US012807654B2

(12) United States Patent
Hasemi et al.

(10) Patent No.: US 12,807,654 B2
(45) Date of Patent: Nov. 24, 2026

(54) IMMUNOGLOBULIN-BINDING PROTEIN

(71) Applicant: TOSOH CORPORATION, Yamaguchi (JP)

(72) Inventors: Takatoshi Hasemi, Kanagawa (JP); Akihiro Iwase, Kanagawa (JP); Satoshi Endo, Kanagawa (JP); Toru Tanaka, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 374 days.

(21) Appl. No.: 18/703,851

(22) PCT Filed: Oct. 24, 2022

(86) PCT No.: PCT/JP2022/039585
§ 371 (c)(1),
(2) Date: Apr. 23, 2024

(87) PCT Pub. No.: WO2023/074642
PCT Pub. Date: May 4, 2023

(65) Prior Publication Data

US 2025/0002543 A1 Jan. 2, 2025

(30) Foreign Application Priority Data

Oct. 25, 2021 (JP) ................................ 2021-174138
Jan. 14, 2022 (JP) ................................ 2022-004574
Apr. 25, 2022 (JP) ................................ 2022-071239
Apr. 25, 2022 (JP) ................................ 2022-071240
Oct. 6, 2022 (JP) ................................ 2022-161841
Oct. 6, 2022 (JP) ................................ 2022-161843

(51) Int. Cl.
*A61K 38/00* (2006.01)
*C07K 1/22* (2006.01)
*C07K 14/195* (2006.01)
*C07K 17/00* (2006.01)
*C12P 21/02* (2006.01)

(52) U.S. Cl.
CPC .............. *C07K 14/195* (2013.01); *C07K 1/22* (2013.01); *C07K 17/00* (2013.01); *C12P 21/02* (2013.01)

(58) Field of Classification Search
CPC ........ C07K 14/195; C07K 1/22; C07K 17/00; C12P 21/02; C12N 5/10; C40B 40/08
See application file for complete search history.

(56) References Cited

U.S. PATENT DOCUMENTS

| | | | |
|---|---|---|---|
| 2018/0305414 A1 | 10/2018 | Majima et al. | |
| 2019/0119333 A1 | 4/2019 | Yoshida | |
| 2020/0262873 A1 | 8/2020 | Yasuoka et al. | |
| 2021/0163545 A1 | 6/2021 | Yasuoka et al. | |

FOREIGN PATENT DOCUMENTS

| | | | | |
|---|---|---|---|---|
| EP | 4074733 A1 | 10/2022 | | |
| JP | 2016-79149 A | 5/2016 | | |
| JP | WO2019059399 A1 * | 10/2020 | .......... C07K 14/195 | |
| WO | 2016/096643 A1 | 6/2016 | | |
| WO | 2017/069158 A1 | 4/2017 | | |
| WO | 2017/191748 A1 | 11/2017 | | |
| WO | 2019/059399 A1 | 3/2019 | | |
| WO | 2019/059400 A1 | 3/2019 | | |
| WO | 2021/109177 A1 | 6/2021 | | |

OTHER PUBLICATIONS

Rodrigo et al., "Antibody Fragments and Their Purification by Protein L Affinity Chromatography," *Antibodies*, 4, 2015, pp. 259-277.
Gulich et al., "Protein engineering of an IgG-binding domain allows milder elution conditions during affinity chromatography," *Journal of Biotechnology*, 76, 2000, pp. 233-244.
International Search Report dated Jan. 17, 2023, issued in PCT/JP2022/039585, with English translation thereof.
International Preliminary Report on Patentability dated Apr. 30, 2024, including Written Opinion dated Jan. 17, 2023, issued in PCT/JP2022/039585, with English translation thereof.

* cited by examiner

*Primary Examiner* — Jeanette M Lieb
(74) *Attorney, Agent, or Firm* — Greenblum & Bernstein, P.L.C.

(57) ABSTRACT

An immunoglobulin-binding protein has an improved chemical stability, especially having an improved alkaline stability, or an immunoglobulin-binding protein capable of allowing antibody elution under mild pH conditions, and an adsorbent on which the protein is immobilized. The alkaline stability or the antibody elution property is improved by including an amino acid sequence which is the same as an amino acid sequence of an immunoglobulin-binding domain of protein L derived from a bacterium belonging to the genus *Finegoldia* except that the amino acid residue(s) at a particular position(s) of the domain in the amino acid sequence is/are substituted with another particular amino acid residues(s).

12 Claims, No Drawings

Specification includes a Sequence Listing.

IMMUNOGLOBULIN-BINDING PROTEIN

TECHNICAL FIELD

An ST.26 sequence listing in electronic (XML text file) format is filed with this application and is incorporated herein by reference. The name of the XML text file is "P71152_Sequence_Listing.xml"; the file was created on Jun. 7, 2024; the size of the file is 595,707 bytes.

The present invention relates to a protein that specifically binds to immunoglobulin. In one aspect, the present invention relates to an immunoglobulin-binding protein having excellent alkali stability. In another aspect, the present invention relates to an immunoglobulin-binding protein that allows antibody elution under mild pH conditions.

BACKGROUND ART

Antibody drugs are pharmaceuticals utilizing an antibody (immunoglobulin), which is a molecule responsible for immune functions in living organisms. By virtue of diversity of the variable region of each antibody, antibody drugs are capable of binding to target molecules with high specificity and affinity. Antibody drugs therefore have fewer side effects. Because of this, and the fact that such drugs have become applicable to a wider range of diseases in recent years, the market for antibody drugs has been rapidly expanding.

Production of an antibody drug includes a culture step and a purification step, wherein productivity in the culture step is improved by modification of antibody-producing cells and optimization of culture conditions. The purification step employs affinity chromatography for crude purification. This is followed by intermediate purification, final purification, and then virus removal before the formulation.

In the purification step, an affinity support that specifically recognizes antibody molecules is used. As a ligand protein for the support, protein A derived from a bacterium belonging to the genus *Staphylococcus* is commonly used since it has an antibody (immunoglobulin)-binding property. However, since protein A is a protein that specifically binds to the Fc region of antibody, it has not been applicable to purification of antibodies that lack the Fc region, such as single-chain Fv (scFv), Fab, F(ab')$_2$, IgA, and bispecific T cell-engaging (BiTE) antibodies. On the other hand, since protein L derived from a bacterium belonging to the genus *Finegoldia* is a protein that binds to the κ light chain of immunoglobulin, use of protein L as the ligand protein enables purification of even an antibody that lacks the Fc region, whose purification is impossible by the protein A.

In the production of the antibody drug, the affinity support is used a plurality of times for reduction of the production cost. After using the affinity support, a step of removing impurities remaining on the support is carried out. Usually, in the step of removing impurities remaining on the support, cleaning-in-place using sodium hydroxide is carried out to regenerate the affinity support. Therefore, the ligand protein needs to have a sufficient chemical stability (especially alkaline stability) so that the antibody-binding capacity can be maintained even after the regeneration step.

Examples of protein L having an improved alkaline stability include the protein L described in Patent Document 1, which was prepared by substituting asparagine at a particular position(s) with glutamine, the protein L described in Patent Document 2, which was prepared by partially deleting N-terminal amino acid residues including proline, and substituting a portion susceptible to alkaline hydrolysis composed of consecutive asparagine and glycine with other amino acids, the protein L described in Patent Document 3, which was prepared by substituting lysine with a basic amino acid other than lysine or with an amino acid containing a hydroxy group, and the protein L described in Patent Document 4, which was prepared by utilizing a domain that does not contain a portion composed of consecutive asparagine and glycine. However, since use of the protein L's disclosed in these documents as ligand proteins requires alkali washing with 20 mM to 50 mM aqueous sodium hydroxide solution (Non-Patent Document 1), their alkaline stabilities have been insufficient for use in the process-scale purification.

Furthermore, in the purification step for an antibody drug, adsorption of antibody molecules to an affinity support under neutral pH conditions is followed by a step of eluting the antibody molecules from the support under acidic pH conditions. Since such acidic pH conditions damage the antibody molecules to cause their aggregation, the pH during the elution is preferably high (in other words, near neutral).

Known examples of a method of increasing the antibody elution pH include a method in which an oligopeptide containing a flexible amino acid residue is inserted into an immunoglobulin-binding protein (Non-Patent Document 2), and a method in which a particular amino acid residue in an immunoglobulin-binding protein is substituted with a histidine residue (Patent Document 5). However, the methods described in these documents have been reported to decrease the chemical stability of the immunoglobulin-binding protein. Thus, there has been a demand for an immunoglobulin-binding protein which does not decrease the chemical stability, and which has a high antibody elution pH (in other words, which allows antibody elution under mild pH conditions).

PRIOR ART DOCUMENTS

Patent Documents

[Patent Document 1] WO 2016/096643
[Patent Document 2] WO 2017/191748
[Patent Document 3] WO 2017/069158
[Patent Document 4] JP 2016-079149 A
[Patent Document 5] WO 2019/059400

Non-Patent Documents

[Non-Patent Document 1] Rodrigo G. et al., Antibodies, 2015, 4, 259-277
[Non-Patent Document 2] Susanne Gulich et al., Journal of Biotechnology, 2000, 76, 233-244

SUMMARY OF THE INVENTION

Problems to be Solved by the Invention

An object of an aspect of the present invention is to provide an immunoglobulin-binding protein having an improved chemical stability, especially having an improved alkaline stability, and an adsorbent on which the protein is immobilized. An object of another object of the present invention is to provide an immunoglobulin-binding protein that allows antibody elution under mild pH conditions, and an adsorbent on which the protein is immobilized.

Means for Solving the Problems

As a result of intensive study to solve the above problem, the present inventors identified amino acid residues responsible for improvement of the stability or for the antibody elution property in an immunoglobulin-binding domain of protein L (FpL) derived from a bacterium belonging to the genus *Finegoldia*, and discovered that substitution of these amino residues with other particular amino acid residues provides a solution to the above problem, thereby completing the present invention.

More specifically, one aspect of the present invention includes the following modes.

[1]

A protein including an amino acid sequence which is the same as an amino acid sequence of an immunoglobulin-binding domain of protein L derived from a bacterium belonging to the genus *Finegoldia* except that the amino acid sequence of the former protein has one or more amino acid substitutions selected from at least the following (1) to (53), the protein having immunoglobulin-binding activity:

(1) substitution of the amino acid residue corresponding to the asparagine at position 50 of SEQ ID NO:1 with tyrosine;
(2) substitution of the amino acid residue corresponding to the glutamic acid at position 1 of SEQ ID NO:1 with glycine or valine;
(3) substitution of the amino acid residue corresponding to the proline at position 3 of SEQ ID NO:1 with serine;
(4) substitution of the amino acid residue corresponding to the glutamic acid at position 4 of SEQ ID NO:1 with lysine or glycine;
(5) substitution of the amino acid residue corresponding to the glutamic acid at position 5 of SEQ ID NO:1 with valine;
(6) substitution of the amino acid residue corresponding to the lysine at position 7 of SEQ ID NO:1 with alanine;
(7) substitution of the amino acid residue corresponding to the glutamic acid at position 8 of SEQ ID NO:1 with glycine;
(8) substitution of the amino acid residue corresponding to the glutamic acid at position 9 of SEQ ID NO:1 with valine;
(9) substitution of the amino acid residue corresponding to the isoleucine at position 17 of SEQ ID NO:1 with phenylalanine;
(10) substitution of the amino acid residue corresponding to the glycine at position 21 of SEQ ID NO:1 with arginine;
(11) substitution of the amino acid residue corresponding to the glutamic acid at position 27 of SEQ ID NO:1 with glycine or arginine;
(12) substitution of the amino acid residue corresponding to the lysine at position 29 of SEQ ID NO:1 with proline;
(13) substitution of the amino acid residue corresponding to the threonine at position 31 of SEQ ID NO:1 with leucine;
(14) substitution of the amino acid residue corresponding to the threonine at position 36 of SEQ ID NO:1 with alanine;
(15) substitution of the amino acid residue corresponding to the alanine at position 41 of SEQ ID NO:1 with threonine;
(16) substitution of the amino acid residue corresponding to the asparagine at position 44 of SEQ ID NO:1 with serine or glycine;
(17) substitution of the amino acid residue corresponding to the glutamic acid at position 49 of SEQ ID NO:1 with threonine or isoleucine;
(18) substitution of the amino acid residue corresponding to the asparagine at position 50 of SEQ ID NO:1 with any of serine, lysine, and aspartic acid;
(19) substitution of the amino acid residue corresponding to the glycine at position 51 of SEQ ID NO:1 with valine;
(20) substitution of the amino acid residue corresponding to the glutamic acid at position 52 of SEQ ID NO:1 with any of valine, glycine, and aspartic acid;
(21) substitution of the amino acid residue corresponding to the tyrosine at position 53 of SEQ ID NO:1 with phenylalanine;
(22) substitution of the amino acid residue corresponding to the threonine at position 54 of SEQ ID NO:1 with isoleucine or methionine;
(23) substitution of the amino acid residue corresponding to the asparagine at position 62 of SEQ ID NO:1 with any of histidine, arginine, leucine, methionine, and tryptophan;
(24) substitution of the amino acid residue corresponding to the asparagine at position 65 of SEQ ID NO:1 with tyrosine;
(25) substitution of the amino acid residue corresponding to the alanine at position 69 of SEQ ID NO:1 with threonine;
(26) substitution of the amino acid residue corresponding to the threonine at position 2 of SEQ ID NO:1 with serine or proline;
(27) substitution of the amino acid residue corresponding to the proline at position 3 of SEQ ID NO:1 with arginine;
(28) substitution of the amino acid residue corresponding to the glutamic acid at position 5 of SEQ ID NO:1 with lysine or arginine;
(29) substitution of the amino acid residue corresponding to the glutamic acid at position 27 of SEQ ID NO:1 with any of valine, lysine, and isoleucine;
(30) substitution of the amino acid residue corresponding to the phenylalanine at position 32 of SEQ ID NO:1 with leucine;
(31) substitution of the amino acid residue corresponding to the lysine at position 38 of SEQ ID NO:1 with alanine;
(32) substitution of the amino acid residue corresponding to the asparagine at position 44 of SEQ ID NO:1 with isoleucine;
(33) substitution of the amino acid residue corresponding to the alanine at position 47 of SEQ ID NO:1 with threonine or arginine;
(34) substitution of the amino acid residue corresponding to the glutamic acid at position 52 of SEQ ID NO:1 with asparagine;
(35) substitution of the amino acid residue corresponding to the threonine at position 2 of SEQ ID NO:1 with alanine;
(36) substitution of the amino acid residue corresponding to the glutamic acid at position 5 of SEQ ID NO:1 with aspartic acid;
(37) substitution of the amino acid residue corresponding to the proline at position 6 of SEQ ID NO:1 with leucine or threonine;
(38) substitution of the amino acid residue corresponding to the lysine at position 7 of SEQ ID NO:1 with proline;
(39) substitution of the amino acid residue corresponding to the valine at position 14 of SEQ ID NO:1 with alanine;

(40) substitution of the amino acid residue corresponding to the isoleucine at position 23 of SEQ ID NO:1 with arginine or valine;

(41) substitution of the amino acid residue corresponding to the lysine at position 29 of SEQ ID NO:1 with phenylalanine;

(42) substitution of the amino acid residue corresponding to the threonine at position 31 of SEQ ID NO:1 with methionine;

(43) substitution of the amino acid residue corresponding to the glutamic acid at position 33 of SEQ ID NO:1 with any of aspartic acid, glycine, and valine;

(44) substitution of the amino acid residue corresponding to the alanine at position 35 of SEQ ID NO:1 with threonine;

(45) substitution of the amino acid residue corresponding to the threonine at position 36 of SEQ ID NO:1 with serine;

(46) substitution of the amino acid residue corresponding to the alanine at position 37 of SEQ ID NO:1 with threonine;

(47) substitution of the amino acid residue corresponding to the alanine at position 41 of SEQ ID NO:1 with isoleucine or tyrosine;

(48) substitution of the amino acid residue corresponding to the asparagine at position 44 of SEQ ID NO:1 with histidine or arginine;

(49) substitution of the amino acid residue corresponding to the glutamic acid at position 52 of SEQ ID NO:1 with leucine or tyrosine;

(50) substitution of the amino acid residue corresponding to the glycine at position 60 of SEQ ID NO:1 with arginine;

(51) substitution of the amino acid residue corresponding to the isoleucine at position 64 of SEQ ID NO:1 with leucine;

(52) substitution of the amino acid residue corresponding to the isoleucine at position 66 of SEQ ID NO:1 with valine; and (53) substitution of the amino acid residue corresponding to the alanine at position 69 of SEQ ID NO:1 with leucine or valine.

[2]

The protein according to [1], which is a protein of any of the following (a) to (c):

(a) a protein including an amino acid sequence which is the same as the amino acid sequence of SEQ ID NO:1 or 18 except that the amino acid sequence of the protein has one or more amino acid substitutions selected from at least the following (1) to (53), the protein having immunoglobulin-binding activity:

(1) substitution of the amino acid residue corresponding to the asparagine at position 50 of SEQ ID NO:1 with tyrosine;

(2) substitution of the amino acid residue corresponding to the glutamic acid at position 1 of SEQ ID NO:1 with glycine or valine;

(3) substitution of the amino acid residue corresponding to the proline at position 3 of SEQ ID NO:1 with serine;

(4) substitution of the amino acid residue corresponding to the glutamic acid at position 4 of SEQ ID NO:1 with lysine or glycine;

(5) substitution of the amino acid residue corresponding to the glutamic acid at position 5 of SEQ ID NO:1 with valine;

(6) substitution of the amino acid residue corresponding to the lysine at position 7 of SEQ ID NO:1 with alanine;

(7) substitution of the amino acid residue corresponding to the glutamic acid at position 8 of SEQ ID NO:1 with glycine;

(8) substitution of the amino acid residue corresponding to the glutamic acid at position 9 of SEQ ID NO:1 with valine;

(9) substitution of the amino acid residue corresponding to the isoleucine at position 17 of SEQ ID NO:1 with phenylalanine;

(10) substitution of the amino acid residue corresponding to the glycine at position 21 of SEQ ID NO:1 with arginine;

(11) substitution of the amino acid residue corresponding to the glutamic acid at position 27 of SEQ ID NO:1 with glycine or arginine;

(12) substitution of the amino acid residue corresponding to the lysine at position 29 of SEQ ID NO:1 with proline;

(13) substitution of the amino acid residue corresponding to the threonine at position 31 of SEQ ID NO:1 with leucine;

(14) substitution of the amino acid residue corresponding to the threonine at position 36 of SEQ ID NO:1 with alanine;

(15) substitution of the amino acid residue corresponding to the alanine at position 41 of SEQ ID NO:1 with threonine;

(16) substitution of the amino acid residue corresponding to the asparagine at position 44 of SEQ ID NO:1 with serine or glycine;

(17) substitution of the amino acid residue corresponding to the glutamic acid at position 49 of SEQ ID NO:1 with threonine or isoleucine;

(18) substitution of the amino acid residue corresponding to the asparagine at position 50 of SEQ ID NO:1 with any of serine, lysine, and aspartic acid;

(19) substitution of the amino acid residue corresponding to the glycine at position 51 of SEQ ID NO:1 with valine;

(20) substitution of the amino acid residue corresponding to the glutamic acid at position 52 of SEQ ID NO:1 with any of valine, glycine, and aspartic acid;

(21) substitution of the amino acid residue corresponding to the tyrosine at position 53 of SEQ ID NO:1 with phenylalanine;

(22) substitution of the amino acid residue corresponding to the threonine at position 54 of SEQ ID NO:1 with isoleucine or methionine;

(23) substitution of the amino acid residue corresponding to the asparagine at position 62 of SEQ ID NO:1 with any of histidine, arginine, leucine, methionine, and tryptophan;

(24) substitution of the amino acid residue corresponding to the asparagine at position 65 of SEQ ID NO:1 with tyrosine;

(25) substitution of the amino acid residue corresponding to the alanine at position 69 of SEQ ID NO:1 with threonine;

(26) substitution of the amino acid residue corresponding to the threonine at position 2 of SEQ ID NO:1 with serine or proline;

(27) substitution of the amino acid residue corresponding to the proline at position 3 of SEQ ID NO:1 with arginine;

(28) substitution of the amino acid residue corresponding to the glutamic acid at position 5 of SEQ ID NO:1 with lysine or arginine;

(29) substitution of the amino acid residue corresponding to the glutamic acid at position 27 of SEQ ID NO:1 with any of valine, lysine, and isoleucine;

(30) substitution of the amino acid residue corresponding to the phenylalanine at position 32 of SEQ ID NO:1 with leucine;

(31) substitution of the amino acid residue corresponding to the lysine at position 38 of SEQ ID NO:1 with alanine;

(32) substitution of the amino acid residue corresponding to the asparagine at position 44 of SEQ ID NO:1 with isoleucine;

(33) substitution of the amino acid residue corresponding to the alanine at position 47 of SEQ ID NO:1 with threonine or arginine;

(34) substitution of the amino acid residue corresponding to the glutamic acid at position 52 of SEQ ID NO:1 with asparagine;

(35) substitution of the amino acid residue corresponding to the threonine at position 2 of SEQ ID NO:1 with alanine;

(36) substitution of the amino acid residue corresponding to the glutamic acid at position 5 of SEQ ID NO:1 with aspartic acid;

(37) substitution of the amino acid residue corresponding to the proline at position 6 of SEQ ID NO:1 with leucine or threonine;

(38) substitution of the amino acid residue corresponding to the lysine at position 7 of SEQ ID NO:1 with proline;

(39) substitution of the amino acid residue corresponding to the valine at position 14 of SEQ ID NO:1 with alanine;

(40) substitution of the amino acid residue corresponding to the isoleucine at position 23 of SEQ ID NO:1 with arginine or valine;

(41) substitution of the amino acid residue corresponding to the lysine at position 29 of SEQ ID NO:1 with phenylalanine;

(42) substitution of the amino acid residue corresponding to the threonine at position 31 of SEQ ID NO:1 with methionine;

(43) substitution of the amino acid residue corresponding to the glutamic acid at position 33 of SEQ ID NO:1 with any of aspartic acid, glycine, and valine;

(44) substitution of the amino acid residue corresponding to the alanine at position 35 of SEQ ID NO:1 with threonine;

(45) substitution of the amino acid residue corresponding to the threonine at position 36 of SEQ ID NO:1 with serine;

(46) substitution of the amino acid residue corresponding to the alanine at position 37 of SEQ ID NO:1 with threonine;

(47) substitution of the amino acid residue corresponding to the alanine at position 41 of SEQ ID NO:1 with isoleucine or tyrosine;

(48) substitution of the amino acid residue corresponding to the asparagine at position 44 of SEQ ID NO:1 with histidine or arginine;

(49) substitution of the amino acid residue corresponding to the glutamic acid at position 52 of SEQ ID NO:1 with leucine or tyrosine;

(50) substitution of the amino acid residue corresponding to the glycine at position 60 of SEQ ID NO:1 with arginine;

(51) substitution of the amino acid residue corresponding to the isoleucine at position 64 of SEQ ID NO:1 with leucine;

(52) substitution of the amino acid residue corresponding to the isoleucine at position 66 of SEQ ID NO:1 with valine; and

(53) substitution of the amino acid residue corresponding to the alanine at position 69 of SEQ ID NO:1 with leucine or valine;

(b) a protein including an amino acid sequence which is the same as the amino acid sequence of SEQ ID NO:1 or 18 except that the amino acid sequence of the protein has one or more amino acid substitutions selected from at least (1) to (53), and also has substitution, deletion, insertion, and/or addition of one or several amino acid residues at one or several positions other than (1) to (53), the protein having immunoglobulin-binding activity; and (c) a protein including an amino acid sequence having a homology of not less than 70% to the amino acid sequence of SEQ ID NO:1 or 18 or a partial sequence thereof, wherein the amino acid sequence of the protein has one or more amino acid substitutions selected from at least (1) to (53), the protein having immunoglobulin-binding activity.

[3]

The protein according to [1] or [2], which is a protein of any of the following (d) to (f):

(d) a protein including an amino acid sequence which is the same as the amino acid sequence of SEQ ID NO:1 or 18 except that the amino acid sequence of the protein has at least the following amino acid substitution (1), the protein having immunoglobulin-binding activity:

(1) substitution of the amino acid residue corresponding to the asparagine at position 50 of SEQ ID NO:1 with tyrosine;

(e) a protein including an amino acid sequence which is the same as the amino acid sequence of SEQ ID NO:1 or 18 except that the amino acid sequence of the protein has at least the amino acid substitution (1), and also has substitution, deletion, insertion, and/or addition of one or several amino acid residues at one or several positions other than the above amino acid substitution, the protein having immunoglobulin-binding activity; and (f) a protein including an amino acid sequence having a homology of not less than 70% to the amino acid sequence of SEQ ID NO:1 or 18 or a partial sequence thereof, wherein the amino acid sequence of the protein has at least the amino acid substitution (1), the protein having immunoglobulin-binding activity.

[4]

The protein according to any of [1] to [3], further including one or more amino acid substitutions selected from at least the following (54) to (64):

(54) substitution of the amino acid residue corresponding to the lysine at position 7 of SEQ ID NO:1 with glutamine;

(55) substitution of the amino acid residue corresponding to the lysine at position 13 of SEQ ID NO:1 with valine;

(56) substitution of the amino acid residue corresponding to the lysine at position 29 of SEQ ID NO:1 with valine or isoleucine;

(57) substitution of the amino acid residue corresponding to the proline at position 6 of SEQ ID NO:1 with alanine;

(58) substitution of the amino acid residue corresponding to the glutamic acid at position 8 of SEQ ID NO:1 with arginine;

(59) substitution of the amino acid residue corresponding to the asparagine at position 15 of SEQ ID NO:1 with valine;

(60) substitution of the amino acid residue corresponding to the isoleucine at position 23 of SEQ ID NO:1 with phenylalanine or leucine;

(61) substitution of the amino acid residue corresponding to the glutamic acid at position 34 of SEQ ID NO:1 with any of aspartic acid, phenylalanine, leucine, and valine;

(62) substitution of the amino acid residue corresponding to the lysine at position 38 of SEQ ID NO:1 with leucine;

(63) substitution of the amino acid residue corresponding to the asparagine at position 50 of SEQ ID NO:1 with methionine; and

(64) substitution of the amino acid residue corresponding to the tyrosine at position 53 of SEQ ID NO:1 with serine.

[5]

The protein according to any of [1] to [4], wherein one or more lysine residues selected from at least the following (I) to (VII) are substituted with a basic amino acid(s) other than lysine, and/or with an amino acid residue(s) containing a hydroxy group:

(I) the lysine residue corresponding to position 7 of SEQ ID NO: 1;

(II) the lysine residue corresponding to position 13 of SEQ ID NO: 1;

(III) the lysine residue corresponding to position 22 of SEQ ID NO: 1;

(IV) the lysine residue corresponding to position 29 of SEQ ID NO: 1;

(V) the lysine residue corresponding to position 38 of SEQ ID NO: 1;

(VI) the lysine residue corresponding to position 48 of SEQ ID NO: 1; and (VII) the lysine residue corresponding to position 67 of SEQ ID NO: 1.

[6]

The protein according to any of [1] to [5], further including one or more amino acid substitutions selected from substitution of the amino acid residue corresponding to the glutamic acid at position 49 of SEQ ID NO:1 with aspartic acid, substitution of the amino acid residue corresponding to the proline at position 6 of SEQ ID NO:1 with serine, substitution of the amino acid residue corresponding to the asparagine at position 44 of SEQ ID NO:1 with aspartic acid, substitution of the amino acid residue corresponding to the glutamic acid at position 49 of SEQ ID NO:1 with valine, substitution of the amino acid residue corresponding to the asparagine at position 62 of SEQ ID NO:1 with tyrosine, substitution of the amino acid residue corresponding to the asparagine at position 23 of SEQ ID NO:1 with aspartic acid, and substitution of the amino acid residue corresponding to the asparagine at position 44 of SEQ ID NO:1 with aspartic acid.

[7]

The protein according to any of [1] to [6], wherein the protein includes at least any of the following amino acid substitutions (W), (X), (Y), (Z), (AA), (AB), (AC), (AD), and (AE):

(W) substitution of the amino acid residue corresponding to the lysine at position 7 of SEQ ID NO:1 with alanine, substitution of the amino acid residue corresponding to the lysine at each of positions 13, 38, 48, and 67 of SEQ ID NO:1 with arginine, substitution of the amino acid residue corresponding to the lysine at position 22 of SEQ ID NO:1 with glutamine, substitution of the amino acid residue corresponding to the lysine at position 29 of SEQ ID NO:1 with isoleucine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, and substitution of the amino acid residue corresponding to the glutamic acid at position 52 of SEQ ID NO:1 with glycine;

(X) substitution of the amino acid residue corresponding to the lysine at position 7 of SEQ ID NO:1 with alanine, substitution of the amino acid residue corresponding to the lysine at each of positions 13, 22, 38, 48, and 67 of SEQ ID NO:1 with arginine, substitution of the amino acid residue corresponding to the lysine at position 29 of SEQ ID NO:1 with isoleucine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with glycine, and substitution of the amino acid residue corresponding to the tyrosine at position 53 of SEQ ID NO:1 with phenylalanine;

(Y) substitution of the amino acid residue corresponding to the glutamic acid at position 4 of SEQ ID NO:1 with glycine, substitution of the amino acid residue corresponding to the lysine at position 7 of SEQ ID NO:1 with alanine, substitution of the amino acid residue corresponding to the lysine at each of positions 13, 22, 38, 48, and 67 of SEQ ID NO:1 with arginine, substitution of the amino acid residue corresponding to the lysine at position 29 of SEQ ID NO:1 with isoleucine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with aspartic acid, and substitution of the amino acid residue corresponding to the tyrosine at position 53 of SEQ ID NO:1 with phenylalanine;

(Z) substitution of the amino acid residue corresponding to the glutamic acid at position 4 of SEQ ID NO:1 with glycine, substitution of the amino acid residue corresponding to the lysine at position 7 of SEQ ID NO:1 with alanine, substitution of the amino acid residue corresponding to the lysine at each of positions 13, 22, 38, 48, and 67 of SEQ ID NO:1 with arginine, substitution of the amino acid residue corresponding to the glutamic acid at position 27 of SEQ ID NO:1 with arginine, substitution of the amino acid residue corresponding to the lysine at position 29 of SEQ ID NO:1 with isoleucine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with aspartic acid, and substitution of the amino acid residue corresponding to the tyrosine at position 53 of SEQ ID NO:1 with phenylalanine;

(AA) substitution of the amino acid residue corresponding to the glutamic acid at position 4 of SEQ ID NO:1 with glycine, substitution of the amino acid residue corresponding to the proline at position 6 of SEQ ID NO:1 with serine, substitution of the amino acid residue corresponding to the lysine at position 7 of SEQ ID NO:1 with alanine, substitution of the amino acid residue corresponding to the lysine at each of positions 13, 22, 48, and 67 of SEQ ID NO:1 with arginine, substitution of the amino acid residue corresponding to the lysine at position 29 of SEQ ID NO:1 with isoleucine, substitution of the amino acid residue corresponding to the lysine at position 38 of SEQ ID NO:1 with glutamic acid, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with aspartic acid, and substitution of the amino acid residue corresponding to the tyrosine at position 53 of SEQ ID NO:1 with phenylalanine;

(AB) substitution of the amino acid residue corresponding to the glutamic acid at position 4 of SEQ ID NO:1 with glycine, substitution of the amino acid residue corresponding to the proline at position 6 of SEQ ID NO:1 with serine, substitution of the amino acid residue corresponding to the lysine at position 7 of SEQ ID NO:1 with alanine, substitution of the amino acid residue corresponding to the lysine at each of positions 13, 22, 48, and 67 of SEQ ID NO:1 with arginine, substitution of the amino acid residue corresponding to the lysine at position 29 of SEQ ID NO:1 with isoleucine, substitution of the amino acid residue corresponding to the lysine at position 38 of SEQ ID NO:1 with glutamic acid, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with valine, substitution of the amino acid residue corresponding to the tyrosine at position 53 of SEQ ID NO:1 with phenylalanine, and substitution of the amino acid residue corresponding to the alanine at position 69 of SEQ ID NO:1 with valine;

(AC) substitution of the amino acid residue corresponding to the glutamic acid at position 4 of SEQ ID NO:1 with glycine, substitution of the amino acid residue corresponding to the proline at position 6 of SEQ ID NO:1 with serine, substitution of the amino acid residue corresponding to the lysine at position 7 of SEQ ID NO:1 with alanine, substitution of the amino acid residue corresponding to the lysine at each of positions 13, 22, 48, and 67 of SEQ ID NO:1 with arginine, substitution of the amino acid residue corresponding to the lysine at position 29 of SEQ ID NO:1 with isoleucine, substitution of the amino acid residue corresponding to the lysine at position 38 of SEQ ID NO:1 with glutamic acid, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the tyrosine at position 53 of SEQ ID NO:1 with phenylalanine, and substitution of the amino acid residue corresponding to the alanine at position 69 of SEQ ID NO:1 with valine;

(AD) substitution of the amino acid residue corresponding to the glutamic acid at position 4 of SEQ ID NO:1 with glycine, substitution of the amino acid residue corresponding to the proline at position 6 of SEQ ID NO:1 with serine, substitution of the amino acid residue corresponding to the lysine at position 7 of SEQ ID NO:1 with alanine, substitution of the amino acid residue corresponding to the lysine at each of positions 13, 22, 48, and 67 of SEQ ID NO:1 with arginine, substitution of the amino acid residue corresponding to the isoleucine at position 23 of SEQ ID NO:1 with arginine, substitution of the amino acid residue corresponding to the lysine at position 29 of SEQ ID NO:1 with isoleucine, substitution of the amino acid residue corresponding to the lysine at position 38 of SEQ ID NO:1 with glutamic acid, substitution of the amino acid residue corresponding to the asparagine at position 44 of SEQ ID NO:1 with arginine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the tyrosine at position 53 of SEQ ID NO:1 with phenylalanine, and substitution of the amino acid residue corresponding to the alanine at position 69 of SEQ ID NO:1 with valine; and (AE) substitution of the amino acid residue corresponding to the glutamic acid at position 4 of SEQ ID NO:1 with glycine, substitution of the amino acid residue corresponding to the proline at position 6 of SEQ ID NO:1 with serine, substitution of the amino acid residue corresponding to the lysine at position 7 of SEQ ID NO:1 with alanine, substitution of the amino acid residue corresponding to the lysine at each of positions 13, 22, and 67 of SEQ ID NO:1 with arginine, substitution of the amino acid residue corresponding to the isoleucine at position 23 of SEQ ID NO:1 with arginine, substitution of the amino acid residue corresponding to the lysine at position 29 of SEQ ID NO:1 with isoleucine, substitution of the amino acid residue corresponding to the lysine at position 38 of SEQ ID NO:1 with glutamic acid, substitution of the amino acid residue corresponding to the asparagine at position 44 of SEQ ID NO:1 with arginine, substitution of the amino acid residue corresponding to the lysine at position 48 of SEQ ID NO:1 with histidine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the tyrosine at position 53 of SEQ ID NO:1 with phenylalanine, substitution of the amino acid residue corresponding to the isoleucine at position 64 of SEQ ID NO:1 with leucine, and substitution of the amino acid residue corresponding to the alanine at position 69 of SEQ ID NO:1 with valine.

[8]

The protein according to any of [1] to [7], wherein the protein includes the amino acid sequence of any of SEQ ID NOs:179, 186, 199, 224, 240, 271, 275, 408, and 413.

[9]

A method of producing a protein having immunoglobulin-binding activity, the method including the steps of:

culturing a recombinant host containing a polynucleotide encoding the protein according to any of [1] to [8], or a recombinant host containing an expression vector containing the polynucleotide, to allow expression of the protein; and recovering the expressed protein.

[10]

The production method according to [9], wherein the host is *Escherichia coli.*

[11]

A column packed with an immunoglobulin adsorbent including:

an insoluble support; and a protein according to any of [1] to [8] immobilized on the insoluble support.

[12]

A method of separating immunoglobulin contained in a solution, the method including the steps of:

applying a solution containing immunoglobulin to the column according to [11], to allow adsorption of the immunoglobulin to the immunoglobulin adsorbent packed in the column; and eluting the immunoglobulin that has adsorbed to the immunoglobulin adsorbent.

Further, one aspect of the present invention includes the following modes.

[A1]

A protein including an amino acid sequence which is the same as an amino acid sequence of an immunoglobulin-binding domain of protein L derived from a bacterium belonging to the genus *Finegoldia* except that the amino acid sequence of the former protein has one or more amino acid substitutions selected from at least the following (1) to (53), the protein having immunoglobulin-binding activity:

(1) substitution of the amino acid residue corresponding to the asparagine at position 50 of SEQ ID NO:1 with tyrosine;

(2) substitution of the amino acid residue corresponding to the glutamic acid at position 1 of SEQ ID NO:1 with glycine or valine;

(3) substitution of the amino acid residue corresponding to the proline at position 3 of SEQ ID NO:1 with serine;

(4) substitution of the amino acid residue corresponding to the glutamic acid at position 4 of SEQ ID NO:1 with lysine or glycine;

(5) substitution of the amino acid residue corresponding to the glutamic acid at position 5 of SEQ ID NO:1 with valine;

(6) substitution of the amino acid residue corresponding to the lysine at position 7 of SEQ ID NO:1 with alanine;

(7) substitution of the amino acid residue corresponding to the glutamic acid at position 8 of SEQ ID NO:1 with glycine;

(8) substitution of the amino acid residue corresponding to the glutamic acid at position 9 of SEQ ID NO:1 with valine;

(9) substitution of the amino acid residue corresponding to the isoleucine at position 17 of SEQ ID NO:1 with phenylalanine;

(10) substitution of the amino acid residue corresponding to the glycine at position 21 of SEQ ID NO:1 with arginine;

(11) substitution of the amino acid residue corresponding to the glutamic acid at position 27 of SEQ ID NO:1 with glycine or arginine;

(12) substitution of the amino acid residue corresponding to the lysine at position 29 of SEQ ID NO:1 with proline;

(13) substitution of the amino acid residue corresponding to the threonine at position 31 of SEQ ID NO:1 with leucine;

(14) substitution of the amino acid residue corresponding to the threonine at position 36 of SEQ ID NO:1 with alanine;

(15) substitution of the amino acid residue corresponding to the alanine at position 41 of SEQ ID NO:1 with threonine;

(16) substitution of the amino acid residue corresponding to the asparagine at position 44 of SEQ ID NO:1 with serine or glycine;

(17) substitution of the amino acid residue corresponding to the glutamic acid at position 49 of SEQ ID NO:1 with threonine or isoleucine;

(18) substitution of the amino acid residue corresponding to the asparagine at position 50 of SEQ ID NO:1 with any of serine, lysine, and aspartic acid;

(19) substitution of the amino acid residue corresponding to the glycine at position 51 of SEQ ID NO:1 with valine;

(20) substitution of the amino acid residue corresponding to the glutamic acid at position 52 of SEQ ID NO:1 with any of valine, glycine, and aspartic acid;

(21) substitution of the amino acid residue corresponding to the tyrosine at position 53 of SEQ ID NO:1 with phenylalanine;

(22) substitution of the amino acid residue corresponding to the threonine at position 54 of SEQ ID NO:1 with isoleucine or methionine;

(23) substitution of the amino acid residue corresponding to the asparagine at position 62 of SEQ ID NO:1 with any of histidine, arginine, leucine, methionine, and tryptophan;

(24) substitution of the amino acid residue corresponding to the asparagine at position 65 of SEQ ID NO:1 with tyrosine;

(25) substitution of the amino acid residue corresponding to the alanine at position 69 of SEQ ID NO:1 with threonine;

(26) substitution of the amino acid residue corresponding to the threonine at position 2 of SEQ ID NO:1 with serine or proline;

(27) substitution of the amino acid residue corresponding to the proline at position 3 of SEQ ID NO:1 with arginine;

(28) substitution of the amino acid residue corresponding to the glutamic acid at position 5 of SEQ ID NO:1 with lysine or arginine;

(29) substitution of the amino acid residue corresponding to the glutamic acid at position 27 of SEQ ID NO:1 with any of valine, lysine, and isoleucine;

(30) substitution of the amino acid residue corresponding to the phenylalanine at position 32 of SEQ ID NO:1 with leucine;

(31) substitution of the amino acid residue corresponding to the lysine at position 38 of SEQ ID NO:1 with alanine;

(32) substitution of the amino acid residue corresponding to the asparagine at position 44 of SEQ ID NO:1 with isoleucine;

(33) substitution of the amino acid residue corresponding to the alanine at position 47 of SEQ ID NO:1 with threonine or arginine;
(34) substitution of the amino acid residue corresponding to the glutamic acid at position 52 of SEQ ID NO:1 with asparagine;
(35) substitution of the amino acid residue corresponding to the threonine at position 2 of SEQ ID NO:1 with alanine;
(36) substitution of the amino acid residue corresponding to the glutamic acid at position 5 of SEQ ID NO:1 with aspartic acid;
(37) substitution of the amino acid residue corresponding to the proline at position 6 of SEQ ID NO:1 with leucine or threonine;
(38) substitution of the amino acid residue corresponding to the lysine at position 7 of SEQ ID NO:1 with proline;
(39) substitution of the amino acid residue corresponding to the valine at position 14 of SEQ ID NO:1 with alanine;
(40) substitution of the amino acid residue corresponding to the isoleucine at position 23 of SEQ ID NO:1 with arginine or valine;
(41) substitution of the amino acid residue corresponding to the lysine at position 29 of SEQ ID NO:1 with phenylalanine;
(42) substitution of the amino acid residue corresponding to the threonine at position 31 of SEQ ID NO:1 with methionine;
(43) substitution of the amino acid residue corresponding to the glutamic acid at position 33 of SEQ ID NO:1 with any of aspartic acid, glycine, and valine;
(44) substitution of the amino acid residue corresponding to the alanine at position 35 of SEQ ID NO:1 with threonine;
(45) substitution of the amino acid residue corresponding to the threonine at position 36 of SEQ ID NO:1 with serine;
(46) substitution of the amino acid residue corresponding to the alanine at position 37 of SEQ ID NO:1 with threonine;
(47) substitution of the amino acid residue corresponding to the alanine at position 41 of SEQ ID NO:1 with isoleucine or tyrosine;
(48) substitution of the amino acid residue corresponding to the asparagine at position 44 of SEQ ID NO:1 with histidine or arginine;
(49) substitution of the amino acid residue corresponding to the glutamic acid at position 52 of SEQ ID NO:1 with leucine or tyrosine;
(50) substitution of the amino acid residue corresponding to the glycine at position 60 of SEQ ID NO:1 with arginine;
(51) substitution of the amino acid residue corresponding to the isoleucine at position 64 of SEQ ID NO:1 with leucine;
(52) substitution of the amino acid residue corresponding to the isoleucine at position 66 of SEQ ID NO:1 with valine; and
(53) substitution of the amino acid residue corresponding to the alanine at position 69 of SEQ ID NO:1 with leucine or valine.

[A2]

The protein according to [A1], which is a protein of any of the following (a) to (c):

(a) a protein including an amino acid sequence which is the same as the amino acid sequence of SEQ ID NO:1 or 18 except that the amino acid sequence of the protein has one or more amino acid substitutions selected from at least the following (1) to (53), the protein having immunoglobulin-binding activity:

(1) substitution of the amino acid residue corresponding to the asparagine at position 50 of SEQ ID NO:1 with tyrosine;
(2) substitution of the amino acid residue corresponding to the glutamic acid at position 1 of SEQ ID NO:1 with glycine or valine;
(3) substitution of the amino acid residue corresponding to the proline at position 3 of SEQ ID NO:1 with serine;
(4) substitution of the amino acid residue corresponding to the glutamic acid at position 4 of SEQ ID NO:1 with lysine or glycine;
(5) substitution of the amino acid residue corresponding to the glutamic acid at position 5 of SEQ ID NO:1 with valine;
(6) substitution of the amino acid residue corresponding to the lysine at position 7 of SEQ ID NO:1 with alanine;
(7) substitution of the amino acid residue corresponding to the glutamic acid at position 8 of SEQ ID NO:1 with glycine;
(8) substitution of the amino acid residue corresponding to the glutamic acid at position 9 of SEQ ID NO:1 with valine;
(9) substitution of the amino acid residue corresponding to the isoleucine at position 17 of SEQ ID NO:1 with phenylalanine;
(10) substitution of the amino acid residue corresponding to the glycine at position 21 of SEQ ID NO:1 with arginine;
(11) substitution of the amino acid residue corresponding to the glutamic acid at position 27 of SEQ ID NO:1 with glycine or arginine;
(12) substitution of the amino acid residue corresponding to the lysine at position 29 of SEQ ID NO:1 with proline;
(13) substitution of the amino acid residue corresponding to the threonine at position 31 of SEQ ID NO:1 with leucine;
(14) substitution of the amino acid residue corresponding to the threonine at position 36 of SEQ ID NO:1 with alanine;
(15) substitution of the amino acid residue corresponding to the alanine at position 41 of SEQ ID NO:1 with threonine;
(16) substitution of the amino acid residue corresponding to the asparagine at position 44 of SEQ ID NO:1 with serine or glycine;
(17) substitution of the amino acid residue corresponding to the glutamic acid at position 49 of SEQ ID NO:1 with threonine or isoleucine;
(18) substitution of the amino acid residue corresponding to the asparagine at position 50 of SEQ ID NO:1 with any of serine, lysine, and aspartic acid;
(19) substitution of the amino acid residue corresponding to the glycine at position 51 of SEQ ID NO:1 with valine;
(20) substitution of the amino acid residue corresponding to the glutamic acid at position 52 of SEQ ID NO:1 with any of valine, glycine, and aspartic acid;
(21) substitution of the amino acid residue corresponding to the tyrosine at position 53 of SEQ ID NO:1 with phenylalanine;

(22) substitution of the amino acid residue corresponding to the threonine at position 54 of SEQ ID NO:1 with isoleucine or methionine;
(23) substitution of the amino acid residue corresponding to the asparagine at position 62 of SEQ ID NO:1 with any of histidine, arginine, leucine, methionine, and tryptophan;
(24) substitution of the amino acid residue corresponding to the asparagine at position 65 of SEQ ID NO:1 with tyrosine;
(25) substitution of the amino acid residue corresponding to the alanine at position 69 of SEQ ID NO:1 with threonine;
(26) substitution of the amino acid residue corresponding to the threonine at position 2 of SEQ ID NO:1 with serine or proline;
(27) substitution of the amino acid residue corresponding to the proline at position 3 of SEQ ID NO:1 with arginine;
(28) substitution of the amino acid residue corresponding to the glutamic acid at position 5 of SEQ ID NO:1 with lysine or arginine;
(29) substitution of the amino acid residue corresponding to the glutamic acid at position 27 of SEQ ID NO:1 with any of valine, lysine, and isoleucine;
(30) substitution of the amino acid residue corresponding to the phenylalanine at position 32 of SEQ ID NO:1 with leucine;
(31) substitution of the amino acid residue corresponding to the lysine at position 38 of SEQ ID NO:1 with alanine;
(32) substitution of the amino acid residue corresponding to the asparagine at position 44 of SEQ ID NO:1 with isoleucine;
(33) substitution of the amino acid residue corresponding to the alanine at position 47 of SEQ ID NO:1 with threonine or arginine;
(34) substitution of the amino acid residue corresponding to the glutamic acid at position 52 of SEQ ID NO:1 with asparagine;
(35) substitution of the amino acid residue corresponding to the threonine at position 2 of SEQ ID NO:1 with alanine;
(36) substitution of the amino acid residue corresponding to the glutamic acid at position 5 of SEQ ID NO:1 with aspartic acid;
(37) substitution of the amino acid residue corresponding to the proline at position 6 of SEQ ID NO:1 with leucine or threonine;
(38) substitution of the amino acid residue corresponding to the lysine at position 7 of SEQ ID NO:1 with proline;
(39) substitution of the amino acid residue corresponding to the valine at position 14 of SEQ ID NO:1 with alanine;
(40) substitution of the amino acid residue corresponding to the isoleucine at position 23 of SEQ ID NO:1 with arginine or valine;
(41) substitution of the amino acid residue corresponding to the lysine at position 29 of SEQ ID NO:1 with phenylalanine;
(42) substitution of the amino acid residue corresponding to the threonine at position 31 of SEQ ID NO:1 with methionine;
(43) substitution of the amino acid residue corresponding to the glutamic acid at position 33 of SEQ ID NO:1 with any of aspartic acid, glycine, and valine;
(44) substitution of the amino acid residue corresponding to the alanine at position 35 of SEQ ID NO:1 with threonine;
(45) substitution of the amino acid residue corresponding to the threonine at position 36 of SEQ ID NO:1 with serine;
(46) substitution of the amino acid residue corresponding to the alanine at position 37 of SEQ ID NO:1 with threonine;
(47) substitution of the amino acid residue corresponding to the alanine at position 41 of SEQ ID NO:1 with isoleucine or tyrosine;
(48) substitution of the amino acid residue corresponding to the asparagine at position 44 of SEQ ID NO:1 with histidine or arginine;
(49) substitution of the amino acid residue corresponding to the glutamic acid at position 52 of SEQ ID NO:1 with leucine or tyrosine;
(50) substitution of the amino acid residue corresponding to the glycine at position 60 of SEQ ID NO:1 with arginine;
(51) substitution of the amino acid residue corresponding to the isoleucine at position 64 of SEQ ID NO:1 with leucine;
(52) substitution of the amino acid residue corresponding to the isoleucine at position 66 of SEQ ID NO:1 with valine; and
(53) substitution of the amino acid residue corresponding to the alanine at position 69 of SEQ ID NO:1 with leucine or valine;
(b) a protein including an amino acid sequence which is the same as the amino acid sequence of SEQ ID NO:1 or 18 except that the amino acid sequence of the protein has one or more amino acid substitutions selected from at least (1) to (53), and also has substitution, deletion, insertion, and/or addition of one or several amino acid residues at one or several positions other than (1) to (53), the protein having immunoglobulin-binding activity; and
(c) a protein including an amino acid sequence having a homology of not less than 70% to the amino acid sequence of SEQ ID NO:1 or 18 or a partial sequence thereof, wherein the amino acid sequence of the protein has one or more amino acid substitutions selected from at least (1) to (53), the protein having immunoglobulin-binding activity.

[A3]

The protein according to [A1] or [A2], which is a protein of any of the following (d) to (f):

(d) a protein including an amino acid sequence which is the same as the amino acid sequence of SEQ ID NO:1 or 18 except that the amino acid sequence of the protein has at least the following amino acid substitution (1), the protein having immunoglobulin-binding activity:
(1) substitution of the amino acid residue corresponding to the asparagine at position 50 of SEQ ID NO:1 with tyrosine;
(e) a protein including an amino acid sequence which is the same as the amino acid sequence of SEQ ID NO:1 or 18 except that the amino acid sequence of the protein has at least the amino acid substitution (1), and also has substitution, deletion, insertion, and/or addition of one or several amino acid residues at one or several positions other than the above amino acid substitution, the protein having immunoglobulin-binding activity; and
(f) a protein including an amino acid sequence having a homology of not less than 70% to the amino acid sequence of SEQ ID NO:1 or 18 or a partial sequence thereof, wherein the amino acid sequence of the protein has at least the amino acid substitution (1), the protein having immunoglobulin-binding activity.

[A4]

The protein according to any of [A1] to [A3], wherein one or more lysine residues selected from at least the following (I) to (VII) are substituted with a basic amino acid(s) other than lysine, and/or with an amino acid residue(s) containing a hydroxy group:

(I) the lysine residue corresponding to position 7 of SEQ ID NO: 1;

(II) the lysine residue corresponding to position 13 of SEQ ID NO: 1;

(III) the lysine residue corresponding to position 22 of SEQ ID NO: 1;

(IV) the lysine residue corresponding to position 29 of SEQ ID NO: 1;

(V) the lysine residue corresponding to position 38 of SEQ ID NO:1;

(VI) the lysine residue corresponding to position 48 of SEQ ID NO: 1; and (VII) the lysine residue corresponding to position 67 of SEQ ID NO:1.

[A5]

The protein according to any of [A1] to [A4], further including one or more amino acid substitutions selected from substitution of the amino acid residue corresponding to the glutamic acid at position 49 of SEQ ID NO:1 with aspartic acid, substitution of the amino acid residue corresponding to the proline at position 6 of SEQ ID NO:1 with serine, substitution of the amino acid residue corresponding to the asparagine at position 44 of SEQ ID NO:1 with aspartic acid, substitution of the amino acid residue corresponding to the glutamic acid at position 49 of SEQ ID NO:1 with valine, substitution of the amino acid residue corresponding to the asparagine at position 62 of SEQ ID NO:1 with tyrosine, substitution of the amino acid residue corresponding to the asparagine at position 23 of SEQ ID NO:1 with aspartic acid, and substitution of the amino acid residue corresponding to the asparagine at position 44 of SEQ ID NO:1 with aspartic acid.

[A6]

The protein according to any of [A1] to [A5], wherein the protein includes at least any of the following amino acid substitutions (W), (X), (Y), (Z), (AA), (AB), and (AC):

(W) substitution of the amino acid residue corresponding to the lysine at position 7 of SEQ ID NO:1 with alanine, substitution of the amino acid residue corresponding to the lysine at each of positions 13, 38, 48, and 67 of SEQ ID NO:1 with arginine, substitution of the amino acid residue corresponding to the lysine at position 22 of SEQ ID NO:1 with glutamine, substitution of the amino acid residue corresponding to the lysine at position 29 of SEQ ID NO:1 with isoleucine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, and substitution of the amino acid residue corresponding to the glutamic acid at position 52 of SEQ ID NO:1 with glycine;

(X) substitution of the amino acid residue corresponding to the lysine at position 7 of SEQ ID NO:1 with alanine, substitution of the amino acid residue corresponding to the lysine at each of positions 13, 22, 38, 48, and 67 of SEQ ID NO:1 with arginine, substitution of the amino acid residue corresponding to the lysine at position 29 of SEQ ID NO:1 with isoleucine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with glycine, and substitution of the amino acid residue corresponding to the tyrosine at position 53 of SEQ ID NO:1 with phenylalanine;

(Y) substitution of the amino acid residue corresponding to the glutamic acid at position 4 of SEQ ID NO:1 with glycine, substitution of the amino acid residue corresponding to the lysine at position 7 of SEQ ID NO:1 with alanine, substitution of the amino acid residue corresponding to the lysine at each of positions 13, 22, 38, 48, and 67 of SEQ ID NO:1 with arginine, substitution of the amino acid residue corresponding to the lysine at position 29 of SEQ ID NO:1 with isoleucine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with aspartic acid, and substitution of the amino acid residue corresponding to the tyrosine at position 53 of SEQ ID NO:1 with phenylalanine;

(Z) substitution of the amino acid residue corresponding to the glutamic acid at position 4 of SEQ ID NO:1 with glycine, substitution of the amino acid residue corresponding to the lysine at position 7 of SEQ ID NO:1 with alanine, substitution of the amino acid residue corresponding to the lysine at each of positions 13, 22, 38, 48, and 67 of SEQ ID NO:1 with arginine, substitution of the amino acid residue corresponding to the glutamic acid at position 27 of SEQ ID NO:1 with arginine, substitution of the amino acid residue corresponding to the lysine at position 29 of SEQ ID NO:1 with isoleucine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with aspartic acid, and substitution of the amino acid residue corresponding to the tyrosine at position 53 of SEQ ID NO:1 with phenylalanine;

(AA) substitution of the amino acid residue corresponding to the glutamic acid at position 4 of SEQ ID NO:1 with glycine, substitution of the amino acid residue corresponding to the proline at position 6 of SEQ ID NO:1 with serine, substitution of the amino acid residue corresponding to the lysine at position 7 of SEQ ID NO:1 with alanine, substitution of the amino acid residue corresponding to the lysine at each of positions 13, 22, 48, and 67 of SEQ ID NO:1 with arginine, substitution of the amino acid residue corresponding to the lysine at position 29 of SEQ ID NO:1 with isoleucine, substitution of the amino acid residue corresponding to the lysine at position 38 of SEQ ID NO:1 with glutamic acid, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with aspartic acid, and substitution of the amino acid residue corresponding to the tyrosine at position 53 of SEQ ID NO:1 with phenylalanine;

(AB) substitution of the amino acid residue corresponding to the glutamic acid at position 4 of SEQ ID NO:1 with glycine, substitution of the amino acid residue corresponding to the proline at position 6 of SEQ ID NO:1 with serine, substitution of the amino acid residue corresponding to the lysine at position 7 of SEQ ID NO:1 with alanine, substitution of the amino acid residue corresponding to the lysine at each of positions 13, 22, 48, and 67 of SEQ ID NO:1 with arginine, substitution of the amino acid residue corresponding to the lysine at position 29 of SEQ ID NO:1 with isoleucine, substitution of the amino acid residue corresponding to the lysine at position 38 of SEQ ID NO:1 with glutamic acid, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with valine, substitution of the amino acid residue corresponding to the tyrosine at position 53 of SEQ ID NO:1 with phenylalanine, and substitution of the amino acid residue corresponding to the alanine at position 69 of SEQ ID NO:1 with valine; and (AC) substitution of the amino acid residue corresponding to the glutamic acid at position 4 of SEQ ID NO:1 with glycine, substitution of the amino acid residue corresponding to the proline at position 6 of SEQ ID NO:1 with serine, substitution of the amino acid residue corresponding to the lysine at position 7 of SEQ ID NO:1 with alanine, substitution of the amino acid residue corresponding to the lysine at each of positions 13, 22, 48, and 67 of SEQ ID NO:1 with arginine, substitution of the amino acid residue corresponding to the lysine at position 29 of SEQ ID NO:1 with isoleucine, substitution of the amino acid residue corresponding to the lysine at position 38 of SEQ ID NO:1 with glutamic acid, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the tyrosine at position 53 of SEQ ID NO:1 with phenylalanine, and substitution of the amino acid residue corresponding to the alanine at position 69 of SEQ ID NO:1 with valine.

[A7]

The protein according to any of [A1] to [A6], wherein the protein includes the amino acid sequence of any of SEQ ID NOs:179, 186, 199, 224, 240, 271, and 275.

[A8]

A polynucleotide encoding the protein according to any of [A1] to [A7].

[A9]

An expression vector including the polynucleotide according to [A8].

[A10]

A recombinant host including the following (A) or (B):

(A) a polynucleotide encoding the protein according to any of [A1] to [A7]; or (B) an expression vector containing a polynucleotide encoding the protein according to any of [A1] to [A7].

[A11]

The recombinant host according to [A10], wherein the host is *Escherichia coli.*

[A12]

A method of producing a protein having immunoglobulin-binding activity, the method including the steps of:

culturing a recombinant host containing a polynucleotide encoding the protein according to any of [A1] to [A7], or a recombinant host containing an expression vector containing the polynucleotide, to allow expression of the protein; and recovering the expressed protein.

[A13]

The production method according to [A12], wherein the host is *Escherichia coli.*

[A14]

An immunoglobulin adsorbent including:

an insoluble support; and a protein according to any of [A1] to [A7] immobilized on the insoluble support.

[A15]

A method of separating immunoglobulin contained in a solution, the method including the steps of:

applying a solution containing immunoglobulin to a column packed with the adsorbent according to [A13], to allow adsorption of the immunoglobulin to the adsorbent; and eluting the immunoglobulin that has adsorbed to the adsorbent.

Further, one aspect of the present invention includes the following modes.

[B1]

A protein including an amino acid sequence which is the same as an amino acid sequence of an immunoglobulin-binding domain of protein L derived from a bacterium belonging to the genus *Finegoldia* except that the amino acid sequence of the former protein has one or more amino acid substitutions selected from at least the following (54) to (64), the protein having immunoglobulin-binding activity:

(54) substitution of the amino acid residue corresponding to the lysine at position 7 of SEQ ID NO: 1 with glutamine;

(55) substitution of the amino acid residue corresponding to the lysine at position 13 of SEQ ID NO: 1 with valine;

(56) substitution of the amino acid residue corresponding to the lysine at position 29 of SEQ ID NO: 1 with valine or isoleucine;

(57) substitution of the amino acid residue corresponding to the proline at position 6 of SEQ ID NO: 1 with alanine;

(58) substitution of the amino acid residue corresponding to the glutamic acid at position 8 of SEQ ID NO:1 with arginine;

(59) substitution of the amino acid residue corresponding to the asparagine at position 15 of SEQ ID NO: 1 with valine;

(60) substitution of the amino acid residue corresponding to the isoleucine at position 23 of SEQ ID NO: 1 with phenylalanine or leucine;
(61) substitution of the amino acid residue corresponding to the glutamic acid at position 34 of SEQ ID NO: 1 with any of aspartic acid, phenylalanine, leucine, and valine;
(62) substitution of the amino acid residue corresponding to the lysine at position 38 of SEQ ID NO: 1 with leucine;
(63) substitution of the amino acid residue corresponding to the asparagine at position 50 of SEQ ID NO: 1 with methionine; and
(64) substitution of the amino acid residue corresponding to the tyrosine at position 53 of SEQ ID NO: 1 with serine.

[B2]

The protein according to [B1], which is a protein of any of the following (a) to (c):

(a) a protein including an amino acid sequence which is the same as the amino acid sequence of SEQ ID NO:1 or 18 except that the amino acid sequence of the protein has one or more amino acid substitutions selected from at least (54) to (64), the protein having immunoglobulin-binding activity:
(b) a protein including an amino acid sequence which is the same as the amino acid sequence of SEQ ID NO:1 or 18 except that the amino acid sequence of the protein has one or more amino acid substitutions selected from at least (54) to (64), and also has substitution, deletion, insertion, and/or addition of one or several amino acid residues at one or several positions other than (54) to (64), the protein having immunoglobulin-binding activity; and
(c) a protein including an amino acid sequence having a homology of not less than 70% to the amino acid sequence of SEQ ID NO:1 or 18 or a partial sequence thereof, wherein the amino acid sequence of the protein has one or more amino acid substitutions selected from at least (54) to (64), the protein having immunoglobulin-binding activity.

[B3]

The protein according to [B1] or [B2], further including one or more amino acid substitutions selected from at least the following (1) to (53):

(1) substitution of the amino acid residue corresponding to the asparagine at position 50 of SEQ ID NO: 1 with tyrosine;
(2) substitution of the amino acid residue corresponding to the glutamic acid at position 1 of SEQ ID NO: 1 with glycine or valine;
(3) substitution of the amino acid residue corresponding to the proline at position 3 of SEQ ID NO: 1 with serine;
(4) substitution of the amino acid residue corresponding to the glutamic acid at position 4 of SEQ ID NO: 1 with lysine or glycine;
(5) substitution of the amino acid residue corresponding to the glutamic acid at position 5 of SEQ ID NO: 1 with valine;
(6) substitution of the amino acid residue corresponding to the lysine at position 7 of SEQ ID NO: 1 with alanine;
(7) substitution of the amino acid residue corresponding to the glutamic acid at position 8 of SEQ ID NO: 1 with glycine;
(8) substitution of the amino acid residue corresponding to the glutamic acid at position 9 of SEQ ID NO: 1 with valine;
(9) substitution of the amino acid residue corresponding to the isoleucine at position 17 of SEQ ID NO: 1 with phenylalanine;
(10) substitution of the amino acid residue corresponding to the glycine at position 21 of SEQ ID NO: 1 with arginine;
(11) substitution of the amino acid residue corresponding to the glutamic acid at position 27 of SEQ ID NO: 1 with glycine or arginine;
(12) substitution of the amino acid residue corresponding to the lysine at position 29 of SEQ ID NO: 1 with proline;
(13) substitution of the amino acid residue corresponding to the threonine at position 31 of SEQ ID NO: 1 with leucine;
(14) substitution of the amino acid residue corresponding to the threonine at position 36 of SEQ ID NO: 1 with alanine;
(15) substitution of the amino acid residue corresponding to the alanine at position 41 of SEQ ID NO: 1 with threonine;
(16) substitution of the amino acid residue corresponding to the asparagine at position 44 of SEQ ID NO: 1 with serine or glycine;
(17) substitution of the amino acid residue corresponding to the glutamic acid at position 49 of SEQ ID NO: 1 with threonine or isoleucine;
(18) substitution of the amino acid residue corresponding to the asparagine at position 50 of SEQ ID NO: 1 with any of serine, lysine, and aspartic acid;
(19) substitution of the amino acid residue corresponding to the glycine at position 51 of SEQ ID NO: 1 with valine;
(20) substitution of the amino acid residue corresponding to the glutamic acid at position 52 of SEQ ID NO: 1 with any of valine, glycine, and aspartic acid;
(21) substitution of the amino acid residue corresponding to the tyrosine at position 53 of SEQ ID NO: 1 with phenylalanine;
(22) substitution of the amino acid residue corresponding to the threonine at position 54 of SEQ ID NO: 1 with isoleucine or methionine;
(23) substitution of the amino acid residue corresponding to the asparagine at position 62 of SEQ ID NO: 1 with any of histidine, arginine, leucine, methionine, and tryptophan;
(24) substitution of the amino acid residue corresponding to the asparagine at position 65 of SEQ ID NO: 1 with tyrosine;
(25) substitution of the amino acid residue corresponding to the alanine at position 69 of SEQ ID NO: 1 with threonine;
(26) substitution of the amino acid residue corresponding to the threonine at position 2 of SEQ ID NO: 1 with serine or proline;
(27) substitution of the amino acid residue corresponding to the proline at position 3 of SEQ ID NO: 1 with arginine;
(28) substitution of the amino acid residue corresponding to the glutamic acid at position 5 of SEQ ID NO: 1 with lysine or arginine;
(29) substitution of the amino acid residue corresponding to the glutamic acid at position 27 of SEQ ID NO: 1 with any of valine, lysine, and isoleucine;

(30) substitution of the amino acid residue corresponding to the phenylalanine at position 32 of SEQ ID NO: 1 with leucine;

(31) substitution of the amino acid residue corresponding to the lysine at position 38 of SEQ ID NO: 1 with alanine;

(32) substitution of the amino acid residue corresponding to the asparagine at position 44 of SEQ ID NO: 1 with isoleucine;

(33) substitution of the amino acid residue corresponding to the alanine at position 47 of SEQ ID NO: 1 with threonine or arginine;

(34) substitution of the amino acid residue corresponding to the glutamic acid at position 52 of SEQ ID NO: 1 with asparagine;

(35) substitution of the amino acid residue corresponding to the threonine at position 2 of SEQ ID NO: 1 with alanine;

(36) substitution of the amino acid residue corresponding to the glutamic acid at position 5 of SEQ ID NO:1 with aspartic acid;

(37) substitution of the amino acid residue corresponding to the proline at position 6 of SEQ ID NO: 1 with leucine or threonine;

(38) substitution of the amino acid residue corresponding to the lysine at position 7 of SEQ ID NO: 1 with proline;

(39) substitution of the amino acid residue corresponding to the valine at position 14 of SEQ ID NO: 1 with alanine;

(40) substitution of the amino acid residue corresponding to the isoleucine at position 23 of SEQ ID NO: 1 with arginine or valine;

(41) substitution of the amino acid residue corresponding to the lysine at position 29 of SEQ ID NO: 1 with phenylalanine;

(42) substitution of the amino acid residue corresponding to the threonine at position 31 of SEQ ID NO: 1 with methionine;

(43) substitution of the amino acid residue corresponding to the glutamic acid at position 33 of SEQ ID NO: 1 with any of aspartic acid, glycine, and valine;

(44) substitution of the amino acid residue corresponding to the alanine at position 35 of SEQ ID NO: 1 with threonine;

(45) substitution of the amino acid residue corresponding to the threonine at position 36 of SEQ ID NO: 1 with serine;

(46) substitution of the amino acid residue corresponding to the alanine at position 37 of SEQ ID NO: 1 with threonine;

(47) substitution of the amino acid residue corresponding to the alanine at position 41 of SEQ ID NO: 1 with isoleucine or tyrosine;

(48) substitution of the amino acid residue corresponding to the asparagine at position 44 of SEQ ID NO: 1 with histidine or arginine;

(49) substitution of the amino acid residue corresponding to the glutamic acid at position 52 of SEQ ID NO: 1 with leucine or tyrosine;

(50) substitution of the amino acid residue corresponding to the glycine at position 60 of SEQ ID NO: 1 with arginine;

(51) substitution of the amino acid residue corresponding to the isoleucine at position 64 of SEQ ID NO: 1 with leucine;

(52) substitution of the amino acid residue corresponding to the isoleucine at position 66 of SEQ ID NO: 1 with valine; and

(53) substitution of the amino acid residue corresponding to the alanine at position 69 of SEQ ID NO: 1 with leucine or valine.

[B4]

The protein according to any of [B1] to [B3], wherein one or more lysine residues selected from at least the following (I) to (VII) are substituted with a basic amino acid(s) other than lysine, and/or with an amino acid residue(s) containing a hydroxy group:

(I) the lysine residue corresponding to position 7 of SEQ ID NO:1;

(II) the lysine residue corresponding to position 13 of SEQ ID NO:1;

(III) the lysine residue corresponding to position 22 of SEQ ID NO:1;

(IV) the lysine residue corresponding to position 29 of SEQ ID NO:1;

(V) the lysine residue corresponding to position 38 of SEQ ID NO:1;

(VI) the lysine residue corresponding to position 48 of SEQ ID NO:1; and (VII) the lysine residue corresponding to position 67 of SEQ ID NO:1.

[B5]

The protein according to any of [B1] to [B4], further including one or more amino acid substitutions selected from substitution of the amino acid residue corresponding to the glutamic acid at position 49 of SEQ ID NO:1 with aspartic acid, substitution of the amino acid residue corresponding to the proline at position 6 of SEQ ID NO: 1 with serine, substitution of the amino acid residue corresponding to the asparagine at position 44 of SEQ ID NO:1 with aspartic acid, substitution of the amino acid residue corresponding to the glutamic acid at position 49 of SEQ ID NO: 1 with valine, substitution of the amino acid residue corresponding to the asparagine at position 62 of SEQ ID NO:1 with tyrosine, substitution of the amino acid residue corresponding to the asparagine at position 23 of SEQ ID NO: 1 with aspartic acid, and substitution of the amino acid residue corresponding to the asparagine at position 44 of SEQ ID NO: 1 with aspartic acid.

[B6]

The protein according to any of [B1] to [B5], wherein the protein includes at least the following amino acid substitution (X) or (Y):

(X) substitution of the amino acid residue corresponding to the glutamic acid at position 4 of SEQ ID NO:1 with glycine, substitution of the amino acid residue corresponding to the proline at position 6 of SEQ ID NO:1 with serine, substitution of the amino acid residue corresponding to the lysine at position 7 of SEQ ID NO:1 with alanine, substitution of the amino acid residue corresponding to the lysine at each of positions 13, 22, 48, and 67 of SEQ ID NO:1 with arginine, substitution of the amino acid residue corresponding to the isoleucine at position 23 of SEQ ID NO:1 with arginine, substitution of the amino acid residue corresponding to the lysine at position 29 of SEQ ID NO:1 with isoleucine, substitution of the amino acid residue corresponding to the lysine at position 38 of SEQ ID NO: 1 with glutamic acid, substitution of the amino acid residue corresponding to the asparagine at position 44 of SEQ ID NO:1 with arginine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the tyrosine at position 53 of SEQ ID NO:1 with phenylalanine, and substitution of the amino acid residue corresponding to the alanine at position 69 of SEQ ID NO: 1 with valine; or (Y) substitution of the amino acid residue corresponding to the glutamic acid at position 4 of SEQ ID NO:1 with glycine, substitution of the amino acid residue corresponding to the proline at position 6 of SEQ ID NO:1 with serine, substitution of the amino acid residue corresponding to the lysine at position 7 of SEQ ID NO:1 with alanine, substitution of the amino acid residue corresponding to the lysine at each of positions 13, 22, and 67 of SEQ ID NO:1 with arginine, substitution of the amino acid residue corresponding to the isoleucine at position 23 of SEQ ID NO: 1 with arginine, substitution of the amino acid residue corresponding to the lysine at position 29 of SEQ ID NO:1 with isoleucine, substitution of the amino acid residue corresponding to the lysine at position 38 of SEQ ID NO:1 with glutamic acid, substitution of the amino acid residue corresponding to the asparagine at position 44 of SEQ ID NO: 1 with arginine, substitution of the amino acid residue corresponding to the lysine at position 48 of SEQ ID NO:1 with histidine, substitution of the amino acid residue corresponding to the glutamic acid at position 49 of SEQ ID NO: 1 with aspartic acid, substitution of the amino acid residue corresponding to the asparagine at each of positions 50 and 62 of SEQ ID NO:1 with tyrosine, substitution of the amino acid residue corresponding to the tyrosine at position 53 of SEQ ID NO:1 with phenylalanine, substitution of the amino acid residue corresponding to the isoleucine at position 64 of SEQ ID NO: 1 with leucine, and substitution of the amino acid residue corresponding to the alanine at position 69 of SEQ ID NO: 1 with valine.

[B7]

The protein according to any of [B1] to [B6], wherein the protein includes the amino acid sequence of SEQ ID NO:408 or 413.

[B8]

A polynucleotide encoding the protein according to any of [B1] to [B7].

[B9]

An expression vector including the polynucleotide according to [B8].

[B10]

A recombinant host including the following (A) or (B):

(A) a polynucleotide encoding the protein according to any of [B1] to [B7]; or (B) an expression vector containing a polynucleotide encoding the protein according to any of [B1] to [B7].

[B11]

The recombinant host according to [B10], wherein the host is *Escherichia coli.*

[B12]

A method of producing an immunoglobulin-binding protein, the method including the steps of:

culturing a recombinant host containing a polynucleotide encoding the protein according to any of [B1] to [B7], or a recombinant host containing an expression vector containing the polynucleotide, to allow expression of the protein; and recovering the expressed protein.

[B13]

The production method according to [B12], wherein the host is *Escherichia coli.*

[B14]

An immunoglobulin adsorbent including:

an insoluble support; and a protein according to any of [B1] to [B7] immobilized on the insoluble support.

[B15]

A method of separating immunoglobulin contained in a solution, the method including the steps of:

applying a solution containing immunoglobulin to a column packed with the adsorbent according to [B14], to allow adsorption of the immunoglobulin to the adsorbent; and changing the pH to elute the immunoglobulin that has adsorbed to the adsorbent.

[B16]

The method according to [B15], wherein the pH change is a decrease in the pH.

MODE FOR CARRYING OUT THE INVENTION

The present invention is described below in detail.

The protein of the present invention is a particular immunoglobulin-binding protein. The "immunoglobulin-binding protein" herein means a protein having a binding capacity to immunoglobulin. Thus, the protein of the present invention has a binding capacity to a particular immunoglobulin. More specifically, the protein of the present invention may have a binding capacity to the κ light chain of immunoglobulin. In the present description, the binding capacity to immunoglobulin is also referred to as "immunoglobulin-binding activity" or "antibody-binding activity". The immunoglobulin-binding activity can be measured, for example, by the ELISA (Enzyme-Linked ImmunoSorbent Assay) method. The ELISA method can be carried out under, for example, the conditions described in Examples.

The protein of an aspect of the present invention is a protein including an amino acid sequence which is the same as an amino acid sequence of an immunoglobulin-binding domain of protein L derived from a bacterium belonging to the genus *Finegoldia* (also referred to as "FpL") except that the amino acid sequence of the protein of an aspect of the present invention has an amino acid substitution(s) at a particular position(s). In the present description, an amino acid sequence of an immunoglobulin-binding domain of FpL having no amino acid substitution at the particular position(s) is hereinafter also referred to as "unmodified amino acid sequence", and an amino acid sequence of an immunoglobulin-binding domain of FpL having the amino acid substitution(s) at the particular position(s) is hereinafter also referred to as "modified amino acid sequence". In other words, the modified amino acid sequence may be an amino acid sequence which is the same as the unmodified amino acid sequence except that the modified amino acid sequence has the amino acid substitution(s) at the particular position(s). The protein of an aspect of the present invention may be, for example, a protein containing an amino acid sequence which is the same as the unmodified amino acid sequence except that the amino acid sequence of the protein has the amino acid substitution(s) at the particular position(s). Further, the protein of an aspect of the present invention may be, for example, a protein containing the modified amino acid sequence. The unmodified amino acid sequence may or may not be a naturally occurring amino acid sequence. The unmodified amino acid sequence may be modified, for example, to have a desired property. The unmodified amino acid sequence may have, for example, an amino acid substitution(s) other than the amino acid substitution(s) at the particular position(s).

Examples of the bacterium belonging to the genus *Finegoldia* from which the FpL is derived include *Finegoldia magna*. Examples of the immunoglobulin-binding domain of protein L derived from *Finegoldia magna* include:

domain B1 (the amino acid residues at positions 104 to 173 of SEQ ID NO:209 (GenBank No. AAA25612));
domain B2 (the amino acid residues at positions 176 to 245 of SEQ ID NO:209;
domain B3 (the amino acid residues at positions 248 to 317 of SEQ ID NO:209;
domain B4 (the amino acid residues at positions 320 to 389 of SEQ ID NO: 209;
domain B5 (the amino acid residues at positions 393 to 462 of SEQ ID NO:209;
domain C1 (the amino acid residues at positions 249 to 317 of SEQ ID NO:210 (GenBank No. AAA67503); SEQ ID NO:112);
domain C2 (the amino acid residues at positions 320 to 389 of SEQ ID NO:210; SEQ ID NO:113);
domain C3 (the amino acid residues at positions 394 to 463 of SEQ ID NO:210; SEQ ID NO:1); and
domain C4 (the amino acid residues at positions 468 to 537 of SEQ ID NO:210; SEQ ID NO:18).

In the present description, the unmodified amino acid sequence may be (i) the entire amino acid sequence of the FpL immunoglobulin-binding domain; or
(ii) a partial amino acid sequence of the domain, as long as the binding activity to the immunoglobulin is retained.

Regarding (ii), the immunoglobulin-binding domain of FpL is composed of four n-sheets and one α-helix, loop portions connecting these to each other, and an N-terminal loop region. However, amino acid residues in regions not responsible for the binding to immunoglobulin, such as the N-terminal loop region, may be absent. More specifically, for example, the immunoglobulin-binding capacity is known to be retained even in the absence of the amino acid residues from the glutamic acid at position 1 to the glutamic acid at position 9, which correspond to the N-terminal loop region of domain C3 (SEQ ID NO:1) of FpL (Housden N. G. et. al. Biochemical Society Transaction, 2003, 31, 716-718). It can thus be said that the partial amino acid sequence of (ii) is not limited as long as it contains at least an amino acid sequence of a binding site for immunoglobulin. In other words, examples of the partial amino acid sequence of (ii) include a partial sequence containing an amino acid sequence of a binding site for immunoglobulin.

In the present description, specific examples of the modified amino acid sequence include an amino acid sequence which is the same as an amino acid sequence of an immunoglobulin-binding domain described above such as the amino acid sequence of SEQ ID NO:1, except that the modified amino acid sequence has an amino acid substitution(s) at a particular position(s). Thus, specific examples of the protein of the present invention include a protein containing an amino acid sequence which is the same as an amino acid sequence of an immunoglobulin-binding domain described above such as the amino acid sequence of SEQ ID NO: 1, except that the amino acid sequence of the protein has an amino acid substitution(s) at a particular position(s). In other words, the protein of an aspect of the present invention may be, for example, a protein containing the same amino acid sequence as an amino acid sequence of an immunoglobulin-binding domain described above such as the amino acid sequence of SEQ ID NO: 1, except for the presence of an amino acid substitution(s) at a particular position(s).

In the present description, the fact that a protein contains an amino acid sequence is also referred to as "a protein contains amino acid residues having an amino acid sequence", and the fact that a protein or an amino acid sequence has an amino acid substitution(s) is also referred to as "an amino acid substitution(s) occur(s) in a protein or an amino acid sequence". Amino acids constituting a protein or an amino acid sequence are also referred to as "amino acid residues".

The protein of an aspect of the present invention may be an immunoglobulin-binding protein having an improved alkaline stability. More specifically, the protein of an aspect of the present invention may be an immunoglobulin-binding protein having an improved alkaline stability compared to an immunoglobulin-binding protein having no modified amino acid sequence (for example, having an unmodified amino acid sequence). More specifically, the protein of an aspect of the present invention may be an immunoglobulin-binding protein having an improved alkaline stability compared to an immunoglobulin-binding protein having no amino acid substitution at the particular position(s). In other words, the protein of an aspect of the present invention may be an immunoglobulin-binding protein whose alkaline stability has been improved due to the presence of the amino acid substitution(s) at the particular position(s). Further, in other words, the amino acid substitution(s) at the particular position(s) may improve the alkaline stability of the immunoglobulin-binding protein.

The "alkaline stability" may mean resistance against deactivation under alkaline conditions. The improvement of the alkaline stability can be measured, for example, as improvement of the remaining activity after alkali treatment. The "activity" herein means the immunoglobulin-binding activity. The alkali treatment can be carried out, for example, under the conditions described in Examples.

The protein of an aspect of the present invention may be an immunoglobulin-binding protein that allows antibody elution under mild pH conditions. More specifically, the protein of an aspect of the present invention may be an immunoglobulin-binding protein that allows antibody elution under milder pH conditions compared to an immunoglobulin-binding protein having no modified amino acid sequence (for example, having an unmodified amino acid sequence). More specifically, the protein of an aspect of the present invention may be an immunoglobulin-binding protein that allows antibody elution under milder pH conditions compared to an immunoglobulin-binding protein having no amino acid substitution at the particular position(s). In other words, the protein an aspect of the present invention may be an immunoglobulin-binding protein that has become capable of allowing antibody elution under mild pH conditions due to the presence of the amino acid substitution(s) at the particular position(s). Further, in other words, the amino acid substitution(s) at the particular position(s) may allow antibody elution from the immunoglobulin-binding protein under mild pH conditions.

The "mild pH conditions" may mean pH conditions close to neutrality. Thus, the term "allow antibody elution under mild conditions" may mean that antibody elution is possible under pH conditions close to neutrality. Further, since a typical antibody elution pH can be acidic, the term "allow antibody elution under mild conditions" may mean the fact that the antibody elution pH is elevated. The antibody elution pH can be measured, for example, under the conditions described in Examples.

The protein of an aspect of the present invention may be an immunoglobulin-binding protein which has an improved alkaline stability, and in addition, which allows antibody elution under mild pH conditions.

The amino acid substitution(s) at the particular position(s) include(s) a first-group mutation and/or a second-group mutation. Of the first-group mutation and the second-group mutation, only the first-group mutation may be included; only the second-group mutation may be included; or both the first-group mutation and the second-group mutation may be included; as the amino acid substitution(s) at the particular position(s). The amino acid substitution(s) at the particular position(s) may include at least the first-group mutation, and may additionally include the second-group mutation. The amino acid substitution(s) at the particular position(s) may include at least the second-group mutation, and may additionally include the first-group mutation.

The first-group mutation may be a mutation that improves the alkaline stability of the immunoglobulin-binding protein. Thus, in cases where the amino acid substitution(s) at the particular position(s) include(s) the first-group mutation, the amino acid substitution(s) at the particular position(s) may be a mutation(s) that improve(s) the alkaline stability of the immunoglobulin-binding protein. In cases where, for example, the protein of an aspect of the present invention is an immunoglobulin-binding protein having an improved alkaline stability, the amino acid substitution(s) at the particular position(s) may include the first-group mutation. In cases where, for example, the protein of an aspect of the present invention is an immunoglobulin-binding protein having an improved alkaline stability, the amino acid substitution(s) at the particular position(s) may include at least the first-group mutation, and may additionally include the second-group mutation. Further, a protein of an aspect of the present invention having at least the first-group mutation may be an immunoglobulin-binding protein having an improved alkaline stability.

The second-group mutation may be a mutation that allows antibody elution from the immunoglobulin-binding protein under mild pH conditions. Thus, in cases where the amino acid substitution(s) at the particular position(s) include(s) the second-group mutation, the amino acid substitution(s) at the particular position(s) may be a mutation(s) that allow(s) antibody elution from the immunoglobulin-binding protein under mild pH conditions. In cases where, for example, the protein of an aspect of the present invention is an immunoglobulin-binding protein that allows antibody elution under mild pH conditions, the amino acid substitution(s) at the particular position(s) may include the second-group mutation. In cases where, for example, the protein of an aspect of the present invention is an immunoglobulin-binding protein that allows antibody elution under mild pH conditions, the amino acid substitution(s) at the particular position(s) may include at least the second-group mutation, and may additionally include the first-group mutation. Further, a protein of an aspect of the present invention having at least the second-group mutation may be an immunoglobulin-binding protein that allows antibody elution under mild pH conditions.

In cases where the amino acid substitutions at the particular positions include both the first-group mutation and the second-group mutation, the amino acid substitutions at the particular positions may be mutations which improve the alkaline stability of the immunoglobulin-binding protein, and in addition, which allow antibody elution from the immunoglobulin-binding protein under mild pH conditions. Further, the protein of an aspect of the present invention having both the first-group mutation and the second-group mutation may be an immunoglobulin-binding protein which has an improved alkaline stability, and in addition, which allows antibody elution under mild pH conditions.

Specifically, the first-group mutation is at least one or more amino acid substitutions selected from Asn50Tyr (this expression represents the fact that the amino acid residue corresponding to the asparagine at position 50 of SEQ ID NO:1 is substituted with tyrosine; the same applies to the other amino acid substitutions hereinafter), Glu1Gly, Glu1Val, Pro3Ser, Glu4Lys, Glu4Gly, Glu5Val, Lys7Ala, Glu8Gly, Glu9Val, Ile17Phe, Gly21Arg, Glu27Gly, Glu27Arg, Lys29Pro, Thr31Leu, Thr36Ala, Ala41Thr, Asn44Ser, Asn44Gly, Glu49Thr, Glu49Ile, Asn50Ser, Asn50Lys, Asn50Asp, Gly51Val, Glu52Val, Glu52Gly, Glu52Asp, Tyr53Phe, Thr54Ile, Thr54Met, Asn62His, Asn62Arg, Asn62Leu, Asn62Met, Asn62Trp, Asn65Tyr, Ala69Thr, Thr2Ser, Thr2Pro, Pro3Arg, Glu5Lys, Glu5Arg, Glu27Val, Glu27Lys, Glu27Ile, Phe32Leu, Lys38Ala, Asn44Ile, Ala47Thr, Ala47Arg, Glu52Asn, Thr2Ala, Glu5Asp, Pro6Leu, Pro6Thr, Lys7Pro, Val14Ala, Ile23Arg, Ile23Val, Lys29Phe, Thr31Met, Glu33Asp, Glu33Gly, Glu33Val, Ala35Thr, Thr36Ser, Ala37Thr, Ala41Ile, Ala41Tyr, Asn44His, Asn44Arg, Glu52Leu, Glu52Tyr, Gly60Arg, Ile64Leu, Ile66Val, Ala69Leu, and Ala69Val.

In other words, the first-group mutation is one or more amino acid substitutions selected from (1) Asn50Tyr;
(2) Glu1Gly or Glu1 Val;
(3) Pro3 Ser;
(4) Glu4Lys or Glu4Gly;
(5) Glu5Val;
(6) Lys7Ala;
(7) Glu8Gly;
(8) Glu9Val;
(9) Ile17Phe;
(10) Gly21Arg;
(11) Glu27Gly or Glu27Arg;
(12) Lys29Pro;
(13) Thr31Leu;
(14) Thr36Ala;
(15) Ala41Thr;
(16) Asn44Ser or Asn44Gly;
(17) Glu49Thr or Glu49Ile;
(18) any of Asn50Ser, Asn50Lys, and Asn50Asp;
(19) Gly 51 Val;
(20) any of Glu52Val, Glu52Gly, and Glu52Asp;
(21) Tyr53Phe;
(22) Thr54Ile or Thr54Met;
(23) any of Asn62His, Asn62Arg, Asn62Leu, Asn62Met, and Asn62Trp;
(24) Asn65Tyr;
(25) Ala69Thr;
(26) Thr2Ser or Thr2Pro;
(27) Pro3 Arg;
(28) Glu5Lys or Glu5Arg;
(29) any of Glu27Val, Glu27Lys, and Glu27Ile;
(30) Phe32Leu;
(31) Lys38Ala;
(32) Asn44Ile;
(33) Ala47Thr or Ala47Arg;
(34) Glu52Asn;
(35) Thr2Ala;
(36) Glu5Asp;

(37) Pro6Leu or Pro6Thr;
(38) Lys7Pro;
(39) Val 14Ala;
(40) Ile23 Arg or Ile23 Val;
(41) Lys29Phe;
(42) Thr31Met;
(43) any of Glu33 Asp, Glu33Gly, and Glu33 Val;
(44) Ala35Thr;
(45) Thr36Ser;
(46) Ala37Thr;
(47) Ala41Ile or Ala41Tyr;
(48) Asn44His or Asn44Arg;
(49) Glu52Leu or Glu52Tyr;
(50) Gly60Arg;
(51) Ile64Leu;
(52) Ile66 Val; and
(53) Ala69Leu or Ala69Val.

Thus, the protein of an aspect of the present invention may have one or more amino acid substitutions selected from the amino acid substitutions (1) to (53). The protein of an aspect of the present invention may have, for example, 1, 2, 3, 4, 5, 6, 7, 8, or 9 amino acid substitutions, or may have not less than 10 amino acid substitutions selected from the amino acid substitutions (1) to (53). Among these, the amino acid substitution (1) (Asn50Tyr) is an amino acid substitution that gives an especially improved alkaline stability. Thus, an immunoglobulin-binding protein having at least the amino acid substitution (1) (Asn50Tyr) may be a preferred example of the protein of the present invention. In other words, the protein of an aspect of the present invention may have at least the amino acid substitution (1) (Asn50Tyr). More specifically, among the amino acid substitutions (1) to (53), the protein of an aspect of the present invention may have only the amino acid substitution (1) (Asn50Tyr), or may have a combination of the amino acid substitution (1) (Asn50Tyr) and one or more amino acid substitutions selected from the amino acid substitutions (2) to (53). The amino acid substitution(s) at the particular position(s) may include, for example, one or more (for example, 1, 2, 3, 4, 5, 6, 7, 8, 9, or not less than 10) amino acid substitutions selected from the amino acid substitutions (1) to (53).

Specifically, the second-group mutation is at least one or more amino acid substitutions selected from Lys7Gln, Lys13Val, Lys29Val, Lys29Ile, Pro6Ala, Glu8Arg, Asn15Val, Ile23Phe, Ile23Leu, Glu34Asp, Glu34Phe, Glu34Leu, Glu34Val, Lys38Leu, Asn50Met, and Tyr53Ser.

In other words, the second-group mutation is one or more amino acid substitutions selected from

(54) Lys7Gln;
(55) Lys13Val;
(56) Lys29Val or Lys29Ile;
(57) Pro6Ala;
(58) Glu8Arg;
(59) Asn15Val;
(60) Ile23Phe or Ile23Leu;
(61) any of Glu34Asp, Glu34Phe, Glu34Leu, and Glu34Val;
(62) Lys38Leu;
(63) Asn50Met; and
(64) Tyr53Ser.

Thus, the protein of an aspect of the present invention may have one or more amino acid substitutions selected from the amino acid substitutions (54) to (64). The protein of an aspect of the present invention may have, for example, 1, 2, 3, 4, 5, 6, 7, 8, or 9 amino acid substitutions, or may have not less than 10 amino acid substitutions selected from the amino acid substitutions (54) to (64). The amino acid substitution(s) at the particular position(s) may include, for example, one or more (for example, 1, 2, 3, 4, 5, 6, 7, 8, 9, or not less than 10) amino acid substitutions selected from the amino acid substitutions (54) to (64).

In other words, the protein of an aspect of the present invention has one or more amino acid substitutions selected from the amino acid substitutions (1) to (64). Specifically, the protein of an aspect of the present invention has one or more amino acid substitutions selected from the amino acid substitutions (1) to (53), and/or one or more amino acid substitutions selected from the amino acid substitutions (54) to (64). For example, the protein of an aspect of the present invention may have 1, 2, 3, 4, 5, 6, 7, 8, 9, or not less than 10 amino acid substitutions selected from the amino acid substitutions (1) to (53), and/or 1, 2, 3, 4, 5, 6, 7, 8, 9, or not less than 10 amino acid substitutions selected from the amino acid substitutions (54) to (64). For example, the protein of an aspect of the present invention may have at least a combination of the amino acid substitution (1) (Asn50Tyr) and one or more amino acid substitutions selected from the amino acid substitutions (54) to (64). A protein of an aspect of the present invention having at least a combination of the amino acid substitution (1) (Asn50Tyr) and one or more amino acid substitutions selected from the amino acid substitutions (2) to (53) can be a preferred example of the immunoglobulin-binding protein which has an improved alkaline stability, and in addition, which allows antibody elution under mild pH conditions.

Among the amino acid substitutions (1) to (64), amino acid substitutions at the same position are not selected at the same time. For example, the amino acid substitution (3) and the amino acid substitution (27) are not selected at the same time.

In cases where the protein of an aspect of the present invention has two or more amino acid substitutions, the combination of these amino acid substitutions is not limited as long as the combination includes the first-group mutation and/or second-group mutation.

In one aspect, examples of the combination of amino acid substitutions selected from the amino acid substitutions (1) to (53) (also referred to as "combination of first-group mutations") include:

the amino acid substitutions Asn50Tyr and Glu52Gly;
the amino acid substitutions Ile17Phe and Asn50Ser;
the amino acid substitutions Glu8Gly and Glu52Val;
the amino acid substitutions Glu27Gly, Ala41Thr, Asn50Lys, and Asn65Tyr;
the amino acid substitutions Pro3Ser, Asn50Asp, and Thr54Ile;
the amino acid substitutions Asn44Ser, Asn50Tyr, and Glu52Gly;
the amino acid substitutions Asn44Ser and Asn50Tyr;
the amino acid substitutions Asn50Tyr and Glu52Val;
the amino acid substitutions Asn44Gly, Asn50Tyr, and Glu52Val;
the amino acid substitutions Asn44Gly, Asn50Ser, and Glu52Val;
the amino acid substitutions Lys7Ala and Gly21Arg;
the amino acid substitutions Lys7Ala, Asn50Tyr, and Glu52Gly;
the amino acid substitutions Lys7Ala, Gly21Arg, Asn50Tyr, and Glu52Gly;
the amino acid substitutions Glu1Gly, Lys7Ala, Asn50Tyr, and Glu52Gly;
the amino acid substitutions Glu1Val, Lys7Ala, Asn50Tyr, and Glu52Gly;

the amino acid substitutions Glu4Lys, Lys7Ala, Asn50Tyr, and Glu52Gly;
the amino acid substitutions Lys7Ala, Glu27Arg, Asn50Tyr, and Glu52Gly;
the amino acid substitutions Lys7Ala, Thr36Ala, Asn50Tyr, and Glu52Gly;
the amino acid substitutions Lys7Ala, Glu9Val, Asn50Tyr, and Glu52Gly;
the amino acid substitutions Lys7Ala, Asn50Tyr, Glu52Gly, and Tyr53Phe;
the amino acid substitutions Lys7Ala, Asn50Tyr, Glu52Gly, and Thr54Met;
the amino acid substitutions Lys7Ala, Asn50Tyr, Glu52Gly, and Ala69Thr;
the amino acid substitutions Glu1Val, Lys7Ala, Asn50Tyr, Glu52Gly, and Tyr53Phe;
the amino acid substitutions Glu4Gly, Lys7Ala, Asn50Tyr, Glu52Gly, and Tyr53Phe;
the amino acid substitutions Asn50Tyr, Glu52Gly, and Tyr53Phe;
the amino acid substitutions Lys7Ala, Gly21Arg, Asn50Tyr, Glu52Gly, and Tyr53Phe;
the amino acid substitutions Lys7Ala, Asn50Tyr, Glu52Asp, and Tyr53Phe;
the amino acid substitutions Glu4Gly, Lys7Ala, Asn50Tyr, Glu52Asp, and Tyr53Phe;
the amino acid substitutions Asn50Tyr, Glu52Asp, and Tyr53Phe;
the amino acid substitutions Glu4Gly, Asn50Tyr, Glu52Gly, and Tyr53Phe;
the amino acid substitutions Glu4Gly, Lys7Ala, Lys38Ala, Asn50Tyr, Glu52Asp, and Tyr53Phe;
the amino acid substitutions Glu4Gly, Lys7Ala, Phe32Leu, Ala47Thr, Asn50Tyr, Glu52Asp, and Tyr53Phe;
the amino acid substitutions Thr2Ser, Glu4Gly, Lys7Ala, Asn50Tyr, Glu52Asp, and Tyr53Phe;
the amino acid substitutions Glu4Gly, Lys7Ala, Glu27Lys, Asn50Tyr, Glu52Asp, and Tyr53Phe;
the amino acid substitutions Thr2Pro, Pro3Arg, Glu4Gly, Lys7Ala, Glu9Val, Asn50Tyr, Glu52Asn, and Tyr53Phe;
the amino acid substitutions Glu4Gly, Lys7Ala, Glu27Ile, Asn50Tyr, Glu52Asp, and Tyr53Phe;
the amino acid substitutions Glu4Gly, Lys7Ala, Asn44Ile, Asn50Tyr, Glu52Asp, and Tyr53Phe;
the amino acid substitutions Glu4Gly, Glu5Lys, Lys7Ala, Asn44Ile, Asn50Tyr, Glu52Asp, and Tyr53Phe;
the amino acid substitutions Pro3Arg, Glu4Gly, Lys7Ala, Asn50Tyr, Glu52Asp, and Tyr53Phe;
the amino acid substitutions Glu4Gly, Glu5Lys, Lys7Ala, Asn50Tyr, Glu52Asp, and Tyr53Phe;
the amino acid substitutions Glu4Gly, Lys7Ala, Glu27Val, Asn50Tyr, Glu52Asp, and Tyr53Phe;
the amino acid substitutions Glu4Gly, Glu5Arg, Lys7Ala, Asn50Tyr, Glu52Asp, and Tyr53Phe;
the amino acid substitutions Glu4Gly, Lys7Ala, Glu27Arg, Asn50Tyr, Glu52Asp, and Tyr53Phe;
the amino acid substitutions Glu4Gly, Lys7Ala, Ala47Arg, Asn50Tyr, Glu52Asp, and Tyr53Phe;
the amino acid substitutions Glu4Gly, Lys7Ala, Asn50Tyr, Glu52Asp, Tyr53Phe, and Ala69Val;
the amino acid substitutions Glu4Gly, Lys7Ala, Lys29Phe, Asn50Tyr, Glu52Asp, and Tyr53Phe;
the amino acid substitutions Glu4Gly, Lys7Ala, Glu8Gly, Glu33Val, Asn50Tyr, Glu52Asp, and Tyr53Phe;
the amino acid substitutions Glu4Gly, Lys7Ala, Ile23Arg, Asn50Tyr, Glu52Asp, and Tyr53Phe;
the amino acid substitutions Glu4Gly, Lys7Ala, Ala41Ile, Asn50Tyr, Glu52Asp, and Tyr53Phe;
the amino acid substitutions Glu4Gly, Lys7Ala, Ala41Tyr, Asn50Tyr, Glu52Asp, and Tyr53Phe;
the amino acid substitutions Glu4Gly, Lys7Ala, Asn50Tyr, Glu52Leu, and Tyr53Phe;
the amino acid substitutions Glu4Gly, Lys7Ala, Asn50Tyr, Glu52Val, and Tyr53Phe;
the amino acid substitutions Glu4Gly, Lys7Ala, Asn50Tyr, Glu52Val, Tyr53Phe, and Ala69Val;
the amino acid substitutions Glu4Gly, Lys7Ala, Asn50Tyr, Glu52Leu, Tyr53Phe, and Ala69Val;
the amino acid substitutions Glu4Gly, Lys7Ala, Asn50Tyr, Tyr53Phe, and Ala69Val;
the amino acid substitutions Pro3Arg, Glu4Gly, Lys7Ala, Asn50Tyr, Tyr53Phe, and Ala69Val;
the amino acid substitutions Pro3Arg, Glu4Gly, Lys7Ala, Asn50Tyr, Tyr53Phe, Ile66Val, and Ala69Val;
the amino acid substitutions Pro3Arg, Glu4Gly, Lys7Ala, Thr31Met, Asn50Tyr, Tyr53Phe, and Ala69Val;
the amino acid substitutions Glu4Gly, Pro6Leu, Lys7Ala, Asn50Tyr, Tyr53Phe, and Ala69Val;
the amino acid substitutions Glu4Gly, Lys7Ala, Ala35Thr, Asn50Tyr, Tyr53Phe, and Ala69Val;
the amino acid substitutions Glu4Gly, Lys7Ala, Glu33Gly, Asn50Tyr, Tyr53Phe, and Ala69Val;
the amino acid substitutions Glu4Gly, Glu5Asp, Pro6Leu, Lys7Ala, Asn50Tyr, Tyr53Phe, and Ala69Val;
the amino acid substitutions Glu4Gly, Lys7Ala, Asn50Tyr, Tyr53Phe, and Ala69Leu;
the amino acid substitutions Glu4Gly, Lys7Ala, Ala37Thr, Asn50Tyr, Tyr53Phe, and Ala69Val;
the amino acid substitutions Glu4Gly, Lys7Ala, Glu33Asp, Asn50Tyr, Glu52Gly, Tyr53Phe, and Ala69Val;
the amino acid substitutions Thr2Ala, Glu4Gly, Lys7Pro, Asn50Tyr, Tyr53Phe, and Ala69Val;
the amino acid substitutions Glu4Gly, Lys7Ala, Ile23Val, Asn50Tyr, Tyr53Phe, and Ala69Val;
the amino acid substitutions Glu4Gly, Pro6Thr, Lys7Ala, Asn50Tyr, Tyr53Phe, and Ala69Val;
the amino acid substitutions Glu4Gly, Lys7Ala, Thr36Ser, Asn50Tyr, Tyr53Phe, and Ala69Val;
the amino acid substitutions Glu4Gly, Lys7Ala, Val14Ala, Asn50Tyr, Tyr53Phe, and Ala69Val;
the amino acid substitutions Glu4Gly, Lys7Ala, Gly21Arg, Asn50Tyr, Tyr53Phe, and Ala69Val;
the amino acid substitutions Glu4Gly, Lys7Ala, Asn44Arg, Asn50Tyr, Tyr53Phe, and Ala69Val;
the amino acid substitutions Glu4Gly, Lys7Ala, Asn44His, Asn50Tyr, Tyr53Phe, and Ala69Val;
the amino acid substitutions Glu4Gly, Lys7Ala, Asn50Tyr, Glu52Tyr, Tyr53Phe, and Ala69Val;
the amino acid substitutions Glu4Gly, Lys7Ala, Asn50Tyr, Tyr53Phe, Gly60Arg, and Ala69Val; and
the amino acid substitutions Glu4Gly, Lys7Ala, Asn50Tyr, Tyr53Phe, Ile64Leu, and Ala69Val.

In one aspect, examples of the combination of amino acid substitutions selected from the amino acid substitutions (54) to (64) (also referred to as "combination of second-group mutations") include:

the amino acid substitutions Pro6Ala and Lys29Ile;
the amino acid substitutions Glu8Arg and Lys29Ile;
the amino acid substitutions Ile23Phe and Lys29Ile;
the amino acid substitutions Ile23Leu and Lys29Ile;

the amino acid substitutions Lys29Ile and Lys38Leu;
the amino acid substitutions Lys29Ile and Asn50Met;
the amino acid substitutions Lys59Ile and Tyr53Ser;
the amino acid substitutions Asn15Val and Lys29Ile;
the amino acid substitutions Lys29Ile and Glu34Asp;
the amino acid substitutions Lys29Ile and Glu34Phe;
the amino acid substitutions Lys29Ile and Glu34Leu; and
the amino acid substitutions Lys29Ile and Glu34Val.

In one aspect, examples of the combination of amino acid substitutions selected from the amino acid substitutions (1) to (64) include a combination of any of the combinations of the first-group mutations exemplified above and any of the combinations of the second-group mutations exemplified above.

In another aspect, examples of the combination of amino acid substitutions include a combination of one or more amino acid substitutions selected from at least the amino acid substitutions (1) to (64) (specifically, one or more amino acid substitutions selected from the amino acid substitutions (1) to (53) and/or one or more amino acid substitutions selected from the amino acid substitutions (54) to (64)) and substitution of one or more lysine (Lys) residues selected from at least the following (I) to (VII) with a basic amino acid(s) other than lysine (arginine (Arg) and/or histidine (His)) and/or with an amino acid(s) containing a hydroxy group (serine (Ser), threonine (Thr), and/or tyrosine (Tyr)).

(I) The lysine residue corresponding to position 7 of SEQ ID NO:1
(II) The lysine residue corresponding to position 13 of SEQ ID NO:1
(III) The lysine residue corresponding to position 22 of SEQ ID NO:1
(IV) The lysine residue corresponding to position 29 of SEQ ID NO:1
(V) The lysine residue corresponding to position 38 of SEQ ID NO:1
(VI) The lysine residue corresponding to position 48 of SEQ ID NO:1
(VII) The lysine residue corresponding to position 67 of SEQ ID NO:1

The protein of an aspect of the present invention may have substitution of one, two, three, four, five, six, or seven lysine residues selected from (I) to (VII).

However, in cases where the substitution of the lysine residue (I) is selected, the amino acid substitutions (6) Lys7Ala and (38) Lys7Pro are overwritten by the substitution of the lysine residue (I);

in cases where the substitution of the lysine residue (IV) is selected, the amino acid substitutions (12) Lys29Pro and (41) Lys29Phe are overwritten by the substitution of the lysine residue (IV); and in cases where the substitution of the lysine residue (V) is selected, the amino acid substitution (31) Lys38Ala is overwritten by the substitution of the lysine residue (V).

Further, in cases where the substitution of the lysine residue (I) is selected, the amino acid substitution (54) Lys7Gln is overwritten by the substitution of the lysine residue (I);

in cases where the substitution of the lysine residue (II) is selected, the amino acid substitution (55) Lys13Val is overwritten by the substitution of the lysine residue (II);

in cases where the substitution of the lysine residue (IV) is selected, the amino acid substitution (56) Lys29Val or Lys29Ile is overwritten by the substitution of the lysine residue (IV); and in cases where the substitution of the lysine residue (V) is selected, the amino acid substitution (62) Lys38Leu is overwritten by the substitution of the lysine residue (V).

Alternatively, among the amino acid substitutions of (I) to (VII), amino acid substitutions at the same positions as those of the one or more amino acid substitutions selected from (1) to (64) do not need to be selected. More specifically, for example, in cases where at least the amino acid substitution (6) Lys7Ala, (38) Lys7Pro, or (54) Lys7Gln is selected from the amino acid substitutions (1) to (64), the amino acid substitution (I) does not need to be selected. Further, the combination of the amino acid substitutions is selected such that one or more amino acid substitutions selected from at least the amino acid substitutions (1) to (64) remain. Thus, for example, in cases where the amino acid substitution (6) Lys7Ala, (38) Lys7Pro, or (54) Lys7Gln alone is selected from the amino acid substitutions (1) to (64), the amino acid substitution (I) cannot be selected. Further, the combination of the amino acid substitutions may be selected such that one or more amino acid substitutions selected from at least the amino acid substitutions (1) to (53) remain. Further, the combination of the amino acid substitutions may be selected such that one or more amino acid substitutions selected from at least the amino acid substitutions (54) to (64) remain.

Each lysine residue other than those substituted with a basic amino acid(s) and/or with an amino acid(s) containing a hydroxy group (in other words, each lysine residue not selected among the lysine residues of (I) to (VII)) may be left unsubstituted (as a lysine residue), or may be substituted with an amino acid that is neither a basic amino acid nor an amino acid containing a hydroxy group. Examples of the latter case include substitution of a lysine residue with glutamine or isoleucine, and the above-described amino acid substitutions (6) Lys7Ala, (12) Lys29Pro, (31) Lys38Ala, (38) Lys7Pro, (41) Lys29Phe, (55) Lys13Val, (56 (partial)) Lys29Val, and (62) Lys38Leu.

In another aspect, specific examples of the combination of amino acid substitutions including a first-group mutation include:

the amino acid substitutions Lys7Arg, Lys13Arg, Gly21Arg, Lys22Arg, Lys29Arg, Lys38Arg, Lys48Arg, and Lys67Arg;
the amino acid substitutions Lys7Arg, Lys13Arg, Lys22Arg, Lys29Arg, Lys38Arg, Lys48Arg, Gly51Val, and Lys67Arg;
the amino acid substitutions Lys7Arg, Lys13Arg, Lys22Arg, Lys29Arg, Lys38Arg, Lys48Arg, Asn50Tyr, Glu52Gly, and Lys67Arg;
the amino acid substitutions Lys7Ala, Lys13Arg, Gly21Arg, Lys22Gln, Lys29Ile, Lys38Arg, Lys48Arg, and Lys67Arg;
the amino acid substitutions Lys7Ala, Lys13Arg, Lys22Gln, Lys29Ile, Lys38Arg, Lys48Arg, Asn50Tyr, Glu52Gly, and Lys67Arg;
the amino acid substitutions Lys7Ala, Lys13Arg, Gly21Arg, Lys22Gln, Lys29Ile, Lys38Arg, Lys48Arg, Asn50Tyr, Glu52Gly, and Lys67Arg;
the amino acid substitutions Glu1Gly, Lys7Ala, Lys13Arg, Lys22Gln, Lys29Ile, Lys38Arg, Lys48Arg, Asn50Tyr, Glu52Gly, and Lys67Arg;

the amino acid substitutions Glu1Val, Lys7Ala, Lys13Arg, Lys22Gln, Lys29Ile, Lys38Arg, Lys48Arg, Asn50Tyr, Glu52Gly, and Lys67Arg;
the amino acid substitutions Lys7Ala, Lys13Arg, Lys22Arg, Lys29Ile, Lys38Arg, Lys48Arg, Asn50Tyr, Glu52Gly, and Lys67Arg;
the amino acid substitutions Glu4Lys, Lys7Ala, Lys13Arg, Lys22Gln, Lys29Ile, Lys38Arg, Lys48Arg, Asn50Tyr, Glu52Gly, and Lys67Arg;
the amino acid substitutions Lys7Ala, Lys13Arg, Lys22Thr, Lys29Ile, Lys38Arg, Lys48Arg, Asn50Tyr, Glu52Gly, and Lys67Arg;
the amino acid substitutions Lys7Ala, Lys13Arg, Lys22Gln, Glu27Arg, Lys29Ile, Lys38Arg, Lys48Arg, Asn50Tyr, Glu52Gly, and Lys67Arg;
the amino acid substitutions Lys7Ala, Lys13Arg, Lys22Gln, Lys29Ile, Thr36Ala, Lys38Arg, Lys48Arg, Asn50Tyr, Glu52Gly, and Lys67Arg;
the amino acid substitutions Lys7Ala, Glu9Val, Lys13Arg, Lys22Gln, Lys29Ile, Lys38Arg, Lys48Arg, Asn50Tyr, Glu52Gly, and Lys67Arg;
the amino acid substitutions Lys7Ala, Lys13Arg, Lys22Arg, Lys29Ile, Lys38Arg, Lys48Arg, Asn50Tyr, Glu52Gly, and Lys67Arg;
the amino acid substitutions Lys7Ala, Lys13Arg, Lys22Gln, Lys29Ile, Lys38Arg, Lys48Arg, Asn50Tyr, Glu52Gly, Tyr53Phe, and Lys67Arg;
the amino acid substitutions Lys7Ala, Lys13Arg, Lys22Gln, Lys29Ile, Lys38Arg, Lys48Arg, Asn50Tyr, Glu52Gly, Thr54Met, and Lys67Arg;
the amino acid substitutions Lys7Ala, Lys13Arg, Lys22Gln, Lys29Ile, Lys38Arg, Lys48Arg, Asn50Tyr, Glu52Gly, Lys67Arg, and Ala69Thr;
the amino acid substitutions Lys7Ala, Lys13Arg, Lys22Arg, Lys29Ile, Lys38Arg, Lys48Arg, Asn50Tyr, Glu52Gly, Tyr53Phe, and Lys67Arg;
the amino acid substitutions Lys7Ala, Lys13Arg, Lys22Arg, Lys29Ile, Lys38Arg, Lys48Arg, Asn50Tyr, Glu52Gly, Thr54Met, and Lys67Arg;
the amino acid substitutions Glu1Val, Lys7Ala, Lys13Arg, Lys22Arg, Lys29Ile, Lys38Arg, Lys48Arg, Asn50Tyr, Glu52Gly, Tyr53Phe, and Lys67Arg;
the amino acid substitutions Glu4Gly, Lys7Ala, Lys13Arg, Lys22Arg, Lys29Ile, Lys38Arg, Lys48Arg, Asn50Tyr, Glu52Gly, Tyr53Phe, and Lys67Arg;
the amino acid substitutions Lys7Ser, Lys13Arg, Lys22Arg, Lys29Ile, Lys38Arg, Lys48Arg, Asn50Tyr, Glu52Gly, Tyr53Phe, and Lys67Arg;
the amino acid substitutions Lys7Ala, Lys13Arg, Gly21Arg, Lys22Arg, Lys29Ile, Lys38Arg, Lys48Arg, Asn50Tyr, Glu52Gly, Tyr53Phe, and Lys67Arg;
the amino acid substitutions Lys7Ala, Lys13Arg, Lys22Arg, Lys29Ile, Lys38Arg, Lys48Arg, Asn50Tyr, Glu52Asp, Tyr53Phe, and Lys67Arg;
the amino acid substitutions Glu4Gly, Lys7Ala, Lys13Arg, Lys22Arg, Lys29Ile, Lys38Arg, Lys48Arg, Asn50Tyr, Glu52Asp, Tyr53Phe, and Lys67Arg;
the amino acid substitutions Lys7Ser, Lys13Arg, Lys22Arg, Lys29Ile, Lys38Arg, Lys48Arg, Asn50Tyr, Glu52Asp, Tyr53Phe, and Lys67Arg;
the amino acid substitutions Glu4Gly, Lys7Ser, Lys13Arg, Lys22Arg, Lys29Ile, Lys38Arg, Lys48Arg, Asn50Tyr, Glu52Gly, Tyr53Phe, and Lys67Arg;
the amino acid substitutions Glu4Gly, Lys7Ala, Lys13Arg, Lys22Arg, Lys29Ile, Lys38Ala, Lys48Arg, Asn50Tyr, Glu52Asp, Tyr53Phe, and Lys67Arg;
the amino acid substitutions Glu4Gly, Lys7Ala, Lys13Arg, Lys22Arg, Lys29Ile, Phe32Leu, Lys38Arg, Ala47Thr, Lys48Arg, Asn50Tyr, Glu52Asp, Tyr53Phe, and Lys67Arg;
the amino acid substitutions Thr2Ser, Glu4Gly, Lys7Ala, Lys13Arg, Lys22Arg, Lys29Ile, Lys38Arg, Lys48Arg, Asn50Tyr, Glu52Asp, Tyr53Phe, and Lys67Arg;
the amino acid substitutions Glu4Gly, Lys7Ala, Lys13Arg, Lys22Arg, Glu27Lys, Lys29Ile, Lys38Arg, Lys48Arg, Asn50Tyr, Glu52Asp, Tyr53Phe, and Lys67Arg;
the amino acid substitutions Thr2Pro, Pro3Arg, Glu4Gly, Lys7Ala, Glu9Val, Lys13Arg, Lys22Arg, Lys29Ile, Lys38Arg, Lys48Arg, Asn50Tyr, Glu52Asn, Tyr53Phe, and Lys67Arg;
the amino acid substitutions Glu4Gly, Lys7Ala, Lys13Arg, Lys22Arg, Glu27Ile, Lys29Ile, Lys38Arg, Lys48Arg, Asn50Tyr, Glu52Asp, Tyr53Phe, and Lys67Arg;
the amino acid substitutions Glu4Gly, Lys7Ala, Lys13Arg, Lys22Arg, Lys29Ile, Lys38Arg, Asn44Ile, Lys48Arg, Asn50Tyr, Glu52Asp, Tyr53Phe, and Lys67Arg;
the amino acid substitutions Glu4Gly, Glu5Lys, Lys7Ala, Lys13Arg, Lys22Arg, Lys29Ile, Lys38Arg, Asn44Ile, Lys48Arg, Asn50Tyr, Glu52Asp, Tyr53Phe, and Lys67Arg;
the amino acid substitutions Pro3Arg, Glu4Gly, Lys7Ala, Lys13Arg, Lys22Arg, Lys29Ile, Lys38Arg, Lys48Arg, Asn50Tyr, Glu52Asp, Tyr53Phe, and Lys67Arg;
the amino acid substitutions Glu4Gly, Glu5Lys, Lys7Ala, Lys13Arg, Lys22Arg, Lys29Ile, Lys38Arg, Lys48Arg, Asn50Tyr, Glu52Asp, Tyr53Phe, and Lys67Arg;
the amino acid substitutions Glu4Gly, Lys7Ala, Lys13Arg, Lys22Arg, Glu27Val, Lys29Ile, Lys38Arg, Lys48Arg, Asn50Tyr, Glu52Asp, Tyr53Phe, and Lys67Arg;
the amino acid substitutions Glu4Gly, Glu5Arg, Lys7Ala, Lys13Arg, Lys22Arg, Lys29Ile, Lys38Arg, Lys48Arg, Asn50Tyr, Glu52Asp, Tyr53Phe, and Lys67Arg;
the amino acid substitutions Glu4Gly, Lys7Ala, Lys13Arg, Lys22Arg, Glu27Arg, Lys29Ile, Lys38Arg, Lys48Arg, Asn50Tyr, Glu52Asp, Tyr53Phe, and Lys67Arg;
the amino acid substitutions Glu4Gly, Lys7Ala, Lys13Arg, Lys22Arg, Lys29Ile, Lys38Arg, Ala47Arg, Lys48Arg, Asn50Tyr, Glu52Asp, Tyr53Phe, and Lys67Arg;
the amino acid substitutions Glu4Gly, Lys7Ala, Lys13Arg, Lys22Arg, Lys29Ile, Lys48Arg, Asn50Tyr, Glu52Asp, Tyr53Phe, and Lys67Arg;
the amino acid substitutions Glu4Gly, Lys7Ala, Lys13Arg, Lys22Arg, Lys29Ile, Lys38Glu, Lys48Arg, Asn50Tyr, Glu52Asp, Tyr53Phe, and Lys67Arg;
the amino acid substitutions Glu4Gly, Lys7Ala, Lys13Arg, Lys22Arg, Lys29Ile, Lys48Arg, Asn50Tyr, Glu52Asp, Tyr53Phe, Lys67Arg, and Ala69Val;
the amino acid substitutions Glu4Gly, Lys7Ala, Lys13Arg, Lys22Arg, Lys29Phe, Lys48Arg, Asn50Tyr, Glu52Asp, Tyr53Phe, and Lys67Arg;
the amino acid substitutions Glu4Gly, Lys7Ala, Glu8Gly, Lys13Arg, Lys22Arg, Lys29Ile, Glu33Val, Lys48Arg, Asn50Tyr, Glu52Asp, Tyr53Phe, and Lys67Arg;
the amino acid substitutions Glu4Gly, Lys7Ala, Lys13Arg, Lys22Arg, Ile23Arg, Lys29Ile, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Ala41Ile, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Ala41Tyr, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Lys48Arg, Asn50Tyr, Glu52Leu, Tyr53Phe, and Lys67Arg;

the amino acid substitutions Glu4Gly, Lys7Ala, Lys13Arg, Lys22Arg, Lys29Ile, Lys48Arg, Asn50Tyr, Glu52Val, Tyr53Phe, and Lys67Arg;

the amino acid substitutions Glu4Gly, Lys7Ala, Lys13Arg, Lys22Arg, Lys29Ile, Lys48Arg, Asn50Tyr, Glu52Val, Tyr53Phe, Lys67Arg, and Ala69Val;

the amino acid substitutions Glu4Gly, Lys7Ala, Lys13Arg, Lys22Arg, Lys29Ile, Lys38Glu, Lys48Arg, Asn50Tyr, Glu52Val, Tyr53Phe, Lys67Arg, and Ala69Val;

the amino acid substitutions Glu4Gly, Lys7Ala, Lys13Arg, Lys22Arg, Lys29Ile, Lys48Arg, Asn50Tyr, Glu52Leu, Tyr53Phe, Lys67Arg, and Ala69Val;

the amino acid substitutions Glu4Gly, Lys7Ala, Lys13Arg, Lys22Arg, Lys29Ile, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Lys38Glu, Lys48Arg, Asn50Tyr, Tyr53Phe, Lys67Arg, and Ala69Val;

the amino acid substitutions Pro3Arg, Glu4Gly, Lys7Ala, Lys13Arg, Lys22Arg, Lys29Ile, Lys48Arg, Asn50Tyr, Tyr53Phe, Lys67Arg, and Ala69Val;

the amino acid substitutions Pro3Arg, Glu4Gly, Lys7Ala, Lys13Arg, Lys22Arg, Lys29Ile, Lys38Arg, Lys48Arg, Asn50Tyr, Tyr53Phe, Lys67Arg, and Ala69Val;

the amino acid substitutions Pro3Arg, Glu4Gly, Lys7Ala, Lys13Arg, Lys22Arg, Lys29Ile, Lys48Arg, Asn50Tyr, Tyr53Phe, Ilr66Val, Lys67Arg, and Ala69Val;

the amino acid substitutions Pro3Arg, Glu4Gly, Lys7Ala, Lys13Arg, Lys22Arg, Lys29Ile, Thr31Met, Lys48Arg, Asn50Tyr, Tyr53Phe, Lys67Arg, and Ala69Val;

the amino acid substitutions Glu4Gly, Pro6Leu, Lys7Ala, Lys13Arg, Lys22Arg, Lys29Ile, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Ala35Thr, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Glu33Gly, Lys48Arg, Asn50Tyr, Tyr53Phe, Lys67Arg, and Ala69Val;

the amino acid substitutions Glu4Gly, Glu5Asp, Pro6Leu, Lys7Ala, Lys13Arg, Lys22Arg, Lys29Ile, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Lys48Arg, Asn50Tyr, Tyr53Phe, Lys67Arg, and Ala69Leu;

the amino acid substitutions Glu4Gly, Lys7Ala, Lys13Arg, Lys22Arg, Lys29Ile, Ala37Thr, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Glu33Asp, Lys48Arg, Asn50Tyr, Glu52Gly, Tyr53Phe, Lys67Arg, and Ala69Val;

the amino acid substitutions Thr2Ala, Glu4Gly, Lys7Pro, Lys13Arg, Lys22Arg, Lys29Ile, Lys48Arg, Asn50Tyr, Tyr53Phe, Lys67Arg, and Ala69Val;

the amino acid substitutions Glu4Gly, Lys7Ala, Lys13Arg, Lys22Arg, Ile23Val, Lys29Ile, Lys48Arg, Asn50Tyr, Tyr53Phe, Lys67Arg, and Ala69Val;

the amino acid substitutions Glu4Gly, Pro6Thr, Lys7Ala, Lys13Arg, Lys22Arg, Lys29Ile, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Thr36Ser, Lys48Arg, Asn50Tyr, Tyr53Phe, Lys67Arg, and Ala69Val;

the amino acid substitutions Glu4Gly, Lys7Ala, Lys13Arg, Val14Ala, Lys22Arg, Lys29Ile, Lys48Arg, Asn50Tyr, Tyr53Phe, Lys67Arg, and Ala69Val;

the amino acid substitutions Glu4Gly, Lys7Ala, Lys13Arg, Gly21Arg, Lys22Arg, Lys29Ile, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Asn44Arg, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Asn44His, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Lys48Arg, Asn50Tyr, Glu52Tyr, Tyr53Phe, Lys67Arg, and Ala69Val;

the amino acid substitutions Glu4Gly, Lys7Ala, Lys13Arg, Lys22Arg, Lys29Ile, Lys48Arg, Asn50Tyr, Tyr53Phe, Gly60Arg, Lys67Arg, and Ala69Val; and the amino acid substitutions Glu4Gly, Lys7Ala, Lys13Arg, Lys22Arg, Lys29Ile, Lys48Arg, Asn50Tyr, Tyr53Phe, Ile64Leu, Lys67Arg, and Ala69Val.

In another aspect, specific examples of the combination of amino acid substitutions including a second-group mutation include:

the amino acid substitutions Lys7Gln, Lys13Arg, Lys22Arg, Lys29Arg, Lys48Arg, and Lys67Arg;

the amino acid substitutions Lys7Arg, Lys13Val, Lys22Arg, Lys29Arg, Lys48Arg, and Lys67Arg;

the amino acid substitutions Lys7Arg, Lys13Arg, Lys22Arg, Lys29Val, Lys48Arg, and Lys67Arg;

the amino acid substitutions Lys7Arg, Lys13Arg, Lys22Arg, Lys29Ile, Lys48Arg, and Lys67Arg;

the amino acid substitutions Lys7Ala, Lys13Arg, Lys29Ile, Lys38Arg, Lys48Arg, and Lys67Arg;

the amino acid substitutions Lys7Ala, Lys13Arg, Lys29Ile, Lys38Arg, Lys48Arg, Asn50Tyr, Glu52Gly, and Lys67Arg;

the amino acid substitutions Lys7Ala, Glu9Val, Lys29Ile, Lys38Arg, Lys48Arg, Asn50Tyr, Glu52Gly, and Lys67Arg;

the amino acid substitutions Lys7Ala, Lys13Arg, Lys22Arg, Lys29Ile, Lys38Arg, Lys48Arg, Asn50Tyr, Glu52Gly, and Lys67Arg;

the amino acid substitutions Lys7Ala, Lys13Arg, Lys29Ile, Lys38Arg, Lys48Arg, Asn50Tyr, Glu52Gly, Tyr53Phe, and Lys67Arg;

the amino acid substitutions Lys7Ala, Lys13Arg, Lys29Ile, Lys38Arg, Lys48rg, Asn50Tyr, Glu52Gly, Thr54Met, and Lys67Arg;

the amino acid substitutions Lys7Ala, Lys13Arg, Lys29Ile, Lys38Arg, Lys48rg, Asn50Tyr, Glu52Gly, Lys67Arg, and Ala69Thr;

the amino acid substitutions Lys7Ala, Lys13Arg, Lys22Arg, Lys29Ile, Lys38Arg, Lys48Arg, Asn50Tyr, Glu52Gly, Tyr53Phe, and Lys67Arg;

the amino acid substitutions Glu1Val, Lys7Ala, Lys13Arg, Lys22Arg, Lys29Ile, Lys38Arg, Lys48Arg, Asn50Tyr, Glu52Gly, Tyr53Phe, and Lys67Arg;

the amino acid substitutions Glu4Gly, Lys7Ala, Lys13Arg, Lys22Arg, Lys29Ile, Lys38Arg, Lys48Arg, Asn50Tyr, Glu52Gly, Tyr53Phe, and Lys67Arg;

the amino acid substitutions Lys7Ser, Lys13Arg, Lys22Arg, Lys29Ile, Lys38Arg, Lys48Arg, Asn50Tyr, Glu52Gly, Tyr53Phe, and Lys67Arg;

the amino acid substitutions Lys7Ala, Lys13Arg, Gly21Arg, Lys22Arg, Lys29Ile, Lys38Arg, Lys48Arg, Asn50Tyr, Glu52Gly, Tyr53Phe, and Lys67Arg;

the amino acid substitutions Lys7Ala, Lys13Arg, Lys22Arg, Lys29Ile, Lys38Arg, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Lys38Glu, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Lys48Arg, Asn50Tyr, Glu52Asp, Tyr53Phe, Lys67Arg, and Ala69Val;

the amino acid substitutions Glu4Gly, Lys7Ala, Glu8Gly, Lys13Arg, Lys22Arg, Lys29Ile, Glu33Val, Lys48Arg, Asn50Tyr, Glu52Asp, Tyr53Phe, and Lys67Arg;

the amino acid substitutions Glu4Gly, Lys7Ala, Lys13Arg, Lys22Arg, Ile23Arg, Lys29Ile, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Ala41Ile, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Ala41Tyr, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Lys48Arg, Asn50Tyr, Glu52Leu, Tyr53Phe, and Lys67Arg;

the amino acid substitutions Glu4Gly, Lys7Ala, Lys13Arg, Lys22Arg, Lys29Ile, Lys48Arg, Asn50Tyr, Glu52Val, Tyr53Phe, and Lys67Arg;

the amino acid substitutions Glu4Gly, Pro6Ala, Lys7Ala, Lys13Arg, Lys22Arg, Lys29Ile, Lys48Arg, Asn50Tyr, Glu52Asp, Tyr53Phe, and Lys67Arg;

the amino acid substitutions Glu4Gly, Lys7Ala, Glu8Gly, Lys13Arg, Lys22Arg, Lys29Ile, Lys48Arg, Asn50Tyr, Glu52Asp, Tyr53Phe, and Lys67Arg;

the amino acid substitutions Glu4Gly, Lys7Ala, Glu8Arg, Lys13Arg, Lys22Arg, Lys29Ile, Lys48Arg, Asn50Tyr, Glu52Asp, Tyr53Phe, and Lys67Arg;

the amino acid substitutions Glu4Gly, Lys7Ala, Lys13Arg, Gly21Arg, Lys22Arg, Lys29Ile, Lys48Arg, Asn50Tyr, Glu52Asp, Tyr53Phe, and Lys67Arg;

the amino acid substitutions Glu4Gly, Lys7Ala, Lys13Arg, Lys22Arg, Ile23Phe, Lys29Ile, Lys48Arg, Asn50Tyr, Glu52Asp, Tyr53Phe, and Lys67Arg;

the amino acid substitutions Glu4Gly, Lys7Ala, Lys13Arg, Lys22Arg, Ile23Leu, Lys29Ile, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Glu33Val, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Lys38His, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Lys38Leu, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Asn44His, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Asn44Arg, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Asn44His, Lys48Arg, Asn50Tyr, Glu52Asp, Tyr53Phe, and Lys67Arg;

the amino acid substitutions Glu4Gly, Lys7Ala, Lys13Arg, Lys22Arg, Lys29Ile, Lys48Arg, Asn50Met, Glu52Asp, Tyr53Phe, and Lys67Arg;

the amino acid substitutions Glu4Gly, Lys7Ala, Lys13Arg, Lys22Arg, Lys29Ile, Lys48Arg, Asn50Tyr, Glu52Tyr, Tyr53Phe, and Lys67Arg;

the amino acid substitutions Glu4Gly, Lys7Ala, Lys13Arg, Lys22Arg, Lys29Ile, Lys48Arg, Asn50Tyr, Glu52Asp, Tyr53Ser, and Lys67Arg;

the amino acid substitutions Glu4Gly, Lys7Ala, Lys13Arg, Lys22Arg, Lys29Ile, Lys48Arg, Asn50Tyr, Glu52Val, Tyr53Phe, Lys67Arg, and Ala69Val;

the amino acid substitutions Glu4Gly, Lys7Ala, Lys13Arg, Lys22Arg, Lys29Ile, Lys38Glu, Lys48Arg, Asn50Tyr, Glu52Val, Tyr53Phe, Lys67Arg, and Ala69Val;

the amino acid substitutions Glu4Gly, Lys7Ala, Lys13Arg, Lys22Arg, Lys29Ile, Lys48Arg, Asn50Tyr, Glu52Leu, Tyr53Phe, Lys67Arg, and Ala69Val;

the amino acid substitutions Glu4Gly, Lys7Ala, Lys13Arg, Lys22Arg, Lys29Ile, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Lys38Glu, Lys48Arg, Asn50Tyr, Tyr53Phe, Lys67Arg, and Ala69Val;

the amino acid substitutions Glu4Gly, Lys7Ala, Lys13Arg, Val14Ala, Lys22Arg, Lys29Ile, Lys48Arg, Asn50Tyr, Tyr53Phe, Lys67Arg, and Ala69Val;

the amino acid substitutions Glu4Gly, Lys7Ala, Lys13Arg, Gly21Arg, Lys22Arg, Lys29Ile, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Asn44Arg, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Asn44His, Lys48Arg, Asn50Tyr, Tyr53Phe, Lys67Arg, and Ala69Val;

the amino acid substitutions Glu4Gly, Lys7Ala, Lys13Arg, Lys22Arg, Lys29Ile, Lys48Arg, Asn50Tyr, Glu52Tyr, Tyr53Phe, Lys67Arg, and Ala69Val;

the amino acid substitutions Glu4Gly, Lys7Ala, Lys13Arg, Lys22Arg, Lys29Ile, Lys48Arg, Asn50Tyr, Tyr53Phe, Gly60Arg, Lys67Arg, and Ala69Val;

the amino acid substitutions Glu4Gly, Lys7Ala, Lys13Arg, Lys22Arg, Lys29Ile, Lys48Arg, Asn50Tyr, Tyr53Phe, Ile64Leu, Lys67Arg, and Ala69Val;

the amino acid substitutions Glu4Gly, Lys7Ala, Lys13Arg, Lys22Arg, Ile23Arg, Lys29Ile, Asn44Arg, Lys48Arg, Asn50Tyr, Tyr53Phe, Lys67Arg, and Ala69Val;

the amino acid substitutions Glu4Gly, Lys7Ala, Lys13Arg, Lys22Arg, Ile23Arg, Lys29Ile, Asn44His, Lys48Arg, Asn50Tyr, Tyr53Phe, Lys67Arg, and Ala69Val;

the amino acid substitutions Glu4Gly, Lys7Ala, Lys13Arg, Lys22Arg, Ile23Arg, Lys29Ile, Lys48Arg, Asn50Tyr, Tyr53Phe, Ile64Leu, Lys67Arg, and Ala69Val;

- the amino acid substitutions Glu4Gly, Lys7Ala, Lys13Arg, Lys22Arg, Lys29Ile, Asn44Arg, Lys48Arg, Asn50Tyr, Tyr53Phe, Ile64Leu, Lys67Arg, and Ala69Val;
- the amino acid substitutions Glu4Gly, Lys7Ala, Lys13Arg, Lys22Arg, Lys29Ile, Asn44His, Lys48Arg, Asn50Tyr, Tyr53Phe, Ile64Leu, Lys67Arg, and Ala69Val;
- the amino acid substitutions Glu4Gly, Lys7Ala, Lys13Arg, Lys22Arg, Ile23Arg, Lys29Ile, Asn44Arg, Lys48His, Asn50Tyr, Tyr53Phe, Ile64Leu, Lys67Arg, and Ala69Val;
- the amino acid substitutions Glu4Gly, Lys7Ala, Lys13Arg, Lys22Arg, Lys29Ile, Asn44His, Lys48His, Asn50Tyr, Tyr53Phe, Ile64Leu, Lys67Arg, and Ala69Val;
- the amino acid substitutions Glu4Gly, Lys7Ala, Lys13Arg, Asn15Val, Lys22Arg, Lys29Ile, Lys48Arg, Asn50Tyr, Glu52Asp, Tyr53Phe, and Lys67Arg;
- the amino acid substitutions Glu4Gly, Lys7Ala, Lys13Arg, Lys22Arg, Lys29Ile, Glu34Asp, Lys48Arg, Asn50Tyr, Glu52Asp, Tyr53Phe, and Lys67Arg;
- the amino acid substitutions Glu4Gly, Lys7Ala, Lys13Arg, Lys22Arg, Lys29Ile, Glu34Phe, Lys48Arg, Asn50Tyr, Glu52Asp, Tyr53Phe, and Lys67Arg;
- the amino acid substitutions Glu4Gly, Lys7Ala, Lys13Arg, Lys22Arg, Lys29Ile, Glu34Leu, Lys48Arg, Asn50Tyr, Glu52Asp, Tyr53Phe, and Lys67Arg; and
- the amino acid substitutions Glu4Gly, Lys7Ala, Lys13Arg, Lys22Arg, Lys29Ile, Glu34Val, Lys48Arg, Asn50Tyr, Glu52Asp, Tyr53Phe, and Lys67Arg.

In another aspect, specific examples of the combination of amino acid substitutions especially include:

- the amino acid substitutions Lys7Ala, Lys13Arg, Lys22Gln, Lys29Ile, Lys38Arg, Lys48Arg, Asn50Tyr, Glu52Gly, and Lys67Arg;
- the amino acid substitutions Lys7Ala, Lys13Arg, Lys22Arg, Lys29Ile, Lys38Arg, Lys48Arg, Asn50Tyr, Glu52Gly, Tyr53Phe, and Lys67Arg;
- the amino acid substitutions Glu4Gly, Lys7Ala, Lys13Arg, Lys22Arg, Lys29Ile, Lys38Arg, Lys48Arg, Asn50Tyr, Glu52Asp, Tyr53Phe, and Lys67Arg;
- the amino acid substitutions Glu4Gly, Lys7Ala, Lys13Arg, Lys22Arg, Glu27Arg, Lys29Ile, Lys38Arg, Lys48Arg, Asn50Tyr, Glu52Asp, Tyr53Phe, and Lys67Arg;
- the amino acid substitutions Glu4Gly, Lys7Ala, Lys13Arg, Lys22Arg, Lys29Ile, Lys38Glu, Lys48Arg, Asn50Tyr, Glu52Asp, Tyr53Phe, and Lys67Arg;
- the amino acid substitutions Glu4Gly, Lys7Ala, Lys13Arg, Lys22Arg, Lys29Ile, Lys38Glu, Lys48Arg, Asn50Tyr, Glu52Val, Tyr53Phe, Lys67Arg, and Ala69Val;
- the amino acid substitutions Glu4Gly, Lys7Ala, Lys13Arg, Lys22Arg, Lys29Ile, Lys38Glu, Lys48Arg, Asn50Tyr, Tyr53Phe, Lys67Arg, and Ala69Val;
- the amino acid substitutions Glu4Gly, Lys7Ala, Lys13Arg, Lys22Arg, Ile23Arg, Lys29Ile, Lys38Glu, Asn44Arg, Lys48Arg, Asn50Tyr, Tyr53Phe, Lys67Arg, and Ala69Val; and
- the amino acid substitutions Glu4Gly, Lys7Ala, Lys13Arg, Lys22Arg, Ile23Arg, Lys29Ile, Lys38Glu, Asn44Arg, Lys48His, Asn50Tyr, Tyr53Phe, Ile64Leu, Lys67Arg, and Ala69Val.

The protein of an aspect of the present invention may further include at least one other amino acid substitution. Examples of the other amino acid substitution include Glu49Asp, Pro6Ser, Asn44Asp, Glu49Val, Asn62Tyr, Ile23Thr, and Ala41Arg. The other amino acid substitution may be an amino acid substitution that improves the alkaline stability of the immunoglobulin-binding protein. For example, each of the amino acid substitutions Asn44Asp, Glu49Val, Asn62Tyr, Ile23Thr, and Ala41Arg may be an amino acid substitution that improves the alkaline stability of the immunoglobulin-binding protein. The protein of an aspect of the present invention may have, for example, one, two, three, four, five, or six amino acid substitutions among these other amino acid substitutions.

However,

- in cases where the amino acid substitution Glu49Asp is selected, the amino acid substitution (17) (Glu49Thr or Glu49Ile) is overwritten by the amino acid substitution Glu49Asp;
- in cases where the amino acid substitution Pro6Ser is selected, the amino acid substitution (37) (one of Pro6Leu and Pro6Thr) is overwritten by the amino acid substitution Pro6Ser;
- in cases where the amino acid substitution Asn44Asp is selected, the amino acid substitution (16) (Asn44Ser or Asn44Gly), the amino acid substitution (32) (Asn44Ile), and the amino acid substitution (48) (Asn44His or Asn44Arg) are overwritten by the amino acid substitution Asn44Asp;
- in cases where the amino acid substitution Glu49Val is selected, the amino acid substitution (17) (Glu49Thr or Glu49Ile) is overwritten by the amino acid substitution Glu49Val;
- in cases where the amino acid substitution Asn62Tyr is selected, the amino acid substitution (23) (one of Asn62His, Asn62Arg, Asn62Leu, Asn62Met, and Asn62Trp) is overwritten by the amino acid substitution Asn62Tyr;
- in cases where the amino acid substitution Ile23Thr is selected, the amino acid substitution (40) (Ile23Arg or Ile23Val) and the amino acid substitution (60) (Ile23Phe or Ile23Leu) are overwritten by the amino acid substitution Ile23Thr; and
- in cases where the amino acid substitution Ala41Arg is selected, the amino acid substitution (15) (Ala41Thr) and the amino acid substitution (47) (Ala41Ile or Ala41Tyr) are overwritten by the amino acid substitution Ala41Arg.

Alternatively, among the other amino acid substitutions, amino acid substitutions at the same positions as those of the one or more amino acid substitutions selected from (1) to (64) do not need to be selected. More specifically, for example, in cases where at least the amino acid substitution (17) (Glu49Thr or Glu49Ile) is selected from the amino acid substitutions (1) to (64), the amino acid substitutions Glu49Asp and Glu49Val do not need to be selected. Further, the combination of the amino acid substitutions is selected such that at least one or more amino acid substitutions selected from (1) to (64) remain. Thus, for example, in cases where the amino acid substitution (17) (Glu49Thr or Glu49Ile) alone is selected from the amino acid substitutions (1) to (64), the amino acid substitutions Glu49Asp and Glu49Val cannot be selected. Further, the combination of the amino acid substitutions may be selected such that at least one or more amino acid substitutions selected from the amino acid substitutions (1) to (53) remain. Further, the combination of the amino acid substitutions may be selected such that at least one or more amino acid substitutions selected from the amino acid substitutions (54) to (64) remain. Thus, examples of the modified amino acid sequence also include an amino acid sequence which is the same as an unmodified amino acid sequence exemplified above (such as the amino acid sequence of SEQ ID NO:1) except that the modified amino acid sequence has the amino acid substitution(s) at the particular position(s) and the other amino acid substitution(s) such as Glu49Asp or Pro6Ser. Thus, examples of the protein of the present invention also include a protein containing an amino acid sequence which is the same as an unmodified amino acid sequence exemplified above (such as the amino acid sequence of SEQ ID NO:1) except that the amino acid sequence of the protein has the amino acid substitution(s) at the particular position(s) and the other amino acid substitution(s) such as Glu49Asp or Pro6Ser. In other words, the protein of an aspect of the present invention may be, for example, a protein containing the same amino acid sequence as an unmodified amino acid sequence exemplified above (such as the amino acid sequence of SEQ ID NO:1) except for the presence of the amino acid substitution(s) at the particular position(s) and the other amino acid substitution(s) such as Glu49Asp or Pro6Ser. Glu49Asp and Pro6Ser, exemplified as the other amino acid substitutions, are amino acid substitutions capable of binding to the κ light chain of immunoglobulin irrespective of the subgroup thereof.

Examples of the combination of amino acid substitutions including the other amino acid substitution(s) include a combination that includes, in addition to a combination of amino acid substitutions exemplified above, one, two, three, four, five, or six other amino acid substitutions described above. In particular, examples of the combination of amino acid substitutions including the other amino acid substitution(s) include a combination that includes, in addition to a combination of amino acid substitutions exemplified above, at least the amino acid substitution Asn62Tyr.

Examples of a protein of the present invention further including the other amino acid substitution(s) include the following proteins. These proteins are preferred from the viewpoint of the fact that they have improved alkaline stabilities, and that they are capable of binding to the κ light chain of immunoglobulin irrespective of the subgroup thereof.

An immunoglobulin-binding protein containing an amino acid sequence which is the same as the amino acid sequence of SEQ ID NO:1 except that the amino acid sequence of the immunoglobulin-binding protein has the amino acid substitutions Lys7Ala, Lys13Arg, Lys22Gln, Lys29Ile, Lys38Arg, Lys48Arg, Glu49Asp, Asn50Tyr, Glu52Gly, Asn62Tyr, and Lys67Arg (an immunoglobulin-binding protein containing the amino acid sequence of SEQ ID NO: 179).

An immunoglobulin-binding protein containing an amino acid sequence which is the same as the amino acid sequence of SEQ ID NO:1 except that the amino acid sequence of the immunoglobulin-binding protein has the amino acid substitutions Lys7Ala, Lys13Arg, Lys22Arg, Lys29Ile, Lys38Arg, Lys48Arg, Glu49Asp, Asn50Tyr, Glu52Gly, Tyr53Phe, Asn62Tyr, and Lys67Arg (an immunoglobulin-binding protein containing the amino acid sequence of SEQ ID NO:186).

An immunoglobulin-binding protein containing an amino acid sequence which is the same as the amino acid sequence of SEQ ID NO:1 except that the amino acid sequence of the immunoglobulin-binding protein has the amino acid substitutions Glu4Gly, Lys7Ala, Lys13Arg, Lys22Arg, Lys29Ile, Lys38Arg, Lys48Arg, Glu49Asp, Asn50Tyr, Glu52Asp, Tyr53Phe, Asn62Tyr, and Lys67Arg (an immunoglobulin-binding protein containing the amino acid sequence of SEQ ID NO:199).

An immunoglobulin-binding protein containing an amino acid sequence which is the same as the amino acid sequence of SEQ ID NO:1 except that the amino acid sequence of the immunoglobulin-binding protein has the amino acid substitutions Glu4Gly, Lys7Ala, Lys13Arg, Lys22Arg, Glu27Arg, Lys29Ile, Lys38Arg, Lys48Arg, Glu49Asp, Asn50Tyr, Glu52Asp, Tyr53Phe, Asn62Tyr, and Lys67Arg (an immunoglobulin-binding protein containing the amino acid sequence of SEQ ID NO:224).

An immunoglobulin-binding protein containing an amino acid sequence which is the same as the amino acid sequence of SEQ ID NO:1 except that the amino acid sequence of the immunoglobulin-binding protein has the amino acid substitutions Glu4Gly, Pro6Ser, Lys7Ala, Lys13Arg, Lys22Arg, Lys29Ile, Lys38Glu, Lys48Arg, Glu49Asp, Asn50Tyr, Glu52Asp, Tyr53Phe, Asn62Tyr, and Lys67Arg (an immunoglobulin-binding protein containing the amino acid sequence of SEQ ID NO:240).

An immunoglobulin-binding protein containing an amino acid sequence which is the same as the amino acid sequence of SEQ ID NO:1 except that the amino acid sequence of the immunoglobulin-binding protein has the amino acid substitutions Glu4Gly, Pro6Ser, Lys7Ala, Lys13Arg, Lys22Arg, Lys29Ile, Lys38Glu, Lys48Arg, Glu49Asp, Asn50Tyr, Glu52Val, Tyr53Phe, Asn62Tyr, Lys67Arg, and Ala69Val (an immunoglobulin-binding protein containing the amino acid sequence of SEQ ID NO:271).

An immunoglobulin-binding protein containing an amino acid sequence which is the same as the amino acid sequence of SEQ ID NO:1 except that the amino acid sequence of the immunoglobulin-binding protein has the amino acid substitutions Glu4Gly, Pro6Ser, Lys7Ala, Lys13Arg, Lys22Arg, Lys29Ile, Lys38Glu, Lys48Arg, Glu49Asp, Asn50Tyr, Tyr53Phe, Asn62Tyr, Lys67Arg, and Ala69Val (an immunoglobulin-binding protein containing the amino acid sequence of SEQ ID NO:275).

Examples of the protein of the present invention further including the other amino acid substitution(s) also include the following proteins. These proteins are preferred from the viewpoint of the fact that they have improved alkaline stabilities, that they are capable of binding to the κ light chain of immunoglobulin irrespective of the subgroup thereof. Further, immunoglobulin adsorbents of an aspect of the present invention obtained by immobilizing these proteins on an insoluble support are preferred from the viewpoint of the fact that the immunoglobulin adsorbents allow elution of immunoglobulins (antibodies) containing a κ light chain, irrespective of the subgroup thereof, under milder pH conditions compared to conventional immunoglobulin adsorbents.

An immunoglobulin-binding protein containing an amino acid sequence which is the same as the amino acid sequence of SEQ ID NO:1 except that the amino acid sequence of the immunoglobulin-binding protein has the amino acid substitutions Glu4Gly, Pro6Ser, Lys7Ala, Lys13Arg, Lys22Arg, Ile23Arg, Lys29Ile, Lys38Glu, Asn44Arg, Lys48Arg, Glu49Asp, Asn50Tyr, Tyr53Phe, Asn62Tyr, Lys67Arg, and Ala69Val (an immunoglobulin-binding protein containing the amino acid sequence of SEQ ID NO:408).

An immunoglobulin-binding protein containing an amino acid sequence which is the same as the amino acid sequence of SEQ ID NO:1 except that the amino acid sequence of the immunoglobulin-binding protein has the amino acid substitutions Glu4Gly, Pro6Ser, Lys7Ala, Lys13Arg, Lys22Arg, Ile23Arg, Lys29Ile, Lys38Glu, Asn44Arg, Lys48His, Glu49Asp, Asn50Tyr, Tyr53Phe, Asn62Tyr, Ile64Leu, Lys67Arg, and Ala69Val (an immunoglobulin-binding protein containing the amino acid sequence of SEQ ID NO:413).

In other words, examples of the amino acid substitutions included in the protein of an aspect of the present invention include the following:

- the amino acid substitutions Lys7Ala, Lys13Arg, Lys22Gln, Lys29Ile, Lys38Arg, Lys48Arg, Glu49Asp, Asn50Tyr, Glu52Gly, Asn62Tyr, and Lys67Arg;
- the amino acid substitutions Lys7Ala, Lys13Arg, Lys22Arg, Lys29Ile, Lys38Arg, Lys48Arg, Glu49Asp, Asn50Tyr, Glu52Gly, Tyr53Phe, Asn62Tyr, and Lys67Arg;
- the amino acid substitutions Glu4Gly, Lys7Ala, Lys13Arg, Lys22Arg, Lys29Ile, Lys38Arg, Lys48Arg, Glu49Asp, Asn50Tyr, Glu52Asp, Tyr53Phe, Asn62Tyr, and Lys67Arg;
- the amino acid substitutions Glu4Gly, Lys7Ala, Lys13Arg, Lys22Arg, Glu27Arg, Lys29Ile, Lys38Arg, Lys48Arg, Glu49Asp, Asn50Tyr, Glu52Asp, Tyr53Phe, Asn62Tyr, and Lys67Arg;
- the amino acid substitutions Glu4Gly, Pro6Ser, Lys7Ala, Lys13Arg, Lys22Arg, Lys29Ile, Lys38Glu, Lys48Arg, Glu49Asp, Asn50Tyr, Glu52Asp, Tyr53Phe, Asn62Tyr, and Lys67Arg;
- the amino acid substitutions Glu4Gly, Pro6Ser, Lys7Ala, Lys13Arg, Lys22Arg, Lys29Ile, Lys38Glu, Lys48Arg, Glu49Asp, Asn50Tyr, Glu52Val, Tyr53Phe, Asn62Tyr, Lys67Arg, and Ala69Val;
- the amino acid substitutions Glu4Gly, Pro6Ser, Lys7Ala, Lys13Arg, Lys22Arg, Lys29Ile, Lys38Glu, Lys48Arg, Glu49Asp, Asn50Tyr, Tyr53Phe, Asn62Tyr, Lys67Arg, and Ala69Val;
- the amino acid substitutions Glu4Gly, Pro6Ser, Lys7Ala, Lys13Arg, Lys22Arg, Ile23Arg, Lys29Ile, Lys38Glu, Asn44Arg, Lys48Arg, Glu49Asp, Asn50Tyr, Tyr53Phe, Asn62Tyr, Lys67Arg, and Ala69Val; and
- the amino acid substitutions Glu4Gly, Pro6Ser, Lys7Ala, Lys13Arg, Lys22Arg, Ile23Arg, Lys29Ile, Lys38Glu, Asn44Arg, Lys48His, Glu49Asp, Asn50Tyr, Tyr53Phe, Asn62Tyr, Ile64Leu, Lys67Arg, and Ala69Val.

In the present description, an amino acid sequence which is the same as the amino acid sequence of SEQ ID NO:1 except for the presence of an amino acid substitution(s) exemplified above (that is, the amino acid substitution(s) at the particular position(s) described above and optionally the other amino acid substitution(s) such as Glu49Asp or Pro6Ser) is also referred to as "SEQ ID NO:1-derived substituted amino acid sequence". The SEQ ID NO:1-derived substituted amino acid sequence is, in other words, an amino acid sequence which is the same as the amino acid sequence of SEQ ID NO:1 except that an amino acid substitution(s) exemplified above (that is, the amino acid substitution(s) at the particular position(s) described above and optionally the other amino acid substitution(s) such as Glu49Asp or Pro6Ser) occurred. Further, the SEQ ID NO:1-derived substituted amino acid sequence is, in other words, an amino acid sequence which is the same as the amino acid sequence of SEQ ID NO:1 except that the SEQ ID NO:1-derived substituted amino acid sequence has an amino acid substitution(s) exemplified above (that is, the amino acid substitution(s) at the particular position(s) described above and optionally the other amino acid substitution(s) such as Glu49Asp or Pro6Ser). The SEQ ID NO:1-derived substituted amino acid sequence is an example of the modified amino acid sequence in the present description.

Examples of the modified amino acid sequence in the present description also include a variant sequence of a modified amino acid sequence exemplified above (such as a SEQ ID NO:1-derived substituted amino acid sequence). Thus, examples of the protein of an aspect of the present invention also include a protein which contains a variant sequence of a modified amino acid sequence exemplified above (such as a SEQ ID NO:1-derived substituted amino acid sequence), and which has immunoglobulin-binding activity. The following description is given by way of examples of the case of a variant sequence of a SEQ ID NO:1-derived substituted amino acid sequence. However, the description is also applicable to variant sequences of any modified amino acid sequence.

The variant sequence of a SEQ ID NO:1-derived substituted amino acid sequence is set such that the amino acid substitution(s) at the particular position(s) remain(s) (in other words, such that the protein of an aspect of the present invention has the amino acid substitution(s) at the particular position(s)). The variant sequence of a SEQ ID NO:1-derived substituted amino acid sequence may also be set such that the other amino acid substitution(s) such as Glu49Asp or Pro6Ser remain(s) (in other words, such that the protein of an aspect of the present invention has the other amino acid substitution(s) such as Glu49Asp or Pro6Ser). Further, the variant sequence of a SEQ ID NO:1-derived substituted amino acid sequence may additionally have one or more amino acid substitutions not contained in the SEQ ID NO:1-derived substituted amino acid sequence selected from, for example, the amino acid substitutions exemplified above (that is, the amino acid substitutions at the particular positions described above and optionally the other amino acid substitutions such as Glu49Asp or Pro6Ser). For example, in cases where the SEQ ID NO: 1-derived substituted amino acid sequence does not have the other amino acid substitution(s) such as Glu49Asp or Pro6Ser, the variant sequence of the SEQ ID NO:1-derived substituted amino acid sequence may have the other amino acid substitution(s).

Examples of the variant sequence of a SEQ ID NO:1-derived substituted amino acid sequence include an amino acid sequence which is the same as the SEQ ID NO:1-derived substituted amino acid sequence except that the amino acid sequence of the variant sequence contains substitution, deletion, insertion, and/or addition of one or several amino acid residues at one or several positions. In other words, the protein of an aspect of the present invention, as long as it has immunoglobulin-binding activity, may contain not only an amino acid substitution(s) exemplified above (that is, the amino acid substitution(s) at the particular position(s) described above and optionally the other amino acid substitution(s) such as Glu49Asp or Pro6Ser), but also substitution, deletion, insertion, and/or addition of one or several amino acid residues at one or several positions in terms of the amino acid sequence of SEQ ID NO: 1. Thus, examples of the protein of the present invention also include a protein containing the same amino acid sequence as the amino acid sequence of SEQ ID NO:1 except for the presence of an amino acid substitution(s) exemplified above (that is, the amino acid substitution(s) at the particular position(s) described above and optionally the other amino acid substitution(s) such as Glu49Asp or Pro6Ser), and also for the presence of substitution, deletion, insertion, and/or addition of one or several amino acid residues at one or several positions, which protein has immunoglobulin-binding activity. In other words, the protein of an aspect of the present invention may be, for example, a protein containing an amino acid sequence which is the same as the amino acid sequence of SEQ ID NO:1 except that the amino acid sequence of the protein has an amino acid substitution(s) exemplified above (that is, the amino acid substitution(s) at the particular position(s) described above and optionally the other amino acid substitution(s) such as Glu49Asp or Pro6Ser), and that the amino acid sequence of the protein also contains substitution, deletion, insertion, and/or addition of one or several amino acid residues at one or several positions, which protein has immunoglobulin-binding activity. The substitution, deletion, insertion, and/or addition of the amino acid residue(s) is/are selected such that the amino acid substitution(s) at the particular position(s) remain(s). In other words, the substitution, deletion, insertion, and/or addition of the amino acid residue(s) may occur, for example, at a position(s) other than the particular position(s) described above. Further, the substitution, deletion, insertion, and/or addition of the amino acid residue(s) may be selected such that the other amino acid substitution(s) remain(s). In other words, the substitution, deletion, insertion, and/or addition of the amino acid residue(s) may occur, for example, at a position(s) other than the position(s) of the other amino acid substitution(s). Further, the substitution, deletion, insertion, and/or addition of the amino acid residue(s) may include, for example, one or more amino acid substitutions which are selected from the amino acid substitutions exemplified above and which are not included in the SEQ ID NO:1-derived substituted amino acid sequence. The term “one or several” specifically means, for example, any of 1 to 20, 1 to 10, 1 to 9, 1 to 8, 1 to 7, 1 to 6, 1 to 5, 1 to 4, 1 to 3, 1 to 2, and 1 depending on the position(s) of the amino acid residue(s) in the spatial structure of the protein, and on the type(s) of the amino acid residue(s). Examples of the substitution of the amino acid residue(s) include conservative substitutions, in which substitution occurs between amino acids having similar physical properties and/or chemical properties. It is known to those skilled in the art that, in cases of conservative substitutions, the protein function is generally maintained between a protein in which the substitution has occurred and a protein in which the substitution has not occurred. Examples of conservative substitutions include substitutions between glycine and alanine, between serine and proline, and between glutamic acid and alanine (Protein Structure and Function, Medical Science International, Ltd., 9, 2005). Examples of the substitution, deletion, insertion, and/or addition of the amino acid residue(s) also include those generated by naturally occurring mutations (mutants or variants), such as those based on a difference between individuals or species of the microorganism from which the protein or a gene encoding it is derived.

Examples of the variant sequence of the SEQ ID NO:1-derived substituted amino acid sequence also include amino acid sequences having high homology to the SEQ ID NO:1-derived substituted amino acid sequence. Thus, examples of the protein of the present invention also include a protein containing an amino acid sequence having high homology to an amino acid sequence which is the same as the amino acid sequence of SEQ ID NO:1 except for the presence of an amino acid substitution(s) exemplified above (that is, the amino acid substitution(s) at the particular position(s) described above and optionally the other amino acid substitution(s) such as Glu49Asp or Pro6Ser), which protein has immunoglobulin-binding activity. The change in the amino acid sequence within such a range of homology is selected such that the amino acid substitution(s) at the particular position(s) remain(s). In other words, the change in the amino acid sequence within such a range of homology may occur, for example, at a position(s) other than the particular position(s) described above. Further, the change in the amino acid sequence within such a range of homology may be selected such that the other amino acid substitution(s) remain(s). In other words, the change in the amino acid sequence within such a range of homology may occur, for example, at a position(s) other than the position(s) of the other amino acid substitution(s). Further, the change in the amino acid sequence within such a range of homology may include, for example, one or more amino acid substitutions which are selected from the amino acid substitutions exemplified above and which are not contained in the SEQ ID NO:1-derived substituted amino acid sequence. “Homology” may mean the similarity or the identity, or may especially mean the identity. “Homology to an amino acid sequence” means the homology to the entire amino acid sequence. “High homology” may mean a homology of not less than 70%, not less than 80%, not less than 90%, or not less than 95%. “Identity” between amino acid sequences means the ratio of amino acid residues whose types are identical between those amino acid sequences (Experimental Medicine, February 2013, Vol. 31, No. 3, Yodosha Co., Ltd.). “Similarity” between amino acid sequences means the sum of the ratio of amino acid residues whose types are identical, and the ratio of amino acid residues whose side chains have similar properties, between those amino acid sequences (Experimental Medicine, February 2013, Vol. 31, No. 3, Yodosha Co., Ltd.). The amino acid residues whose side chains have similar properties are as described above. The homology between amino acid sequences can be determined using an alignment program such as BLAST (Basic Local Alignment Search Tool) or FASTA.

Examples of the modified amino acid sequence also include an amino acid sequence which is the same as a variant sequence exemplified above except that the modified amino acid sequence further includes one or more amino acid substitutions selected from the amino acid substitutions exemplified above (that is, the amino acid substitutions at the particular positions described above and optionally the other amino acid substitutions such as Glu49Asp or Pro6Ser). For example, the modified amino acid sequence may be an amino acid sequence which is the same as a variant sequence having the amino acid substitution(s) at at least the particular position(s) described above except that the modified amino acid sequence further includes the other amino acid substitution(s).

Examples of the unmodified amino acid sequence also include a variant sequence of an unmodified amino acid sequence exemplified above (such as the amino acid sequence of SEQ ID NO:1). Thus, examples of the modified amino acid sequence also include an amino acid sequence which is the same as a variant sequence of an unmodified amino acid sequence exemplified above (such as the amino acid sequence of SEQ ID NO:1) except that the modified amino acid sequence has an amino acid substitution(s) exemplified above (that is, the amino acid substitution(s) at the particular position(s) described above and optionally the other amino acid substitution(s) such as Glu49Asp or Pro6Ser). Thus, examples of the protein of the present invention also include a protein containing an amino acid sequence which is the same as a variant sequence of an unmodified amino acid sequence exemplified above (such as the amino acid sequence of SEQ ID NO:1) except that the variant sequence in the protein has an amino acid substitution(s) exemplified above (that is, the amino acid substitution(s) at the particular position(s) described above and optionally the other amino acid substitution(s) such as Glu49Asp or Pro6Ser), which protein has immunoglobulin-binding activity. In other words, the protein of an aspect of the present invention may be, for example, a protein containing the same amino acid sequence as a variant sequence of an unmodified amino acid sequence exemplified above (such as the amino acid sequence of SEQ ID NO:1) except for the presence of an amino acid substitution(s) exemplified above. The variant sequence of an unmodified amino acid sequence exemplified above (such as the amino acid sequence of SEQ ID NO:1) may or may not be actually present in a bacterium belonging to the genus *Finegoldia*. Thus, "amino acid sequence of an immunoglobulin-binding domain of protein L derived from a bacterium belonging to the genus *Finegoldia* (amino acid sequence of an immunoglobulin-binding domain of FpL)" is not limited to an amino acid sequence of an immunoglobulin-binding domain of protein L actually present in a bacterium belonging to the genus *Finegoldia*, and also includes an amino acid sequence which is a variant sequence of the amino acid sequence of the domain, and which is not actually present (that is, which is a hypothetical amino acid sequence) in a bacterium belonging to the genus *Finegoldia*. The following description is given by way of examples of the case of a variant sequence of the amino acid sequence of SEQ ID NO:1. However, this description is also applicable to variant sequences of any unmodified amino acid sequence.

Examples of the variant sequence of the amino acid sequence of SEQ ID NO:1 include an amino acid sequence which is the same as the amino acid sequence of SEQ ID NO:1 except that the variant sequence contains substitution, deletion, insertion, and/or addition of one or several amino acid residues at one or several positions. Thus, examples of the protein of an aspect of the present invention also include a protein containing an amino acid sequence which is the same as the amino acid sequence of SEQ ID NO:1 except that the amino acid sequence of the protein contains substitution, deletion, insertion, and/or addition of one or several amino acid residues at one or several positions, and that the amino acid sequence of the protein further includes an amino acid substitution(s) exemplified above (that is, the amino acid substitution(s) at the particular position(s) described above and optionally the other amino acid substitution(s) such as Glu49Asp or Pro6Ser), which protein has immunoglobulin-binding activity. The substitution, deletion, insertion, and/or addition of the amino acid residue(s) may occur, for example, at a position(s) other than the particular position(s) described above. The substitution, deletion, insertion, and/or addition of the amino acid residue(s) may occur, for example, at a position(s) other than the position(s) of the other amino acid substitution(s).

Examples of the variant sequence of the amino acid sequence of SEQ ID NO:1 also include amino acid sequences having high homology to the amino acid sequence of SEQ ID NO:1. Thus, examples of the protein of the present invention also include a protein containing an amino acid sequence having high homology to the amino acid sequence of SEQ ID NO:1, wherein the amino acid sequence (amino acid sequence having high homology to the amino acid sequence of SEQ ID NO:1) has an amino acid substitution(s) exemplified above (that is, the amino acid substitution(s) at the particular position(s) described above and optionally the other amino acid substitution(s) such as Glu49Asp or Pro6Ser), which protein has immunoglobulin-binding activity. The change(s) in the amino acid residue(s) within such a range of homology may occur, for example, at a position(s) other than the particular position(s) described above. The change(s) in the amino acid residue(s) within such a range of homology may occur, for example, at a position(s) other than the position(s) of the other amino acid substitution(s).

To the variant sequence of the amino acid sequence of SEQ ID NO:1, the description on the variant sequence of a SEQ ID NO:1-derived substituted amino acid sequence is applicable.

In the present description, "amino acid at position X in the amino acid sequence of SEQ ID NO: 1" means the amino acid present at the Xth position as counted from the N-terminus of the amino acid sequence of SEQ ID NO:1. "Amino acid residue corresponding to the amino acid at position X of the amino acid sequence of SEQ ID NO: 1" in a particular amino acid sequence means the amino acid residue, in the particular amino acid sequence, which is placed at the same position as the amino acid at position X of the amino acid sequence of SEQ ID NO:1 in an alignment of the particular amino acid sequence with the amino acid sequence of SEQ ID NO:1. For example, in a case of the amino acid substitution Asn50Tyr, "amino acid residue corresponding to the asparagine at position 50 of SEQ ID NO:1" in a particular amino acid sequence means the amino acid residue, in the particular amino acid sequence, which is placed at the same position as the asparagine at position 50 of the amino acid sequence of SEQ ID NO:1 in an alignment of the particular amino acid sequence with the amino acid sequence of SEQ ID NO: 1. "Amino acid residue corresponding to the amino acid at position X of the amino acid sequence of SEQ ID NO: 1" in the amino acid sequence of SEQ ID NO:1 means the amino acid at position X of the amino acid sequence of SEQ ID NO:1 itself. Thus, the positions of the amino acid substitutions exemplified above (that is, the amino acid substitutions at the particular positions described above and optionally the other amino acid substitutions) do not necessarily represent the absolute positions in the protein of the present invention, but represent relative positions based on the amino acid sequence of SEQ ID NO: 1. Thus, for example, in cases where the protein of an aspect of the present invention contains insertion, deletion, or addition of an amino acid residue(s) in the N-terminal side relative to the positions of the amino acid substitutions exemplified above, the absolute positions of the amino acid substitutions may change in accordance therewith. The positions of the amino acid substitutions exemplified above in the protein of an aspect of the present invention can be specified by, for example, alignment of the amino acid sequence of the protein of an aspect of the present invention with the amino acid sequence of SEQ ID NO: 1. The alignment can be carried out by, for example, using an alignment program such as BLAST or FASTA. The same applies to the positions of the amino acid substitutions exemplified above in any amino acid sequence such as a variant sequence of the amino acid sequence of SEQ ID NO:1. The amino acid residues before the occurrence of the amino acid substitutions exemplified above (that is, the amino acid substitutions at the particular positions described above and optionally the other amino acid substitutions such as Glu49Asp or Pro6Ser) represent the types of the unsubstituted amino acid residues in the amino acid sequence of SEQ ID NO:1, and may or may not be conserved in unmodified amino acid sequences other than the amino acid sequence of SEQ ID NO:1.

The protein of an aspect of the present invention may contain only one modified amino acid sequence, or may contain a plurality of modified amino acid sequences. The protein of an aspect of the present invention may contain, for example, not less than 2, not less than 3, not less than 4, or not less than 5 modified amino acid sequences; may contain not more than 10, not more than 7, not more than 5, not more than 4, not more than 3, or not more than 2 modified amino acid sequences; or may contain modified amino acid sequences in a number specified by a consistent combination of these numbers. In cases where the protein of an aspect of the present invention contains a plurality of modified amino acid sequences, these plurality of modified amino acid sequences may be either the same or different. The plurality of modified amino acid sequences may be in a mode in which they are directly linked to each other, or may be in a mode in which they are linked through an appropriate linker(s) (such as an oligopeptide(s) composed of 5 to 25 amino acid residues) to each other.

The protein of an aspect of the present invention may be composed of a modified amino acid sequence(s), or may further contain another amino acid sequence. Thus, the protein of an aspect of the present invention may further contain another amino acid sequence, for example, in the N-terminal side or the C-terminal side thereof. In other words, in the protein of an aspect of the present invention, another amino acid sequence may be added to, for example, the N-terminal side or the C-terminal side of the modified amino acid sequence. Examples of the other amino acid sequence include an oligopeptide. Examples of the oligopeptide used as the other amino acid sequence include an oligopeptide other than the linker. The other amino acid sequence is not limited as long as it does not deteriorate the immunoglobulin-binding activity or the stability of the protein of an aspect of the present invention. For example, the type and the length of the other amino acid sequence are not limited as long as the immunoglobulin-binding capacity or the stability of the protein of an aspect of the present invention is not deteriorated.

The protein of an aspect of the present invention may contain, for example, part of another immunoglobulin-binding domain as well as the immunoglobulin-binding domain selected. For example, in cases where the protein of an aspect of the present invention contains a modified amino acid sequence of domain C3 of FpL, the protein of an aspect of the present invention may also contain part of the region in the N-terminal side of domain C3 of FpL (domain C1 or domain C2), or part of the region in the C-terminal side of domain C3 of FpL (domain C4).

The protein of an aspect of the present invention may contain, for example, in its N-terminal side or C-terminal side, an oligopeptide useful for the purpose of specifically detecting or separating a target substance. Examples of such an oligopeptide include polyhistidine and polyarginine. Further, the protein of an aspect of the present invention may contain, for example, in its N-terminal side or C-terminal side, an oligopeptide useful for immobilizing the protein of an aspect of the present invention on a solid phase such as a support for chromatography. Examples of such an oligopeptide include oligopeptides containing lysine or cysteine.

In cases where the protein of an aspect of the present invention contains the above-described other amino acid sequence, for example, the protein of an aspect of the present invention may be produced in a form already containing the other amino acid sequence, or the above-described other amino acid sequence may be separately produced and added to the protein. In cases where the protein of an aspect of the present invention contains the above-described other amino acid sequence, the protein of an aspect of the present invention can be typically produced by expression from a polynucleotide encoding the entire amino acid sequence of the protein of an aspect of the present invention containing the above-described other amino acid sequence. More specifically, for example, a polynucleotide encoding the other amino acid sequence may be linked to a polynucleotide encoding the protein of an aspect of the present invention (which, for example, does not contain the other amino acid sequence) such that the other amino acid sequence is added to the N-terminal side or the C-terminal side of the protein of an aspect of the present invention, and then the protein of an aspect of the present invention may be expressed. Further, for example, the other amino acid sequence may be chemically synthesized, and chemically bound to the N-terminal side or the C-terminal side of the protein of an aspect of the present invention (which, for example, does not contain the other amino acid sequence).

The protein of an aspect of the present invention can be produced by, for example, expression from a polynucleotide encoding the protein of an aspect of the present invention. In the present description, the polynucleotide encoding the protein of an aspect of the present invention is also referred to as "polynucleotide of an aspect of the present invention". More specifically, the polynucleotide of an aspect of the present invention may be a polynucleotide containing a nucleotide sequence encoding the protein of an aspect of the present invention.

The polynucleotide of an aspect of the present invention can be obtained, for example, by a chemical synthesis method, or by a DNA amplification method utilizing the PCR method or the like. The DNA amplification method can be carried out using, as a template, a polynucleotide containing a nucleotide sequence to be amplified, such as a nucleotide sequence encoding the protein of an aspect of the present invention. Examples of the polynucleotide to be used as the template include genomic DNA of an organism that expresses the protein of an aspect of the present invention, cDNA of the protein of an aspect of the present invention, and vectors containing the polynucleotide of an aspect of the present invention.

The nucleotide sequence of the polynucleotide of an aspect of the present invention can be designed by, for example, conversion from the amino acid sequence of the protein of an aspect of the present invention. In the conversion from the amino acid sequence to the nucleotide sequence, a standard codon table may be used. The conversion is preferably carried out taking into account the codon usage in the host to be transformed with the polynucleotide of an aspect of the present invention. For example, in cases where the host is *Escherichia coli*, the conversion may be carried out while avoiding use of the codons AGA/AGG/CGG/CGA for arginine (Arg), ATA for isoleucine (Ile), CTA for leucine (Leu), GGA for glycine (Gly), and CCC for proline (Pro) since the usage of each of these codons is low (that is, the codons are the so-called rare codons). Analysis of the codon usage is possible by, for example, utilizing a public database (such as the Codon Usage Database provided on the website of Kazusa DNA Research Institute).

The polynucleotide of an aspect of the present invention may be obtained at once as the entire sequence of the polynucleotide, or may be obtained by obtaining polynucleotides composed of partial sequences of the polynucleotide and then linking the obtained polynucleotides to each other. The above description on the method of obtaining the polynucleotide of an aspect of the present invention is applicable not only to cases where the entire sequence is obtained at once, but also to cases where its partial sequences are obtained.

The polynucleotide of an aspect of the present invention may be designed such that it is linked to a polynucleotide encoding the amino acid sequence of any polypeptide, to encode a fusion-type amino acid sequence.

The protein of an aspect of the present invention can be produced by, for example, culturing a recombinant host containing the polynucleotide of an aspect of the present invention (hereinafter simply referred to as "recombinant host of an aspect of the present invention") to allow expression of the protein, and then recovering the expressed protein. The recombinant host of an aspect of the present invention can be obtained by, for example, transforming a host using the polynucleotide of an aspect of the present invention. The host is not limited as long as the protein of an aspect of the present invention can be expressed by transformation of the host with the polynucleotide of an aspect of the present invention. Examples of the host include animal cells, insect cells, and microorganisms. Among these, examples of the animal cells include COS cells, CHO (Chinese Hamster Ovary) cells, Hela cells, NIH3T3 cells, and HEK293 cells; examples of the insect cells include Sf9 cells and BTI-TN-5B1-4 cells; and examples of the microorganisms include yeasts and bacteria. Examples of the yeasts include yeasts belonging to the genus *Saccharomyces*, such as *Saccharomyces cerevisiae*; yeasts belonging to the genus *Pichia*, such as *Pichia pastoris*; and yeasts belonging to the genus *Schizosaccharomyces*, such as *Schizosaccharomyces pombe*. Examples of the bacteria include bacteria belonging to the genus *Escherichia*, such as *Escherichia coli*. Examples of the *Escherichia coli* include the JM109 strain and the BL21 (DE3) strain. A yeast or *Escherichia coli* is preferably used as the host from the viewpoint of productivity. *Escherichia coli* is more preferably used as the host.

In the recombinant host of an aspect of the present invention, the polynucleotide of an aspect of the present invention may be retained in a mode that allows its expression. More specifically, the polynucleotide of an aspect of the present invention may be retained such that it is expressed under the regulation of a promoter that functions in the host. In cases where *Escherichia coli* is used as the host, examples of the promoter that functions in the host include the trp promoter, tac promoter, trc promoter, lac promoter, T7 promoter, recA promoter, and lpp promoter.

In the recombinant host of an aspect of the present invention, the polynucleotide of an aspect of the present invention may be present on a vector that self-replicates outside the genomic DNA. Thus, a host may be transformed with an expression vector containing the polynucleotide of an aspect of the present invention (hereinafter simply referred to as "expression vector of an aspect of the present invention", to prepare the recombinant host of an aspect of the present invention. The expression vector of an aspect of the present invention can be obtained by, for example, inserting the polynucleotide of an aspect of the present invention into an appropriate position in an expression vector. The expression vector is not limited as long as it can be stably present and is capable of replication in the host to be transformed therewith. In cases where the host is *Escherichia coli*, examples of the expression vector include the pET plasmid vector, pUC plasmid vector, and pTrc plasmid vector. The expression vector of an aspect of the present invention may contain a selection marker such as an antibiotic resistance gene. The appropriate position described above means a position where the insertion does not destroy regions responsible for the replication function, selection marker, and transferability of the expression vector. In the process of inserting the polynucleotide of an aspect of the present invention into the expression vector, the polynucleotide is preferably inserted in a state where it is linked to a functional polynucleotide such as a promoter required for its expression.

In the recombinant host of an aspect of the present invention, the polynucleotide of an aspect of the present invention may be introduced in the genomic DNA. The introduction of the polynucleotide of an aspect of the present invention into the genomic DNA can be carried out by, for example, utilizing a gene transfer method based on homologous recombination. Examples of the gene transfer method based on homologous recombination include a method using linear DNA, such as the Red-driven integration method (Datsenko, K. A., and Wanner, B. L., Proc. Natl. Acad. Sci. USA., 97: 6640-6645(2000)); a method using a vector containing a temperature-sensitive origin of replication; a method using a vector not having an origin of replication that functions in the host; and a transduction method using a phage.

The transformation of the host using a polynucleotide such as the expression vector of an aspect of the present invention can be carried out by, for example, a method commonly used by those skilled in the art. For example, in cases where *Escherichia coli* is selected as the host, the transformation may be carried out by the competent cell method, heat shock method, electroporation method, or the like. By performing screening for a host containing the polynucleotide of an aspect of the present invention by an appropriate method after the transformation, the recombinant host of an aspect of the present invention can be obtained.

Information on genetic engineering methods, such as expression vectors and promoters available for various microorganisms, may be obtained by utilization of known documents such as "Fundamental Microbiology 8: Genetic Engineering. Kyoritsu Shuppan Co., Ltd. (1987)".

In cases where the recombinant host of an aspect of the present invention contains the expression vector of an aspect of the present invention, the expression vector of an aspect of the present invention can be prepared from the recombinant host of an aspect of the present invention. For example, from a culture obtained by culturing the recombinant host of an aspect of the present invention, the expression vector of an aspect of the present invention can be prepared by the alkaline extraction method, or by using a commercially available extraction kit such as a QIAprep Spin Miniprep kit (manufactured by QIAGEN).

By culturing the recombinant host of an aspect of the present invention, the protein of an aspect of the present invention can be expressed. Further, by culturing the recombinant host of an aspect of the present invention, the protein of an aspect of the present invention can be expressed, and, by recovering the expressed protein, the protein of an aspect of the present invention can be produced. Thus, the present description discloses a method of producing the protein of an aspect of the present invention, the method including the steps of: culturing the recombinant host of an aspect of the present invention to allow expression of the protein of an aspect of the present invention; and recovering the expressed protein. The medium composition and the culture conditions may be appropriately set depending on conditions such as the type of the host and properties of the protein of an aspect of the present invention. For example, the medium composition and the culture conditions may be set such that the host can be grown and can express the protein of an aspect of the present invention. Examples of media that can be used therefor include media appropriately containing a carbon source, a nitrogen source, an inorganic salt, and/or other organic components and/or inorganic components. Specifically, in cases where the host is *Escherichia coli*, one preferred example of the medium is LB (Luria-Bertani) medium supplemented with necessary nutrient sources (1% (w/v) tryptone, 0.5% (w/v) yeast extract, and 1% (w/v) NaCl). For selective growth of the recombinant host of an aspect of the present invention based on the presence or absence of the expression vector of an aspect of the present invention introduced, the culture is preferably carried out with a medium supplemented with an antibiotic corresponding to an antibiotic resistance gene contained in the expression vector. For example, in cases where the expression vector contains a kanamycin resistance gene, the medium may be supplemented with kanamycin. The same applies to cases where the polynucleotide of an aspect of the present invention is introduced in the genomic DNA. The medium may also contain one or more reducing agents selected from the group consisting of glutathione, cysteine, cystatin, thioglycolate, and dithiothreitol. The medium may also contain a reagent, such as glycine, which promotes secretion of protein from the transformant into the culture liquid. For example, in cases where the host is *Escherichia coli*, glycine is preferably added at not more than 2% (w/v) to the medium. For example, in cases where the host is *Escherichia coli*, the culture temperature may be generally 10° C. to 40° C., preferably 20° C. to 37° C., more preferably about 25° C. For example, in cases where the host is *Escherichia coli*, the pH of the medium is pH 6.8 to pH 7.4, preferably about pH 7.0. In cases where the protein of an aspect of the present invention is expressed under the regulation of an inducible promoter, the induction is preferably carried out so as to allow favorable expression of the protein of an aspect of the present invention. For the induction of the expression, for example, an inducer in accordance with the type of the promoter may be used. Examples of the inducer may include IPTG (isopropyl-β-D-thiogalactopyranoside). For example, in cases where the host is *Escherichia coli*, an appropriate amount of IPTG may be added when the turbidity (absorbance at 600 nm) of the culture liquid has reached about 0.5 to 1.0, and the culture may then be continued to induce expression of the protein of an aspect of the present invention. The IPTG may be added at a concentration of, for example, 0.005 mM to 1.0 mM, preferably 0.01 mM to 0.5 mM. The induction of the expression such as IPTG induction can be carried out, for example, under conditions well known in the art.

The protein of an aspect of the present invention may be recovered by separation from the culture by a method suitable for the mode of its expression. In the present description, the "culture" means the entire culture liquid obtained by culturing, or part thereof. The part is not limited as long as it is a part containing the protein of an aspect of the present invention. Examples of the part include cultured cells of the transformant of an aspect of the present invention, and the medium after culturing (that is, the culture supernatant). For example, in cases where the protein of an aspect of the present invention is accumulated in the culture supernatant, the cells may be separated by a centrifugation operation, and the protein of an aspect of the present invention may then be recovered from the resulting culture supernatant. In cases where the protein of an aspect of the present invention is accumulated in the cells (including periplasm), the cells may be collected by a centrifugation operation, and then an enzyme treatment agent, a surfactant, or the like may be added thereto to disrupt the cells, followed by recovering the protein of an aspect of the present invention from the disruption product. The recovery of the protein of an aspect of the present invention from the culture supernatant or the disrupted cells can be carried out by, for example, a known method used for separation and purification of protein. Examples of the recovery method include ammonium sulfate fractionation, ion-exchange chromatography, hydrophobic chromatography, affinity chromatography, gel filtration chromatography, and isoelectric precipitation.

The protein of an aspect of the present invention can be used for, for example, separation or analysis of immunoglobulin (antibody). In cases where the protein of an aspect of the present invention is used for the above purpose, it may be used, for example, in the form of an immunoglobulin adsorbent including: an insoluble support; and a protein of an aspect of the present invention immobilized on the insoluble support (hereinafter simply referred to as "immunoglobulin adsorbent of an aspect of the present invention"). In the present description, the "separation of immunoglobulin" includes not only separation of an immunoglobulin from a solution in which impurities are present, but also separation of immunoglobulins from each other based on their structures, properties, activities, and/or the like. The insoluble support is not limited as long as it is a support insoluble in aqueous solutions. Examples of the insoluble support include supports using a polysaccharide such as agarose, alginate (alginic acid salt), carrageenan, chitin, cellulose, dextrin, dextran, or starch as a raw material; supports using a synthetic polymer such as polyvinyl alcohol, polymethacrylate, poly(2-hydroxyethyl methacrylate), or polyurethane as a raw material; and supports using a ceramic such as silica as a raw material. Among these, supports using a polysaccharide as a raw material, and supports using a synthetic polymer as a raw material, are preferred as the insoluble support. Examples of the preferred supports include polymethacrylate gels in which hydroxy groups are introduced, such as TOYOPEARL (manufactured by Tosoh Corporation); agarose gels such as Sepharose (manufactured by Cytiva); and cellulose gels such as Cellufine (manufactured by JNC Corporation). The shape of the insoluble support is not limited. The insoluble support may have, for example, a shape which allows packing of a column therewith. The insoluble support may be, for example, a granular matter or a nongranular matter. The insoluble support may be, for example, porous or nonporous.

The immunoglobulin (antibody) to be separated or analyzed in an aspect of the present invention is not limited as long as the protein of an aspect of the present invention can bind thereto. More specifically, the immunoglobulin may contain a κ light chain. The immunoglobulin may or may not contain another region such as an Fc region, in addition to the κ light chain. The immunoglobulin may be an immunoglobulin having no Fc region, such as single-chain Fv (scFv), Fab, $F(ab')_2$, IgA, or bispecific T cell-engaging (BiTE) antibody. The immunoglobulin may be either a monoclonal antibody or a poly clonal antibody. The immunoglobulin may be, for example, any of IgG, IgM, IgA, IgD, and IgE. The IgG may be, for example, any of IgG1, IgG2, IgG3, and IgG4. The source of the immunoglobulin is not limited. The immunoglobulin may be derived from a single organism, or may be derived from a combination of two or more kinds of organisms. Examples of the immunoglobulin include chimeric antibodies, humanized antibodies, and human antibodies; and variants (such as amino acid substitution mutants) thereof. Examples of the immunoglobulin also include those having artificially modified structures, such as bispecific antibodies, fusion antibodies containing a κ light chain and another protein, and complexes containing a κ light chain and a drug (ADC). The "immunoglobulin" also includes antibody drugs.

The protein of an aspect of the present invention may be immobilized on the insoluble support by, for example, covalent bonding. More specifically, for example, the protein of an aspect of the present invention can be immobilized on the insoluble support by covalently binding the protein to the insoluble support through an active group contained in the insoluble support. Thus, the insoluble support may contain an active group, for example, on its surface. Examples of the active group include an N-hydroxysuccinimide (NHS)-activated ester group, an epoxy group, a carboxy group, a maleimide group, a haloacetyl group, a tresyl group, a formyl group, and haloacetamide. As the insoluble support containing an active group, for example, a commercially available insoluble support containing an active group may be used as it is, or an active group may be introduced to an insoluble support before use. Examples of commercially available supports containing an active group include TOYOPEARL AF-Epoxy-650M, TOYOPEARL AF-Tresyl-650M (these are manufactured by Tosoh Corporation), HiTrap NHS-activated HP Columns, NHS-activated Sepharose 4 Fast Flow, Epoxy-activated Sepharose 6B (these are manufactured by Cytiva), and SulfoLink Coupling Resin (manufactured by Thermo Fisher Scientific Inc.).

Examples of the method of introducing the active group to the surface of the support include a method in which one of two or more active sites contained in a compound is reacted with a hydroxy group, an epoxy group, a carboxy group, an amino group, or the like present on the surface of the support.

Examples of a compound for introduction of an epoxy group to the hydroxy group or amino group present on the surface of the support include epichlorohydrin, ethanediol diglycidyl ether, butanediol diglycidyl ether, and hexanediol diglycidyl ether.

Examples of a compound for introduction of a carboxy group to the epoxy group present on the surface of the support include 2-mercaptoacetic acid, 3-mercaptopropionic acid, 4-mercaptobutyric acid, 6-mercaptobutyric acid, glycine, 3-aminopropionic acid, 4-aminobutyric acid, and 6-aminohexanoic acid.

Examples of a compound for introduction of a maleimide group to the hydroxy group, epoxy group, carboxy group, or amino group present on the surface of the support include N-(ε-maleimidocaproic acid)hydrazide, N-(ε-maleimidopropionic acid)hydrazide, 4-(4-N-maleimidophenyl)acetic acid hydrazide, 2-aminomaleimide, 3-aminomaleimide, 4-aminomaleimide, 6-aminomaleimide, 1-(4-aminophenyl) maleimide, 1-(3-aminophenyl)maleimide, 4-(maleimido) phenyl isocyanate, 2-maleimidoacetic acid, 3-maleimidopropionic acid, 4-maleimidobutyric acid, 6-maleimidohexanoic acid, N-(α-maleimidoacetoxy)succinimide ester, (m-maleimidobenzoyl) N-hydroxysuccinimide ester, succinimidyl-4-(maleimidomethyl)cyclohexane-1-carbonyl-(6-aminohexanoic acid), succinimidyl-4-(maleimidomethyl)cyclohexane-1-carboxylic acid, (p-maleimidobenzoyl) N-hydroxysuccinimide ester, and (m-maleimidobenzoyl) N-hydroxysuccinimide ester.

Examples of a compound for introduction of a haloacetyl group to the hydroxy group or amino group present on the surface of the support include chloroacetic acid, bromoacetic acid, iodoacetic acid, chloroacetic chloride, bromoacetic chloride, bromoacetic bromide, chloroacetic anhydride, bromoacetic anhydride, iodoacetic anhydride, 2-(iodoacetamido)acetic acid-N-hydroxysuccinimide ester, 3-(bromoacetamido)propionic acid-N-hydroxysuccinimide ester, and 4-(iodoacetyl)aminobenzoic acid-N-hydroxysuccinimide ester.

Examples of the method of introducing the active group to the surface of the support also include a method in which ω-alkenylalkane glycidyl ether is reacted with the hydroxy group or amino group present on the surface of the support, and then the ω-alkenyl site is halogenated with a halogenating agent to cause its activation. Examples of the ω-alkenylalkane glycidyl ether include allylglycidyl ether, 3-butenylglycidyl ether, and 4-pentenylglycidyl ether. Examples of the halogenating agent include N-chlorosuccinimide, N-bromosuccinimide, and N-iodosuccinimide.

Examples of the method of introducing the active group to the surface of the support also include a method in which the active group is introduced to the carboxy group present on the surface of the support using a condensing agent and an additive. Examples of the condensing agent include 1-ethyl-3-(3-dimethylaminopropyl)carbodiimide (EDC), dicyclohexylcarbodiamide, and carbonyldiimidazole. Examples of the additive include N-hydroxysuccinimide (NHS), 4-nitrophenol, and 1-hydroxybenztriazole.

The immobilization of the protein of an aspect of the present invention on the insoluble support can be carried out, for example, in a buffer. Examples of the buffer include acetate buffer, phosphate buffer, MES (2-morpholinoethanesulfonic acid) buffer, HEPES (4-(2-hydroxyethyl)-1-piperazineethanesulfonic acid) buffer, Tris buffer, and borate buffer. The reaction temperature for the immobilization may be appropriately set depending on, for example, conditions such as reactivity of the active group and stability of the protein of an aspect of the present invention. The reaction temperature for the immobilization may be, for example, 5° C. to 50° C., and is preferably 10° C. to 35° C.

The immunoglobulin adsorbent of an aspect of the present invention may be in the form of a column packed with the adsorbent from the viewpoint of using it for separation of immunoglobulin (antibody). For example, a solution containing immunoglobulin is applied to a column packed with the immunoglobulin adsorbent of an aspect of the present invention to allow adsorption of the immunoglobulin to the adsorbent, and then the immunoglobulin that has adsorbed to the adsorbent is eluted. By this, the immunoglobulin can be separated. Thus, the present description discloses, for example, a method of separating immunoglobulin contained in a solution, the method including the steps of: applying a solution containing immunoglobulin to a column packed with the immunoglobulin adsorbent of an aspect of the present invention, to allow adsorption of the immunoglobulin to the adsorbent; and eluting the immunoglobulin that has adsorbed to the adsorbent. The solution containing immunoglobulin may be applied to the column using, for example, liquid transferring means such as a pump. The solvent of the solution containing immunoglobulin may be preliminarily replaced using an appropriate buffer before the application to the column. Before the application of the solution containing immunoglobulin to the column, the column may be equilibrated using an appropriate buffer. By the equilibration of the column, for example, separation of the immunoglobulin with higher purity can be expected. Examples of the buffer used for the solvent replacement or the equilibration include phosphate buffer, acetate buffer, and MES buffer. The buffer may be further supplemented with, for example, an inorganic salt such as 1 mM to 1000 mM sodium chloride. The buffer used for the solvent replacement and the buffer used for the equilibration may be either the same or different. In cases where components other than the immunoglobulin, such as impurities, are remaining in the column after passing the solution containing immunoglobulin through the column, such components may be removed from the column before the elution of the immunoglobulin that has adsorbed to the immunoglobulin adsorbent. The components other than the immunoglobulin can be removed from the column by, for example, using an appropriate buffer. To the buffer used for the removal of the components other than the immunoglobulin, for example, the description on the buffer used for the solvent replacement or the equilibration is applicable. The immunoglobulin that has adsorbed to the immunoglobulin adsorbent can be eluted by, for example, reducing the interaction between the immunoglobulin and the ligand (the protein of an aspect of the present invention). Examples of the means for reducing the interaction between the immunoglobulin and the ligand (the protein of an aspect of the present invention) include changing of the pH, addition of a counter peptide, increasing of the temperature, and changing of the salt concentration. Examples of the means for reducing the interaction between the immunoglobulin and the ligand (the protein of an aspect of the present invention) especially include changing of the pH. Thus, examples of the step of eluting the immunoglobulin that has adsorbed to the adsorbent especially include a step of changing the pH to elute the immunoglobulin that has adsorbed to the adsorbent. Examples of the pH change include a decrease in the pH. Examples of the decrease in the pH include a decrease in the pH due to a buffer. More specifically, the immunoglobulin that has adsorbed to the immunoglobulin adsorbent can be eluted by, for example, using an appropriate eluent. Examples of the eluent include buffers that are more acidic than the buffers used for the solvent replacement or the equilibration. Examples of the buffers that are more acidic include citrate buffer, glycine-HCl buffer, and acetate buffer. Thus, by using the buffers that are more acidic, the pH can be decreased. The pH of the eluent may be set within a range in which the function (for example, the binding capacity to antigen) of the immunoglobulin is not deteriorated. For example, the pH of the eluent may be not less than 2, not less than 2.1, not less than 2.2, not less than 2.3, not less than 2.4, not less than 2.5, not less than 2.6, not less than 2.7, not less than 2.8, not less than 2.9, not less than 3, not less than 3.1, or not less than 3.2; may be not more than 4, not more than 3.5, not more than 3.2, not more than 3.1, not more than 3, not more than 2.9, not more than 2.8, not more than 2.7, not more than 2.6, or not more than 2.5; or may be a pH specified by a consistent combination of these pHs. More specifically, the pH of the eluent may be, for example, 2 to 4, 2.2 to 4, or 2.4 to 4.

In cases where the elution of the immunoglobulin that has adsorbed to the immunoglobulin adsorbent is carried out by decreasing the pH by a buffer, and the protein of an aspect of the present invention as a component of the immunoglobulin adsorbent of an aspect of the present invention is an immunoglobulin-binding protein that allows antibody elution under mild pH conditions, the pH of the eluent can be increased (that is, the immunoglobulin can be eluted under conditions at a higher pH (at a pH closer to neutrality)) compared to cases with an immunoglobulin adsorbent containing: an insoluble support; and an immunoglobulin-binding protein having an unmodified amino acid sequence, immobilized on the insoluble support. For example, a protein of an aspect of the present invention having one or more amino acid substitutions selected from at least Gly21Arg and Gly51Val, and any of Asn62His, Asn62Arg, and Asn62Trp, can be an immunoglobulin-binding protein that allows antibody elution under mild pH conditions. Further, for example, a protein of an aspect of the present invention having at least the second-group mutation can be an immunoglobulin-binding protein that allows antibody elution under mild pH conditions. Thus, in cases where a protein of an aspect of the present invention that is an immunoglobulin-binding protein that allows antibody elution under mild pH conditions is used as the immunoglobulin-binding protein that is a component of the immunoglobulin adsorbent, elution of the immunoglobulin can be carried out under milder pH conditions (that is, under conditions closer to neutrality) compared to cases where an immunoglobulin-binding protein having an unmodified amino acid sequence is used. The pH of the eluent in such cases may be within the pH range of the eluent exemplified above. For example, the pH of the eluent may be not less than 2.5, not less than 2.6, not less than 2.7, not less than 2.8, not less than 2.9, not less than 2.95, not less than 3, not less than 3.05, not less than 3.1, not less than 3.15, or not less than 3.2; may be not more than 4, not more than 3.5, not more than 3.3, not more than 3.2, not more than 3.1, or not more than 3; or may be a pH specified by a consistent combination of these pHs. More specifically, the pH of the eluent may be, for example, 2.5 to 4, 2.8 to 4, 2.95 to 4, 3 to 4, or 3.05 to 4.

By separating the immunoglobulin (antibody) by the above method, a separated immunoglobulin can be obtained. Thus, in one aspect, the method of separating immunoglobulin may be a method of producing immunoglobulin, more specifically, a method of producing separated immunoglobulin. The immunoglobulin is obtained as, for example, an eluted fraction containing the immunoglobulin. Thus, a fraction containing the eluted immunoglobulin can be collected. The collection of the fraction may be carried out by, for example, an ordinary method. Examples of the method of collecting the fraction include a method in which collection containers are replaced at certain time or volume intervals, a method in which collection containers are replaced depending on the shape of the chromatogram of the eluate, and a method in which fractions are collected using an automatic fraction collector such as an autosampler. Further, immunoglobulin can be recovered from a fraction containing the immunoglobulin. The recovery of the immunoglobulin from the fraction containing the immunoglobulin may be carried out by, for example, a known method used for separation and purification of protein.

EXAMPLES

The present invention is described below more concretely by way of Examples. However, the present invention is not limited to the Examples. It should be noted that Reference Examples do not constitute the present invention.

Example 1 Preparation of Protein L Immunoglobulin-Binding Domain C3 Expression Vector (1) A polynucleotide (SEQ ID NO:2) encoding an amino acid sequence of immunoglobulin-binding domain C3 (the amino acid residues at positions 394 to 463 of GenBank No. AAA67503 (SEQ ID NO:210); hereinafter also referred to as "FpL_C3") of protein L (hereinafter referred to as FpL) having the amino acid sequence of SEQ ID NO:1 derived from a bacterium belonging to the genus *Finegoldia* (*Finegoldia magna*) was synthesized. In the synthesis, a recognition sequence for the restriction enzyme NcoI (5'-CCATGG-3') was added to the 5'-end side, and a nucleotide sequence encoding six histidine residues (5'-CATCACCAC- CATCACCAC-3'; SEQ ID NO:232), a stop codon, and a recognition sequence for the restriction enzyme HindIII (5'-AAGCTT-3') were added to the 3'-end side.

(2) The polynucleotide obtained by the synthesis, containing SEQ ID NO:2, was treated with the restriction enzymes NcoI and HindIII, and then subjected to agarose gel electrophoresis to confirm a band having the size of the product of interest. The band of interest was excised, and then a polynucleotide was purified using a QIAquick Gel Extraction kit (manufactured by QIAGEN).

(3) Using a DNA Ligation Kit (manufactured by Takara Bio Inc.), the polynucleotide obtained in (2) was ligated to the plasmid pET-26b, which had been preliminarily digested with the restriction enzymes NcoI and HindIII. Using the ligation product, the *Escherichia coli* BL21 (DE3) strain was transformed, and then the resulting transformant was cultured (37° C., 16 hours) on LB (Luria-Bertani) plate medium supplemented with 50 μg/mL kanamycin.

(4) The transformant (recombinant *Escherichia coli*) obtained in (3) was subjected to selection and then to culture in LB medium supplemented with 50 μg/mL kanamycin, followed by purification using a QIAprep Spin Miniprep kit (manufactured by QIAGEN), to obtain a vector (which was named pET-FpL_C3) capable of expressing FpL C3.

(5) The polynucleotide encoding FpL_C3, and its vicinity, in the expression vector pET-FpL_C3 obtained in (4) were subjected to cycle sequencing reaction using a Big Dye Terminator Cycle Sequencing ready Reaction kit (manufactured by Thermo Fisher Scientific Inc.), which is based on the chain terminator method. The nucleotide sequence was analyzed using an ABI Prism 3700 DNA analyzer (manufactured by Thermo Fisher Scientific Inc.), which is a fully automated DNA sequencer. In the analysis, oligonucleotides having the sequence of SEQ ID NO:3 (5'-TAATACGACTCACTATAGGG-3') or SEQ ID NO:4 (5'-TATGCTAGTTATTGCTCAG-3') were used as sequencing primers.

As a result of the sequence analysis, it could be confirmed that the expression vector pET-FpL_C3 contains a polynucleotide having the sequence of SEQ ID NO:2 inserted therein.

Example 2 Introduction of Mutations into FpL_C3 and Preparation of Library (Part 1)

Into the polynucleotide portion (SEQ ID NO:2) encoding the immunoglobulin-binding protein in the expression vector pET-FpL_C3 prepared in Example 1, mutations were randomly introduced by error-prone PCR.

(1) pET-FpL_C3 prepared in Example 1 was used as a template DNA to perform error-prone PCR. For the error-prone PCR, a reaction liquid having the composition shown in Table 1 was prepared, and the reaction liquid was heat-treated at 95° C. for 2 minutes, followed by performing 30 cycles of reaction in which each cycle included a first step at 95° C. for 30 seconds, a second step at 50° C. for 30 seconds, and a third step at 72° C. for 90 seconds, and then finally performing heat treatment at 72° C. for 7 minutes. By the error-prone PCR, mutations were well introduced into the polynucleotide (SEQ ID NO:2) encoding FpL_C3. The average mutation introduction rate was 1.6%.

TABLE 1

| Components | Volume |
|---|---|
| 10 ng/μL template DNA | 1 μL |
| 2.5 mM dNTP mixture | 8 μL |
| 10 μM PCR forward primer (SEQ ID NO: 3) | 4 μL |
| 10 μM PCR reverse primer (SEQ ID NO: 4) | 4 μL |
| 10 mM $MnCl_2$ | 2 μL |
| 10 mM $MgCl_2$ | 12 μL |
| Go Taq DNA polymerase (manufactured by Promega) | 1 μL |
| $H_2O$ | Up to 100 μL |

(2) The PCR product obtained was purified, and then digested with the restriction enzymes NcoI and HindIII, followed by ligation into the expression vector pET-26b, which had been preliminarily digested with the restriction enzymes NcoI and HindIII.

(3) After completion of the ligation reaction, the *Escherichia coli* BL21 (DE3) strain was transformed using the reaction liquid, and then cultured (37° C., 16 hours) on LB plate medium supplemented with 50 μg/mL kanamycin. The resulting colonies, formed on the plate, were provided as a random mutant library.

Example 3 Screening of FpL_C3 Amino Acid Substitution Mutants (Part 1) (1) The random mutant library (transformants) prepared in Example 2, or the transformant prepared in Example 1, which expresses FpL_C3 (SEQ ID NO:1), was inoculated to 250 μL of 2×YT liquid medium (1.6% (w/v) tryptone, 1% (w/v) yeast extract, 0.5% (w/v) sodium chloride) supplemented with 50 μg/mL kanamycin, and subjected to shake culture using a 96-deep-well plate at 37° C. overnight.

(2) Thereafter, 5 μL of the culture liquid of (1) was subcultured into 500 μL of 2×YT liquid medium supplemented with 50 μg/mL kanamycin, 0.3% (w/v) glycine, and 0.01 mM IPTG (isopropyl-β-D-thiogalactopyranoside), and further subjected to shake culture using a 96-deep-well plate at 20° C. overnight.

(3) Thereafter, each culture supernatant obtained by a centrifugation operation was mixed with an equal amount of 1.0 M NaOH, and then subjected to alkali treatment at 38° C. for 15 minutes.

(4) The antibody-binding activity of the immunoglobulin-binding protein subjected to the alkali treatment was measured by the ELISA method as described below. The antibody-binding activity of the immunoglobulin-binding protein subjected to the alkali treatment of (3) was divided by the antibody-binding activity of the immunoglobulin-binding protein without the alkali treatment of (3), to calculate the remaining activity.

(4-1) A human antibody prepared at 10 μg/mL using Tris-Buffered Saline (TBS) (gamma globulin preparation, manufactured by The Chemo-Sero-Therapeutic Research Institute) was dispensed into wells of 96-well microplates, followed by immobilization (4° C., 16 hours). Thereafter, blocking was carried out using skim milk (manufactured by Becton Dickinson) which was prepared at 2% (w/v) using TBS.

(4-2) Each well of the 96-well microplates was washed with a washing buffer (0.05 M Tris buffer (pH 7.5) containing 0.15 M NaCl and 0.05% (w/v) Tween 20 (trade name); hereinafter also referred to as "washing buffer A"), and a solution containing the immunoglobulin-binding protein to be evaluated for its antibody-binding activity was added thereto, followed by reacting the immunoglobulin-binding protein with the immobilized gamma globulin (30° C., 1 hour).

(4-3) Thereafter, the wells were washed with washing buffer A, and 100 μL/well of Anti-6-His Antibody (manufactured by BETHYL LABORATORIES) diluted to 100 ng/mL was added thereto, followed by allowing the reaction to proceed (30° C., 1 hour).

(4-4) Thereafter, the wells were washed with washing buffer A, and 50 μL/well of TMB Peroxidase Substrate (manufactured by KPL) was added thereto. Subsequently, 50 μL/well of 1 M phosphoric acid was added to stop the reaction, and the absorbance was measured at 450 nm using a microplate reader (manufactured by TECAN).

(5) About 1600 strains of transformants were evaluated to select, among these, transformants expressing an immunoglobulin-binding protein having an improved alkaline stability compared to the wild-type FpL_C3 (having no amino acid substitution) (SEQ ID NO:1).

(6) Each selected transformant was cultured, and an expression vector was prepared therefrom using a QIAprep Spin Miniprep kit (manufactured by QIAGEN).

(7) The nucleotide sequence of the polynucleotide region encoding the immunoglobulin-binding protein inserted in the expression vector obtained was analyzed by the method described in Example 1(5), to identify the position of each amino acid substitution.

(8) Each transformant selected in (5), which expresses the immunoglobulin-binding protein, was inoculated to 2 mL of 2×YT liquid medium supplemented with 50 μg/mL kanamycin. Preculture was carried out by aerobically performing shake culture at 37° C. overnight.

(9) To 20 mL of 2×YT liquid medium supplemented with 50 μg/mL of kanamycin, 200 NL of the preculture liquid was inoculated, and shake culture was aerobically carried out at 37° C.

(10) Two hours after the beginning of the culture, the culture temperature was changed to 20° C., and IPTG was added thereto to a final concentration of 0.01 mM. Shake culture was then aerobically carried out at 20° C. overnight.

(11) Thereafter, the bacterial cells were collected by centrifugation, and a protein extract was prepared therefrom using the BugBuster Protein Extraction Reagent (manufactured by Merck).

(12) The antibody-binding activity of the immunoglobulin-binding protein in the protein extract prepared in (11) was measured using the ELISA method described in (4).

(13) The protein extract was diluted with TBS such that each protein had the same concentration. The resulting dilution was equally divided into two aliquots. An equal amount of 0.2 M NaOH was added to one of these (alkali-treated), and an equal amount of TBS was added to the other (alkali-untreated), followed by mixing each resulting mixture. Each mixture was then left to stand at 25° C. for 5 hours.

(14) After addition of 4 volumes of 1 M Tris buffer (pH 7.0), the antibody-binding activity of each of the alkali-treated protein solution (which had been treated with 0.1 M (final concentration) NaOH at 25° C. for 5 hours) and the alkali-untreated protein solution was measured by the ELISA method described in (4). The antibody-binding activity of the alkali-treated immunoglobulin-binding protein was divided by the antibody-binding activity of the alkali-untreated immunoglobulin-binding protein, to calculate the remaining activity for evaluation of the alkaline stability.

The results are shown in Table 2. It can be said that an immunoglobulin-binding protein having the same amino acid sequence as SEQ ID NO:1 except that the immunoglobulin-binding protein has one or more amino acid substitutions selected from at least Pro3Ser (this expression represents the fact that the amino acid residue corresponding to the proline at position 3 of SEQ ID NO:1 is substituted with serine; the same applies hereinafter), Glu5Val, Glu8Gly, Ile17Phe, Glu27Gly, Ala41Thr, Asn44Ser, Glu49Val, Asn50Ser, Asn50Tyr, Asn50Lys, Asn50Asp, Glu52Val, Glu52Gly, Thr54Ile, Asn62Tyr, and Asn65Tyr has an improved alkaline stability compared to the wild-type FpL_C3 (SEQ ID NO:1).

In particular, an immunoglobulin-binding protein having the amino acid substitutions Asn50Tyr and Glu52Gly (SEQ ID NO:11; which was named FpL_C3 2a) showed remarkable improvement of the alkaline stability (wild-type FpL_C3: 40%, FpL_C3 2a: 94%). Since an immunoglobulin-binding protein having the amino acid substitution Glu52Gly alone (SEQ ID NO:16) did not show remarkable improvement of the alkaline stability (wild-type FpL_C3: 40%, SEQ ID NO: 16: 48%), the amino acid substitution that improves the alkaline stability is assumed to be the amino acid substitution Asn50Tyr.

TABLE 2

| Amino acid substitutions | SEQ ID NO: | Remaining activity [%] |
|---|---|---|
| FpL_C3 (wild-type) | 1 | 40 |
| Asn62Tyr | 5 | 62 |
| Ile17Phe, Asn50Ser | 6 | 70 |
| Lys22Arg, Lys29Arg, Asn44Ser | 7 | 74 |
| Glu8Gly, Glu52Val, Asn62Tyr | 8 | 61 |
| Glu49Val | 9 | 60 |
| Lys22Arg | 10 | 62 |
| Asn50Tyr, Glu52Gly | 11 | 94 |
| Glu27Gly, Ala41Thr, Asn50Lys, Asn65Tyr | 12 | 72 |
| Asn50Ser | 13 | 70 |
| Glu5Val | 14 | 43 |
| Pro3Ser, Asn50Asp, Thr54Ile | 15 | 70 |
| Glu52Gly | 16 | 48 |
| Lys38Arg | 17 | 52 |

※Alkali treatment: 25° C., 0.1M NaOH(final concentration), 5 h

Example 4 Preparation of FpL Immunoglobulin-Binding Domain C4 Expression Vector (1) A polynucleotide (SEQ ID NO:19) encoding an amino acid sequence of immunoglobulin-binding domain C4 (the amino acid residues at positions 468 to 537 of GenBank No. AAA67503 (SEQ ID NO:210); hereinafter also referred to as "FpL_C4") of FpL having the amino acid sequence of SEQ ID NO:18 was synthesized. In the synthesis, a recognition sequence for the restriction enzyme NcoI (5'-CCATGG-3') was added to the 5'-end side, and a nucleotide sequence encoding six histidine residues (SEQ ID NO:232), a stop codon, and a recognition sequence for the restriction enzyme HindIII (5'-AAGCTT-3') were added to the 3'-end side.

(2) By the same method as in Example 1(2), the polynucleotide containing SEQ ID NO:19 synthesized in (1) was purified.

(3) By the same method as in Example 1(3), the polynucleotide obtained in (2) was ligated to the plasmid pET-26b, which had been preliminarily digested with the restriction enzymes NcoI and HindIII, and then the resulting ligation product was used to transform the *Escherichia coli* BL21 (DE3) strain, followed by culturing the resulting transformant.

(4) After selection of the transformant (recombinant *Escherichia coli*) obtained in (3), culturing and plasmid purification were carried out by the same method as in Example 1(4), to obtain a vector (which was named pET-FpL_C4) capable of expressing FpL_C4.

(5) The polynucleotide encoding FpL_C4 of SEQ ID NO:19 and its vicinity in the expression vector pET-FpL_C4 obtained in (4) were subjected to sequence analysis by the same method as in Example 1(5).

As a result of the sequence analysis, it could be confirmed that the expression vector pET-FpL_C4 contains a polynucleotide having the sequence of SEQ ID NO:19 inserted therein.

Example 5 Introduction of Mutations into FpL_C4 and Preparation of Library

Into the polynucleotide portion (SEQ ID NO: 19) encoding the immunoglobulin-binding protein in the expression vector pET-FpL_C4, which was prepared in Example 4, mutations were randomly introduced by error-prone PCR by the same method as in Example 2, to prepare a library. The mutation introduction rate was 3.5%.

Example 6 Screening of FpL_C4 Amino Acid Substitution Mutants (1) The random mutant library (transformants) prepared in Example 5, or the transformant prepared in Example 4, which expresses FpL_C4 (SEQ ID NO:18), was cultured by the same method as in Example 3(1) to (2).

(2) Thereafter, each culture supernatant obtained by a centrifugation operation was mixed with an equal amount of 1.0 M NaOH, and then subjected to alkali treatment at 42° C. for 15 minutes.

(3) The remaining activity was calculated using the ELISA method described in Example 3(4).

(4) About 600 strains of transformants were evaluated to select, among these, transformants expressing an immunoglobulin-binding protein having an improved alkaline stability compared to the wild-type FpL_C4 (having no amino acid substitution) (SEQ ID NO:18).

(5) Each selected transformant was cultured, and an expression vector was prepared therefrom using a QIAprep Spin Miniprep kit (manufactured by QIAGEN).

(6) The nucleotide sequence of the polynucleotide region encoding the immunoglobulin-binding protein inserted in the expression vector obtained was analyzed by the method described in Example 1(5), to identify the position of each amino acid substitution.

(7) Each transformant expressing an immunoglobulin-binding protein selected in (4) was cultured by the same method as in Example 3(8) to (10), and a protein extract was prepared therefrom by the method described in Example 3(11).

(8) The antibody-binding activity of the immunoglobulin-binding protein in the protein extract prepared in (7) was measured using the ELISA method described in Example 3(4).

(9) Alkali treatment was carried out by the same method as in Example 3(13) except that the treatment time was 15 hours. Thereafter, the remaining activity was calculated by the same method as in Example 3(14), to evaluate the alkaline stability.

The results are shown in Table 3. It can be said that an immunoglobulin-binding protein having the same amino acid sequence as SEQ ID NO:18 except that the immunoglobulin-binding protein has one or more amino acid substitutions selected from at least Glu1Gly and Asn50Asp has an improved alkaline stability compared to the wild-type FpL_C4 (SEQ ID NO:18).

TABLE 3

| Amino acid substitutions | SEQ ID NO: | Remaining activity [%] |
|---|---|---|
| FpL_C4 (wild-type) | 18 | 45 |
| Glu1Gly | 20 | 49 |
| Asn50Asp | 21 | 61 |
| Lys22Arg | 22 | 51 |

※Alkali treatment: 25° C., 0.1M NaOH(final concentration), 15 h

Example 7 Preparation of FpL_C3 Amino Acid Substitution-Integrated Mutants (Part 1)

(1) Design of FpL_C3 Amino Acid Substitution-Integrated Mutants Amino acid substitutions found to be responsible for the improvement of the alkaline stability of the immunoglobulin-binding protein in Example 3 were integrated into FpL_C3 (SEQ ID NO: 1) in an attempt to further improve the alkaline stability. More specifically, the 12 kinds of immunoglobulin-binding proteins shown in the following (a) to (1) were designed and prepared.

(a) A protein (SEQ ID NO:23; which was named FpL_C3 3a) prepared by introducing the amino acid substitutions Asn50Tyr, Glu52Gly, and Asn62Tyr into FpL_C3
(b) A protein (SEQ ID NO:27; which was named FpL_C3 3b) prepared by introducing the amino acid substitutions Glu49Val, Asn50Tyr, and Glu52Gly into FpL_C3
(c) A protein (SEQ ID NO:30; which was named FpL_C3 3c) prepared by introducing the amino acid substitutions Asn44Ser, Asn50Tyr, and Glu52Gly into FpL_C3
(d) A protein (SEQ ID NO:33; which was named FpL_C3 3d) prepared by introducing the amino acid substitutions Asn44Asp, Asn50Tyr, and Glu52Gly into FpL_C3
(e) A protein (SEQ ID NO:36; which was named FpL_C3 3e) prepared by introducing the amino acid substitutions Glu49Val, Asn50Tyr, and Asn62Tyr into FpL_C3
(f) A protein (SEQ ID NO:38; which was named FpL_C3 4a) prepared by introducing the amino acid substitutions Asn44Ser, Glu49Val, Asn50Tyr, and Asn62Tyr into FpL_C3
(g) A protein (SEQ ID NO:40; which was named FpL_C3 4b) prepared by introducing the amino acid substitutions Asn44Asp, Glu49Val, Asn50Tyr, and Asn62Tyr into FpL_C3
(h) A protein (SEQ ID NO:42; which was named FpL_C3 4c) prepared by introducing the amino acid substitutions Glu49Val, Asn50Tyr, Glu52Gly, and Asn62Tyr into FpL_C3
(i) A protein (SEQ ID NO:44; which was named FpL_C3 4d) prepared by introducing the amino acid substitutions Asn44Ser, Asn50Tyr, Glu52Gly, and Asn62Tyr into FpL_C3
(j) A protein (SEQ ID NO:46; which was named FpL4e) prepared by introducing the amino acid substitutions Asn44Asp, Glu49Val, Asn50Tyr, and Asn62Tyr into FpL_C3
(k) A protein (SEQ ID NO:48; which was named FpL_C3 5a) prepared by introducing the amino acid substitutions Asn44Ser, Glu49Val, Asn50Tyr, Glu52Gly, and Asn62Tyr into FpL_C3

(l) A protein (SEQ ID NO:50; which was named FpL_C3 5b) prepared by introducing the amino acid substitutions Asn44Asp, Glu49Val, Asn50Tyr, Glu52Gly, and Asn62Tyr into FpL_C3

(2) Preparation of FpL_C3 Amino Acid Substitution-Integrated Mutants

The methods of the preparation of the 12 kinds of immunoglobulin-binding proteins shown in (a) to (l) are described below.

(a) FpL_C3 3a

This protein was prepared by selecting Asn62Tyr among the amino acid substitutions that were found to improve the alkaline stability in Example 3, and introducing this amino acid substitution into FpL_C3 2a (SEQ ID NO:11).

(a-1) Mutagenesis using inverse PCR was carried out to prepare a polynucleotide containing a nucleotide sequence encoding FpL_C3 3a (SEQ ID NO:23). For the inverse PCR, an expression vector (hereinafter also referred to as "pET-FpL_C3 2a") containing a polynucleotide (SEQ ID NO:24) encoding FpL_C3 2a was used as a template DNA; an oligonucleotide having the sequence of SEQ ID NO:25 was used as a PCR Forward Primer; and an oligonucleotide having the sequence of SEQ ID NO:26 was used as a PCR Reverse Primer. After preparing a reaction liquid having the composition shown in Table 4, the reaction liquid was heat-treated at 98° C. for 2 minutes, followed by performing 30 cycles of reaction in which each cycle included a first step at 95° C. for 10 seconds, a second step at 50° C. for 5 seconds, and a third step at 72° C. for 6 minutes, and then finally performing heat treatment at 72° C. for 7 minutes.

TABLE 4

| Components | Volume |
|---|---|
| 1 ng/μL template DNA | 1 μL |
| 10 μM PCR forward primer | 1 μL |
| 10 μM PCR reverse primer | 1 μL |
| PrimeSTAR HS (premix) (manufactured by Takara Bio Inc.) | 25 μL |
| $H_2O$ | Up to 50 μL |

(a-2) The polynucleotide obtained was purified, and then treated with the restriction enzyme DpnI, followed by transforming the *Escherichia coli* BL21 (DE3) strain using the treated product.

(a-3) The transformant obtained was cultured in LB medium supplemented with 50 μg/mL kanamycin, and then an expression vector (which was named pET-FpL_C3 3a) was extracted using a QIAprep Spin Miniprep kit (manufactured by QIAGEN).

(a-4) The nucleotide sequence of pET-FpL_C3 3a was analyzed by the same method as in Example 1(5).

As a result of the sequence analysis, it could be confirmed that the expression vector pET-FpL_C3 3a contains a polynucleotide encoding FpL_C3 3a (SEQ ID NO:23) inserted therein.

(b) FpL_C3 3b

This protein was prepared by selecting Glu49Val among the amino acid substitutions that were found to improve the alkaline stability in Example 3, and introducing this amino acid substitution into FpL_C3 2a (SEQ ID NO:11).

(b-1) Mutagenesis using inverse PCR was carried out to prepare a polynucleotide containing a nucleotide sequence encoding FpL_C3 3b (SEQ ID NO:27). The inverse PCR was carried out by the same method as in (a-1) except that pET-FpL_C3 2a was used as a template DNA, that an oligonucleotide having the sequence of SEQ ID NO:28 was used as a PCR Forward Primer, and that an oligonucleotide having the sequence of SEQ ID NO:29 was used as a PCR Reverse Primer.

(b-2) The polynucleotide obtained was purified, and then treated with the restriction enzyme DpnI, followed by transforming the *Escherichia coli* BL21 (DE3) strain using the treated product.

(b-3) The transformant obtained was subjected to culturing and extraction of an expression vector (which was named pET-FpL_C3 3b) by the same method as in (a-3). The nucleotide sequence of the expression vector was analyzed by the same method as in Example 1(5).

As a result of the sequence analysis, it could be confirmed that the expression vector pET-FpL_C3 3b contains a polynucleotide encoding FpL_C3 3b (SEQ ID NO:27) inserted therein.

(c) FpL_C3 3c

This protein was prepared by selecting Asn44Ser among the amino acid substitutions that were found to improve the alkaline stability in Example 3, and introducing this amino acid substitution into FpL_C3 2a (SEQ ID NO:11).

(c-1) Mutagenesis using inverse PCR was carried out to prepare a polynucleotide containing a nucleotide sequence encoding FpL_C3 3c (SEQ ID NO:30). The inverse PCR was carried out by the same method as in (a-1) except that an oligonucleotide having the sequence of SEQ ID NO:31 was used as a PCR Forward Primer, and that an oligonucleotide having the sequence of SEQ ID NO:32 was used as a PCR Reverse Primer.

(c-2) The polynucleotide obtained was purified, and then treated with the restriction enzyme DpnI, followed by transforming the *Escherichia coli* BL21 (DE3) strain using the treated product.

(c-3) The transformant obtained was subjected to culturing and extraction of an expression vector (which was named pET-FpL_C3 3c) by the same method as in (a-3). The nucleotide sequence of the expression vector was analyzed by the same method as in Example 1(5).

As a result of the sequence analysis, it could be confirmed that the expression vector pET-FpL_C3 3c contains a polynucleotide encoding FpL_C3 3c (SEQ ID NO:30) inserted therein.

(d) FpL_C3 3d

This protein was prepared by selecting Asn44Asp among the amino acid substitutions that were found to improve the alkaline stability in Example 3, and introducing this amino acid substitution into FpL_C3 2a (SEQ ID NO:11).

(d-1) Mutagenesis using inverse PCR was carried out to prepare a polynucleotide containing a nucleotide sequence encoding FpL_C3 3d (SEQ ID NO:33). The inverse PCR was carried out by the same method as in (a-1) except that an oligonucleotide having the sequence of SEQ ID NO:34 was used as a PCR Forward Primer, and that an oligonucleotide having the sequence of SEQ ID NO:35 was used as a PCR Reverse Primer.

(d-2) The polynucleotide obtained was purified, and then treated with the restriction enzyme DpnI, followed by transforming the *Escherichia coli* BL21 (DE3) strain using the treated product.

(d-3) The transformant obtained was subjected to culturing and extraction of an expression vector (which was named pET-FpL_C3 3d) by the same method as in (a-3). The nucleotide sequence of the expression vector was analyzed by the same method as in Example 1(5).

As a result of the sequence analysis, it could be confirmed that the expression vector pET-FpL_C3 3d contains a polynucleotide encoding FpL_C3 3d (SEQ ID NO:33) inserted therein.

(e) FpL_C3 3e (e-1) A polynucleotide (SEQ ID NO:37) encoding FpL_C3 3e (SEQ ID NO:36) was synthesized. In the synthesis, a recognition sequence for the restriction enzyme NcoI (5'-CCATGG-3') was added to the 5'-end side, and a nucleotide sequence encoding six histidine residues (5'-CATCACCACCATCACCAC-3'; SEQ ID NO:232), a stop codon, and a recognition sequence for the restriction enzyme HindIII (5'-AAGCTT-3') were added to the 3'-end side.

(e-2) By the same method as in Example 1(2), the polynucleotide synthesized in (e-1) was purified.

(e-3) By the same method as in Example 1(3), the polynucleotide obtained in (e-2) was ligated to the plasmid pET-26b, which had been preliminarily digested with the restriction enzymes NcoI and HindIII, and then the resulting ligation product was used to transform the *Escherichia coli* BL21 (DE3) strain, followed by culturing the resulting transformant.

(e-4) The transformant obtained was subjected to culturing and plasmid purification by the same method as in Example 1(4), to obtain an expression vector (which was named pET-FpL_C3 3e). The nucleotide sequence of the expression vector was analyzed by the same method as in Example 1(5).

As a result of the sequence analysis, it could be confirmed that the expression vector pET-FpL_C3 3e contains a polynucleotide (SEQ ID NO:37) encoding FpL_C3 3e (SEQ ID NO:36) inserted therein.

(f) FpL_C3 4a

A transformant and an expression vector (which was named pET-FpL_C3 4a) were obtained by the same method as in (e) except that a polynucleotide (SEQ ID NO:39) encoding FpL_C3 4a (SEQ ID NO:38) was used as the polynucleotide encoding an immunoglobulin-binding protein. As a result of nucleotide sequence analysis of the expression vector pET-FpL_C3 4a, it could be confirmed that pET-FpL_C3 4a contains a polynucleotide (SEQ ID NO:39) encoding FpL_C3 4a (SEQ ID NO:38) inserted therein.

(g) FpL_C3 4b

A transformant and an expression vector (which was named pET-FpL_C3 4b) were obtained by the same method as in (e) except that a polynucleotide (SEQ ID NO:41) encoding FpL_C3 4b (SEQ ID NO:40) was used as the polynucleotide encoding an immunoglobulin-binding protein. As a result of nucleotide sequence analysis of the expression vector pET-FpL_C3 4b, it could be confirmed that pET-FpL_C3 4b contains a polynucleotide (SEQ ID NO:41) encoding FpL_C3 4b (SEQ ID NO:40) inserted therein.

(h) FpL_C3 4c

A transformant and an expression vector (which was named pET-FpL_C3 4c) were obtained by the same method as in (e) except that a polynucleotide (SEQ ID NO:43) encoding FpL_C3 4c (SEQ ID NO:42) was used as the polynucleotide encoding an immunoglobulin-binding protein. As a result of nucleotide sequence analysis of the expression vector pET-FpL_C3 4c, it could be confirmed that pET-FpL_C3 4c contains a polynucleotide (SEQ ID NO:43) encoding FpL_C3 4c (SEQ ID NO:42) inserted therein.

(i) FpL_C3 4d

A transformant and an expression vector (which was named pET-FpL_C3 4d) were obtained by the same method as in (e) except that a polynucleotide (SEQ ID NO:45) encoding FpL_C3 4d (SEQ ID NO:44) was used as the polynucleotide encoding an immunoglobulin-binding protein. As a result of nucleotide sequence analysis of the expression vector pET-FpL_C3 4d, it could be confirmed that pET-FpL_C3 4d contains a polynucleotide (SEQ ID NO:45) encoding FpL_C3 4d (SEQ ID NO:44) inserted therein.

(j) FpL_C3 4e

A transformant and an expression vector (which was named pET-FpL_C3 4e) were obtained by the same method as in (e) except that a polynucleotide (SEQ ID NO:47) encoding FpL_C3 4e (SEQ ID NO:46) was used as the polynucleotide encoding an immunoglobulin-binding protein. As a result of nucleotide sequence analysis of the expression vector pET-FpL_C3 4e, it could be confirmed that pET-FpL_C3 4e contains a polynucleotide (SEQ ID NO:47) encoding FpL_C3 4e (SEQ ID NO:46) inserted therein.

(k) FpL_C3 5a

A transformant and an expression vector (which was named pET-FpL_C3 5a) were obtained by the same method as in (e) except that a polynucleotide (SEQ ID NO:49) encoding FpL_C3 5a (SEQ ID NO:48) was used as the polynucleotide encoding an immunoglobulin-binding protein. As a result of nucleotide sequence analysis of the expression vector pET-FpL_C3 5a, it could be confirmed that pET-FpL_C3 5a contains a polynucleotide (SEQ ID NO:49) encoding FpL_C3 5a (SEQ ID NO:48) inserted therein.

(l) FpL_C3 5b

A transformant and an expression vector (which was named pET-FpL_C3 5b) were obtained by the same method as in (e) except that a polynucleotide (SEQ ID NO:51) encoding FpL_C3 5b (SEQ ID NO:50) was used as the polynucleotide encoding an immunoglobulin-binding protein. As a result of nucleotide sequence analysis of the expression vector pET-FpL_C3 5b, it could be confirmed that pET-FpL_C3 5b contains a polynucleotide (SEQ ID NO:51) encoding FpL_C3 5b (SEQ ID NO:50) inserted therein.

Example 8 Evaluation of Alkaline Stabilities of FpL_C3 Amino Acid Substitution-Integrated Mutants (1) Transformants each of which expresses one of the wild-type FpL_C3 (SEQ ID NO:1) prepared in Example 1, the mutant-type (amino-acid-substituted) immunoglobulin-binding protein FpL_C3 2a (SEQ ID NO: 11) obtained in Example 3, and the mutant-type immunoglobulin-binding proteins FpL_C3 3a (SEQ ID NO:23), FpL_C3 3b (SEQ ID NO:27), FpL_C3 3c (SEQ ID NO:30), FpL_C3 3d (SEQ ID NO:33), FpL_C3 3e (SEQ ID NO:36), FpL_C3 4a (SEQ ID NO:38), FpL_C3 4b (SEQ ID NO:40), FpL_C3 4c (SEQ ID NO:42), FpL_C3 4d (SEQ ID NO:44), FpL_C3 4e (SEQ ID NO:46), FpL_C3 5a (SEQ ID NO:48), and FpL_C3 5b (SEQ ID NO:50) prepared in Example 7 were cultured by the same method as in Example 3(8) to (10), and protein extracts were prepared therefrom by the method described in Example 3(11).

(2) The antibody-binding activity of the immunoglobulin-binding protein in each protein extract prepared in (1) was measured using the ELISA method described in Example 3(4).

(3) Alkali treatment was carried out by the same method as in Example 3(13) except that the concentration of the NaOH used for the treatment was 0.4 M (final concentration, 0.2 M), and that the treatment time was 15 hours. Thereafter, the remaining activity was calculated by the same method as in Example 3(14), to evaluate the alkaline stability.

The results are shown in Table 5. All mutant-type immunoglobulin-binding proteins evaluated in the present Example showed higher remaining activities compared to the wild-type FpL_C3 (SEQ ID NO:1), indicating that these mutant-type immunoglobulin-binding proteins have improved alkaline stability. Further, based on comparison of the results for FpL_C3 3a (SEQ ID NO:23), FpL_C3 3b (SEQ ID NO:27), FpL_C3 3c (SEQ ID NO:30), FpL_C3 3d (SEQ ID NO:33), and FpL_C3 3e (SEQ ID NO:36), the mutant-type immunoglobulin-binding proteins having the amino acid substitution Asn62Tyr (FpL_C3 3a and FpL_C3 3e) had especially improved alkaline stabilities. It can therefore be seen that the amino acid substitution Asn62Tyr largely contributes to the improvement of the alkaline stability of the immunoglobulin-binding protein.

[Table 5]

TABLE 5

| | Amino acid substitutions | | | | | SEQ ID | Remaining activity |
|---|---|---|---|---|---|---|---|
| Name | Asn44 | Glu49 | Asn50 | Glu52 | Asn62 | NO: | [%] |
| FpL_C3 (wild-type) | — | — | — | — | — | 1 | 8 |
| FpL_C3 2a | — | — | Tyr | Gly | — | 11 | 23 |
| FpL_C3 3a | — | — | Tyr | Gly | Tyr | 23 | 59 |
| FpL_C3 3b | — | Val | Tyr | Gly | — | 27 | 45 |
| FpL_C3 3c | Ser | — | Tyr | Gly | — | 30 | 17 |
| FpL_C3 3d | Asp | — | Tyr | Gly | — | 33 | 32 |
| FpL_C3 3e | — | Val | Tyr | — | Tyr | 36 | 55 |
| FpL_C3 4a | Ser | Val | Tyr | — | Tyr | 38 | 59 |
| FpL_C3 4b | Asp | Val | Tyr | — | Tyr | 40 | 49 |
| FpL_C3 4c | — | Val | Tyr | Gly | Tyr | 42 | 51 |
| FpL_C3 4d | Ser | — | Tyr | Gly | Tyr | 44 | 35 |
| FpL_C3 4e | Asp | Val | Tyr | — | Tyr | 46 | 32 |
| FpL_C3 5a | Ser | Val | Tyr | Gly | Tyr | 48 | 52 |
| FpL_C3 5b | Asp | Val | Tyr | Gly | Tyr | 50 | 37 |

※Alkali treatment: 25° C., 0.2M NaOH(final concentration), 15 h

[SEQ ID NO:53] complementary sequence of SEQ ID NO:52

[SEQ ID NO:54]

Positions 1 to 75: region corresponding to positions 30 to 104 of SEQ ID NO:2

Positions 1 to 24: portion for linking to SEQ ID NO:52

Positions 51 to 75: portion for linking to SEQ ID NO:56

[SEQ ID NO:55] complementary sequence of SEQ ID NO:54

[SEQ ID NO:56]

Positions 1 to 75: region corresponding to positions 80 to 156 of SEQ ID NO:2

Positions 1 to 25: portion for linking to SEQ ID NO:54

Positions 51 to 77: portion for linking to SEQ ID NO:58

[SEQ ID NO:57] complementary sequence of SEQ ID NO:56

[SEQ ID NO:58]

Positions 1 to 76: region corresponding to positions 130 to 205 of SEQ ID NO:2

Positions 1 to 27: portion for linking to SEQ ID NO:56

Positions 47 to 76: portion for linking to SEQ ID NO:60

Example 9 Introduction of Mutations into FpL_C3 and Preparation of Library (Part 2)

Based on the results of Example 3, oligonucleotides containing mixed bases were designed such that the amino acid residue at each of particular positions in a mutant-type immunoglobulin-binding protein is selected among a plurality of alternatives. By linking the oligonucleotides to each other, a mutant library was prepared. Details of the preparation are described below concretely.

(1) A polynucleotide encoding the wild-type FpL_C3 having the sequence of SEQ ID NO:2 was divided into five segments, and oligonucleotides (SEQ ID NOs:52 to 61) were designed such that the amino acid residue at position 44, the amino acid residue at position 49, the amino acid residue at position 50, the amino acid residue at position 52, and the amino acid residue at position 62 are selected among a plurality of alternatives. The following are details of the designed oligonucleotides.

[SEQ ID NO:52]

Positions 1 to 24: portion for linking to pET26b

Positions 28 to 80: region corresponding to positions 1 to 53 of SEQ ID NO:2

Positions 57 to 80: portion for linking to SEQ ID NO:54

[SEQ ID NO:59] complementary sequence of SEQ ID NO:58

[SEQ ID NO:60]

Positions 1 to 35: region corresponding to positions 176 to 210 of SEQ ID NO:2

Positions 1 to 30: portion for linking to SEQ ID NO:58

Positions 36 to 53: region encoding six histidine residues

Positions 54 to 56: region encoding a stop codon

Positions 57 to 80: portion for linking to pET26b

[SEQ ID NO:61] complementary sequence of SEQ ID NO:60

Mixed bases were introduced such that positions 51 to 53 of SEQ ID NO:56 encode Asn (asparagine), Asp (aspartic acid), Ser (serine), or Gly (glycine) for the amino acid corresponding to position 44 of SEQ ID NO:1, such that positions 66 to 68 of SEQ ID NO:56 encode Glu (glutamic acid) or Val (valine) for the amino acid corresponding to position 49 of SEQ ID NO: 1, such that positions 69 to 71 of SEQ ID NO:56 encode Asn, Asp, Ser, or Cys (cysteine) for the amino acid corresponding to position 50 of SEQ ID NO:1, and such that positions 75 to 77 of SEQ ID NO:56 encode Gly or Val for the amino acid corresponding to position 52 of SEQ ID NO: 1.

In addition, mixed bases were introduced such that positions 55 to 57 of SEQ ID NO:58 encode Asn or Tyr (tyrosine) for the amino acid corresponding to position 62 of SEQ ID NO:1.

(2) After diluting the synthesized polynucleotides (SEQ ID NOs: 52 to 61) to 0.05 μmol, these were ligated to the expression vector pET-26b, which had been preliminarily digested with the restriction enzymes NcoI and HindIII, using NEBuilder (manufactured by New England Biolabs).

(3) After completion of the reaction, the *Escherichia coli* BL21 (DE3) strain was transformed using the reaction liquid, and then cultured (37° C., 16 hours) on LB plate medium supplemented with 50 μg/mL kanamycin. The resulting colonies, formed on the plate, were provided as a random mutant library.

Example 10 Screening of FpL_C3 Amino Acid Substitution Mutants (Part 2)

(1) FpL_C3 2a prepared in Example 3 and the mutant library (transformants) prepared in Example 9 were cultured by the same method as in Example 3(1) to (2).

(2) Thereafter, each culture supernatant obtained by a centrifugation operation was mixed with an equal amount of 1.0 M NaOH, and then subjected to alkali treatment at 43° C. for 15 minutes.

(3) The remaining activity was calculated using the ELISA method described in Example 3(4).

(4) About 540 strains of transformants were evaluated to select, among these, transformants expressing an immunoglobulin-binding protein having an improved alkaline stability compared to FpL_C3 2a (SEQ ID NO:11).

(5) Each selected transformant was cultured, and an expression vector was prepared therefrom using a QIAprep Spin Miniprep kit (manufactured by QIAGEN).

(6) The nucleotide sequence of the polynucleotide region encoding the immunoglobulin-binding protein inserted in the expression vector obtained was analyzed by the method described in Example 1(5), to identify the position of each amino acid substitution.

(7) Each transformant expressing an immunoglobulin-binding protein selected in (4), the transformant expressing FpL_C3 (SEQ ID NO:1) prepared in Example 1, or the transformant expressing FpL_C3 2a (SEQ ID NO:11) obtained in Example 3 was cultured by the same method as in Example 3(8) to (10), and a protein extract was prepared therefrom by the same method as in Example 3(11).

(8) The antibody-binding activity of the immunoglobulin-binding protein in each protein extract prepared in (7) was measured using the ELISA method described in Example 3(4).

(9) Alkali treatment was carried out by the same method as in Example 3(13) except that the treatment time was 15 hours. Thereafter, the remaining activity was calculated by the same method as in Example 3(14), to evaluate the alkaline stability.

Table 6 shows a summary of the results for the immunoglobulin-binding proteins expressed by the transformants selected in (4), on the position of each amino acid substitution (in terms of SEQ ID NO:1), the remaining activity [%] after the alkali treatment, and the antibody-binding activity (absorbance) of the alkali-untreated protein solution. In the present screening, the following three mutant-type immunoglobulin-binding proteins were obtained:

- a protein (which was named FpL_C3 4f; SEQ ID NO:62) prepared by introducing the amino acid substitutions Asn44Asp, Asn50Tyr, Glu52Val, and Asn62Tyr into FpL_C3;
- a protein (which was named FpL_C3 5c; SEQ ID NO:63) prepared by introducing the amino acid substitutions Asn44Gly, Glu49Val, Asn50Tyr, Glu52Val, and Asn62Tyr into FpL_C3; and
- a protein (which was named FpL_C3 5d; SEQ ID NO:64) prepared by introducing the amino acid substitutions Asn44Gly, Glu49Val, Asn50Ser, Glu52Val, and Asn62Tyr into FpL_C3.

All three mutant-type immunoglobulin-binding proteins had improved alkaline stabilities compared to FpL_C3 2a. It can thus be said that an immunoglobulin-binding protein having the same amino acid sequence as SEQ ID NO:1 except that the immunoglobulin-binding protein has one or more amino acid substitutions selected from at least Asn44Asp, Asn44Gly, Glu49Val, Asn50Ser, Glu52Val, and Asn62Tyr has an improved alkaline stability. However, the immunoglobulin-binding protein having the amino acid substitution Asn50Ser (FpL_C3 5d) showed a much lower antibody-binding activity of the alkali-untreated protein solution compared to the immunoglobulin-binding proteins having the amino acid substitution Asn50Tyr (FpL_C3 2a, FpL_C3 4f, and FpL_C3 5c).

TABLE 6

| | Amino acid substitutions | | | | | SEQ ID | Remaining activity | Antibody-binding |
|---|---|---|---|---|---|---|---|---|
| Name | Asn44 | Glu49 | Asn50 | Glu52 | Asn62 | NO: | [%] | activity |
| FpL_C3 (wild-type) | — | — | — | — | — | 1 | 8 | 0.80 |
| FpL_C3 2a | — | — | Tyr | Gly | — | 11 | 23 | 0.72 |
| FpL_C3 4f | Asp | — | Tyr | Val | Tyr | 62 | 40 | 0.90 |
| FpL_C3 5c | Gly | Val | Tyr | Val | Tyr | 63 | 27 | 0.74 |
| FpL_C3 5d | Gly | Val | Ser | Val | Tyr | 64 | 66 | 0.46 |

※Alkali treatment: 25° C., 0.1M NaOH(final concentration), 15 h

Example 11 Introduction of Mutations into FpL_C3 and Preparation of Library (Part 3)

(1) pET-FpL_C3 prepared in Example 1 was used as a template to prepare a saturation substitution mutant library for the amino acid residues at positions 21, 22, 31, 49, 51, and 62. According to the 22c-trick method (Sabrina Kille et. al., ACS Synthetic Biology, 2013, 2, 83-92), primers were designed such that appropriate mixed bases could be placed at the mutation introduction sites, and such that inverse PCR could be carried out focusing on the mutation introduction sites (SEQ ID NOs:65 to 100). These primers were mixed to provide a combination of six primers for each substitution site according to the compositions shown in Table 7 and Table 8, to prepare PCR primer mixtures (Forward/Reverse primer mix).

TABLE 7

| Components<br>Forward/reverse primer mix | Volume |
|---|---|
| 10 μM Forward primer 1 | 24 μL |
| 10 μM Forward primer 2 | 18 μL |
| 10 μM Forward primer 3 | 2 μL |
| 10 μM Reverse primer 1 | 24 μL |
| 10 μM Reverse primer 2 | 18 μL |
| 10 μM Reverse primer 3 | 2 μL |

TABLE 8

| SEQ | Position of amino acid substitution | | | | | |
|---|---|---|---|---|---|---|
| ID NO: | Gly21 | Lys22 | Thr31 | Glu49 | Gly51 | Asn62 |
| Forward primer 1 | 65 | 71 | 77 | 83 | 89 | 95 |
| Forward primer 2 | 66 | 72 | 78 | 84 | 90 | 96 |
| Forward primer 3 | 67 | 73 | 79 | 85 | 91 | 97 |
| Reverse primer 1 | 68 | 74 | 80 | 86 | 92 | 98 |
| Reverse primer 2 | 69 | 75 | 81 | 87 | 93 | 99 |
| Reverse primer 3 | 70 | 76 | 82 | 88 | 94 | 100 |

(2) pET-FpL_C3 prepared in Example 1 was used as a template DNA to perform site-directed mutagenesis by inverse PCR. For the inverse PCR, a reaction liquid having the composition shown in Table 9 was prepared, and the reaction liquid was heat-treated at 98° C. for 2 minutes, followed by performing 30 cycles of reaction in which each cycle included a first step at 95° C. for 10 seconds, a second step at 50° C. for 5 seconds, and a third step at 72° C. for 6 minutes, and then finally performing heat treatment at 72° C. for 7 minutes.

TABLE 9

| Components | Volume |
|---|---|
| 1 ng/μL template DNA | 1 μL |
| Forward/reverse primer mix | 1 μL |
| PrimeSTAR HS (premix) (manufactured by Takara Bio Inc.) | 25 μL |
| $H_2O$ | Up to 50 μL |

(3) After purification of the PCR product obtained, the *Escherichia coli* BL21 (DE3) strain was transformed using the reaction liquid, and then cultured (37° C., 16 hours) on LB plate medium supplemented with 50 μg/mL kanamycin. The resulting colonies, formed on the plate, were provided as a site-directed mutant library.

Example 12 Screening of FpL_C3 Amino Acid Substitution Mutants (Part 3)

(1) The transformant capable of expressing FpL_C3 prepared in Example 1 and the site-directed amino acid substitution mutant library (transformants) prepared in Example 11 were cultured by the same method as in Example 3(1) to (2).

(2) Thereafter, each culture supernatant obtained by a centrifugation operation was subjected to alkali treatment by the same method as in Example 3(3), and the remaining activity was calculated by the ELISA method described in Example 3(4).

(3) About 500 strains of transformants were evaluated to select, among these, transformants expressing an immunoglobulin-binding protein having an improved alkaline stability compared to the wild-type FpL_C3 (SEQ ID NO:1).

(4) Each selected transformant was cultured, and an expression vector was prepared therefrom using a QIAprep Spin Miniprep kit (manufactured by QIAGEN).

(5) The nucleotide sequence of the polynucleotide region encoding the immunoglobulin-binding protein inserted in the expression vector obtained was analyzed by the method described in Example 1(5), to identify the position of each amino acid substitution.

(6) Each transformant expressing an immunoglobulin-binding protein selected in (3) or the transformant expressing FpL_C3 (SEQ ID NO:1) prepared in Example 1 was cultured by the same method as in Example 3(8) to (10), and a protein extract was prepared therefrom by the same method as in Example 3(11).

(7) The antibody-binding activity of the immunoglobulin-binding protein in each protein extract prepared in (6) was measured using the ELISA method described in Example 3(4).

(8) Alkali treatment was carried out by the method described in Example 3(13). Thereafter, the remaining activity was calculated by the same method as in Example 3(14), to evaluate the alkaline stability.

Table 10 shows a summary of the results for the immunoglobulin-binding proteins expressed by the transformants selected in (3), on the position of each amino acid substitution (in terms of SEQ ID NO:1) and the remaining activity [%] after the alkali treatment. It can be said that an immunoglobulin-binding protein having the same amino acid sequence as SEQ ID NO:1 except that the immunoglobulin-binding protein has one or more amino acid substitutions selected from at least Gly21Arg, Lys22Thr, Thr31Leu, Glu49Thr, Glu49Ile, Gly51Val, Asn62His, Asn62Arg, Asn62Leu, Asn62Met, Asn62Tyr, and Asn62Trp has an improved alkaline stability compared to the wild-type FpL_C3 (SEQ ID NO:1).

From Table 10, it can be seen that the alkaline stability can be improved by substituting the asparagine at position 62 (Asn62) of SEQ ID NO:1 with a relatively bulky amino acid such as histidine (His), arginine (Arg), leucine (Leu), methionine (Met), tyrosine (Tyr), or tryptophan (Trp). In particular, it can be seen that the amino acid substitution Asn62Tyr (SEQ ID NO:5) leads to the highest improvement of the alkaline stability (wild-type FpL_C3: 46%, Asn62Tyr: 66%). Regarding the positions other than Asn62, the alkaline stability was found to be improved especially by the amino acid substitutions Gly21Arg, Glu49Thr, and Gly51Val.

TABLE 10

| Amino acid substitutions | SEQ ID NO: | Remaining activity [%] |
|---|---|---|
| FpL_C3 (wild-type) | 1 | 46 |
| Gly21Arg | 101 | 68 |
| Lys22Thr | 102 | 51 |
| Thr31Leu | 103 | 48 |
| Glu49Thr | 104 | 68 |
| Glu49Ile | 105 | 51 |

TABLE 10-continued

| Amino acid substitutions | SEQ ID NO: | Remaining activity [%] |
|---|---|---|
| Gly51Val | 106 | 55 |
| Asn62His | 107 | 48 |
| Asn62Arg | 108 | 57 |
| Asn62Leu | 109 | 57 |
| Asn62Met | 110 | 60 |
| Asn62Tyr | 5 | 66 |
| Asn62Trp | 111 | 57 |

※Alkali treatment: 25° C., 0.1M NaOH(final concentration), 5 h

Reference Example 1

(1) Design of Immunoglobulin-Binding Proteins (Lysine-Substituted Mutants)

WO 2017/069158 discloses an immunoglobulin-binding protein having an improved alkaline stability prepared by substituting a lysine residue(s) contained in an immunoglobulin-binding domain(s) of FpL with a basic amino acid(s) other than lysine and/or with an amino acid(s) containing a hydroxy group. In order to confirm the effect according to the above document, immunoglobulin-binding proteins were prepared by substituting lysine residues contained in immunoglobulin-binding domains of FpL with arginine residues, which are a basic amino acid other than lysine. More specifically, the following four kinds of immunoglobulin-binding proteins (α) to (δ) were designed.

(α) An immunoglobulin-binding protein (SEQ ID NO: 114, hereinafter also referred to as "FpL_C1KR") prepared by substituting all lysine residues (specifically, the lysine residues at positions 12, 28, 33, 46, 47, 59, and 66 of SEQ ID NO:112) contained in the immunoglobulin-binding domain C1 of FpL (the amino acid residues at positions 249 to 317 of GenBank No. AAA67503; SEQ ID NO:112; hereinafter also referred to as "FpL_C1") with arginine residues (β) An immunoglobulin-binding protein (SEQ ID NO: 115, hereinafter also referred to as "FpL_C2KR") prepared by substituting all lysine residues (specifically, the lysine residues at positions 2, 7, 13, 22, 29, 38, 48, and 67 of SEQ ID NO:113) contained in the immunoglobulin-binding domain C2 of FpL (the amino acid residues at positions 320 to 389 of GenBank No. AAA67503; SEQ ID NO:113; hereinafter also referred to as "FpL_C2") with arginine residues (γ) An immunoglobulin-binding protein (SEQ ID NO: 116, hereinafter also referred to as "FpL_C3KR") prepared by substituting all lysine residues in FpL_C3 (SEQ ID NO:1) (specifically, the lysine residues at positions 7, 13, 22, 29, 38, 48, and 67 of SEQ ID NO:1) with arginine residues (δ) An immunoglobulin-binding protein (SEQ ID NO: 117, hereinafter also referred to as "FpL_C4KR") prepared by substituting all lysine residues in FpL_C4 (SEQ ID NO:18) (specifically, the lysine residues at positions 7, 13, 22, 29, 48, and 67 of SEQ ID NO:18) with arginine residues (2) Preparation of Immunoglobulin-Binding Proteins (Lysine-Substituted Mutants)

(α) FpL_C1KR (α-1) A polynucleotide (SEQ ID NO:120) encoding FpL_C1KR (SEQ ID NO:114) was synthesized. In the synthesis, a recognition sequence for the restriction enzyme NcoI (5'-CCATGG-3') was added to the 5'-end side, and a nucleotide sequence encoding six histidine residues (5'-CATCACCACCATCACCAC-3'; SEQ ID NO:232), a stop codon, and a recognition sequence for the restriction enzyme HindIII (5'-TAAGCTT-3') were added to the 3'-end side.

(α-2) By the same method as in Example 1(2), the polynucleotide synthesized in (α-1) was purified.

(α-3) By the same method as in Example 1(3), the polynucleotide obtained in (α-2) was ligated to the plasmid pET-26b, which had been preliminarily digested with the restriction enzymes NcoI and HindIII, and then the resulting ligation product was used to transform the *Escherichia coli* BL21 (DE3) strain, followed by culturing the resulting transformant.

(α-4) The transformant obtained was subjected to culturing and plasmid purification by the same method as in Example 1(4), to obtain an expression vector (which was named pET-FpL_C1KR). The nucleotide sequence of the expression vector was analyzed by the same method as in Example 1(5). As a result of the sequence analysis, it could be confirmed that the expression vector pET-FpL_C1KR contains a polynucleotide (SEQ ID NO:120) encoding FpL_C1KR (SEQ ID NO:114) inserted therein.

(β) FpL_C2KR

A transformant and an expression vector (which was named pET-FpL_C2KR) were obtained by the same method as in (a) except that a polynucleotide (SEQ ID NO:121) encoding FpL_C2KR (SEQ ID NO:115) was used as the polynucleotide encoding an immunoglobulin-binding protein. As a result of nucleotide sequence analysis of the expression vector pET-FpL_C2KR, it could be confirmed that pET-FpL_C2KR contains a polynucleotide (SEQ ID NO:121) encoding FpL_C2KR (SEQ ID NO:115) inserted therein.

(γ) FpL_C3KR

A transformant and an expression vector (which was named pET-FpL_C3KR) were obtained by the same method as in (a) except that a polynucleotide (SEQ ID NO:122) encoding FpL_C3KR (SEQ ID NO:116) was used as the polynucleotide encoding an immunoglobulin-binding protein. As a result of nucleotide sequence analysis of the expression vector pET-FpL_C3KR, it could be confirmed that pET-FpL_C3KR contains a polynucleotide (SEQ ID NO:122) encoding FpL_C3KR (SEQ ID NO:116) inserted therein.

(δ) FpL_C4KR

A transformant and an expression vector (which was named pET-FpL_C4KR) were obtained by the same method as in (a) except that a polynucleotide (SEQ ID NO:123) encoding FpL_C4KR (SEQ ID NO:117) was used as the polynucleotide encoding an immunoglobulin-binding protein. As a result of nucleotide sequence analysis of the expression vector pET-FpL_C4KR, it could be confirmed that pET-FpL_C4KR contains a polynucleotide (SEQ ID NO:123) encoding FpL_C4KR (SEQ ID NO:117) inserted therein.

(3) Preparation of Immunoglobulin-Binding Proteins (Wild-Type)

(ε) FpL_C1

A transformant and an expression vector (which was named pET-FpL_C1) were obtained by the same method as in (a) except that a polynucleotide (SEQ ID NO:118) encoding FpL_C1 (SEQ ID NO:112) was used as the polynucleotide encoding an immunoglobulin-binding protein. As a result of nucleotide sequence analysis of the expression vector pET-FpL_C1, it could be confirmed that pET-FpL_C1 contains a polynucleotide (SEQ ID NO:118) encoding FpL_C1 (SEQ ID NO:112) inserted therein.

(ζ) FpL_C2

A transformant and an expression vector (which was named pET-FpL_C1) were obtained by the same method as in (a) except that a polynucleotide (SEQ ID NO:119) encoding FpL_C1 (SEQ ID NO:113) was used as the polynucleotide encoding an immunoglobulin-binding protein. As a result of nucleotide sequence analysis of the expression vector pET-FpL_C2, it could be confirmed that pET-FpL_C2 contains a polynucleotide (SEQ ID NO:119) encoding FpL_C2 (SEQ ID NO:113) inserted therein.

Reference Example 2

(1) Transformants each of which expresses one of FpL_C3 (SEQ ID NO:1) prepared in Example 1, FpL_C4 (SEQ ID NO:18) prepared in Example 4, and FpL_C1 (SEQ ID NO:112), FpL_C2 (SEQ ID NO:113), FpL_C1KR (SEQ ID NO:114), FpL_C2KR (SEQ ID NO:115), FpL_C3KR (SEQ ID NO:116), and FpL_C4KR (SEQ ID NO:117) prepared in Reference Example 1 were cultured by the same method as in Example 3(8) to (10), and protein extracts were prepared therefrom by the same method as in Example 3(11). Each extract was centrifuged, and the resulting supernatant was passed through a filter for clarification.

(2) The supernatant clarified in (1) was applied to a column packed with Ni-NTA Sepharose 6 Fast Flow (manufactured by Cytiva) which had been equilibrated in advance with 0.05 M Tris buffer (pH 7.5) containing 0.5 M NaCl and 0.02 M imidazole (hereinafter referred to as washing buffer B). The column was then washed with washing buffer B in an amount of 10 volumes with respect to the support packed in the column, and then 0.05 M Tris buffer (pH 7.5) containing 0.5 M NaCl and 0.5 M imidazole was passed therethrough, to collect a fraction corresponding to the immunoglobulin-binding protein.

(3) The absorbance of the collected fraction was measured with a spectrophotometer, to quantify the immunoglobulin-binding protein contained in the fraction. Further, SDS-PAGE (SDS-polyacrylamide electrophoresis) was performed to confirm that the protein was purified with high purity.

(4) Alkali treatment was carried out by the same method as in Example 3(13) except that the concentration of the NaOH used for the treatment was 1.0 M (final concentration, 0.5 M), that the treatment temperature was 42° C., and that the treatment time was 15 minutes. Thereafter, the remaining activity was calculated by the same method as in Example 3(14), to evaluate the alkaline stability.

The results are shown in Table 11. FpL_C2 (SEQ ID NO:113), FpL_C3 (SEQ ID NO:1), and FpL_C4 (SEQ ID NO: 18) showed improved alkaline stabilities by the substitution of all lysine resin residues with arginine residues (FpL_C2KR (SEQ ID NO:115), FpL_C3KR (SEQ ID NO:116), and FpL_C4KR (SEQ ID NO:117)).

TABLE 11

| Name | SEQ ID NO: | Remaining activity [%] |
|---|---|---|
| FpL_C1 | 112 | 39 |
| FpL_C2 | 113 | 50 |
| FpL_C3 | 1 | 44 |
| FpL_C4 | 18 | 78 |
| FpL_C1KR | 114 | 27 |
| FpL_C2KR | 115 | 72 |
| FpL_C3KR | 116 | 85 |
| FpL_C4KR | 117 | 87 |

※Alkali treatment: 42° C., 0.5M NaOH(final concentration), 15 min

Example 13 Introduction of Mutations into FpL_C4KR and Preparation of Library (1) pET-FpL_C4KR obtained in Reference Example 1(2)(δ) was used as a template to prepare a saturation substitution mutant library for the amino acid residues at positions 7 and 29. Primers were designed similarly to Example 11(1) according to the 22c-trick method such that appropriate mixed bases could be placed at the mutation introduction sites, and such that inverse PCR could be carried out focusing on the mutation introduction sites (SEQ ID NOs: 124 to 135). These primers were mixed to provide a combination of six primers for each substitution site according to the compositions shown in Table 7 and Table 12, to prepare PCR primer mixtures (Forward/Reverse primer mix).

TABLE 12

| | Position of amino acid substitution | |
|---|---|---|
| SEQ ID NO: | Lys7 | Lys29 |
| Forward primer 1 | 124 | 130 |
| Forward primer 2 | 125 | 131 |
| Forward primer 3 | 126 | 132 |
| Reverse primer 1 | 127 | 133 |
| Reverse primer 2 | 128 | 134 |
| Reverse primer 3 | 129 | 135 |

(2) Site-directed mutagenesis by inverse PCR was carried out by the same method as in Example 11(2) except that pET-FpL_C4KR was used as a template DNA.

(3) After purification of the PCR product obtained, the *Escherichia coli* BL21 (DE3) strain was transformed using the reaction liquid, and then cultured (37° C., 16 hours) on LB plate medium supplemented with 50 μg/mL kanamycin. The resulting colonies, formed on the plate, were provided as a site-directed mutant library.

Example 14 Screening of FpL_C4KR Amino Acid Substitution Mutants (1) The transformant expressing FpL_C4KR (SEQ ID NO:117) prepared in Reference Example 1(2)(δ), and the site-directed amino acid substitution mutant library (transformants) prepared in Example 13 were cultured by the same method as in Example 3(1) to (2).

(2) Thereafter, each culture supernatant obtained by a centrifugation operation was subjected to alkali treatment by the same method as in Example 3(3), and the remaining activity was calculated by the ELISA method described in Example 3(4).

(3) About 200 strains of transformants were evaluated to select, among these, transformants expressing an immunoglobulin-binding protein having an improved alkaline stability compared to FpL_C4KR (SEQ ID NO:117).

(4) Each selected transformant was cultured, and an expression vector was prepared therefrom using a QIAprep Spin Miniprep kit (manufactured by QIAGEN).

(5) The nucleotide sequence of the polynucleotide region encoding the immunoglobulin-binding protein inserted in the expression vector obtained was analyzed by the method described in Example 1(5), to identify the position of each amino acid substitution.

(6) Each transformant expressing an immunoglobulin-binding protein selected in (3) or the transformant expressing FpL_C4KR (SEQ ID NO:117) prepared in Reference Example 1 was cultured by the same method as in Example 3(8) to (10), and a protein extract was prepared therefrom by the same method as in Example 3(11).

(7) The antibody-binding activity of the immunoglobulin-binding protein in each protein extract prepared in (6) was measured using the ELISA method described in Example 3(4).

(8) Alkali treatment was carried out by the method described in Example 3(13). Thereafter, the remaining activity was calculated by the same method as in Example 3(14), to evaluate the alkaline stability.

Table 13 shows a summary of the results for the immunoglobulin-binding proteins expressed by the transformants selected in (3), on the position of each amino acid substitution (in terms of SEQ ID NO:117) and the remaining activity [%] after the alkali treatment. It can be said that an immunoglobulin-binding protein having the same amino acid sequence as SEQ ID NO:117 except that the immunoglobulin-binding protein has at least the amino acid substitution(s) Lys(Arg)7Ala (this expression represents the fact that the amino acid residue corresponding to the lysine at position 7 of SEQ ID NO:1 (the lysine at position 7 of SEQ ID NO:18) is once substituted with arginine, and then substituted with alanine; the same applies hereinafter) and/or Lys(Arg)29Pro has an improved alkaline stability compared to FpL_C4KR (SEQ ID NO:117).

TABLE 13

| Amino acid substitution (into FpL_C4KR) | SEQ ID NO: | Remaining activity [%] |
|---|---|---|
| w/o substitution(FpL_C4KR) | 117 | 83 |
| Lys(Arg)7Ala | 136 | 86 |
| Lys(Arg)29Pro | 137 | 84 |

※Alkali treatment: 25° C., 0.1M NaOH(final concentration), 5 h

Example 15 Preparation of FpL_C3KR Amino Acid Substitution-Integrated Mutants (1) Design of FpL_C3KR Amino Acid Substitution-Integrated Mutants Amino acid substitutions found to be responsible for the improvement of the alkaline stability of the immunoglobulin-binding protein in Example 8 and Example 12 were integrated into FpL_C3KR (SEQ ID NO:116) in an attempt to further improve the stability. More specifically, the four kinds of immunoglobulin-binding proteins shown in the following (m) to (p) were designed and prepared.

(m) A protein (which was named FpL_C3KR 1a) prepared by introducing the amino acid substitution Gly21Arg into FpL_C3KR (n) A protein (which was named FpL_C3KR 1b) prepared by introducing the amino acid substitution Gly51Val into FpL_C3KR (o) A protein (which was named FpL_C3KR 1c) prepared by introducing the amino acid substitution Asn62Tyr into FpL_C3KR (p) A protein (which was named FpL_C3KR 3a) prepared by introducing the amino acid substitutions Asn50Tyr, Glu52Gly, and Asn62Tyr into FpL_C3KR (2) Preparation of FpL_C3KR Amino Acid Substitution-Integrated Mutants The methods of the preparation of the four kinds of immunoglobulin-binding proteins shown in (m) to (p) are described below.

(m) FpL_C3KR 1a

This protein was prepared by selecting Gly21Arg among the amino acid substitutions that were found to improve the alkaline stability in Example 12, and introducing this amino acid residue into FpL_C3KR (SEQ ID NO:116).

(m-1) Mutagenesis using inverse PCR was carried out to prepare a polynucleotide containing a nucleotide sequence encoding FpL_C3KR 1a (SEQ ID NO:138). The inverse PCR was carried out by the same method as in Example 7(2) (a-1) except that pET-FpL_C3KR was used as a template DNA, that an oligonucleotide having the sequence of SEQ ID NO:146 was used as a PCR Forward Primer, and that an oligonucleotide having the sequence of SEQ ID NO: 147 was used as a PCR Reverse Primer.

(m-2) The polynucleotide obtained was purified, and then treated with the restriction enzyme DpnI, followed by transforming the *Escherichia coli* BL21 (DE3) strain using the restriction enzyme-treated product.

(m-3) The transformant obtained was subjected to culturing and extraction of an expression vector (which was named pET-FpL_C3KR Ta) by the same method as in Example 7(2) (a-3). The nucleotide sequence of the expression vector was analyzed by the same method as in Example 1(5).

As a result of the sequence analysis, it could be confirmed that the expression vector pET-FpL_C3KR 1a contains a polynucleotide encoding FpL_C3KR Ta (SEQ ID NO:138) inserted therein.

(n) FpL_C3KR 1b

This protein was prepared by selecting Gly51Val among the amino acid substitutions that were found to improve the alkaline stability in Example 12, and introducing this amino acid residue into FpL_C3KR (SEQ ID NO:116).

(n-1) Mutagenesis using inverse PCR was carried out to prepare a polynucleotide containing a nucleotide sequence encoding FpL_C3KR 1b (SEQ ID NO:139). The inverse PCR was carried out by the same method as in Example 7(2) (a-1) except that a polynucleotide containing pET-FpL_C3KR was used as a template DNA, that an oligonucleotide having the sequence of SEQ ID NO: 148 was used as a PCR Forward Primer, and that an oligonucleotide having the sequence of SEQ ID NO:149 was used as a PCR Reverse Primer.

(n-2) The polynucleotide obtained was purified, and then treated with the restriction enzyme DpnI, followed by transforming the *Escherichia coli* BL21 (DE3) strain using the restriction enzyme-treated product.

(n-3) The transformant obtained was subjected to culturing and extraction of an expression vector (which was named pET-FpL_C3KR 1b) by the same method as in Example 7(2) (a-3). The nucleotide sequence of the expression vector was analyzed by the same method as in Example 1(5).

As a result of the sequence analysis, it could be confirmed that the expression vector pET-FpL_C3KR 1b contains a polynucleotide encoding FpL_C3KR 1b (SEQ ID NO:139) inserted therein.

(o) FpL_C3KR 1c (o-1) The nucleotide sequence of the expression vector pET-FpL_C3KR 1c, containing pET26b and a polynucleotide (SEQ ID NO: 150) encoding FpL_C3KR 1c (SEQ ID NO:140), was designed, and divided into the following three regions.

First region: the nucleotide sequence of pET26b, a nucleotide sequence encoding the amino acid residues at positions 1 to 20 of FpL_C3KR 1c (the nucleotide sequence of positions 1 to 60 of SEQ ID NO:150), a nucleotide sequence encoding the amino acid residues at positions 53 to 70 of FpL_C3KR 1c (the nucleotide sequence of positions 157 to 210 of SEQ ID NO:150), a nucleotide sequence encoding six histidine residues (SEQ ID NO:232), a stop codon, and a recognition sequence for the restriction enzyme HindIII (5'-TAAGCTT-3')

Second region: a nucleotide sequence encoding the amino acid residues at positions 16 to 37 of FpL_C3KR 1c (polynucleotides having the sequences of SEQ ID NOs:153 [forward] and 154 [reverse])

Third region: a nucleotide sequence encoding the amino acid residues at positions 33 to 57 of FpL_C3KR1c (polynucleotides having the sequences of SEQ ID NOs:155 [forward] and 156 [reverse])

(o-2) By inverse PCR, the polynucleotide of the first region was prepared. The inverse PCR was carried out by the same method as in Example 7(2) (a-1) except that pET-FpL_C4KR was used as a template DNA, that an oligonucleotide having the sequence of SEQ ID NO:151 was used as a PCR Forward Primer, and that an oligonucleotide having the sequence of SEQ ID NO: 152 was used as a PCR Reverse Primer. After the inverse PCR, a polynucleotide containing the first region was purified.

(o-3) The polynucleotide of the first region prepared in (o-2) and polynucleotides of the second region and the third region designed in (o-1) (prepared by direct chemical synthesis) were ligated to each other using NEBuilder (manufactured by New England Biolabs). To the reaction liquid, each polynucleotide for the three regions (each of the five kinds of polynucleotides) was added at 0.05 pmol.

(o-4) The resulting ligated polynucleotide was used to transform the *Escherichia coli* BL21 (DE3) strain.

(o-5) The transformant obtained was subjected to culturing and extraction of an expression vector by the same method as in Example 7(2) (a-3). The nucleotide sequence of the expression vector was analyzed by the same method as in Example 1(5).

As a result of the sequence analysis, it could be confirmed that the expression vector pET-FpL_C3KR 1c contains a polynucleotide (SEQ ID NO:150) encoding FpL_C3KR 1c (SEQ ID NO:140) inserted therein.

(p) FpL_C3KR 3a (p-1) The nucleotide sequence of the expression vector pET-FpL_C3KR 3a, containing pET26b and a polynucleotide (SEQ ID NO: 157) encoding FpL_C3KR 3a (SEQ ID NO:141), was designed, and divided into the following three regions.

First region: the nucleotide sequence of pET26b, a nucleotide sequence encoding the amino acid residues at positions 1 to 20 of FpL_C3KR 3a (the nucleotide sequence of positions 1 to 60 of SEQ ID NO:141), a nucleotide sequence encoding the amino acid residues at positions 53 to 70 of FpL_C3KR 3a (the nucleotide sequence of positions 157 to 210 of SEQ ID NO:141), a nucleotide sequence encoding six histidine residues (SEQ ID NO:232), a stop codon, and a recognition sequence for the restriction enzyme HindIII (5'-TAAGCTT-3')

Second region: a nucleotide sequence encoding the amino acid residues at positions 16 to 37 of FpL_C3KR 3a (polynucleotides having the sequences of SEQ ID NOs:153 [forward] and 154 [reverse])

Third region: a nucleotide sequence encoding the amino acid residues at positions 33 to 57 of FpL_C3KR 3a (polynucleotides having the sequences of SEQ ID NOs:158 [forward] and 159 [reverse])

(p-2) By the inverse PCR described in (o-2), a polynucleotide of the first region was prepared. The polynucleotide was then purified.

(p-3) The polynucleotide of the first region prepared in (p-2) and polynucleotides of the second region and the third region designed in (p-1) (prepared by direct chemical synthesis) were ligated to each other by the same method as in (o-3).

(p-4) The resulting ligated polynucleotide was used to transform the *Escherichia coli* BL21 (DE3) strain.

(p-5) The transformant obtained was subjected to culturing and extraction of an expression vector by the same method as in Example 7(2) (a-3). The nucleotide sequence of the expression vector was analyzed by the same method as in Example 1(5).

As a result of the sequence analysis, it could be confirmed that the expression vector pET-FpL_C3KR 3a contains a polynucleotide (SEQ ID NO:157) encoding FpL_C3KR 3a (SEQ ID NO:141) inserted therein.

Example 16 Preparation of FpL_C3 Amino Acid Substitution-Integrated Mutants (Part 2) (1) Design of FpL_C3 Amino Acid Substitution-Integrated Mutants Some of the arginine residues in FpL_C3KR (SEQ ID NO:116) that had been introduced by substitution from lysine residues were substituted with other amino acid residues (specifically, the amino acid substitutions Lys (Arg) 7Ala, Lys (Arg) 22Gln, and Lys (Arg) 29Ile were introduced), to prepare the immunoglobulin-binding protein FpL_C3KX (SEQ ID NO: 142). Thereafter, amino acid substitutions found to be responsible for improvement of the alkaline stability of the immunoglobulin-binding protein in Example 8 and Example 12 were integrated into FpL_C3KX (SEQ ID NO:142). More specifically, the three kinds of immunoglobulin-binding proteins shown in the following (q) to(s) were designed and prepared.

(q) A protein (which was named FpL_C3KX 1a) prepared by introducing the amino acid substitution Gly21Arg into FpL_C3KX;

(r) A protein (which was named FpL_C3KX 3a) prepared by introducing the amino acid substitutions Asn50Tyr, Glu52Gly, and Asn62Tyr into FpL_C3KX (s) A protein (which was named FpL_C3KX 4g) prepared by introducing the amino acid substitutions Gly21Arg, Asn50Tyr, Glu52Gly, and Asn62Tyr into FpL_C3KX (2) Preparation of FpL_C3 KX (2-1) The nucleotide sequence of the expression vector pET-FpL_C3KX, containing pET26b and a polynucleotide (SEQ ID NO: 161) encoding FpL_C3KX (SEQ ID NO:142), was designed, and divided into the following three regions.

First region: the nucleotide sequence of pET26b, a nucleotide sequence encoding the amino acid residues at positions 1 to 20 of FpL_C3KX (the nucleotide sequence of positions 1 to 60 of SEQ ID NO:161), a nucleotide sequence encoding the amino acid residues at positions 53 to 70 of FpL_C3KX (the nucleotide sequence of positions 157 to 210 of SEQ ID NO:161), a nucleotide sequence encoding six histidine residues (SEQ ID NO:232), a stop codon, and a recognition sequence for the restriction enzyme HindIII (5'-TAAGCTT-3')

Second region: a nucleotide sequence encoding the amino acid residues at positions 16 to 37 of FpL_C3KX (polynucleotides having the sequences of SEQ ID NOs:163 [forward] and 164 [reverse])

Third region: a nucleotide sequence encoding the amino acid residues at positions 33 to 57 of FpL_C3KX (polynucleotides having the sequences of SEQ ID NOs:155 [forward] and 156 [reverse])

(2-2) By inverse PCR, a polynucleotide containing the first region was prepared. The inverse PCR was carried out by the same method as in Example 7(2) (a-1) except that the expression vector pET-FpL_C4KR K7A, containing a polynucleotide (SEQ ID NO:160) encoding FpL_C4KR K7A (an immunoglobulin-binding protein prepared by introducing the amino acid substitution Lys(Arg)7Ala into FpL_C4KR; SEQ ID NO: 136), was used as a template DNA, that an oligonucleotide having the sequence of SEQ ID NO:162 was used as a PCR Forward Primer, and that an oligonucleotide having the sequence of SEQ ID NO: 152 was used as a PCR Reverse Primer. After the inverse PCR, a polynucleotide containing the first region was purified.

(2-3) The polynucleotide of the first region prepared in (2-2) and polynucleotides of the second region and the third region designed in (2-1) (prepared by direct chemical synthesis) were ligated to each other by the same method as in Example 15(2) (o-3).

(2-4) The resulting ligated polynucleotide was used to transform the *Escherichia coli* BL21 (DE3) strain.

(2-5) The transformant obtained was subjected to culturing and extraction of an expression vector by the same method as in Example 7(2) (a-3). The nucleotide sequence of the expression vector was analyzed by the same method as in Example 1(5).

As a result of the sequence analysis, it could be confirmed that the expression vector pET-FpL_C3KX contains a polynucleotide (SEQ ID NO:161) encoding FpL_C3KX (SEQ ID NO: 142) inserted therein.

(3) Preparation of FpL_C3KX Amino Acid Substitution-Integrated Mutants

The methods of the preparation of the three kinds of immunoglobulin-binding proteins shown in (q) to (s) are described below.

(q) FpL_C3KX 1a (q-1) The nucleotide sequence of the expression vector pET-FpL_C3KX 1a, containing pET26b and a polynucleotide (SEQ ID NO:165) encoding FpL_C3KX 1a (SEQ ID NO:143), was designed, and divided into the following three regions.

First region: the nucleotide sequence of pET26b, a nucleotide sequence encoding the amino acid residues at positions 1 to 20 of FpL_C3KX 1a (the nucleotide sequence of positions 1 to 60 of SEQ ID NO:165), a nucleotide sequence encoding the amino acid residues at positions 53 to 70 of FpL_C3KX 1a (the nucleotide sequence of positions 157 to 210 of SEQ ID NO:165), a nucleotide sequence encoding six histidine residues (SEQ ID NO:232), a stop codon, and a recognition sequence for the restriction enzyme HindIII (5'-TAAGCTT-3')

Second region: a nucleotide sequence encoding the amino acid residues at positions 16 to 37 of FpL_C3KX 1a (polynucleotides having the sequences of SEQ ID NOs:166 [forward] and 167 [reverse])

Third region: a nucleotide sequence encoding the amino acid residues at positions 33 to 57 of FpL_C3KX 1a (polynucleotides having the sequences of SEQ ID NOs:155 [forward] and 156 [reverse])

(q-2) By the inverse PCR described in (2-2), a polynucleotide of the first region was prepared. The polynucleotide was then purified.

(q-3) The polynucleotide of the first region prepared in (q-2) and polynucleotides of the second region and the third region designed in (q-1) (prepared by direct chemical synthesis) were ligated to each other by the same method as in Example 15(2) (o-3).

(q-4) The resulting ligated polynucleotide was used to transform the *Escherichia coli* BL21 (DE3) strain.

(q-5) The transformant obtained was subjected to culturing and extraction of an expression vector (which was named pET-FpL_C3KX 1a) by the same method as in Example 7(2) (a-3). The nucleotide sequence of the expression vector was analyzed by the same method as in Example 1(5).

As a result of the sequence analysis, it could be confirmed that the expression vector pET-FpL_C3KX 1a contains a polynucleotide (SEQ ID NO:165) encoding FpL_C3KX 1a (SEQ ID NO:143) inserted therein.

(r) FpL_C3KX 3a (r-1) The nucleotide sequence of the expression vector pET-FpL_C3KX 3a, containing pET26b and a polynucleotide (SEQ ID NO: 168) encoding FpL_C3KX 3a (SEQ ID NO:144), was designed, and divided into the following three regions.

First region: the nucleotide sequence of pET26b, a nucleotide sequence encoding the amino acid residues at positions 1 to 20 of FpL_C3KX 3a (the nucleotide sequence of positions 1 to 60 of SEQ ID NO:168), a nucleotide sequence encoding the amino acid residues at positions 53 to 70 of FpL_C3KX 3a (the nucleotide sequence of positions 157 to 210 of SEQ ID NO:168), a nucleotide sequence encoding six histidine residues (SEQ ID NO:232), a stop codon, and a recognition sequence for the restriction enzyme HindIII (5'-TAAGCTT-3')

Second region: a nucleotide sequence encoding the amino acid residues at positions 16 to 37 of FpL_C3KX 3a (polynucleotides having the sequences of SEQ ID NOs:169 [forward] and 170 [reverse])

Third region: a nucleotide sequence encoding the amino acid residues at positions 33 to 57 of FpL_C3KX 3a (polynucleotides having the sequences of SEQ ID NOs:158 [forward] and 159 [reverse])

(r-2) By inverse PCR, a polynucleotide of the first region was prepared. The inverse PCR was carried out by the same method as in Example 7(2) (a-1) except that pET-FpL_C4KR K7A was used as a template DNA, that an oligonucleotide having the sequence of SEQ ID NO:151 was used as a PCR Forward Primer, and that an oligonucleotide having the sequence of SEQ ID NO:152 was used as a PCR Reverse Primer. After the inverse PCR, a polynucleotide containing the first region was purified.

(r-3) The polynucleotide of the first region prepared in (r-2) and polynucleotides of the second region and the third region designed in (r-1) (prepared by direct chemical synthesis) were ligated to each other by the same method as in Example 15(2) (o-3).

(r-4) The resulting ligated polynucleotide was used to transform the *Escherichia coli* BL21 (DE3) strain.

(r-5) The transformant obtained was subjected to culturing and extraction of an expression vector by the same method as in Example 7(2) (a-3). The nucleotide sequence of the expression vector was analyzed by the same method as in Example 1(5).

As a result of the sequence analysis, it could be confirmed that the expression vector pET-FpL_C3KX 3a contains a polynucleotide (SEQ ID NO:168) encoding FpL_C3KX 3a (SEQ ID NO:144) inserted therein.

(s) FpL_C3KX 4g (s-1) The nucleotide sequence of the expression vector pET-FpL_C3KX 4g, containing pET26b and a polynucleotide (SEQ ID NO:171) encoding FpL_C3KX 4g (SEQ ID NO:145), was designed, and divided into the following three regions.

First region: the nucleotide sequence of pET26b, a nucleotide sequence encoding the amino acid residues at positions 1 to 20 of FpL_C3KX 4g (the nucleotide sequence of positions 1 to 60 of SEQ ID NO:171), a nucleotide sequence encoding the amino acid residues at positions 53 to 70 of FpL_C3KX 4g (the nucleotide sequence of positions 157 to 210 of SEQ ID NO:171), a nucleotide sequence encoding six histidine residues (SEQ ID NO:232), a stop codon, and a recognition sequence for the restriction enzyme HindIII (5'-TAAGCTT-3')

Second region: a nucleotide sequence encoding the amino acid residues at positions 16 to 37 of FpL_C3KX 4g (polynucleotides having the sequences of SEQ ID NOs:166 [forward] and 167 [reverse])

Third region: a nucleotide sequence encoding the amino acid residues at positions 33 to 57 of FpL_C3KX 4g (polynucleotides having the sequences of SEQ ID NOs:158 [forward] and 159 [reverse])

(s-2) By the inverse PCR described in (r-2), a polynucleotide of the first region was prepared. The polynucleotide was then purified.

(s-3) The polynucleotide of the first region prepared in (s-2) and polynucleotides of the second region and the third region designed in (s-1) (prepared by direct chemical synthesis) were ligated to each other by the same method as in Example 15(20) (o-3).

(s-4) The resulting ligated polynucleotide was used to transform the *Escherichia coli* BL21 (DE3) strain.

(s-5) The transformant obtained was subjected to culturing and extraction of an expression vector by the same the mutant-type (amino-acid-substituted) immunoglobulin-binding protein FpL_C3KR (SEQ ID NO:116) prepared in Reference Example 1, the mutant-type immunoglobulin-binding proteins FpL_C3KR 1a (SEQ ID NO:138), FpL_C3KR 1b (SEQ ID NO:139), FpL_C3KR 1c (SEQ ID NO:140), and FpL_C3KR 3a (SEQ ID NO:141) prepared in Example 15, and the mutant-type immunoglobulin-binding proteins FpL_C3KX (SEQ ID NO: 142), FpL_C3KX 1a (SEQ ID NO:143), FpL_C3KX 3a (SEQ ID NO:144), and FpL_C3KX 4g (SEQ ID NO:145) prepared in Example 16 were cultured by the same method as in Example 3(8) to (10), and protein extracts were prepared therefrom by the method described in Example 3(11).

(2) The antibody-binding activity of the immunoglobulin-binding protein in each protein extract prepared in (1) was measured using the ELISA method described in Example 3(4).

(3) Alkali treatment was carried out by the same method as in Example 3(13) except that the concentration of the NaOH used for the treatment was 0.4 M (final concentration, 0.2 M), and that the treatment time was 15 hours. Thereafter, the remaining activity was calculated by the same method as in Example 3(14), to evaluate the alkaline stability.

The results are shown in Table 14. It can be said that the immunoglobulin-binding proteins having one or more amino acid substitutions selected from at least Gly21Arg, Asn50Tyr, Gly51Val, Glu52Gly, and Asn62Tyr have improved alkaline stabilities compared to the immunoglobulin-binding proteins in which these amino acid substitutions were not introduced (FpL_C3KR and FpL_C3KX). In particular, it can be said that the immunoglobulin-binding proteins each having all of the amino acid substitutions Asn50Tyr, Glu52Gly, and Asn62Tyr (FpL_C3KR 3a and FpL_C3KX 3a) have especially improved alkaline stabilities (FpL_C3KR: 54%, FpL_C3KR 3a: 86%) (FpL_C3KX: 10%, FpL_C3KX 3a: 69%).

TABLE 14

| | Amino acid substitution | | | | | | | | | | | | SEQ ID | Remaining activity |
|---|---|---|---|---|---|---|---|---|---|---|---|---|---|---|
| Name | Lys7 | Lys13 | Gly21 | Lys22 | Lys29 | Lys36 | Lys48 | Asn50 | Gly51 | Glu52 | Asn62 | Lys67 | NO: | [%] |
| FpL_C3 | — | — | — | — | — | — | — | — | — | — | — | — | 1 | 8 |
| FpL_C3KR | Arg | Arg | — | Arg | Arg | Arg | Arg | — | — | — | — | Arg | 116 | 54 |
| FpL_C3KR 1a | Arg | Arg | Arg | Arg | Arg | Arg | Arg | — | — | — | — | Arg | 138 | 70 |
| FpL_C3KR 1b | Arg | Arg | — | Arg | Arg | Arg | Arg | — | Val | — | — | Arg | 139 | 69 |
| FpL_C3KR 1c | Arg | Arg | — | Arg | Arg | Arg | Arg | — | — | — | Tyr | Arg | 140 | 65 |
| FpL_C3KR 3a | Arg | Arg | — | Arg | Arg | Arg | Arg | Tyr | — | Gly | Tyr | Arg | 141 | 86 |
| FpL_C3KX | Ala | Arg | — | Gln | Ile | Arg | Arg | — | — | — | — | Arg | 142 | 10 |
| FpL_C3KX 1a | Ala | Arg | Arg | Gln | Ile | Arg | Arg | — | — | — | — | Arg | 143 | 21 |
| FpL_C3KX 3a | Ala | Arg | — | Gln | Ile | Arg | Arg | Tyr | — | Gly | Tyr | Arg | 144 | 69 |
| FpL_C3KX 4g | Ala | Arg | Arg | Gln | Ile | Arg | Arg | Tyr | — | Gly | Tyr | Arg | 145 | 32 |

※Alkali treatment: 25° C., 0.2M NaOH(final concentration), 15 h method as in Example 7(2) (a-3). The nucleotide sequence of the expression vector was analyzed by the same method as in Example 1(5).

As a result of the sequence analysis, it could be confirmed that the expression vector pET-FpL_C3KX 4g contains a polynucleotide (SEQ ID NO:171) encoding FpL_C3KX 4g (SEQ ID NO:145) inserted therein.

Example 17 Evaluation of Alkaline Stabilities of FpL_C3KX Amino Acid Substitution-Integrated Mutants (1) Transformants each of which expresses one of the wild-type FpL_C3 (SEQ ID NO:1) prepared in Example 1,

Example 18 Introduction of Mutations into FpL_C3KX 3a and Preparation of Library Into the polynucleotide portion (SEQ ID NO: 168) encoding the immunoglobulin-binding protein in the expression vector pET-FpL_C3KX 3a prepared in Example 16(r), mutations were randomly introduced by error-prone PCR by the same method as in Example 2, to prepare a library. The average mutation introduction rate was 1.7%.

Example 19 Screening of FpL_C3KX 3a Amino Acid Substitution Mutants (Part 1)

(1) pET-FpL_C3KX 3a (transformant) prepared in Example 16(r) and the random mutant library (transformants) prepared in Example 18 were cultured by the same method as in Example 3(1) to (2).

(2) Thereafter, each culture supernatant obtained by a centrifugation operation was mixed with an equal amount of 1.0 M NaOH, and then subjected to alkali treatment at 42° C. for 30 minutes.

(3) The antibody-binding activity of the immunoglobulin-binding protein subjected to the alkali treatment was measured by the ELISA method described in Example 3(4). The antibody-binding activity of the immunoglobulin-binding protein subjected to the alkali treatment was divided by the antibody-binding activity of the immunoglobulin-binding protein without the alkali treatment, to calculate the remaining activity.

(4) About 900 strains of transformants were evaluated to select, among these, transformants expressing an immunoglobulin-binding protein having an improved alkaline stability compared to FpL_C3KX 3a (SEQ ID NO: 144).

(5) Each selected transformant was cultured, and an expression vector was prepared therefrom using a QIAprep Spin Miniprep kit (manufactured by QIAGEN).

(6) The nucleotide sequence of the polynucleotide region encoding the immunoglobulin-binding protein inserted in the expression vector obtained was analyzed by the method described in Example 1(5), to identify the position of each amino acid mutation.

(7) Each transformant expressing an immunoglobulin-binding protein selected in (4) was cultured by the same method as in Example 3(8) to (10), and a protein extract was prepared therefrom by the same method as in Example 3(11).

(8) The antibody-binding activity of the immunoglobulin-binding protein in the protein extract prepared in (7) was measured using the ELISA method described in Example 3(4).

(9) Alkali treatment was carried out by the same method as in Example 3(13) except that the concentration of the NaOH used for the treatment was 1.0 M (final concentration, 0.5 M), and that the treatment time was 15 hours. Thereafter, the remaining activity was calculated by the same method as in Example 3(14), to evaluate the alkaline stability.

The results are shown in Table 15. It can be said that an immunoglobulin-binding protein having the same amino acid sequence as SEQ ID NO:144 except that the immunoglobulin-binding protein has at least the amino acid substitution Glu1 Gly or Glu1Val has an improved alkaline stability even compared to FpL_C3KX 3a (SEQ ID NO: 144), which has a higher alkaline stability than that of the wild-type FpL_C3 (SEQ ID NO:1).

TABLE 15

| Amino acid substitution (into FpL_C3KX 3a) | SEQ ID NO: | Remaining activity [%] |
|---|---|---|
| w/o substitution(FpL_C3KX 3a) | 144 | 49 |
| Glu1Gly | 172 | 52 |
| Glu1Val | 173 | 61 |
| Lys(Gln)22Arg | 174 | 67 |

※Alkali treatment: 25° C., 0.5M NaOH(final concentration), 15 h

Example 20 Screening of FpL_C3KX 3a Amino Acid Substitution Mutants (Part 2)

(1) From the random mutant library (transformants) prepared in Example 18, about 1400 strains of transformants were newly evaluated by the method described in Example 19(1) to (3). Among these, transformants expressing an immunoglobulin-binding protein having an improved alkaline stability even compared to the alkaline-stability-improved immunoglobulin-binding protein (FpL_C3KX 3a) were selected.

(2) Each selected transformant, or the transformant expressing FpL_C3KX 3a (SEQ ID NO:144) prepared in Example 16(r) was cultured, and an expression vector was prepared therefrom using a QIAprep Spin Miniprep kit (manufactured by QIAGEN).

(3) The nucleotide sequence of the polynucleotide region encoding the immunoglobulin-binding protein inserted in the expression vector obtained was analyzed by the method described in Example 1(5), to identify the position of each amino acid mutation.

(4) The transformants expressing an immunoglobulin-binding protein selected in (1) were cultured by the same method as in Example 3(8) to (10), and protein extracts were prepared therefrom by the same method as in Example 3(11).

(5) The antibody-binding activity of the immunoglobulin-binding protein in each protein extract prepared in (4) was measured using the ELISA method described in Example 3(4).

(6) Alkali treatment was carried out by the same method as in Example 3(13) except that the concentration of the NaOH used for the treatment was 0.4 M (final concentration, 0.2 M), and that the treatment time was 15 hours. Thereafter, the remaining activity was calculated by the same method as in Example 3(14), to evaluate the alkaline stability.

The results are shown in Table 16. It can be said that an immunoglobulin-binding protein having the same amino acid sequence as SEQ ID NO:144 except that the immunoglobulin-binding protein has one or more amino acid substitutions selected from at least Glu4Lys, Glu27Arg, and Thr36Ala has an improved alkaline stability even compared to FpL_C3KX 3a (SEQ ID NO:144), which has a higher alkaline stability than that of the wild-type FpL_C3 (SEQ ID NO: 1).

TABLE 16

| Amino acid substitution (into FpL_C3KX 3a) | SEQ ID NO: | Remaining activity [%] |
|---|---|---|
| w/o substitution(FpL_C3KX 3a) | 144 | 65 |
| Glu4Lys | 175 | 69 |
| Lys(Gln)22Thr | 176 | 82 |
| Glu27Arg | 177 | 72 |
| Thr36Ala | 178 | 68 |
| Glu49Asp | 179 | 64 |

※Alkali treatment: 25° C., 0.2M NaOH(final concentration), 15 h

Example 21 Evaluation of Immunoglobulin κ Light Chain-Binding Capacities of Immunoglobulin-Binding Proteins (Part 1)

The immunoglobulin κ light chain-binding activities of mutant-type immunoglobulin-binding proteins were measured by the following ELISA method, to evaluate effects of amino acid substitution on the human immunoglobulin κ light chain-binding activity.

(1) Transformants each of which expresses one of FpL_C3KR (SEQ ID NO:116) and FpL_C4KR (SEQ ID NO:117) prepared in Reference Example 1, FpL_C3KX 3a (SEQ ID NO: 144) prepared in Example 16, and an immunoglobulin-binding protein (SEQ ID NO:179, hereinafter also referred to as "FpL_C3KX 4h") prepared by introducing the amino acid substitution Glu49Asp into FpL_C3KX 3a obtained in Example 20 were cultured by the same method as in Example 3(8) to (10), and protein extracts were prepared therefrom by the same method as in Example 3(11). Each extract was centrifuged, and the resulting supernatant was passed through a filter for clarification.

(2) The supernatant clarified in (1) was purified by the method described in Reference Example 2(2), and a fraction corresponding to the immunoglobulin-binding protein was collected.

(3) The absorbance of the collected fraction was measured with a spectrophotometer, to quantify each mutant-type immunoglobulin-binding protein contained in the fraction. Further, SDS-PAGE was carried out to confirm that each mutant-type immunoglobulin-binding protein was purified with high purity.

(4) The human immunoglobulin κ light chain-binding activity of each mutant-type immunoglobulin-binding protein was measured by the following ELISA method, to evaluate effects of the amino acid substitutions on the human immunoglobulin κ light chain-binding activity.

(4-1) Polyclonal antibody solutions prepared at 10 μg/mL using TBS were dispensed into wells of a 96-well microplate, followed by immobilization (4° C., 16 hours). One of the following polyclonal antibodies was used:

- a herceptin containing human κ light chain subgroup 1 (Vκ 1) (manufactured by Chugai Pharmaceutical Co., Ltd.);
- a human PDGF R alpha antibody containing human κ light chain subgroup 3 (Vκ3) (manufactured by R&D Systems);
- a human CTLA4 antibody containing human κ light chain subgroup 3 (Vκ3) (manufactured by R&D Systems); and
- a human PCSK9 antibody containing human κ light chain subgroup 4 (Vκ4) (manufactured by R&D Systems).

Thereafter, blocking was carried out using skim milk (manufactured by Becton Dickinson) which was prepared at 2% (w/v) using TBS.

(4-2) Each well of the 96-well microplate was washed with washing buffer A (0.05 M Tris buffer (pH 7.5) containing 0.15 M NaCl and 0.05% (w/v) Tween 20 (trade name)), and a solution containing the immunoglobulin-binding protein to be evaluated for its antibody-binding activity, after dilution to 50 μg/mL, was added thereto, followed by reacting the immunoglobulin-binding protein with the immobilized polyclonal antibody (30° C., 1 hour).

(4-3) Thereafter, the wells were washed with washing buffer A, and 100 μL/well of Anti-6-His Antibody (manufactured by BETHYL LABORATORIES) diluted to 100 ng/mL was added thereto, followed by allowing the reaction to proceed (30° C., 1 hour).

(4-4) Thereafter, the wells were washed with washing buffer A, and 50 κL/well of TMB Peroxidase Substrate (manufactured by KPL) was added thereto. Subsequently, 50 μL/well of 1 M phosphoric acid was added to stop the reaction, and the absorbance was measured at 450 nm using a microplate reader (manufactured by TECAN).

(4-5) The difference in the absorbance was calculated between each well on which a polyclonal antibody was immobilized and a well without the immobilization. Based on the calculated absorbance, the binding capacity of the mutant-type immunoglobulin-binding protein to the polyclonal antibody was evaluated. In cases where the immunoglobulin-binding protein shows a difference in the absorbance between polyclonal antibodies, the immunoglobulin-binding protein is suggested to have different binding capacities to different human κ light chains. In cases where the value is highly variable among polyclonal antibodies, the immunoglobulin-binding protein is suggested to have decreased binding capacity to a particular human κ light chain subgroup(s).

The results are shown in Table 17. Since FpL_C4KR (SEQ ID NO:117) and FpL_C3KX_4h (SEQ ID NO:179) showed low variations among the polyclonal antibodies, they can be said to be capable of binding to human immunoglobulin κ light chains of any subgroup. On the other hand, FpL_C3KR (SEQ ID NO: 116) and FpL_C3KX3a (SEQ ID NO:144) showed decreased binding abilities especially to human Vκ3. These results indicate that a Vκ3-binding ability can be given by introducing the amino acid substitution Glu49Asp.

TABLE 17

| | | Polyclonal antibody-binding activity (abs@450 nm) | | | |
|---|---|---|---|---|---|
| Name | SEQ ID NO: | Herceptin (Vκ1) | PDGF R alpha (Vκ3) | Human CTLA4 (Vκ3) | Human PCSK9 (Vκ4) |
| FpL_C4KR | 117 | 0.65 | 0.59 | 0.66 | 0.55 |
| FpL_C3KR | 116 | 0.92 | 0.21 | 0.32 | 0.77 |
| FpL_C3KX 3a | 144 | 0.87 | 0.12 | 0.21 | 0.76 |
| FpL_C3KX 4h | 179 | 0.69 | 0.56 | 0.63 | 0.62 |

Example 22 Introduction of Mutations into FpL_C3KX 4h and Preparation of Library Into the polynucleotide portion (SEQ ID NO: 180) encoding the immunoglobulin-binding protein in the expression vector pET-FpL_C3KX 4h, which was prepared in Example 20 and expresses FpL_C3KX 4h (SEQ ID NO:179), mutations were randomly introduced by error-prone PCR by the same method as in Example 2, to prepare a library. The average mutation introduction rate was 1.7%.

Example 23 Screening of FpL_C3KX 4h Amino Acid Substitution Mutants (1) The random mutant library (transformants) prepared in Example 22 was cultured by the same method as in Example 3(1) to (2), and then each culture supernatant obtained by a centrifugation operation was subjected to the alkali treatment described in Example 19(2).

(2) The antibody-binding activity of the immunoglobulin-binding protein subjected to the alkali treatment was measured by the ELISA method described in Example 3(4). The antibody-binding activity of the immunoglobulin-binding protein subjected to the alkali treatment was divided by the antibody-binding activity of the immunoglobulin-binding protein without the alkali treatment, to calculate the remaining activity.

(3) About 900 strains of transformants were evaluated to select, among these, transformants expressing an immunoglobulin-binding protein having an improved alkaline stability even compared to the alkaline-stability-improved immunoglobulin-binding protein (FpL_C3KX 4h).

(4) Each selected transformant was cultured, and an expression vector was prepared therefrom using a QIAprep Spin Miniprep kit (manufactured by QIAGEN).

(5) The nucleotide sequence of the polynucleotide region encoding the immunoglobulin-binding protein inserted in the expression vector obtained was analyzed by the method described in Example 1(5), to identify the position of each amino acid mutation.

(6) Each transformant expressing an immunoglobulin-binding protein selected in (5) or the transformant expressing FpL_C3KX 4h (SEQ ID NO: 179) prepared in Example 20 was cultured by the same method as in Example 3(8) to (10), and a protein extract was prepared therefrom by the same method as in Example 3(11). The extract was centrifuged, and the resulting supernatant was passed through a filter for clarification.

(7) The supernatant clarified in (6) was purified by the method described in Reference Example 2(2), and a fraction corresponding to the immunoglobulin-binding protein was collected.

(8) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(9) Alkali treatment was carried out by the same method as in Example 3(13) except that the concentration of the NaOH used for the treatment was 1.0 M (final concentration, 0.5 M), and that the treatment time was 15 hours. Thereafter, the remaining activity was calculated by the same method as in Example 3(14), to evaluate the alkaline stability.

The results are shown in Table 18. It can be said that an immunoglobulin-binding protein having the same amino acid sequence as SEQ ID NO:179 except that the immunoglobulin-binding protein has one or more amino acid substitutions selected from at least Glu9Val, Tyr53Phe, Thr54Met, and Ala69Thr has an improved alkaline stability even compared to FpL_C3KX 4h (SEQ ID NO:179), which has a higher alkaline stability than that of the wild-type FpL_C3 (SEQ ID NO:1).

As a result of comparison of the purification yield after culturing in 20 mL of a medium, it was confirmed that the protein purification yield can be remarkably improved by introduction of the amino acid substitution Lys(Gln)22Arg. The immunoglobulin-binding protein prepared by introducing the amino acid substitution Lys(Gln)22Arg into FpL_C3KX 4h is hereinafter referred to as FpL_C3KX 4i (SEQ ID NO:182).

TABLE 18

| Amino acid substitution (into FpL_C3KX 4h) | SEQ ID NO: | Remaining activity [%] | Protein purification yield[mg/20 mL(medium)] |
|---|---|---|---|
| w/o substitution(FpL_C3KX 4h) | 179 | 45 | 1.57 |
| Glu9Val | 181 | 59 | 0.43 |
| Lys(Gln)22Arg | 182 | 59 | 4.52 |
| Tyr53Phe | 183 | 55 | 1.18 |
| Thr54Met | 184 | 59 | 1.09 |
| Ala69Thr | 185 | 47 | 0.58 |

※Alkali treatment: 25° C., 0.5M NaOH(final concentration), 15 h

Example 24 Preparation of FpL_C3KX 4i Amino Acid Substitution-Integrated Mutants (1) Design of FpL_C3KX 4i Amino Acid Substitution-Integrated Mutants Amino acid substitutions found to be responsible for the improvement of the alkaline stability of the immunoglobulin-binding protein in Example 23 were integrated into FpL_C3KX 4i (SEQ ID NO: 182) in an attempt to further improve the alkaline stability. More specifically, the two kinds of immunoglobulin-binding proteins shown in the following (t) and (u) were designed and prepared.

(t) A protein (SEQ ID NO: 186; which was named FpL_C3KX 5e) prepared by introducing the amino acid substitution Tyr53Phe into FpL_C3KX 4i (u) A protein (SEQ ID NO: 187; which was named FpL_C3KX 5f) prepared by introducing the amino acid substitution Thr54Met into FpL_C3KX 4i (2) Preparation of FpL_C3KX 4i Amino Acid Substitution-Integrated Mutants The methods of the preparation of the two kinds of immunoglobulin-binding proteins shown in (t) and (u) are described below.

(t) FpL_C3KX 5e (t-1) Mutagenesis using inverse PCR was carried out to prepare a polynucleotide containing a nucleotide sequence encoding FpL_C3KX 5e (SEQ ID NO:186). The inverse PCR was carried out by the same method as in Example 7(2) (a-1) except that an expression vector (hereinafter also referred to as "pET-FpL_C3KX 4i") containing a polynucleotide (SEQ ID NO:188) encoding FpL_C3KX 4i (SEQ ID NO:182) was used as a template DNA, that the oligonucleotide of SEQ ID NO:189 was used as a PCR Forward Primer, and that the oligonucleotide of SEQ ID NO:190 was used as a PCR Reverse Primer.

(t-2) The polynucleotide obtained was purified, and then treated with the restriction enzyme DpnI, followed by transforming the *Escherichia coli* BL21 (DE3) strain using the restriction enzyme-treated product.

(t-3) The transformant obtained was subjected to culturing and extraction of an expression vector (which was named pET-FpL_C3KX 5e) by the same method as in Example 7(2) (a-3). The nucleotide sequence of the expression vector was analyzed by the same method as in Example 1(5).

As a result of the sequence analysis, it could be confirmed that the expression vector pET-FpL_C3KX 5e contains a polynucleotide encoding FpL_C3KX 5e (SEQ ID NO:186) inserted therein.

(u) FpL_C3KX 5f (u-1) Mutagenesis using inverse PCR was carried out to prepare a polynucleotide containing a nucleotide sequence encoding FpL_C3KX 5f (SEQ ID NO:187). The inverse PCR was carried out by the same method as in Example 7(2) (a-1) except that pET-FpL_C3KX 4i was used as a template DNA, that the oligonucleotide of SEQ ID NO:191 was used as a PCR Forward Primer, and that the oligonucleotide of SEQ ID NO:192 was used as a PCR Reverse Primer.

(u-2) The polynucleotide obtained was purified, and then treated with the restriction enzyme DpnI, followed by transforming the *Escherichia coli* BL21 (DE3) strain using the restriction enzyme-treated product.

(u-3) The transformant obtained was subjected to culturing and extraction of an expression vector (which was named pET-FpL_C3KX 5f) by the same method as in Example 7(2) (a-3). The nucleotide sequence of the expression vector was analyzed by the same method as in Example 1(5).

As a result of the sequence analysis, it could be confirmed that the expression vector pET-FpL_C3KX 5f contains a polynucleotide encoding FpL_C3KX 5f (SEQ ID NO:187) inserted therein.

Example 25 Evaluation of Alkaline Stabilities of FpL_C3KX 4h Amino Acid Substitution Mutants (1) Transformants each of which expresses one of FpL_C3KX 4h (SEQ ID NO:179) prepared in Example 20, FpL_C3KX 4i (SEQ ID NO:182) obtained in Example 23, and FpL_C3KX 5e (SEQ ID NO:186) and FpL_C3KX 5f (SEQ ID NO:187) prepared in Example 24 were cultured by the same method as in Example 3(8) to (10), and protein extracts were prepared therefrom by the same method as in Example 3(11). Each extract was centrifuged, and the resulting supernatant was passed through a filter for clarification.

(2) The supernatant clarified in (1) was purified by the method described in Reference Example 2(2), and a fraction corresponding to the immunoglobulin-binding protein was collected.

(3) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(4) Alkali treatment was carried out by the same method as in Example 3(13) except that the concentration of the NaOH used for the treatment was 1.0 M (final concentration, 0.5 M), that the treatment temperature was 55° C., and that the treatment time was 15 minutes. Thereafter, the remaining activity was calculated by the same method as in Example 3(14), to evaluate the alkaline stability.

The results are shown in Table 19. It can be said that FpL_C3KX 5e (SEQ ID NO:186) and FpL_C3KX 5f (SEQ ID NO:187) prepared in Example 24 have improved alkaline stabilities even compared to FpL_C3KX 4h (SEQ ID NO:179) and FpL_C3KX 4i (SEQ ID NO:182), which have higher alkaline stabilities than that of the wild-type FpL_C3 (SEQ ID NO:1). In particular, FpL_C3KX 5e showed remarkable improvement in the alkaline stability (FpL_C3KX 4h: 34%, FpL_C3KX 4i: 48%, FpL_C3KX 5e: 73%).

TABLE 19

| | Amino acid substitution | | | SEQ ID | Remaining activity |
|---|---|---|---|---|---|
| Name | Lys22 | Tyr53 | Thr54 | NO: | [%] |
| FpL_C3KX 4h | Gln | — | — | 179 | 34 |
| FpL_C3KX 4i | Arg | — | — | 182 | 48 |
| FpL_C3KX 5e | Arg | Phe | — | 186 | 73 |
| FpL_C3KX 5f | Arg | — | Met | 187 | 61 |

※Alkali treatment: 55° C., 0.5M NaOH(final concentration), 15 min

Example 26 Introduction of Mutations into FpL_C3KX 5e and Preparation of Library Into the polynucleotide portion (SEQ ID NO: 193) encoding the immunoglobulin-binding protein in the expression vector pET-FpL_C3KX 5e prepared in Example 24, mutations were randomly introduced by error-prone PCR by the same method as in Example 2, to prepare a library. The average mutation introduction rate was 1.9%.

Example 27 Screening of FpL_C3KX 5e Amino Acid Substitution Mutants (1) The random mutant library (transformants) prepared in Example 26 was cultured by the same method as in Example 3(1) to (2), and then each culture supernatant obtained by a centrifugation operation was subjected to the alkali treatment described in Example 19(2).

(2) The antibody-binding activity of the immunoglobulin-binding protein subjected to the alkali treatment was measured by the ELISA method described in Example 3(4). The antibody-binding activity of the immunoglobulin-binding protein subjected to the alkali treatment was divided by the antibody-binding activity of the immunoglobulin-binding protein without the alkali treatment, to calculate the remaining activity.

(3) About 900 strains of transformants were evaluated to select, among these, transformants expressing an immunoglobulin-binding protein having an improved alkaline stability even compared to the alkaline-stability-improved immunoglobulin-binding protein (FpL_C3KX 5e).

(4) Each selected transformant was cultured, and an expression vector was prepared therefrom using a QIAprep Spin Miniprep kit (manufactured by QIAGEN).

(5) The nucleotide sequence of the polynucleotide region encoding the immunoglobulin-binding protein inserted in the expression vector obtained was analyzed by the method described in Example 1(5), to identify the position of each amino acid mutation.

(6) Each transformant expressing an immunoglobulin-binding protein selected in (3) or the transformant expressing FpL_C3KX 5e (SEQ ID NO:186) prepared in Example 24 was cultured by the same method as in Example 3(8) to (10), and a protein extract was prepared therefrom by the same method as in Example 3(11). The extract was centrifuged, and the resulting supernatant was passed through a filter for clarification.

(7) The supernatant clarified in (6) was purified by the method described in Reference Example 2(2), and a fraction corresponding to the immunoglobulin-binding protein was collected.

(8) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(9) Alkali treatment was carried out by the same method as in Example 3(13) except that the concentration of the NaOH used for the treatment was 2.0 M (final concentration, 1.0 M), and that the treatment time was 17 hours. Thereafter, the remaining activity was calculated by the same method as in Example 3(14), to evaluate the alkaline stability.

The results are shown in Table 20. It can be said that an immunoglobulin-binding protein having the same amino acid sequence as SEQ ID NO:186 except that the immunoglobulin-binding protein has one or more amino acid substitutions selected from at least Glu1Val, Glu4Gly, Gly21Arg, and Glu(Gly)52Asp has an improved alkaline stability even compared to FpL_C3KX 5e (SEQ ID NO:186), which has a higher alkaline stability than that of the wild-type FpL_C3 (SEQ ID NO:1).

TABLE 20

| Amino acid substitution (into FpL_C3KX 5e) | SEQ ID NO: | Remaining activty [%] |
|---|---|---|
| w/o substitution(FpL_C3KX 5e) | 186 | 41 |
| Glu1Val | 194 | 44 |
| Glu4Gly | 195 | 45 |
| Lys(Ala)7Ser | 196 | 43 |
| Gly21Arg | 197 | 42 |
| Glu(Gly)52Asp | 198 | 49 |

※Alkali treatment: 25° C., 1.0M NaOH(final concentration), 17 h

Example 28 Preparation of FpL_C3KX 5e Amino Acid Substitution-Integrated Mutants (Part 1)

(1) Design of FpL_C3KX 5e Amino Acid Substitution-Integrated Mutants

Amino acid substitutions found to be responsible for the improvement of the alkaline stability of the immunoglobulin-binding protein in Example 27 were integrated into FpL_C3KX 5e in an attempt to further improve the alkaline stability. More specifically, the three kinds of immunoglobulin-binding proteins shown in the following (v) to (x) were designed and prepared.

(v) A protein (SEQ ID NO: 199; which was named FpL_C3KX 6a) prepared by introducing the amino acid substitutions Glu4Gly and Glu(Gly)52Asp into FpL_C3KX 5e (w) A protein (SEQ ID NO:200; which was named FpL_C3KX 5g) prepared by introducing the amino acid substitutions Lys(Ala)7Ser and Glu(Gly)52Asp into FpL_C3KX 5e (x) A protein (SEQ ID NO:201; which was named FpL_C3KX 6b) prepared by introducing the amino acid substitutions Glu4Gly and Lys(Ala)7Ser into FpL_C3KX 5e (2) Preparation of FpL_C3KX 5e Amino Acid Substitution-Integrated Mutants The methods of the preparation of the three kinds of immunoglobulin-binding proteins shown in (v) to (x) are described below.

(v) FpL_C3KX 6a (v-1) Mutagenesis using inverse PCR was carried out to prepare a polynucleotide containing a nucleotide sequence encoding FpL_C3KX 6a. The inverse PCR was carried out by the same method as in Example 7(2) (a-1) except that the expression vector pET-FpL_C3KX 5e E52D, containing a polynucleotide (SEQ ID NO:202) encoding FpL_C3KX 5e E52D (an immunoglobulin-binding protein prepared by introducing the amino acid substitution Glu(Gly)52Asp into FpL_C3KX 5e; SEQ ID NO:198), was used as a template DNA, that an oligonucleotide having the sequence of SEQ ID NO:203 was used as a PCR Forward Primer, and that an oligonucleotide having the sequence of SEQ ID NO:204 was used as a PCR Reverse Primer.

(v-2) The polynucleotide obtained was purified, and then treated with the restriction enzyme DpnI, followed by transforming the *Escherichia coli* BL21 (DE3) strain using the restriction enzyme-treated product.

(v-3) The transformant obtained was subjected to culturing and extraction of an expression vector (which was named pET-FpL_C3KX 6a) by the same method as in Example 7(2) (a-3). The nucleotide sequence of the expression vector was analyzed by the same method as in Example 1(5).

As a result of the sequence analysis, it could be confirmed that the expression vector pET-FpL_C3KX 6a contains a polynucleotide encoding FpL_C3KX 6a (SEQ ID NO:199) inserted therein.

(w) FpL_C3KX 5g (w-1) Mutagenesis using inverse PCR was carried out to prepare a polynucleotide containing a nucleotide sequence encoding FpL_C3KX 5g. The inverse PCR was carried out by the same method as in Example 7(2) (a-1) except that pET-FpL_C3KX 5e E52D was used as a template DNA, that an oligonucleotide having the sequence of SEQ ID NO:205 was used as a PCR Forward Primer, and that an oligonucleotide having the sequence of SEQ ID NO:206 was used as a PCR Reverse Primer.

(w-2) The polynucleotide obtained was purified, and then treated with the restriction enzyme DpnI, followed by transforming the *Escherichia coli* BL21 (DE3) strain using the restriction enzyme-treated product.

(w-3) The transformant obtained was subjected to culturing and extraction of an expression vector (which was named pET-FpL_C3KX 5g) by the same method as in Example 7(2) (a-3). The nucleotide sequence of the expression vector was analyzed by the same method as in Example 1(5).

As a result of the sequence analysis, it could be confirmed that the expression vector pET-FpL_C3KX 5g contains a polynucleotide encoding FpL_C3KX 5g (SEQ ID NO:200) inserted therein.

(x) FpL_C3KX 6b (x-1) Mutagenesis using inverse PCR was carried out to prepare a polynucleotide containing a nucleotide sequence encoding FpL_C3KX 6b. The inverse PCR was carried out by the same method as in Example 7(2) (a-1) except that the expression vector pET-FpL_C3KX 5e E4G, containing a polynucleotide (SEQ ID NO:207) encoding FpL_C3KX 5e E4G (an immunoglobulin-binding protein prepared by introducing the amino acid substitution Glu4Gly into FpL_C3KX 5e; SEQ ID NO:195), was used as a template DNA, that the oligonucleotide of SEQ ID NO:205 was used as a PCR Forward Primer, and that the oligonucleotide of SEQ ID NO:208 was used as a PCR Reverse Primer.

(x-2) The polynucleotide obtained was purified, and then treated with the restriction enzyme DpnI, followed by transforming the *Escherichia coli* BL21 (DE3) strain using the restriction enzyme-treated product.

(x-3) The transformant obtained was subjected to culturing and extraction of an expression vector (which was named pET-FpL_C3KX 6b) by the same method as in Example 7(2) (a-3). The nucleotide sequence of the expression vector was analyzed by the same method as in Example 1(5).

As a result of the sequence analysis, it could be confirmed that the expression vector pET-FpL_C3KX 6b contains a polynucleotide encoding FpL_C3KX 6b (SEQ ID NO:201) inserted therein.

Example 29 Evaluation of Alkaline Stabilities of FpL_C3KX 5e Amino Acid Substitution-Integrated Mutants (Part 1)

(1) Transformants each of which expresses one of FpL_C3KX 5e (SEQ ID NO:186) prepared in Example 24, and FpL_C3KX 6a (SEQ ID NO:199), FpL_C3KX 5g (SEQ ID NO:200), and FpL_C3KX 6b (SEQ ID NO:201) prepared in Example 28 were cultured by the same method as in Example 3(8) to (10), and protein extracts were prepared therefrom by the same method as in Example 3(11). Each extract was centrifuged, and the resulting supernatant was passed through a filter for clarification.

(2) The supernatant clarified in (1) was purified by the method described in Reference Example 2(2), and a fraction corresponding to the immunoglobulin-binding protein was collected.

(3) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(4) Alkali treatment was carried out by the same method as in Example 3(13) except that the concentration of the NaOH used for the treatment was 2.0 M (final concentration, 1.0 M), and that the treatment time was 15 hours. Thereafter, the remaining activity was calculated by the same method as in Example 3(14), to evaluate the alkaline stability.

The results are shown in Table 21. It can be said that all of the FpL_C3KX 6a (SEQ ID NO:199), FpL_C3KX 5g (SEQ ID NO:200), and FpL_C3KX 6b (SEQ ID NO:201) prepared in the present Example have improved alkaline stabilities even compared to FpL_C3KX 5e (SEQ ID NO: 186), which has a higher alkaline stability than that of the wild-type FpL_C3 (SEQ ID NO: 1). In particular, FpL_C3KX 6a showed the highest alkaline stability (FpL_C3KX 5e: 55%, FpL_C3KX 6a: 62%).

TABLE 21

| Namd | Amino acid substitution (into FpL_C3KX 5e) | SEQ ID NO: | Remining activity |
|---|---|---|---|
| FpL_C3KX 5e | — | 186 | 55 |
| FpL_C3KX 6a | Glu4Gly, Glu(Gly)52Asp | 199 | 62 |
| FpL_C3KX 5g | Lys(Ala)7Ser, Glu(Gly)52Asp | 200 | 57 |
| FpL_C3KX 6b | Glu4Gly, Lys(Ala)7Ser | 201 | 56 |

※Alkali treatment: 25° C., 1.0M NaOH(final concentration), 15 h

Example 30 Evaluation of Immunoglobulin Elution pHs of Proteins of Present Invention The wild-type FpL_C3 (SEQ ID NO:1) prepared in Example 1; or the mutant-type (amino-acid-substituted) immunoglobulin-binding protein FpL_C3 G21R (an immunoglobulin-binding protein prepared by introducing the amino acid substitution Gly21Arg into FpL_C3; SEQ ID NO:101), FpL_C3 G51V (an immunoglobulin-binding protein prepared by introducing the amino acid substitution Gly51Val into FpL_C3; SEQ ID NO:106), FpL_C3 N62H (an immunoglobulin-binding protein prepared by introducing the amino acid substitution Asn62His into FpL_C3; SEQ ID NO:107), FpL_C3 N62R (an immunoglobulin-binding protein prepared by introducing the amino acid substitution Asn62Arg into FpL_C3; SEQ ID NO:108), FpL_C3 N62Y (an immunoglobulin-binding protein prepared by introducing the amino acid substitution Asn62Tyr into FpL_C3; SEQ ID NO:5), or FpL_C3 N62W (an immunoglobulin-binding protein prepared by introducing the amino acid substitution Asn62Trp into FpL_C3; SEQ ID NO:111) obtained in Example 12; was subjected to the following method to measure the pH at which immunoglobulin bound thereto can be eluted (hereinafter also simply referred to as "elution pH").

(1) A 50% (w/v) aqueous slurry of IgG Sepharose 6 Fast Flow (manufactured by Cytiva), which is an insoluble support to which immunoglobulin is immobilized, was prepared, and then 0.5 mL of the slurry was fed into a Tricorn 5/50 column (5-mm inner diameter×50-mm length, manufactured by Cytiva), followed by transferring pure water to the column using a pump, to prepare an IgG Sepharose-packed column.

(2) The IgG Sepharose-packed column prepared in (1) was placed in AKTA AVANT 25 (manufactured by Cytiva). The column was equilibrated with 0.1 M citrate buffer (pH 6.5) (hereinafter referred to as liquid A), and then washed with 0.1 M citrate buffer (pH 2.2) (hereinafter referred to as liquid B), followed by performing equilibration again with liquid A.

(3) To the IgG Sepharose-packed column, 100 μL of 1 g/L immunoglobulin-binding protein solution prepared with liquid A was applied, and 5 column volumes of liquid A was transferred to the column, followed by eluting the immunoglobulin-binding protein by 10 minutes of linear gradient elution from 0% to 100% liquid B. The obtained chromatogram was analyzed, and the pH at the position of elution with the highest absorbance was determined as the elution pH.

The results are shown in Table 22. It can be said that an immunoglobulin-binding protein having the same amino acid sequence as SEQ ID NO:1 except that the immunoglobulin-binding protein has one or more amino acid substitutions selected from at least Gly21Arg, Gly51Val, Asn62His, Asn62Arg, Asn62Tyr, and Asn62Trp has an improved elution pH compared to that of the wild-type FpL_C3, in other words, immunoglobulin (antibody) bound to the immunoglobulin-binding protein can be eluted under milder pH conditions.

TABLE 22

| Amino acid substitution | SEQ ID NO: | Elution pH |
|---|---|---|
| FpL_C3(wild-type) | 1 | 2.9 |
| Gly21Arg | 101 | 3.4 |
| Gly51Val | 106 | 3.4 |
| Asn62His | 107 | 3.0 |
| Asn62Arg | 108 | 3.0 |
| Asn62Tyr | 5 | 3.0 |
| Asn62Trp | 111 | 3.0 |

Example 31 Introduction of Mutations into FpL_C3KX 6a and Preparation of Library Into the polynucleotide portion (SEQ ID NO:211) encoding the immunoglobulin-binding protein in the expression vector pET-FpL_C3KX 6a prepared in Example 28, mutations were randomly introduced by error-prone PCR by the same method as in Example 2, to prepare a library. The average mutation introduction rate was 1.8%.

Example 32 Screening of FpL_C3KX 6a Amino Acid Substitution Mutants (1) The random mutant library (transformants) prepared in Example 31 was cultured by the same method as in Example 3(1) to (2), and then each culture supernatant obtained by a centrifugation operation was mixed with an equal amount of 1.0 M NaOH, followed by performing alkali treatment at 62° C. for 30 minutes.

(2) The antibody-binding activity of the immunoglobulin-binding protein subjected to the alkali treatment was measured by the ELISA method described in Example 3(4). The antibody-binding activity of the immunoglobulin-binding protein subjected to the alkali treatment was divided by the antibody-binding activity of the immunoglobulin-binding protein without the alkali treatment, to calculate the remaining activity.

(3) About 1800 strains of transformants were evaluated to select, among these, transformants expressing an immunoglobulin-binding protein having an improved alkaline stability even compared to the alkaline-stability-improved immunoglobulin-binding protein (FpL_C3KX 6a).

(4) Each selected transformant was cultured, and an expression vector was prepared therefrom using a QIAprep Spin Miniprep kit (manufactured by QIAGEN).

(5) The nucleotide sequence of the polynucleotide region encoding the immunoglobulin-binding protein inserted in the expression vector obtained was analyzed by the method described in Example 1(5), to identify the position of each amino acid mutation.

(6) Each transformant expressing an immunoglobulin-binding protein selected in (3), the transformant expressing FpL_C3 (SEQ ID NO:1) prepared in Example 1, the transformant expressing FpL_C4KR (SEQ ID NO: 117) prepared in Reference Example 1, or the transformant expressing FpL_C3KX 6a (SEQ ID NO:199) prepared in Example 28 was cultured by the same method as in Example 3(8) to (10), and a protein extract was prepared therefrom by the same method as in Example 3(11). The extract was centrifuged, and the resulting supernatant was passed through a filter for clarification.

(7) The supernatant clarified in (6) was purified by the method described in Reference Example 2(2), and a fraction corresponding to the immunoglobulin-binding protein was collected.

(8) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(9) Alkali treatment was carried out by the same method as in Example 3(13) except that the concentration of the NaOH used for the treatment was 2.0 M (final concentration, 1.0 M), and that the treatment time was 17 hours. Thereafter, the remaining activity was calculated by the same method as in Example 3(14), to evaluate the alkaline stability.

The results are shown in Table 23. It can be said that an immunoglobulin-binding protein having the same amino acid sequence as SEQ ID NO:199 except that the immunoglobulin-binding protein has one or more amino acid substitutions selected from at least Thr2Pro, Thr2Ser, Pro3Arg, Glu5Lys, Glu9Val, Glu27Lys, Glu27Ile, Glu27Val, Phe32Leu, Lys(Arg)38Ala, Asn44Ile, Ala47Thr, and Glu (Asp)52Asn has an improved alkaline stability even compared to FpL_C3KX 6a (SEQ ID NO:199), which has a higher alkaline stability than that of the wild-type FpL_C3 (SEQ ID NO: 1).

TABLE 23

| Amino acid substitution (into FpL_C3KX 6a) | SEQ ID NO: | Remaining activity [%] |
|---|---|---|
| w/o substitution(FpL_C3KX 6a) | 199 | 43 |
| Lys(Arg)38Ala | 212 | 47 |
| Phe32Leu, Ala47Thr | 213 | 49 |
| Thr2Ser | 214 | 46 |
| Glu27Lys | 215 | 49 |
| Thr2Pro, Pro3Arg, Glu9Val, Glu(Asp)52Asn | 216 | 49 |
| Glu27Ile | 217 | 45 |
| Asn44Ile | 218 | 52 |
| Glu5Lys, Asn44Ile | 219 | 52 |
| Pro3Arg | 220 | 55 |
| Glu5Lys | 221 | 54 |
| Glu27Val | 222 | 51 |
| FpL_C4KR | 117 | 15 |
| FpL_C3(wild-type) | 1 | 6 |

※Alkali treatment: 25° C., 1.0M NaOH(final concentration), 17 h

Example 33 Evaluation of Elution Property of FpL_C3KX 6a Amino Acid Substitution Mutant (1) Transformants each of which expresses FpL_C3 (SEQ ID NO: 1) prepared in Example 1 or FpL_C3KX 6a E27V (a protein prepared by introducing the amino acid substitution Glu27Val into FpL_C3KX 6a; SEQ ID NO:222) obtained in Example 32 were cultured by the same method as in Example 3(8) to (10), and protein extracts were prepared therefrom by the same method as in Example 3(11). Each extract was centrifuged, and the resulting supernatant was passed through a filter for clarification.

(2) The supernatant clarified in (1) was purified by the method described in Reference Example 2(2), and a fraction corresponding to the immunoglobulin-binding protein was collected.

(3) The absorbance of the collected fraction was measured with a spectrophotometer, to quantify each mutant-type immunoglobulin-binding protein contained in the fraction. Further, SDS-PAGE was carried out to confirm that each mutant-type immunoglobulin-binding protein was purified with high purity.

(4) The acid elution property of the mutant-type immunoglobulin-binding protein from the human immunoglobulin κ light chain was measured by the following ELISA method, to evaluate an effect of the amino acid substitution on the acid elution property.

(4-1) Herceptin (manufactured by Chugai Pharmaceutical Co., Ltd.) prepared as a 10 μg/mL solution using TBS was dispensed into wells of a 96-well microplate, followed by immobilization (4° C., 16 hours). Thereafter, blocking was carried out using 2% (w/v) skim milk (manufactured by Becton Dickinson) prepared with TBS.

(4-2) Each well of the 96-well microplate was washed with washing buffer A (0.05 M Tris buffer (pH 7.5) containing 0.15 M NaCl and 0.05% (w/v) Tween 20 (trade name)), and a solution containing the immunoglobulin-binding protein to be evaluated for its antibody-binding activity, after dilution to 2 μg/mL, was added thereto, followed by reacting the immunoglobulin-binding protein with the immobilized monoclonal antibody (30° C., 1 hour).

(4-3) After completion of the reaction, the wells were washed with washing buffer A, and 100 μL/well of 0.05 M citric acid solution (pH 2.7) was added to some of the wells to dissociate the immunoglobulin-binding protein (25° C. for 2 min).

(4-4) The wells were washed with washing buffer A, and 100 μL/well of Anti-6-His Antibody (manufactured by BETHYL LABORATORIES) diluted to 100 ng/mL was added thereto, followed by allowing the reaction to proceed (30° C., 1 hour).

(4-5) Thereafter, the wells were washed with washing buffer A, and 50 μL/well of TMB Peroxidase Substrate (manufactured by KPL) was added thereto. Subsequently, 50 μL/well of 1 M phosphoric acid was added to stop the reaction, and the absorbance was measured at 450 nm using a microplate reader (manufactured by TECAN).

(4-6) Based on the absorbance ratio between each well in which the immunoglobulin-binding protein was dissociated using the citric acid solution in (4-3) and each well without the dissociation, the acid elution rate (the higher the value, the better the acid elution property) of the mutant-type immunoglobulin-binding protein for the monoclonal antibody was evaluated.

The results are shown in Table 24. It can be said that FpL_C3KX 6a E27V (SEQ ID NO:222) more easily allows the acid elution compared to FpL_C3 (SEQ ID NO:1).

TABLE 24

| Name | SEQ ID NO: | Eluion rate [%] |
|---|---|---|
| FpL__C3(wild-type) | 1 | 76 |
| FpL__C3KX 6a__E27V | 222 | 84 |

※Acid elution treatment: 50 mM Sodium citrate, pH 2.7, 2 min

Example 34 Preparation of FpL_C3KX 6a Arginine Substitution Mutants

The three kinds of FpL_C3KX 6a arginine substitution mutants shown in the following (y) to (aa) were designed and prepared.

(y) A protein (SEQ ID NO:223; which was named FpL_C3KX 7a) prepared by introducing the amino acid substitution Glu5Arg into FpL_C3KX 6a (z) A protein (SEQ ID NO:224; which was named FpL_C3KX 7b) prepared by introducing the amino acid substitution Glu27Arg into FpL_C3KX 6a (aa) A protein (SEQ ID NO:225; which was named FpL_C3KX 7c) prepared by introducing the amino acid substitution Ala47Arg into FpL_C3KX 6a The methods of the preparation of the three kinds of immunoglobulin-binding proteins shown in (y), (z), and (aa) are described below.

(y) FpL_C3KX 7a (y-1) Mutagenesis using inverse PCR was carried out to prepare a polynucleotide containing a nucleotide sequence encoding FpL_C3KX 7a (SEQ ID NO:223). The inverse PCR was carried out by the same method as in Example 7(2) (a-1) except that an expression vector (hereinafter also referred to as "pET-FpL_C3KX 6a") containing a polynucleotide (SEQ ID NO:211) encoding FpL_C3KX 6a (SEQ ID NO:199) was used as a template DNA, that the oligonucleotide of SEQ ID NO:226 was used as a PCR Forward Primer, and that the oligonucleotide of SEQ ID NO:227 was used as a PCR Reverse Primer.

(y-2) The polynucleotide obtained was purified, and then treated with the restriction enzyme DpnI, followed by transforming the *Escherichia coli* BL21 (DE3) strain using the restriction enzyme-treated product.

(y-3) The transformant obtained was subjected to culturing and extraction of an expression vector (which was named pET-FpL_C3KX 7a) by the same method as in Example 7(2) (a-3). The nucleotide sequence of the expression vector was analyzed by the same method as in Example 1(5).

As a result of the sequence analysis, it could be confirmed that the expression vector pET-FpL_C3KX 7a contains a polynucleotide encoding FpL_C3KX 7a (SEQ ID NO:223) inserted therein.

(z) FpL_C3KX 7b (z-1) Mutagenesis using inverse PCR was carried out to prepare a polynucleotide containing a nucleotide sequence encoding FpL_C3KX 7b (SEQ ID NO:224). The inverse PCR was carried out by the same method as in Example 7(2) (a-1) except that pET-FpL_C3KX 6a was used as a template DNA, that the oligonucleotide of SEQ ID NO:228 was used as a PCR Forward Primer, and that the oligonucleotide of SEQ ID NO:229 was used as a PCR Reverse Primer.

(z-2) The polynucleotide obtained was purified, and then treated with the restriction enzyme DpnI, followed by transforming the *Escherichia coli* BL21 (DE3) strain using the restriction enzyme-treated product.

(z-3) The transformant obtained was subjected to culturing and extraction of an expression vector (which was named pET-FpL_C3KX 7b) by the same method as in Example 7(2) (a-3). The nucleotide sequence of the expression vector was analyzed by the same method as in Example 1(5).

As a result of the sequence analysis, it could be confirmed that the expression vector pET-FpL_C3KX 7b contains a polynucleotide encoding FpL_C3KX 7b (SEQ ID NO:224) inserted therein.

(aa) FpL_C3KX 7c (aa-1) Mutagenesis using inverse PCR was carried out to prepare a polynucleotide containing a nucleotide sequence encoding FpL_C3KX 7c (SEQ ID NO:225). The inverse PCR was carried out by the same method as in Example 7(2) (a-1) except that pET-FpL_C3KX 6a was used as a template DNA, that the oligonucleotide of SEQ ID NO:230 was used as a PCR Forward Primer, and that the oligonucleotide of SEQ ID NO:231 was used as a PCR Reverse Primer.

(aa-2) The polynucleotide obtained was purified, and then treated with the restriction enzyme DpnI, followed by transforming the *Escherichia coli* BL21 (DE3) strain using the restriction enzyme-treated product.

(aa-3) The transformant obtained was subjected to culturing and extraction of an expression vector (which was named pET-FpL_C3KX 7c) by the same method as in Example 7(2) (a-3). The nucleotide sequence of the expression vector was analyzed by the same method as in Example 1(5).

As a result of the sequence analysis, it could be confirmed that the expression vector pET-FpL_C3KX 7c contains a polynucleotide encoding FpL_C3KX 7c (SEQ ID NO:225) inserted therein.

Example 35 Evaluation of Alkaline Stabilities of FpL_C3KX 6a Arginine Substitution Mutants (1) Transformants each of which expresses one of FpL_C3KX 6a (SEQ ID NO:199) prepared in Example 28, and FpL_C3KX 7a (SEQ ID NO:223), FpL_C3KX 7b (SEQ ID NO:224), and FpL_C3KX 7c (SEQ ID NO:225) prepared in Example 34 were cultured by the same method as in Example 3(8) to (10), and protein extracts were prepared therefrom by the same method as in Example 3(11). Each extract was centrifuged, and the resulting supernatant was passed through a filter for clarification.

(2) The supernatant clarified in (1) was purified by the method described in Reference Example 2(2), and a fraction corresponding to the immunoglobulin-binding protein was collected.

(3) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(4) Alkali treatment was carried out by the same method as in Example 3(13) except that the concentration of the NaOH used for the treatment was 1.0 M (final concentration, 0.5 M), that the treatment temperature was 25° C., and that the treatment time was 14 hours. Thereafter, the remaining activity was calculated by the same method as in Example 3(14), to evaluate the alkaline stability.

The results are shown in Table 25. It can be said that FpL_C3KX 7a (SEQ ID NO:223), FpL_C3KX 7b (SEQ ID NO:224), and FpL_C3KX 7c (SEQ ID NO:225) have improved alkaline stabilities even compared to FpL_C3KX 6a (SEQ ID NO:199), which has a higher alkaline stability than that of the wild-type FpL_C3 (SEQ ID NO:1). In particular, FpL_C3KX 7b showed remarkable improvement in the alkaline stability (FpL_C3KX 6a: 52%, FpL_C3KX 7b: 70%).

TABLE 25

| Name | Amino acid substitution (into FpL_C3KX 6a) | SEQ ID NO: | Remaining activity [%] |
|---|---|---|---|
| FpL_C3KX 6a | — | 199 | 52 |
| FpL_C3KX 7a | Glu5Arg | 223 | 53 |
| FpL_C3KX 7b | Glu27Arg | 224 | 70 |
| FpL_C3KX 7c | Ala47Arg | 225 | 54 |

※ Alkali treatment: 25° C., 0.5M NaOH(final concentration), 14 h

Example 36 Evaluation of Elution Properties of FpL_C3KX 6a Arginine Substitution Mutants (1) Transformants each of which expresses one of FpL_C3KX 6a (SEQ ID NO:199) prepared in Example 28, FpL_C3KX 6a E27V (SEQ ID NO:222) obtained in Example 32, and FpL_C3KX 7b (SEQ ID NO:224) and FpL_C3KX 7c (SEQ ID NO:225) prepared in Example 34 were cultured by the same method as in Example 3(8) to (10), and protein extracts were prepared therefrom by the same method as in Example 3(11). Each extract was centrifuged, and the resulting supernatant was passed through a filter for clarification.

(2) The supernatant clarified in (1) was purified by the method described in Reference Example 2(2), and a fraction corresponding to the immunoglobulin-binding protein was collected.

(3) The absorbance of the collected fraction was measured with a spectrophotometer, to quantify each mutant-type immunoglobulin-binding protein contained in the fraction. Further, SDS-PAGE was carried out to confirm that each mutant-type immunoglobulin-binding protein was purified with high purity.

(4) The acid elution rate of the mutant-type immunoglobulin-binding protein was evaluated by the same method as in example 33(4) except that the pH of the 0.05 M citric acid solution used was 2.4.

The results are shown in Table 26. It can be seen that FpL_C3KX 7b (SEQ ID NO:224) and FpL_C3KX 7c (SEQ ID NO:225), which are arginine substitution mutants of FpL_C3KX 6a, have improved acid elution properties even compared to FpL_KX6a E27V (SEQ ID NO:222), which has a higher acid elution property than that of the wild-type FpL_C3 (SEQ ID NO: 1). In particular, FpL_C3KX 7b showed remarkable improvement in the acid elution property (FpL_C3KX 6a E27V: 53%, FpL_C3KX 7b: 61%).

TABLE 26

| Name | Amino acid substitution (into FpL_C3KX 6a) | SEQ ID NO: | Eluiton rate [%] |
|---|---|---|---|
| FpL_C3KX 6a | — | 199 | 25 |
| FpL_C3KX 6a E27V | Glu27Val | 222 | 53 |
| FpL_C3KX 7b | Glu27Arg | 224 | 61 |
| FpL_C3KX 7c | Ala47Arg | 225 | 59 |

※ Acid elution treatment: 50 mM Sodium citrate, pH 2.4, 2 min

Example 37 Evaluation of Immunoglobulin κ Light Chain-Binding Capacities of Immunoglobulin-Binding Proteins (Part 2)

An effect of introduction of the amino acid substitution Pro6Ser on the human immunoglobulin κ light chain-binding activity was evaluated. More specifically, an immunoglobulin-binding protein was prepared by introducing the amino acid substitution Pro6Ser into FpL_C3KX 5e (SEQ ID NO: 186), and the prepared immunoglobulin-binding protein was evaluated.

(1) Mutagenesis using inverse PCR was carried out to prepare a polynucleotide containing a nucleotide sequence encoding an immunoglobulin-binding protein (which was named FpL_C3KX_5e_P6S; SEQ ID NO:236) which is the same as FpL_C3KX 5e (SEQ ID NO:186) except that the amino acid substitution Pro6Ser is introduced. The inverse PCR was carried out by the same method as in Example 7(2) (a-1) except that pET-FpL_C3KX 5e was used as a template DNA, that the oligonucleotide of SEQ ID NO:234 was used as a PCR Forward Primer, and that the oligonucleotide of SEQ ID NO:235 was used as a PCR Reverse Primer.

(2) The polynucleotide obtained was purified, and then treated with the restriction enzyme DpnI, followed by transforming the *Escherichia coli* BL21 (DE3) strain using the restriction enzyme-treated product.

(3) The transformant obtained was subjected to culturing and extraction of an expression vector (which was named pET-FpL_C3KX_5e_P6S) by the same method as in Example 7(2) (a-3). The nucleotide sequence of the expression vector was analyzed by the same method as in Example 1(5). As a result of the sequence analysis, it could be confirmed that the expression vector pET-FpL_C3KX_5e_P6S contains a polynucleotide encoding FpL_C3KX_5e_P6S (SEQ ID NO:236) inserted therein.

(4) Transformants each of which expresses FpL_C3KX_5e_P6S (SEQ ID NO:236) obtained in (2) or FpL_C3KX 5e (SEQ ID NO:186) prepared in Example 24 were cultured by the same method as in Example 3(8) to (10), and protein extracts were prepared therefrom by the same method as in Example 3(11). Each extract was centrifuged, and the resulting supernatant was passed through a filter for clarification.

(5) The supernatant clarified in (4) was purified by the method described in Reference Example 2(2), and a fraction corresponding to the immunoglobulin-binding protein was collected.

(6) The absorbance of the collected fraction was measured with a spectrophotometer, to quantify each mutant-type immunoglobulin-binding protein contained in the fraction. Further, SDS-PAGE was carried out to confirm that each mutant-type immunoglobulin-binding protein was purified with high purity.

(7) The human immunoglobulin κ light chain-binding activity of each immunoglobulin-binding protein was measured by the same method as in Example 21(4), to evaluate an effect of the amino acid substitution on the human immunoglobulin κ light chain-binding activity. For the evaluation of the binding activity, one of the following polyclonal antibodies was used:

a herceptin containing human κ light chain subgroup 1 (Vκ 1) (manufactured by Chugai Pharmaceutical Co., Ltd.); and a human CTLA4 antibody containing human κ light chain subgroup 3 (Vκ3) (manufactured by R&D Systems).

Reference Example 3

An effect of introduction of the amino acid substitution Lys38Glu on the human immunoglobulin κ light chain-binding activity was evaluated. More specifically, an immunoglobulin-binding protein was prepared by introducing the amino acid substitution Lys(Arg)38Glu into FpL_C3KR (SEQ ID NO: 116), and the prepared immunoglobulin-binding protein was evaluated.

(1) Mutagenesis using inverse PCR was carried out to prepare a polynucleotide containing a nucleotide sequence encoding an immunoglobulin-binding protein (which was named FpL_C3KR_K38E; SEQ ID NO:239) which is the same as FpL_C3KR (SEQ ID NO:116) except that the amino acid substitution Lys(Arg)38Glu is introduced. The inverse PCR was carried out by the same method as in Example 7(2) (a-1) except that pET-FpL_C3KR was used as a template DNA, that the oligonucleotide of SEQ ID NO:237 was used as a PCR Forward Primer, and that the oligonucleotide of SEQ ID NO:238 was used as a PCR Reverse Primer.

(2) The polynucleotide obtained was purified, and then treated with the restriction enzyme DpnI, followed by transforming the *Escherichia coli* BL21 (DE3) strain using the restriction enzyme-treated product.

(3) The transformant obtained in (2) was subjected to culturing and extraction of an expression vector (which was named pET-FpL_C3KX 5e_K38E) by the same method as in Example 7(2) (a-3). The nucleotide sequence of the expression vector was analyzed by the same method as in Example 1(5). As a result of the sequence analysis, it could be confirmed that the expression vector pET-FpL_C3KR_K38E contains a polynucleotide encoding FpL_C3KR_K38E (SEQ ID NO:239) inserted therein.

(4) Transformants each of which expresses FpL_C3KR_K38E (SEQ ID NO:239) obtained in (2) or FpL_C3KR (SEQ ID NO:116) prepared in Reference Example 1 were cultured by the same method as in Example 3(8) to (10), and protein extracts were prepared therefrom by the same method as in Example 3(11). Each extract was centrifuged, and the resulting supernatant was passed through a filter for clarification.

(5) The supernatant clarified in (4) was purified by the method described in Reference Example 2(2), and a fraction corresponding to the immunoglobulin-binding protein was collected.

(6) The absorbance of the collected fraction was measured with a spectrophotometer, to quantify each mutant-type immunoglobulin-binding protein contained in the fraction. Further, SDS-PAGE was carried out to confirm that each mutant-type immunoglobulin-binding protein was purified with high purity.

(7) The human immunoglobulin κ light chain-binding activity of each immunoglobulin-binding protein was measured by the same method as in Example 37(7), to evaluate an effect of the amino acid substitution on the human immunoglobulin κ light chain-binding activity.

The results of both Example 37 and Reference Example 3 are shown in Table 27. It can be seen that a binding ability to VK3 can be given by introducing the amino acid substitution Pro6Ser (Example 37) or Lys(Arg)38Glu (Reference Example 3).

TABLE 27

| Name | SEQ ID NO: | Polyclonal antibody-binding activity (abs@450 nm) Herceptin (Vκ1) | Human CTLA4 (Vκ3) |
|---|---|---|---|
| Example 37 | | | |
| FpL_C3KX 5e | 186 | 0.96 | 0.06 |
| FpL_C3KX 5e_P6S | 236 | 0.98 | 0.78 |
| Reference Example 3 | | | |
| FpL_C3KR | 116 | 0.86 | 0.07 |
| FpL_C3KR_K38E | 239 | 1.02 | 0.98 |

Example 38 Preparation of FpL_C3KX 5e Amino Acid Substitution-Integrated Mutants (Part 2)

An amino acid substitution that gives a Vκ3-binding ability described above and amino acid substitutions found to be responsible for the improvement of the alkaline stability of the immunoglobulin-binding protein in Example 27 were integrated into FpL_C3KX 5e. More specifically, the immunoglobulin-binding protein shown in the following (ab) was designed and prepared.

(ab) A Protein (SEQ ID NO:240; which was Named FpL_C3KX 7d) Prepared by Introducing the Amino Acid Substitutions Glu4Gly, Lys(Arg)38Glu, and Glu(Gly)52Asp into FpL_C3KX 5e (ab-1) A polynucleotide (SEQ ID NO:241) encoding FpL_C3KX 7d (SEQ ID NO:240) was synthesized. In the synthesis, a recognition sequence for the restriction enzyme NcoI (5'-CCATGG-3') was added to the 5'-end side, and a nucleotide sequence encoding six histidine residues (SEQ ID NO:232), a stop codon, and a recognition sequence for the restriction enzyme HindIII (5'-AAGCTT-3') were added to the 3'-end side.

(ab-2) By the same method as in Example 1(2), the polynucleotide synthesized in (ab-1) was purified.

(ab-3) By the same method as in Example 1(3), the polynucleotide obtained in (ab-2) was ligated to the plasmid pET-26b, which had been preliminarily digested with the restriction enzymes NcoI and HindIII, and then the resulting ligation product was used to transform the *Escherichia coli* BL21 (DE3) strain, followed by culturing the resulting transformant.

(ab-4) The transformant obtained was subjected to culturing and plasmid purification by the same method as in Example 1(4), to obtain an expression vector (which was named pET-FpL_C3KX 7d). The nucleotide sequence of the expression vector was analyzed by the same method as in Example 1(5).

As a result of the sequence analysis, it could be confirmed that the expression vector pET-FpL_C3KX 7d contains a polynucleotide (SEQ ID NO:241) encoding FpL_C3KX 7d (SEQ ID NO:240) inserted therein.

Example 39 Evaluation of Alkaline Stabilities of FpL_C3KX 5e Amino Acid Substitution-Integrated Mutants (Part 2)

(1) Transformants each of which expresses FpL_C3KX 5e (SEQ ID NO:186) prepared in Example 24 or FpL_C3KX 7d (SEQ ID NO:240) prepared in Example 38 were cultured by the same method as in Example 3(8) to (10), and protein extracts were prepared therefrom by the method described in Example 3(11). Each extract was centrifuged, and the resulting supernatant was passed through a filter for clarification.

(2) The supernatant clarified in (1) was purified by the method described in Reference Example 2(2), and a fraction corresponding to the immunoglobulin-binding protein was collected.

(3) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(4) Alkali treatment was carried out by the same method as in Example 3(13) except that the concentration of the NaOH used for the treatment was 1.0 M (final concentration, 0.5 M), and that the treatment time was 15 hours. Thereafter, the remaining activity was calculated by the same method as in Example 3(14), to evaluate the alkaline stability.

The results are shown in Table 28. It can be said that FpL_C3KX 7d (SEQ ID NO:240), evaluated in the present Example, has an improved alkaline stability even compared to FpL_C3KX 5e (SEQ ID NO:186), which has a higher alkaline stability than that of the wild-type FpL_C3 (SEQ ID NO: 1).

TABLE 28

| Name | Amino acid substitution (into FpL_C3KX 5e) | SEQ ID NO: | Remaining activity [%] |
|---|---|---|---|
| FpL_C3KX 5e | — | 186 | 54 |
| FpL_C3KX 7d | Glu4Gly, Pro6Ser, Lys(Arg)38Glu, Glu(Gly)52Asp | 240 | 59 |

※ Alkali treatment: 25° C., 0.5M NaOH(final concentration), 15 h

Example 40 Introduction of Mutations into FpL_C3KX 7d and Preparation of Library (Part 1)

Into the polynucleotide portion (SEQ ID NO:241) encoding the immunoglobulin-binding protein in the expression vector pET-FpL_C3KX 7d, which was prepared in Example 38 and expresses FpL_C3KX 7d (SEQ ID NO:240), mutations were randomly introduced by error-prone PCR by the same method as in Example 2, to prepare a library. The average mutation introduction rate was 1.9%.

Example 41 Screening of FpL_C3KX 7d Amino Acid Substitution Mutants (Part 1)

(1) pET-FpL_C3KX 7d (transformant) prepared in Example 38 and the random mutant library (transformants) prepared in Example 40 were cultured by the same method as in Example 3(1) to (2).

(2) Thereafter, each culture supernatant obtained by a centrifugation operation was mixed with an equal amount of 1.0 M NaOH, and then subjected to alkali treatment at 58° C. for 30 minutes.

(3) The antibody-binding activity of the immunoglobulin-binding protein subjected to the alkali treatment was measured by the ELISA method described in Example 3(4). The antibody-binding activity of the immunoglobulin-binding protein subjected to the alkali treatment was divided by the antibody-binding activity of the immunoglobulin-binding protein without the alkali treatment, to calculate the remaining activity.

(4) About 1000 strains of transformants were evaluated to select, among these, transformants expressing an immunoglobulin-binding protein having an improved alkaline stability compared to FpL_C3KX 7d (SEQ ID NO:240).

(5) Each selected transformant was cultured, and an expression vector was prepared therefrom using a QIAprep Spin Miniprep kit (manufactured by QIAGEN).

(6) The nucleotide sequence of the polynucleotide region encoding the immunoglobulin-binding protein inserted in the expression vector obtained was analyzed by the method described in Example 1(5), to identify the position of each amino acid mutation.

(7) Each transformant expressing an immunoglobulin-binding protein selected in (4) or the transformant expressing FpL_C3KX 7d (SEQ ID NO:240) prepared in Example 38 was cultured by the same method as in Example 3(8) to (10), and a protein extract was prepared therefrom by the same method as in Example 3(11). The extract was centrifuged, and the resulting supernatant was passed through a filter for clarification.

(8) The supernatant clarified in (7) was purified by the method described in Reference Example 2(2), and a fraction corresponding to the immunoglobulin-binding protein was collected.

(9) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(10) Alkali treatment was carried out by the same method as in Example 3(13) except that the concentration of the NaOH used for the treatment was 1.0 M (final concentration, 0.5 M), and that the treatment time was 15 hours. Thereafter, the remaining activity was calculated by the same method as in Example 3(14), to evaluate the alkaline stability.

The results are shown in Table 29. It can be said that an immunoglobulin-binding protein having the same amino acid sequence as SEQ ID NO:240 except that the immunoglobulin-binding protein has one or more amino acid substitutions selected from at least Glu8Val, Lys(Ile)29Phe, Glu33Val, and Ala69Val has an improved alkaline stability even compared to FpL_C3KX 7d (SEQ ID NO:240), which has a higher alkaline stability than that of the wild-type FpL_C3 (SEQ ID NO:1).

TABLE 29

| Amino acid substitution | SEQ ID NO: | Remaining activity [%] |
|---|---|---|
| w/o substitution(FpL_C3KX 7d) | 240 | 80 |
| Ala69Val | 242 | 82 |
| Lys(Ile)29Phe | 243 | 93 |
| Glu8Gly, Glu33Val | 244 | 85 |

※ Alkali treatment: 25° C., 0.5M NaOH(final concentration), 15 h

Example 42 Introduction of Mutations into FpL_C3KX 7d and Preparation of Library (Part 2)

(1) The expression vector pET-FpL_C3KX 7d, which was prepared in Example 38, was used as a template to prepare a saturation substitution mutant library for the amino acid residues at positions 23, 41, and 52. Primers were designed similarly to Example 11(1) according to the 22c-trick method such that appropriate mixed bases could be placed at the mutation introduction sites, and such that inverse PCR could be carried out focusing on the mutation introduction sites (SEQ ID NOs:245 to 250, 252 to 257, and 260 to 265).

These primers were mixed to provide a combination of six primers for each substitution site according to the compositions shown in Table 7 and Table 30, to prepare PCR primer mixtures (Forward/Reverse primer mix).

TABLE 30

| | Position of amino acid substitution | | |
|---|---|---|---|
| | Ile23 | Ala41 | Glu52 |
| Forward primer 1 | 245 | 252 | 260 |
| Forward primer 2 | 246 | 253 | 261 |
| Forward primer 3 | 247 | 254 | 262 |
| Reverse primer 1 | 248 | 255 | 263 |
| Reverse primer 2 | 249 | 256 | 264 |
| Reverse primer 3 | 250 | 257 | 265 |

(2) Site-directed mutagenesis by inverse PCR was carried out by the same method as in Example 11(2) except that pET-FpL_C3KX 7d was used as a template DNA.

(3) After purification of the PCR product obtained, the *Escherichia coli* BL21 (DE3) strain was transformed using the reaction liquid, and then cultured (37° C., 16 hours) on LB plate medium supplemented with 50 μg/mL kanamycin. The resulting colonies, formed on the plate, were provided as a site-directed mutant library.

Example 43 Screening of FpL_C3KX 7d Amino Acid Substitution Mutants (Part 2)

(1) pET-FpL_C3KX 7d (transformant) prepared in Example 38 and the site-directed amino acid substitution mutant library (transformants) prepared in Example 42 were cultured by the same method as in Example 3(1) to (2), and each culture supernatant obtained by a centrifugation operation was subjected to the alkali treatment described in Example 41(2).

(2) The antibody-binding activity of the immunoglobulin-binding protein subjected to the alkali treatment was measured by the ELISA method described in Example 3(4). The antibody-binding activity of the immunoglobulin-binding protein subjected to the alkali treatment was divided by the antibody-binding activity of the immunoglobulin-binding protein without the alkali treatment, to calculate the remaining activity.

(3) About 300 strains of transformants were evaluated to select, among these, transformants expressing an immunoglobulin-binding protein having an improved alkaline stability compared to FpL_C3KX 7d (SEQ ID NO:240).

(4) Each selected transformant was cultured, and an expression vector was prepared therefrom using a QIAprep Spin Miniprep kit (manufactured by QIAGEN).

(5) The nucleotide sequence of the polynucleotide region encoding the immunoglobulin-binding protein inserted in the expression vector obtained was analyzed by the method described in Example 1(5), to identify the position of each amino acid mutation.

(6) Each transformant expressing an immunoglobulin-binding protein selected in (3) or the transformant expressing FpL_C3KX 7d (SEQ ID NO:240) prepared in Example 38 was cultured by the same method as in Example 3(8) to (10), and a protein extract was prepared therefrom by the same method as in Example 3(11). The extract was centrifuged, and the resulting supernatant was passed through a filter for clarification.

(7) The supernatant clarified in (6) was purified by the method described in Reference Example 2(2), and a fraction corresponding to the immunoglobulin-binding protein was collected.

(8) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(9) Alkali treatment was carried out by the same method as in Example 3(13) except that the concentration of the NaOH used for the treatment was 1.0 M (final concentration, 0.5 M), and that the treatment time was 15 hours. Thereafter, the remaining activity was calculated by the same method as in Example 3(14), to evaluate the alkaline stability.

The results are shown in Table 31. It can be said that an immunoglobulin-binding protein having the same amino acid sequence as SEQ ID NO:240 except that the immunoglobulin-binding protein has at least the amino acid substitutions Ile23Arg, Ala41Ile, Ala41Tyr, Glu(Gly,Asp) 52Leu (this expression represents the fact that the amino acid residue corresponding to the glutamic acid at position [7] 52 of SEQ ID NO:1 is once substituted with glycine, and then substituted with aspartic acid, further followed by substitution with leucine; the same applies hereinafter), and Glu (Gly,Asp) 52Val has an improved alkaline stability even compared to FpL_C3KX 7d (SEQ ID NO:240), which has a higher alkaline stability than that of the wild-type FpL_C3 (SEQ ID NO:1).

TABLE 31

| Amino acid substitution | SEQ ID NO: | Remaining activity [%] |
|---|---|---|
| w/o substitution(FpL_C3KX 7d) | 240 | 85 |
| Ile23Arg | 251 | 86 |
| Ala41Ile | 258 | 86 |
| Ala41Tyr | 259 | 88 |
| Glu(Gly, Asp)52Leu | 266 | 86 |
| Glu(Gly, Asp)52Val | 267 | 86 |

※Alkali treatment: 25° C., 0.5M NaOH(final concentration), 15 h

Example 44 Preparation of FpL_C3KX 7d Amino Acid Substitution-Integrated Mutants (1) Design of FpL_C3KX 7d Amino Acid Substitution-Integrated Mutants Combinations of the amino acid substitutions found to be responsible for the improvement of the alkaline stability of the immunoglobulin-binding protein in Examples 41 and 43 were integrated into FpL_C3KX 7d (SEQ ID NO:240) in an attempt to further improve the alkaline stability. More specifically, the two kinds of immunoglobulin-binding proteins shown in the following (ac) to (ad) were designed and prepared.

(ac) A protein (SEQ ID NO:271; which was named FpL_C3KX 8a) prepared by introducing the amino acid substitutions Glu(Gly,Asp)52Val and Ala69Val into FpL_C3KX 7d (ad) A protein (SEQ ID NO:274; which was named FpL_C3KX 8b) prepared by introducing the amino acid substitutions Glu(Gly,Asp)52Leu and Ala69Val into FpL_C3KX 7d (2) Preparation of FpL_C3KX 7d Amino Acid Substitution-Integrated Mutants The methods of the preparation of the two kinds of immunoglobulin-binding proteins shown in (ac) to (ad) are described below.

(ac) FpL_C3KX 8a (ac-1) Mutagenesis using inverse PCR was carried out to prepare a polynucleotide containing a nucleotide sequence encoding FpL_C3KX 8a (SEQ ID NO:271). The inverse PCR was carried out by the same method as in Example 7(2) (a-1) except that an expression vector (hereinafter also referred to as "pET-FpL_C3KX 7d_A69V") containing a polynucleotide (SEQ ID NO:268) encoding FpL_C3KX 7d_A69V (an immunoglobulin-binding protein prepared by introducing the amino acid substitution Ala69Val into FpL_C3KX 7d; SEQ ID NO:242) was used as a template DNA, that the oligonucleotide of SEQ ID NO:269 was used as a PCR Forward Primer, and that the oligonucleotide of SEQ ID NO:270 was used as a PCR Reverse Primer.

(ac-2) The polynucleotide obtained was purified, and then treated with the restriction enzyme DpnI, followed by transforming the *Escherichia coli* BL21 (DE3) strain using the restriction enzyme-treated product.

(ac-3) The transformant obtained was subjected to culturing and extraction of an expression vector (which was named pET-FpL_C3KX 8a) by the same method as in Example 7(2) (a-3). The nucleotide sequence of the expression vector was analyzed by the same method as in Example 1(5).

As a result of the sequence analysis, it could be confirmed that the expression vector pET-FpL_C3KX 8a contains a polynucleotide encoding FpL_C3KX 8a (SEQ ID NO:271) inserted therein.

(ad) FpL_C3KX 8b (ad-1) Mutagenesis using inverse PCR was carried out to prepare a polynucleotide containing a nucleotide sequence encoding FpL_C3KX 8b (SEQ ID NO:274). The inverse PCR was carried out by the same method as in Example 7(2) (a-1) except that pET-FpL_C3KX8a_A69V was used as a template DNA, that the oligonucleotide of SEQ ID NO:272 was used as a PCR Forward Primer, and that the oligonucleotide of SEQ ID NO:273 was used as a PCR Reverse Primer.

(ad-2) The polynucleotide obtained was purified, and then treated with the restriction enzyme DpnI, followed by transforming the *Escherichia coli* BL21 (DE3) strain using the restriction enzyme-treated product.

(ad-3) The transformant obtained was subjected to culturing and extraction of an expression vector (which was named pET-FpL_C3KX 8b) by the same method as in Example 7(2) (a-3). The nucleotide sequence of the expression vector was analyzed by the same method as in Example 1(5).

As a result of the sequence analysis, it could be confirmed that the expression vector pET-FpL_C3KX 8b contains a polynucleotide encoding FpL_C3KX 8b (SEQ ID NO:274) inserted therein.

Example 45 Evaluation of Alkaline Stabilities of FpL_C3KX 7d Amino Acid Substitution-Integrated Mutants (1) Transformants each of which expresses one of FpL_C3KX 7d_A69V (SEQ ID NO: 242) obtained in Example 42, and FpL_C3KX 8a (SEQ ID NO:271) and FpL_C3KX8b (SEQ ID NO:274) prepared in Example 44 were cultured by the same method as in Example 3 (8) to (10), and protein extracts were prepared therefrom by the method described in Example 3 (11). Each extract was centrifuged, and the resulting supernatant was passed through a filter for clarification.

(2) The supernatant clarified in (1) was purified by the method described in Reference Example 2(2), and a fraction corresponding to the immunoglobulin-binding protein was collected.

(3) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(4) Alkali treatment was carried out by the same method as in Example 3(13) except that the concentration of the NaOH used for the treatment was 1.0 M (final concentration, 0.5 M), and that the treatment time was 15 hours. Thereafter, the remaining activity was calculated by the same method as in Example 3(14), to evaluate the alkaline stability.

The results are shown in Table 32. It can be said that FpL_C3KX 8a (SEQ ID NO:271) and FpL_C3KX 8b (SEQ ID NO:274) have improved alkaline stabilities even compared to FpL_C3KX 7d_A69V (SEQ ID NO:242), which has a higher alkaline stability than that of the wild-type FpL_C3 (SEQ ID NO: 1).

TABLE 32

| Name | Amino acid substitution (into FpL_C3KX 7d) | SEQ ID NO: | Remaining activity [%] |
|---|---|---|---|
| FpL_C3KX 7d_A69V | Ala69Val | 242 | 75 |
| FpL_C3KX 8a | Ala69Val, Glu(Gly, Asp)52Val | 271 | 81 |
| FpL_C3KX 8b | Ala69Val, Glu(Gly, Asp)52Leu | 274 | 88 |

※ Alkali treatment: 25° C., 0.5M NaOH(final concentration), 15 h

Example 46 Introduction of Mutations into Immunoglobulin-Binding Protein of Present Invention and Preparation of Library Into a polynucleotide (SEQ ID NO:276) encoding FpL_C3KX 7e, which is an immunoglobulin-binding protein of an aspect of the present invention having the amino acid sequence of SEQ ID NO:275, mutations were randomly introduced by error-prone PCR by the same method as in Example 2, to prepare a library. The average mutation introduction rate was 1.0%. FpL_C3KX 7e is an immunoglobulin-binding protein prepared by introducing the amino acid substitutions Glu4Gly, Pro6Ser, Lys7Ala, Lys13Arg, Lys22Arg, Lys29Ile, Lys29Glu, Lys48Arg, Glu49Asp, Asn50Tyr, Tyr53Phe, Asn62Tyr, Lys67Arg, and Ala69Val to the wild-type FpL_C3 (SEQ ID NO:1).

Example 47 Screening of FpL_C3KX 7e Amino Acid Substitution Mutants (1) A transformant capable of expressing FpL_C3KX 7e and the random mutant library (transformants) prepared in Example 46 were cultured by the same method as in Example 3(1) to (2), and then each culture supernatant obtained by a centrifugation operation was subjected to the alkali treatment described in Example 41(2).

(2) The antibody-binding activity of the immunoglobulin-binding protein subjected to the alkali treatment was measured by the ELISA method described in Example 3(4). The antibody-binding activity of the immunoglobulin-binding protein subjected to the alkali treatment was divided by the antibody-binding activity of the immunoglobulin-binding protein without the alkali treatment, to calculate the remaining activity.

(3) About 1800 strains of transformants were evaluated to select, among these, transformants expressing an immunoglobulin-binding protein having an improved alkaline stability compared to FpL_C3KX 7e (SEQ ID NO:275).

(4) Each selected transformant was cultured, and an expression vector was prepared therefrom using a QIAprep Spin Miniprep kit (manufactured by QIAGEN).

(5) The nucleotide sequence of the polynucleotide region encoding the immunoglobulin-binding protein inserted in the expression vector obtained was analyzed by the method described in Example 1(5), to identify the position of each amino acid mutation.

(6) The transformant expressing FpL_C3KX 7e (SEQ ID NO:275) prepared in Example 40 or each transformant expressing an immunoglobulin-binding protein selected in (4) was cultured by the same method as in Example 3(8) to (10), and a protein extract was prepared therefrom by the same method as in Example 3(11). The extract was centrifuged, and the resulting supernatant was passed through a filter for clarification.

(7) The supernatant clarified in (6) was purified by the method described in Reference Example 2(2), and a fraction corresponding to the immunoglobulin-binding protein was collected.

(8) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(9) Alkali treatment was carried out by the same method as in Example 3(13) except that the concentration of the NaOH used for the treatment was 1.0 M (final concentration, 0.5 M), and that the treatment time was 15 hours. Thereafter, the remaining activity was calculated by the same method as in Example 3(14), to evaluate the alkaline stability.

The results are shown in Table 33. It can be said that an immunoglobulin-binding protein having the same amino acid sequence as SEQ ID NO:275 except that the immunoglobulin-binding protein has one or more amino acid substitutions selected from at least Thr2Ala, Pro3Arg, Glu5Asp, Pro(Ser)6Leu, Pro(Ser)6Thr, Lys(Ala)7Pro, Ile23Val, Thr31Met, Glu33Asp, Glu33Gly, Ala35Thr, Thr36Ser, Ala37Thr, Glu52Gly, Ile66Val, and Ala(Val)69Leu has an improved alkaline stability even compared to FpL_C3KX 7e (SEQ ID NO:275), which has a higher alkaline stability than that of the wild-type FpL_C3 (SEQ ID NO: 1).

TABLE 33

| Amino acid substitution | SEQ ID NO: | Remaining activity [%] |
|---|---|---|
| w/o substitution(FpL_C3KX 7e) | 275 | 57 |
| Pro3Arg | 279 | 61 |
| Pro3Arg, Lys(Glu)38Arg | 280 | 68 |
| Pro3Arg, Ile66Val | 281 | 60 |
| Pro3Arg, Thr31Met | 282 | 62 |
| Pro(Ser)6Leu | 283 | 60 |
| Ala35Thr | 284 | 66 |
| Glu33Gly | 285 | 59 |
| Glu5Asp, Pro(Ser)6Leu | 286 | 62 |
| Ala(Val)69Leu | 287 | 58 |
| Ala37Thr | 288 | 60 |
| Glu33Asp, Glu52Gly | 289 | 58 |
| Thr2Ala, Lys(Ala)7Pro | 290 | 69 |
| Ile23Val | 291 | 72 |
| Pro(Ser)6Thr | 292 | 65 |
| Thr36Ser | 293 | 65 |

Example 48 Preparation of FpL_C3KX 7e Amino Acid Substitution Mutants

One of Val14Ala, Gly21Arg, Ile23Thr, Ala41Arg, Asn44Asp, Asn44Arg, Asn44His, Glu52Tyr, Gly60Arg, and Ile64Leu was integrated into FpL_C3KX 7e. These are amino acid substitutions that give improved alkaline stabilities, obtained by substitution with an amino acid residue containing a side chain having a different property, or by a method that introduces, at a position showing different amino acid sequences between domains, a substitution with an amino acid residue found in another domain.

(1) Inverse PCR was carried out by the same method as in Example 7(2) (a-1) except that an expression vector (hereinafter also referred to as "pET-FpL_C3KX 7e") containing a polynucleotide (SEQ ID NO:276) encoding FpL_C3KX 7e (SEQ ID NO:275) was used as a template DNA, and that the combinations of oligonucleotides having the sequences of the SEQ ID NOs in Table 34 were used as combinations of a PCR Forward Primer and a PCR Reverse Primer.

TABLE 34

| Name | Amino acid substitution (into FpL_C3KX 7e) | Primer SEQ ID NO: Forward | Reverse |
|---|---|---|---|
| FpL_C3KX 7e_V14A | Val14Ala | 294 | 295 |
| FpL_C3KX 7e_G21R | Gly21Arg | 297 | 298 |
| FpL_C3KX 7e_I23T | Ile23Thr | 300 | 301 |
| FpL_C3KX 7e_A41R | Ala41Arg | 303 | 304 |
| FpL_C3KX 7e_N44D | Asn44Asp | 306 | 307 |
| FpL_C3KX 7e_N44R | Asn44Arg | 309 | 310 |
| FpL_C3KX 7e_N44H | Asn44His | 312 | 313 |
| FpL_C3KX 7e_E52Y | Glu52Tyr | 315 | 316 |
| FpL_C3KX 7e_G60R | Gly60Arg | 318 | 319 |
| FpL_C3KX 7e_I64L | Ile64Leu | 321 | 322 |

(2) Each polynucleotide obtained in (1) was purified, and then treated with the restriction enzyme DpnI, followed by transforming the *Escherichia coli* BL21 (DE3) strain using the restriction enzyme-treated product.

(3) The transformant obtained was subjected to culturing and extraction of an expression vector by the same method as in Example 7(2) (a-3). The nucleotide sequence of the expression vector was analyzed by the same method as in Example 1(5). As a result, it could be confirmed that the polynucleotide obtained in (1) is inserted in each expression vector.

Example 49 Evaluation of Alkaline Stabilities of FpL_C3KX 7e Amino Acid Substitution Mutants (1) Transformants each of which expresses one of FpL_C3KX 7e and the FpL_C3KX 7e amino acid substitution mutants prepared in Example 48 (10 kinds in total) were cultured by the same method as in Example 3(8) to (10), and protein extracts were prepared therefrom by the method described in Example 3(11). Each extract was centrifuged, and the resulting supernatant was passed through a filter for clarification.

(2) The supernatant clarified in (1) was purified by the method described in Reference Example 2(2), and a fraction corresponding to the immunoglobulin-binding protein was collected.

(3) The absorbance of the collected fraction was measured with a spectrophotometer, to quantify the immunoglobulin-binding protein contained in the fraction. Further, SDS- PAGE was carried out to confirm that each selected immunoglobulin-binding protein was purified with high purity.

(4) Alkali treatment was carried out by the same method as in Example 3(13) except that the concentration of the NaOH used for the treatment was 1.0 M (final concentration, 0.5 M), and that the treatment time was 15 hours. Thereafter, the remaining activity was calculated by the same method as in Example 3(14), to evaluate the alkaline stability.

The results are shown in Table 35. It can be said that all FpL_C3KX 7e amino acid substitution mutants evaluated in the present Example have improved alkaline stabilities even compared to FpL_C3KX 7e (SEQ ID NO:275), which has a higher alkaline stability than that of the wild-type FpL_C3 (SEQ ID NO:1).

TABLE 35

| Amino acid substitution | SEQ ID NO: | Remaining activity [%] |
|---|---|---|
| FpL_C3KX 7e | 275 | 50 |
| FpL_C3KX 7e_V14A | 296 | 56 |
| FpL_C3KX 7e_G21R | 299 | 58 |
| FpL_C3KX 7e_I23T | 302 | 55 |
| FpL_C3KX 7e_A41R | 305 | 67 |
| FpL_C3KX 7e_N44D | 308 | 55 |
| FpL_C3KX 7e_N44R | 311 | 58 |
| FpL_C3KX 7e_N44H | 314 | 64 |
| FpL_C3KX 7e_E52Y | 317 | 64 |
| FpL_C3KX 7e_G60R | 320 | 64 |
| FpL_C3KX 7e_I64L | 323 | 51 |

※Alkali treatment: 25° C., 0.5M NaOH(final concentration), 15 h

Example 50 Multimerization of Protein of Present Invention (Part 1)

A multimer of FpL_C3KX 7e (SEQ ID NO:275) as one mode of the protein of the present invention was prepared by the following method.

(1) Preparation of FpL_C3KX 7e Multimer Expression Vector (1-1) As an FpL_C3KX 7e multimer, a polypeptide (which was named $(FpL\_C3KX7e)_4$-IT-6H3K) having the amino acid sequence of SEQ ID NO:326 was designed. The polypeptide contains four units of FpL_C3KX 7e (SEQ ID NO:275) directly linked to each other, and additionally contains, in the C-terminal side thereof, an oligopeptide (oligopeptide having the amino acid sequence of positions 297 to 319 of SEQ ID NO:36 in WO2017/069158; IT; SEQ ID NO:324) for improving the immobilization rate to an insoluble support, a histidine tag as a purification tag (6H; SEQ ID NO:325), and three lysine residues (3K; hereinafter also referred to as "lysine tag") for improving the immobilization rate to an insoluble support.

(1-2) A polynucleotide (SEQ ID NO:327) was designed such that it encodes $(FpL\_C3KX\ 7e)_4$-IT-6H3K (SEQ ID NO:326), which was designed in (1-1). In the polynucleotide having the sequence of SEQ ID NO:327, positions 1 to 210, positions 211 to 420, positions 421 to 630, and positions 631 to 840 correspond to polynucleotides encoding FpL_C3KX 7e (SEQ ID NO:275); positions 841 to 909 correspond to a polynucleotide (SEQ ID NO:328) encoding the oligopeptide (IT) having the amino acid sequence of SEQ ID NO:324; positions 910 to 927 correspond to an oligonucleotide encoding the histidine tag (6H, SEQ ID NO:325); positions 928 to 936 correspond to an oligonucleotide encoding the lysine tag (3K); and positions 937 to 939 correspond to a stop codon. In SEQ ID NO:327, the sequences of the polynucleotides encoding FpL_C3KX 7e (SEQ ID NO:275) were designed basically using SEQ ID NO:276. However, for positions 187 to 210, positions 421 to 444, and positions 607 to 630 of SEQ ID NO:327, codons different from those in SEQ ID NO:276 were used in the conversion from SEQ ID NO:275, from the viewpoint of ease of cloning.

(1-3) Primers (oligonucleotides) for synthesis of the polynucleotide having the sequence of SEQ ID NO:327, designed in (1-2), were designed and synthesized. More specifically, each of the following was designed and synthesized:

- primers having the sequences of SEQ ID NO:329 and SEQ ID NO:330, for preparation of a polynucleotide fragment having the sequence of the NcoI restriction enzyme site (CCATGG) of the pET26b vector and the sequence of positions 1 to 231 of SEQ ID NO:327;
- primers having the sequences of SEQ ID NO:331 and SEQ ID NO:332, for preparation of a polynucleotide fragment having the sequence of positions 187 to 444 of SEQ ID NO:327;
- primers having the sequences of SEQ ID NO:333 and SEQ ID NO:334, for preparation of a polynucleotide fragment having the sequence of positions 421 to 630 of SEQ ID NO:327;
- primers having the sequences of SEQ ID NO:335 and SEQ ID NO:336, for preparation of a polynucleotide fragment having the sequence of positions 607 to 894 of SEQ ID NO:327;
- primers having the sequences of SEQ ID NO:337 and SEQ ID NO:338, for preparation of a polynucleotide fragment having the sequence of positions 871 to 936 of SEQ ID NO:327; and
- primers having the sequences of SEQ ID NO:339 and SEQ ID NO:340, for preparation of a pET26b vector containing: positions 916 to 936 of SEQ ID NO:327; the downstream side of the HindIII restriction enzyme site (AAGGTT) in the pET26b vector; and the NcoI restriction enzyme site and the upstream side thereof in pET26b; by the inverse PCR method.

(1-4) A reaction liquid having the composition shown in Table 36 was prepared, and the reaction liquid was subjected to PCR by 30 repeated cycles of reaction in which each cycle included a first step at 98° C. for 10 seconds, a second step at 50° C. for 5 seconds, and a third step at 68° C. for 40 seconds. In Table 36, the combination of the template DNA/Forward primer/Reverse primer is one of the combinations shown in <1> to <5> in Table 37.

TABLE 36

| Components | Volume |
|---|---|
| 1 ng/μL template DNA | 1 μL |
| 10 μM Forward primer | 1 μL |
| 10 μM Reverse primer | 1 μL |
| 2 × PrimeSTAR MAX Premix (manufactured by Takara Bio Inc.) | 25 μL |
| $H_2O$ | Up to 50 μL |

TABLE 37

| Combination | <1> | <2> | <3> | <4> | <5> |
|---|---|---|---|---|---|
| template DNA | SEQ ID NO: 275 | SEQ ID NO: 275 | SEQ ID NO: 275 | SEQ ID NO: 275 | pET26b |
| Forward primer | SEQ ID NO: 329 | SEQ ID NO: 331 | SEQ ID NO: 333 | SEQ ID NO: 335 | SEQ ID NO: 339 |
| Reverse primer | SEQ ID NO: 330 | SEQ ID NO: 332 | SEQ ID NO: 334 | SEQ ID NO: 336 | SEQ ID NO: 340 |

(1-5) Each of the total of five kinds of PCR products (polynucleotides) obtained by using the combinations of <1> to <5> was purified, and then TE buffer (10 mM Tris buffer containing 1 mM EDTA) (pH 8.0) containing 0.05 pmol each of the polynucleotides was prepared. Further, 0.05 pmol each of polynucleotides having the sequences of SEQ ID NO:337 and SEQ ID NO:338 were added thereto, and Gibson Assembly reaction using NEBuilder HiFi DNA Assembly Master Mix (manufactured by New England Biolabs) was carried out to ligate these polynucleotides together.

(1-6) Using the ligation product after the reaction in (1-5), the *Escherichia coli* BL21 (DE3) strain was transformed, and then the resulting transformant was cultured (37° C., 16 hours) on LB plate medium supplemented with 50 μg/mL kanamycin.

(1-7) After preparation of a reaction liquid having the composition shown in Table 38, the transformant obtained in (1-6) was added thereto, and colony PCR was carried out under the same conditions as in (1-4). A transformant (recombinant *Escherichia coli*) for which amplification of a PCR product of about 1000 to 1200 base pairs could be confirmed after the colony PCR was selected, and then cultured in LB medium supplemented with 50 μg/mL kanamycin, followed by purification using a QIAprep Spin Miniprep kit (manufactured by QIAGEN), to obtain a vector (which was named pET-(FpL_C3KX 7e)$_4$-IT-6H3K) capable of expressing the immunoglobulin-binding protein (FpL_C3KX 7e)$_4$-IT-6H3K (SEQ ID NO:326).

TABLE 38

| Components | volume |
|---|---|
| 2 × GoTaq Green Master Mix (manufactured by Promega) | 500 μL |
| 10 μM Forward primer (SEQ ID NO: 3) | 100 μL |
| 10 μM Reverse primer (SEQ ID NO: 4) | 100 μL |
| $H_2O$ | Up to 1000 μL |

(1-8) The nucleotide sequence of the expression vector pET-(FpL_C3KX 7e)$_4$-IT-6H3K obtained in (1-7) was analyzed by the same method as in Example 1(5). As a result of the sequence analysis, it could be confirmed that the expression vector contains a polynucleotide having the sequence of SEQ ID NO:327 inserted therein.

(2) Preparation of (FpL_C3KX 7e)$_4$-IT-6H3K (2-1) The recombinant *Escherichia coli* containing pET-(FpL_C3KX 7e)$_4$-IT-6H3K prepared in (1) was inoculated to 20 mL of 2×YT liquid medium (1.6% (w/v) tryptone, 1% (w/v) yeast extract, 0.5% (w/v) sodium chloride) supplemented with 50 μg/mL kanamycin, and preculture was performed (30° C., 16 hours).

(2-2) After the preculture, 10 mL of the culture liquid was inoculated to 1 L of 2×YT liquid medium supplemented with 50 μg/mL kanamycin, and culture was performed at 37° C. for 2 hours to 3 hours, followed by adding 200 μL of 0.5 M IPTG to the culture liquid, and then performing shake culture at 20° C. overnight.

(2-3) The culture liquid after the culture was centrifuged to collect cultured bacterial cells (wet weight, 8 g). An aliquot of the cultured bacterial cells with a wet weight of 2 g was lysed using the BugBuster Protein Extraction Reagent (manufactured by Merck Millipore Corporation), and a supernatant was obtained by centrifugation, followed by passing the supernatant through a filter for clarification.

(2-4) The supernatant clarified in (2-3) was applied to a column packed with Ni Sepharose 6 Fast Flow (manufactured by Cytiva) which had been equilibrated in advance with 0.02 M Tris buffer (pH 7.5) containing 0.5 M sodium chloride and 0.02 M imidazole (hereinafter also simply referred to as "equilibration liquid"). The column was then washed with the equilibration liquid in an amount of 10 volumes with respect to the support packed in the column, and then 0.02 M Tris buffer (pH 7.5) containing 0.5 M sodium chloride and 0.5 M imidazole was passed therethrough to collect a fraction corresponding to the immunoglobulin-binding protein.

(2-5) The absorbance of the collected fraction was measured with a spectrophotometer, to quantify the mass of the protein contained in the fraction. Further, SDS-PAGE was carried out to confirm that the immunoglobulin-binding protein was purified with high purity.

Example 51 Multimerization of Protein of Present Invention (Part 2)

A multimer of FpL_C3KX 6c (SEQ ID NO:341) as another mode of the protein of the present invention was prepared by the following method. The amino acid sequence of FpL_C3KX 6c (SEQ ID NO:341) is the same as the amino acid sequence of FpL_C3KX 7e (SEQ ID NO:275) except that the tyrosine residue at position 50 is reverted to an asparagine residue, which is the same as the amino acid residue in the wild-type FpL_C3 (SEQ ID NO:1).

(1) As an FpL_C3KX 6c multimer, a polypeptide (which was named (FpL_C3KX 6c)$_4$-IT-6H3K) having the amino acid sequence of SEQ ID NO:343 was designed. The polypeptide contains four units of FpL_C3KX 6c (SEQ ID NO:341) directly linked to each other, and additionally contains, in the C-terminal side thereof, an oligopeptide (IT; SEQ ID NO:324) for improving the immobilization rate to an insoluble support, a histidine tag as a purification tag (6H; SEQ ID NO:325), and a lysine tag (3K) for improving the immobilization rate to an insoluble support.

(2) A polynucleotide (SEQ ID NO:344) was designed by the same method as in Example 50(1-2) such that it encodes a polypeptide having the amino acid sequence of SEQ ID NO:343, which was designed in (1). The sequences of the polynucleotides encoding FpL_C3KX 6c (SEQ ID NO:341) were designed basically using SEQ ID NO:342.

(3) PCR was carried out by the same method as in Example 50(1-4) except that one of the combinations shown in <5> to <9> in Table 39 was used as the combination of the template DNA/Forward primer/Reverse primer.

TABLE 39

| Combination | <5> | <6> | <7> | <8> | <9> |
|---|---|---|---|---|---|
| template DNA | pET26b | SEQ ID NO: 342 | SEQ ID NO: 342 | SEQ ID NO: 342 | SEQ ID NO: 342 |
| Forward primer | SEQ ID NO: 339 | SEQ ID NO: 329 | SEQ ID NO: 331 | SEQ ID NO: 333 | SEQ ID NO: 335 |
| Reverse primer | SEQ ID NO: 340 | SEQ ID NO: 330 | SEQ ID NO: 332 | SEQ ID NO: 334 | SEQ ID NO: 336 |

(5) The five kinds of PCR products (polynucleotides) obtained using the combinations <5> to <9> were purified, and Gibson Assembly reaction was carried out by the same method as in Example 50 (1-5), to ligate these polynucleotides together.

(6) The ligation product after the reaction of (5) was used to transform *Escherichia coli* by the same method as in Example 50(1-6), and the transformed *Escherichia coli* was cultured.

(7) Colony PCR was carried out by the same method as in Example 50(1-7). Thereafter, selection of a transformant, culturing of the selected transformant, and plasmid extraction were carried out by the same method as in Example 50(1-7), to obtain an expression vector (which was named pET-(FpL_C3KX 6c) 4-IT-6H3K) capable of expressing the immunoglobulin-binding protein (FpL_C3KX 6c) 4-IT-6H3K (SEQ ID NO:343).

(8) The nucleotide sequence of the expression vector pET-(FpL_C3KX 6c)$_4$-IT-6H3K obtained in (7), was analyzed by the same method as in Example 1(5). As a result of the sequence analysis, it could be confirmed that the expression vector contains a polynucleotide having the sequence of SEQ ID NO:344 inserted therein.

Example 52 Preparation of Immunoglobulin Adsorbent (1) The fraction containing (FpL_C3KX 7e) 4-IT-6H3K (SEQ ID NO:326) prepared in Example 50 or the fraction containing (FpL_C3KX 6c) 4-IT-6H3K (SEQ ID NO: 343) prepared in Example 51 was concentrated using Amicon Ultra (manufactured by Merck Millipore Corporation) to 1/10 volume with respect to the original volume, and sodium phosphate buffer in an amount of 10 volumes with respect to the concentrated solution was added thereto, followed by concentrating the resulting mixture using Amicon Ultra (manufactured by Merck Millipore Corporation) to 1/10 volume with respect to the original volume, to perform concentration and buffer replacement of the protein solution.

(2) A 50% (v/v) slurry was prepared with TOYOPEARL AF-Formyl-650 (manufactured by Tosoh Corporation), which is an insoluble support containing a formyl group as an active group, after replacement with pure water. To a Mini Bio-Spin Column (manufactured by BIORAD), 100 μL of the prepared 50% (v/v) slurry was applied.

(3) To the Mini Bio-Spin Column (manufactured by BIORAD) after the application of the insoluble support, the concentrate of (FpL_C3KX 7e)$_4$-IT-6H3K prepared in Example 50 or the concentrate of (FpL_C3KX 6c)$_4$-IT-6H3K (SEQ ID NO:343) prepared in Example 51 was applied to a final concentration of 10 g/L. Thereafter, the column was shaken at 25° C. to bind the insoluble support contained in the column to the protein by Schiff base formation.

(4) An appropriate amount of 1 M aqueous sodium borohydride solution was applied to the column, and the column was shaken at room temperature for 2 hours to allow reduction of the remaining Schiff bases, to prepare an immunoglobulin adsorbent. The prepared adsorbent was washed with water, subjected to replacement with 20% (v/v) ethanol, and then stored.

Example 53 Evaluation of Alkaline Stabilities of Immunoglobulin Adsorbents (1) Through the column packed with each immunoglobulin adsorbent prepared in Example 52, 0.1 M glycine hydrochloride solution (pH 2.0) (hereinafter also referred to as acidic solution) was passed, and then 0.02 M Tris buffer (pH 7.5) containing 0.15 M sodium chloride (hereinafter also referred to as "washing buffer C") was passed therethrough to wash the column.

(2) An immunoglobulin solution (manufactured by Japan Blood Products Organization) diluted to 60 mg/mL with washing buffer C was applied to the washed column, and then the column was shaken using a constant-temperature shaking incubator (manufactured by TAITEC CORPORATION) at 25° C. at 1000 rpm for 2 hours, to allow adsorption of the immunoglobulin to the insoluble support.

(3) Washing buffer C was passed through the column to wash away unadsorbed immunoglobulin, and then the acidic solution was passed therethrough to elute immunoglobulin that had adsorbed to the adsorbent. The absorbance (wavelength, 280 nm) of the eluate was measured with a spectrophotometer, and the static adsorption amount of the adsorbent was calculated from the amount of immunoglobulin contained in the eluate.

(4) Washing buffer C was passed through the column to equilibrate the immunoglobulin adsorbent, and then 0.5 M sodium hydroxide solution was passed therethrough, followed by leaving the column to stand at 25° C. for 17 hours to perform alkali treatment. Washing buffer C was passed through the column to neutralize the immunoglobulin adsorbent after the alkali treatment.

(5) The static adsorption amount of the adsorbent was calculated by the same method as in (2) and (3), and the ratio between the adsorption amounts before and after the alkali treatment (remaining activity) was calculated to evaluate the alkaline stability The results are shown in Table 40. When FpL_C3KX 6c (SEQ ID NO:341) was used instead of FpL_C3KX 7e (SEQ ID NO:275) as the protein of an aspect of the present invention constituting the multimer, the alkaline stability largely decreased ((FpL_C3KX7e)$_4$-IT-6H3K (SEQ ID NO:326): 66%, (FpL_C3KX 6c)$_4$-IT-6H3K (SEQ ID NO:343): 15%). Since the only difference in the amino acid sequence between FpL_C3KX 6e and FpL_C3KX 7c is position 50 (FpL_C3KX 7e: tyrosine residue, FpL_C3KX 6c: asparagine residue (which is the same as in the wild-type FpL_C3)), it can be seen that the amino acid substitution Asn50Tyr especially contributes to the improvement of the alkaline stability.

TABLE 40

| | Name | SEQ ID NO: | Remaining activity [%] |
|---|---|---|---|
| Example 50 | $(FpL\_C3KX\ 7e)_4$-IT-6H3K | 326 | 66 |
| Example 51 | $(FpL\_C3KX\ 6c)_4$-IT-6H3K | 343 | 15 |

※ Alkali treatment: 25° C., 0.5M NaOH(final concentration), 17 h

Example 54 Preparation of Protein L Immunoglobulin-Binding Domain C4 (FpL_C4) Amino Acid Substitution Mutants (1) Preparation of FpL_C4KR (1-1) The transformant containing pET-FpL_C4KR prepared in Reference Example 1(2)(δ) was inoculated to 2 mL of 2×YT liquid medium supplemented with 50 μg/mL kanamycin, and preculture was performed (30° C., 16 hours).

(1-2) After the preculture, 200 μL of the culture liquid was inoculated to 20 mL of 2×YT liquid medium supplemented with 50 μg/mL kanamycin, and culture was performed at 37° C. for 1.5 hours to 2 hours, followed by adding 4 NL of 0.05 M IPTG to the culture liquid, and then performing shake culture at 20° C. overnight.

(1-3) Thereafter, the cultured bacterial cells were collected by centrifugation, and a protein extract was prepared therefrom using the BugBuster Protein Extraction Reagent (manufactured by Merck Millipore Corporation). The extract was centrifuged, and the resulting supernatant was passed through a filter for clarification.

(1-4) The supernatant clarified in (1-3) was applied to a column packed with Ni-NTA Sepharose 6 Fast Flow (manufactured by Cytiva) which had been equilibrated in advance with washing buffer B (0.05 M Tris buffer (pH 7.5) containing 0.5 M NaCl and 0.02 M imidazole). The column was then washed with washing buffer B in an amount of 10 volumes with respect to the support packed in the column, and then 0.05 M Tris buffer (pH 7.5) containing 0.5 M NaCl and 0.5 M imidazole was passed therethrough, to collect a fraction corresponding to FpL_C4KR.

(1-5) The absorbance of the collected fraction was measured with a spectrophotometer, to quantify FpL_C4KR contained in the fraction. Further, SDS-PAGE was carried out to confirm that FpL_C4KR (SEQ ID NO:117) was purified with high purity.

(2) Introduction of Mutations into FpL_C4KR and Preparation of Library (2-1) pET-FpL_C4KR prepared in Reference Example 1(2)(δ) was used as a template to prepare a saturation substitution mutant library for the amino acid residues at positions 7, 13, 22, and 29. Primers were designed similarly to Example 11(1) according to the 22c-trick method such that appropriate mixed bases could be placed at the mutation introduction sites, and such that inverse PCR could be carried out focusing on the mutation introduction sites (SEQ ID NOs:124 to 129, 345 to 356, and 130 to 135). These primers were mixed to provide a combination of six primers for each substitution site according to the compositions shown in Table 7 and Table 41, to prepare PCR primer mixtures (Forward/Reverse primer mix).

TABLE 41

| | Positions of amino acid substitution | | | |
|---|---|---|---|---|
| SEQ ID NO: | Lys7 | Lys13 | Lys22 | Lys29 |
| Forward primer 1 | 124 | 345 | 351 | 130 |
| Forward primer 2 | 125 | 346 | 352 | 131 |
| Forward primer 3 | 126 | 347 | 353 | 132 |
| Reverse primer 1 | 127 | 348 | 354 | 133 |
| Reverse primer 2 | 128 | 349 | 355 | 134 |
| Reverse primer 3 | 129 | 350 | 356 | 135 |

(2-2) pET-FpL_C4KR prepared in Reference Example 1(2)(δ) was used as a template to perform site-directed mutagenesis by inverse PCR. For the inverse PCR, a reaction liquid having the composition shown in Table 9 was prepared, and the reaction liquid was heat-treated at 98° C. for 2 minutes, followed by performing 30 cycles of reaction in which each cycle included a first step at 95° C. for 10 seconds, a second step at 50° C. for 5 seconds, and a third step at 72° C. for 6 minutes, and then finally performing heat treatment at 72° C. for 7 minutes.

(2-3) After purification of the PCR product obtained, the *Escherichia coli* BL21 (DE3) strain was transformed using the purified product, and then cultured (37° C., 16 hours) on LB plate medium supplemented with 50 μg/mL kanamycin. The resulting colonies, formed on the plate, were provided as a saturation substitution mutant library.

Example 55 Screening of FpL_C4KR Amino Acid Substitution Mutants (1) The transformant capable of expressing FpL_C4KR prepared in Reference Example 1(2)(δ) and the saturation substitution mutant library (transformants) prepared in Example 54(2) were inoculated to 250 μL of 2×YT liquid medium supplemented with 50 μg/mL kanamycin, and subjected to shake culture using a 96-deep-well plate at 37° C. overnight.

(2) Thereafter, 5 μL, of the culture liquid was subcultured into 500 μL of 2×YT liquid medium supplemented with 50 μg/mL kanamycin, 0.3% (w/v) glycine, and 0.01 mM IPTG, and further subjected to shake culture using a 96-deep-well plate at 20° C. overnight.

(3) Thereafter, each culture supernatant obtained by a centrifugation operation was mixed with an equal amount of 1.0 M NaOH, and then subjected to alkali treatment at 38° C. for 15 minutes.

(4) The antibody-binding activity of the immunoglobulin-binding protein subjected to the alkali treatment was measured by the ELISA method shown in Example 3(4). The antibody-binding activity of the immunoglobulin-binding protein subjected to the alkali treatment of (3) was divided by the antibody-binding activity of the immunoglobulin-binding protein without the alkali treatment of (3), to calculate the remaining activity.

(5) About 500 strains of transformants were evaluated to select, among these, transformants expressing an immunoglobulin-binding protein having an improved alkaline stability compared to FpL_C4KR (SEQ ID NO:117).

(6) Each transformant selected in (5) was cultured, and an expression vector was prepared therefrom using a QIAprep Spin Miniprep kit (manufactured by QIAGEN).

(7) The nucleotide sequence of the polynucleotide region encoding the immunoglobulin-binding protein inserted in the expression vector obtained was analyzed by the method described in Example 1(5), to identify the position of each amino acid substitution.

(8) Each transformant expressing an immunoglobulin-binding protein selected in (5) was cultured by the same method as in Example 54(1-1) to (1-2), and a protein extract was prepared therefrom and clarified by the same method as in Example 54(1-3).

(9) The protein extract clarified in (8) was purified by the method described in Example 54(1-4), and a fraction corresponding to the immunoglobulin-binding protein was collected.

(10) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

Example 56 Evaluation of Immunoglobulin Elution pHs of Proteins of Present Invention A pH that allows elution of immunoglobulin bound to FpL_C3 (SEQ ID NO:1) prepared in Example 1, FpL_C4KR (SEQ ID NO:117) prepared in Reference Example 1(2)(δ), or each FpL_C4KR amino acid substitution mutant obtained in Example 55 (hereinafter also simply referred to as "elution pH") was measured by the following method.

(1) A 50% (w/v) aqueous slurry of IgG Sepharose 6 Fast Flow (manufactured by Cytiva), which is an insoluble support to which immunoglobulin is immobilized, was prepared, and then 0.5 mL of the slurry was fed into a Tricom 5/50 column (5-mm inner diameter×50-mm length, manufactured by Cytiva), followed by transferring pure water to the column using a pump, to prepare an IgG Sepharose-packed column.

(2) The IgG Sepharose-packed column prepared in (1) was placed in AKTA AVANT 25 (manufactured by Cytiva). The column was equilibrated with 0.1 M citrate buffer (pH 6.5) (hereinafter referred to as liquid A), and then washed with 0.1 M citrate buffer (pH 2.2) (hereinafter referred to as liquid B), followed by performing equilibration again with liquid A.

(3) To the IgG Sepharose-packed column, 100 μL of each immunoglobulin-binding protein solution prepared at 1 g/L with liquid A was applied, and 5 column volumes of liquid A was transferred to the column, followed by eluting FpL_C3 by 10 minutes of linear gradient elution from 0% to 100% liquid B. The obtained chromatogram was analyzed, and the pH at the position of elution with the highest absorbance was determined as the elution pH.

The results are shown in Table 42. It can be said that an immunoglobulin-binding protein having the same amino acid sequence as SEQ ID NO:117 except that the immunoglobulin-binding protein has one or more amino acid substitutions selected from at least Lys(Arg)7Gln (this expression represents the fact that the amino acid residue corresponding to the lysine at position 7 of SEQ ID NO:1 (the lysine at position 7 of SEQ ID NO:5) is once substituted with arginine, and then substituted with glutamine; the same applies to the other amino acid substitutions hereinafter), Lys(Arg)13Val, Lys(Arg)22Thr, Lys(Arg)29Pro, Lys(Arg)29Val, and Lys(Arg)29Ile has a higher elution pH compared to those of the wild-type FpL_C3 (SEQ ID NO:1) and FpL_C4KR (SEQ ID NO:117), in other words, has a capacity to allow elution of immunoglobulin (antibody) bound to the immunoglobulin-binding protein, under milder pH conditions (that is, under conditions closer to neutrality).

TABLE 42

| Amino acid substitution | SEQ ID NO: | Elution pH |
|---|---|---|
| FpL_C3(wild-type) | 1 | 2.9 |
| FpL_C4KR | 117 | 2.8 |
| Lys(Arg)7Gln | 357 | 3.0 |
| Lys(Arg)13Val | 358 | 3.1 |
| Lys(Arg)22Thr | 359 | 3.2 |
| Lys(Arg)29Pro | 360 | 3.2 |
| Lys(Arg)29Val | 361 | 3.1 |
| Lys(Arg)29Ile | 362 | 3.1 |

Example 57 Design and Preparation of FpL_C3KX 7d Amino Acid Substitution Mutants One of Pro(Ser)6Ala, Glu8Gly, Glu8Arg, Gly21Arg, Ile23Phe, Ile23Leu, Glu33Val, Lys(Arg,Glu)38His, Lys(Arg,Glu)38Leu, Asn44His, Asn44Arg, Lys(Arg)48His, Asn(Tyr)50Met, Glu(Gly,Asp)52Tyr, and Tyr(Phe)53Ser was integrated into FpL_C3KX 7d (SEQ ID NO:240). These are amino acid substitutions that give improved acid elution properties, obtained by substitution with an amino acid residue containing a side chain having a different property, or by a method that introduces, at a position showing different amino acid sequences between domains, a substitution with an amino acid residue found in another domain.

(1) Inverse PCR was carried out by the same method as in Example 7(2) (a-1) except that the expression vector pET-FpL_C3KX 7d, which contains a polynucleotide (SEQ ID NO:241) encoding FpL_C3KX 7d (SEQ ID NO:240), was used as a template DNA, and that the combinations of oligonucleotides having the sequences of the SEQ ID NOs in Table 43 were used as combinations of a PCR Forward Primer and a PCR Reverse Primer.

TABLE 43

| Name | Amino acid substitution (into FpL_C3KX 7d) | Primer SEQ ID NO: Forward | Primer SEQ ID NO: Reverse |
|---|---|---|---|
| FpL_C3KX 7d_P6A | Pro(Ser)6Ala | 363 | 364 |
| FpL_C3KX 7d_E8G | Glu8Gly | 365 | 366 |
| FpL_C3KX 7d_E8R | Glu8Arg | 367 | 368 |
| FpL_C3KX 7d_G21R | Gly21Arg | 369 | 370 |
| FpL_C3KX 7d_I23F | Ile23Phe | 371 | 372 |
| FpL_C3KX 7d_I23L | Ile23Leu | 373 | 374 |
| FpL_C3KX 7d_E33V | Glu33Val | 375 | 376 |
| FpL_C3KX 7d_K38H | Lys(Arg, Glu)38His | 377 | 378 |
| FpL_C3KX 7d_K38L | Lys(Arg, Glu)38Leu | 379 | 380 |
| FpL_C3KX 7d_N44H | Asn44His | 381 | 382 |
| FpL_C3KX 7d_N44R | Asn44Arg | 383 | 384 |
| FpL_C3KX 7d_K48H | Lys(Arg)48His | 385 | 386 |
| FpL_C3KX 7d_N50M | Asn(Tyr)50Met | 387 | 388 |
| FpL_C3KX 7d_E52Y | Glu(Gly, Asp)52Tyr | 389 | 390 |
| FpL_C3KX 7d_Y53S | Tyr(Phe)53Ser | 391 | 392 |

(2) Each polynucleotide obtained in (1) was purified, and then treated with the restriction enzyme DpnI, followed by transforming the *Escherichia coli* BL21 (DE3) strain using the restriction enzyme-treated product.

(3) The transformant obtained was subjected to culturing and extraction of an expression vector by the same method as in Example 1(4). The nucleotide sequence of the expression vector was analyzed by the same method as in Example 1(5). As a result, it could be confirmed that the polynucleotide obtained in (1) is inserted in each expression vector.

Example 58 Evaluation of Acid Elution Properties of FpL_C3KX 7d Amino Acid Substitution Mutants (1) Transformants each of which expresses one of FpL_C3KX 7d (SEQ ID NO:240), and the FpL_C3KX 7d amino acid substitution mutants prepared in Example 57 (15 kinds in total) were cultured by the same method as in Example 54(1-1) to (1-2), and protein extracts were prepared therefrom by the method described in Example 54(1-3). Each extract was centrifuged, and the resulting supernatant was passed through a filter for clarification.

(2) The supernatant clarified in (1) was purified by the method described in Example 54(1-4), and a fraction corresponding to the immunoglobulin-binding protein was collected.

(3) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(4) The protein extract was diluted with TBS such that each protein had the same concentration. The dilution was equally divided into two aliquots. By the ELISA method described in Example 3(4) (acid elution property evaluation), one of the aliquots was subjected to measurement of the antibody-binding activity for a case where 0.05 M sodium citrate buffer (pH 3.0) was added (acid treatment), and the other was subjected to measurement of the antibody-binding activity for a case where TBS was added (acid-untreated). The antibody-binding activity of the acid-treated immunoglobulin-binding protein was divided by the antibody-binding activity of the acid-untreated immunoglobulin-binding protein, to calculate the remaining activity. The elution rate was calculated by subtracting the remaining activity from 1, to evaluate the acid elution property.

The results are shown in Table 44. All FpL_C3KX 7d amino acid substitution mutants evaluated in the present Example had higher elution rates compared to FpL_C3KX 7d (SEQ ID NO:240), which has a higher alkaline stability than that of the wild-type FpL_C3 (SEQ ID NO: 1), indicating that these mutant-type immunoglobulin-binding proteins have improved acid elution properties.

TABLE 44

| Name | SEQ ID NO: | Elution rate [%] |
|---|---|---|
| FpL_C3KX 7d | 240 | 78 |
| FpL_C3KX 7d_P6A | 365 | 82 |
| FpL_C3KX 7d_E8G | 368 | 80 |
| FpL_C3KX 7d_E8R | 371 | 82 |
| FpL_C3KX 7d_G21R | 374 | 82 |
| FpL_C3KX 7d_I23F | 377 | 81 |
| FpL_C3KX 7d_I23L | 380 | 82 |
| FpL_C3KX 7d_E33V | 383 | 86 |
| FpL_C3KX 7d_K38H | 386 | 86 |
| FpL_C3KX 7d_K38L | 389 | 88 |
| FpL_C3KX 7d_N44H | 392 | 82 |
| FpL_C3KX 7d_N44R | 395 | 82 |
| FpL_C3KX 7d_K48H | 398 | 85 |
| FpL_C3KX 7d_N50M | 401 | 86 |
| FpL_C3KX 7d_E52Y | 404 | 85 |
| FpL_C3KX 7d_Y53S | 407 | 83 |

※Acid treatment: 25° C., 50 mM NaOAc buffer(pH 3.0), 15 min

Example 59 Integration of Amino Acid Substitutions into Immunoglobulin-Binding Protein of Present Invention (1) Design of Amino Acid Substitution-Integrated Mutants An amino acid substitution(s) found to be responsible for the improvement of the alkaline stability of the immunoglobulin-binding protein in Examples 43 and 48, and/or an amino acid substitution(s) found to be responsible for the improvement of the immunoglobulin elution property of the immunoglobulin-binding protein in Example 58, were integrated into FpL_C3KX 7e (SEQ ID NO:275). More specifically, the seven kinds of immunoglobulin-binding proteins shown in the following <c> to <i> were designed and prepared.

<c> A protein (SEQ ID NO:408; which was named FpL_C3KX 9a) prepared by introducing the amino acid substitutions Ile23Arg and Asn44Arg into FpL_C3KX 7e <d> A protein (SEQ ID NO:409; which was named FpL_C3KX 9b) prepared by introducing the amino acid substitutions Ile23Arg and Asn44His into FpL_C3KX 7e <e> A protein (SEQ ID NO:410; which was named FpL_C3KX 9c) prepared by introducing the amino acid substitutions Ile23Arg and Ile64Leu into FpL_C3KX 7e <f> A protein (SEQ ID NO:411; which was named FpL_C3KX 9d) prepared by introducing the amino acid substitutions Asn44Arg and Ile64Leu into FpL_C3KX 7e <g> A protein (SEQ ID NO:412; which was named FpL_C3KX 9e) prepared by introducing the amino acid substitutions Asn44His and Ile64Leu into FpL_C3KX 7e <h> A protein (SEQ ID NO:413; which was named FpL_C3KX 10a) prepared by introducing the amino acid substitutions Ile23Arg, Asn44Arg, Lys(Arg)48His, and Ile64Leu into FpL_C3KX 7e <i> A protein (SEQ ID NO:414; which was named FpL_C3KX 10b) prepared by introducing the amino acid substitutions Ile23Arg, Asn44His, Lys(Arg)48His, and Ile64Leu into FpL_C3KX 7e (2) Preparation of FpL_C3KX 7e Amino Acid Substitution-Integrated Mutants The methods of the preparation of the seven kinds of immunoglobulin-binding proteins shown in <c> to <i> are described below.

<c> FpL_C3KX 9a

<c-1> A polynucleotide (SEQ ID NO:214) encoding FpL_C3KX 9a (SEQ ID NO:408) was synthesized. In the synthesis, a recognition sequence for the restriction enzyme NcoI (5'-CCATGG-3') was added to the 5'-end side, and a nucleotide sequence encoding six histidine residues (SEQ ID NO:232), a stop codon, and a recognition sequence for the restriction enzyme HindIII (5'-AAGCTT-3') were added to the 3'-end side.

<c-2> By the same method as in Example 1(2), the polynucleotide synthesized in <c-1> was purified.

<c-3> By the same method as in Example 1(3), the polynucleotide obtained in <c-2> was ligated to the plasmid pET-26b, which had been preliminarily digested with the restriction enzymes NcoI and HindIII, and then the resulting ligation product was used to transform the *Escherichia coli* BL21 (DE3) strain, followed by culturing the resulting transformant.

<c-4> The transformant obtained was subjected to culturing and plasmid purification by the same method as in Example 1(4), to obtain an expression vector (which was named pET-FpL_C3KX 9a). The nucleotide sequence of the expression vector was analyzed by the same method as in Example 1(5).

As a result of the sequence analysis, it could be confirmed that the expression vector pET-FpL_C3KX 9a contains a polynucleotide (SEQ ID NO:415) encoding FpL_C3KX 9a (SEQ ID NO:408) inserted therein.

<d> FpL_C3KX 9b

A transformant and an expression vector (which was named pET-FpL_C3KX 9b) were obtained by the same method as in <c> except that a polynucleotide (SEQ ID NO:416) encoding FpL_C3KX 9b (SEQ ID NO:409) was used as the polynucleotide encoding an immunoglobulin-binding protein. As a result of nucleotide sequence analysis of the expression vector pET-FpL_C3KX 9b, it could be confirmed that pET-FpL_C3KX 9b contains a polynucleotide (SEQ ID NO:416) encoding FpL_C3KX 9b (SEQ ID NO:409) inserted therein.

<e> FpL_C3KX 9c

A transformant and an expression vector (which was named pET-FpL_C3KX 9c) were obtained by the same method as in <c> except that a polynucleotide (SEQ ID NO:417) encoding FpL_C3KX 9c (SEQ ID NO:410) was used as the polynucleotide encoding an immunoglobulin-binding protein. As a result of nucleotide sequence analysis of the expression vector pET-FpL_C3KX 9c, it could be confirmed that pET-FpL_C3KX [9e] 9c contains a polynucleotide (SEQ ID NO:417) encoding FpL_C3KX 9c (SEQ ID NO:410) inserted therein.

<f> FpL_C3KX 9d

A transformant and an expression vector (which was named pET-FpL_C3KX 9d) were obtained by the same method as in <c> except that a polynucleotide (SEQ ID NO:418) encoding FpL_C3KX 9d (SEQ ID NO:411) was used as the polynucleotide encoding an immunoglobulin-binding protein. As a result of nucleotide sequence analysis of the expression vector pET-FpL_C3KX 9d, it could be confirmed that pET-FpL_C3KX 9d contains a polynucleotide (SEQ ID NO:418) encoding FpL_C3KX 9d (SEQ ID NO:411) inserted therein.

<g> FpL_C3KX 9e

A transformant and an expression vector (which was named pET-FpL_C3KX 9e) were obtained by the same method as in <c> except that a polynucleotide (SEQ ID NO:419) encoding FpL_C3KX 9e (SEQ ID NO:412) was used as the polynucleotide encoding an immunoglobulin-binding protein. As a result of nucleotide sequence analysis of the expression vector pET-FpL_C3KX 9e, it could be confirmed that pET-FpL_C3KX 9e contains a polynucleotide (SEQ ID NO:419) encoding FpL_C3KX 9e (SEQ ID NO:412) inserted therein.

<h> FpL_C3KX 10a

A transformant and an expression vector (which was named pET-FpL_C3KX 10a) were obtained by the same method as in <c> except that a polynucleotide (SEQ ID NO:420) encoding FpL_C3KX 10a (SEQ ID NO:413) was used as the polynucleotide encoding an immunoglobulin-binding protein. As a result of nucleotide sequence analysis of the expression vector pET-FpL_C3KX 10a, it could be confirmed that pET-FpL_C3KX 10a contains a polynucleotide (SEQ ID NO:420) encoding FpL_C3KX 10a (SEQ ID NO:413) inserted therein.

<i> FpL_C3KX 10b

A transformant and an expression vector (which was named pET-FpL_C3KX 10b) were obtained by the same method as in <c> except that a polynucleotide (SEQ ID NO:421) encoding FpL_C3KX 10b (SEQ ID NO:414) was used as the polynucleotide encoding an immunoglobulin-binding protein. As a result of nucleotide sequence analysis of the expression vector pET-FpL_C3KX 10b, it could be confirmed that pET-FpL_C3KX 10b contains a polynucleotide (SEQ ID NO:421) encoding FpL_C3KX 10b (SEQ ID NO:414) inserted therein.

Example 60 Evaluation of Acid Elution Properties of FpL_C3KX 7e Amino Acid Substitution Mutants (1) Transformants each of which expresses one of FpL_C3KX 7e (SEQ ID NO:275), and FpL_C3KX 9a (SEQ ID NO:408), FpL_C3KX 9b (SEQ ID NO:409), FpL_C3KX 9c (SEQ ID NO: 410), FpL_C3KX [9c] 9d (SEQ ID NO:411), FpL_C3KX [9d] 9e (SEQ ID NO:412), FpL_C3KX 10a (SEQ ID NO:413), and FpL_C3KX 10b (SEQ ID NO:414) prepared in Example 59 were cultured by the same method as in Example 54(1-1) to (1-2), and protein extracts were prepared therefrom by the method described in Example 54(1-3). Each extract was centrifuged, and the resulting supernatant was passed through a filter for clarification.

(2) The supernatant clarified in (1) was purified by the method described in Example 54(1-4), and a fraction corresponding to the immunoglobulin-binding protein was collected.

(3) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(4) The protein extract was diluted with TBS such that each protein had the same concentration. The dilution was equally divided into two aliquots. By the ELISA method described in Example 3(4) (acid elution property evaluation), one of the aliquots was subjected to measurement of the antibody-binding activity for a case where acid treatment was carried out with 0.05 M sodium citrate (NaOAc) buffer (pH 3.2) for 5 minutes, and the other was subjected to measurement of the antibody-binding activity for a case where TBS was added (acid-untreated). The antibody-binding activity of the acid-treated immunoglobulin-binding protein was divided by the antibody-binding activity of the acid-untreated immunoglobulin-binding protein, to calculate the remaining activity. The elution rate was calculated by subtracting the remaining activity from 1, to evaluate the acid elution property.

The results are shown in Table 45. FpL_C3KX 9a (SEQ ID NO:408), FpL_C3KX 9b (SEQ ID NO:409), FpL_C3KX 9c (SEQ ID NO:410), FpL_C3KX 9d (SEQ ID NO:411), FpL_C3KX 9e (SEQ ID NO:412), FpL_C3KX 10a (SEQ ID NO:413), and FpL_C3KX 10b (SEQ ID NO:414) showed higher elution rates compared to FpL_C3KX 7e (SEQ ID NO:275), indicating that these mutant-type immunoglobulin-binding proteins have improved acid elution properties. In particular, it can be seen that FpL_C3KX 9a (SEQ ID NO:408) and FpL_C3KX 10a (SEQ ID NO:413) have especially improved acid elution properties.

TABLE 45

| Name | Amino acid substitution (into FpL_C3KX 7e) | SEQ ID NO: | Elution rate [%] |
|---|---|---|---|
| FpL_C3KX 7e | — | 275 | 46 |
| FpL_C3KX 9a | Ile23Arg, Asn44Arg | 408 | 70 |
| FpL_C3KX 9b | Ile23Arg, Asn44His | 409 | 68 |
| FpL_C3KX 9c | Ile23Arg, Ile64Leu | 410 | 69 |
| FpL_C3KX 9d | Asn44Arg, Ile64Leu | 411 | 63 |
| FpL_C3KX 9e | Asn44His, Ile64Leu | 412 | 68 |
| FpL_C3KX 10a | Ile23Arg, Asn44Arg, Asn48His, Ile64Leu | 413 | 75 |
| FpL_C3KX 10b | Ile23Arg, Asn44His, Asn48His, Ile64Leu | 414 | 67 |

※Acid treatment: 25° C., 50 mM NaOAc buffer(pH 3.2), 5 min

Example 61 Introduction of Mutations into FpL_C3KX 7e and Preparation of Library (Part 3)

(1) The expression vector pET-FpL_C3KX 7e, which expresses FpL_C3KX 7e (SEQ ID NO:275), was used as a template to prepare a saturation substitution mutant library for the amino acid residues at positions 15 and 34. Primers were designed similarly to Example 11(1) according to the 22c-trick method such that appropriate mixed bases could be placed at the mutation introduction sites, and such that inverse PCR could be carried out focusing on the mutation introduction sites (SEQ ID NOs:422 to 433). These primers were mixed to provide a combination of six primers for each substitution site according to the compositions shown in Table 7 and Table 46, to prepare PCR primer mixtures (Forward/Reverse primer mix).

TABLE 46

| | Position of Amino acid substitution | |
|---|---|---|
| | Asn15 | Glu34 |
| Forward primer 1 | 422 | 428 |
| Forward primer 2 | 423 | 429 |
| Forward primer 3 | 424 | 430 |
| Reverse primer 1 | 425 | 431 |
| Reverse primer 2 | 426 | 432 |
| Reverse primer 3 | 427 | 433 |

(2) Site-directed mutagenesis by inverse PCR was carried out by the same method as in Example 2(2-2) except that pET-FpL_C3KX 7e was used as a template DNA.

(3) After purification of the PCR product obtained, the *Escherichia coli* BL21 (DE3) strain was transformed using the reaction liquid, and then cultured (37° C., 16 hours) on LB plate medium supplemented with 50 μg/mL kanamycin. The resulting colonies, formed on the plate, were provided as a site-directed mutant library.

Example 62 Screening of FpL_C3KX 7e Amino Acid Substitution Mutants (Part 3)

(1) pET-FpL_C3KX 7e (transformant), and the site-directed amino acid substitution mutant library (transformants) prepared in Example 61 were cultured by the same method as in Example 55(1) to (2), and then the alkali treatment described in Example 55(3) was carried out.

(2) The antibody-binding activity of the immunoglobulin-binding protein subjected to the alkali treatment was measured by the ELISA method described in Example 2(4). The antibody-binding activity of the immunoglobulin-binding protein subjected to the alkali treatment was divided by the antibody-binding activity of the immunoglobulin-binding protein without the alkali treatment, to calculate the remaining activity.

(3) About 200 strains of transformants were evaluated to select, among these, transformants expressing an immunoglobulin-binding protein having an improved alkaline stability compared to FpL_C3KX 7e (SEQ ID NO:275).

(4) Each selected transformant was cultured, and an expression vector was prepared therefrom using a QIAprep Spin Miniprep kit (manufactured by QIAGEN).

(5) The nucleotide sequence of the polynucleotide region encoding the immunoglobulin-binding protein inserted in the expression vector obtained was analyzed by the method described in Example 1(5), to identify the position of each amino acid mutation.

(6) Each transformant expressing an immunoglobulin-binding protein selected in (3) or the transformant expressing pET-FpL_C3KX 7e (SEQ ID NO:275) was cultured by the same method as in Example 54(1-1) to (1-2), and a protein extract was prepared therefrom by the same method as in Example 54(1-3). The extract was centrifuged, and the resulting supernatant was passed through a filter for clarification.

(7) The supernatant clarified in (6) was purified by the method described in Example 54(1-4), and a fraction corresponding to the immunoglobulin-binding protein was collected.

(8) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(9) The acid elution property was evaluated by the same method as in Example 60(4).

The results are shown in Table 47. It can be said that an immunoglobulin-binding protein having the same amino acid sequence as SEQ ID NO:275 except that the immunoglobulin-binding protein has one or more amino acid substitutions selected from at least Asn15Val, Glu34Asp, Glu34Phe, Glu34Leu, and Glu34Val has a higher elution rate compared to FpL_C3KX 7e (SEQ ID NO:275), indicating that these mutant-type immunoglobulin-binding proteins have improved acid elution properties.

TABLE 47

| Amino acid substitution | SEQ ID NO: | Elution rate [%] |
|---|---|---|
| w/o substitution(FpL_C3KX 7e) | 275 | 26 |
| Asn15Val | 434 | 29 |
| Glu34Asp | 435 | 46 |
| Glu34Phe | 436 | 64 |
| Glu34Leu | 437 | 51 |
| Glu34Val | 438 | 29 |

※Acid treatment: 25° C., 50 mM NaOAc buffer(pH 3.2), 5 min

Example 63 Evaluation of Alkaline Stability of FpL_C3KX 9a (1) Transformants each of which expresses FpL_C3KX 7e (SEQ ID NO:275) or FpL_C3KX 9a (SEQ ID NO:408) were cultured by the same method as in Example 54(1-1) to (1-2), and protein extracts were prepared therefrom by the method described in Example 54(1-3). Each extract was centrifuged, and the resulting supernatant was passed through a filter for clarification.

(2) The supernatant clarified in (1) was purified by the method described in Example 54(1-4), and a fraction corresponding to the immunoglobulin-binding protein was collected.

(3) The absorbance of the collected fraction was measured with a spectrophotometer, to quantify the immunoglobulin-binding protein contained in the fraction. Further, SDS-PAGE was carried out to confirm that each selected immunoglobulin-binding protein was purified with high purity.

(4) Alkali treatment was carried out by the same method as in Example 2(13) except that the concentration of the NaOH used for the treatment was 2.0 M (final concentration, 1.0 M), and that the treatment time was 15 hours. Thereafter, the remaining activity was calculated by the same method as in Example 2(14), to evaluate the alkaline stability.

The results are shown in Table 48. It could be confirmed that FpL_C3KX 9a (SEQ ID NO:408), evaluated in the present Example, has an alkaline stability equivalent to that of FpL_C3KX 7e (SEQ ID NO:275), which has a higher alkaline stability than that of the wild-type FpL_C3 (SEQ ID NO:1).

TABLE 48

| Name | SEQ ID NO: | Remaining activity [%] |
|---|---|---|
| FpL_C3KX 7e | 275 | 42 |
| FpL_C3KX 9a | 408 | 41 |

※Alkali treatment: 25° C., 1.0M NaOH (final concentration), 15 h

INDUSTRIAL APPLICABILITY

The protein of an aspect of the present invention is characterized in that it includes an amino acid sequence which is the same as an amino acid sequence of an immunoglobulin-binding domain of protein L derived from the genus *Finegoldia* except that the amino acid sequence of the protein has at least one amino acid substitution that improves the alkaline stability, the protein having immunoglobulin-binding activity. In one aspect, an immunoglobulin adsorbent including: an insoluble support; and a protein of an aspect of the present invention immobilized on the insoluble support; has a higher alkaline stability than those of conventional immunoglobulin adsorbents, so that the immunoglobulin adsorbent can be repeatedly used a larger number of times. Thus, use of the immunoglobulin adsorbent enables production of immunoglobulin at lower cost than conventional immunoglobulin adsorbents.

The protein of an aspect of the present invention is characterized in that it includes an amino acid sequence which is the same as an amino acid sequence of an immunoglobulin-binding domain of protein L derived from the genus *Finegoldia* except that the amino acid sequence of the protein has at least one amino acid substitution that improves the antibody elution property, the protein having immunoglobulin-binding activity. An immunoglobulin adsorbent of an aspect of the present invention including: an insoluble support; and a protein of an aspect of the present invention immobilized on the insoluble support; enables elution of immunoglobulin (antibody) under milder pH conditions compared to conventional immunoglobulin adsorbents, so that immunoglobulin with high quality can be obtained.

The invention claimed is:

1. A protein comprising an amino acid sequence which is the same as an amino acid sequence of an immunoglobulin-binding domain of protein L derived from a bacterium belonging to the genus *Finegoldia* except that the amino acid sequence of the former protein has one or more amino acid substitutions selected from at least the following (1) to (53), the protein having immunoglobulin-binding activity:

(1) substitution of the amino acid residue corresponding to the asparagine at position 50 of SEQ ID NO: 1 with tyrosine;

(2) substitution of the amino acid residue corresponding to the glutamic acid at position 1 of SEQ ID NO: 1 with glycine or valine;

(3) substitution of the amino acid residue corresponding to the proline at position 3 of SEQ ID NO: 1 with serine;

(4) substitution of the amino acid residue corresponding to the glutamic acid at position 4 of SEQ ID NO: 1 with lysine or glycine;

(5) substitution of the amino acid residue corresponding to the glutamic acid at position 5 of SEQ ID NO: 1 with valine;

(6) substitution of the amino acid residue corresponding to the lysine at position 7 of SEQ ID NO: 1 with alanine;

(7) substitution of the amino acid residue corresponding to the glutamic acid at position 8 of SEQ ID NO: 1 with glycine;

(8) substitution of the amino acid residue corresponding to the glutamic acid at position 9 of SEQ ID NO: 1 with valine;

(9) substitution of the amino acid residue corresponding to the isoleucine at position 17 of SEQ ID NO: 1 with phenylalanine;

(10) substitution of the amino acid residue corresponding to the glycine at position 21 of SEQ ID NO: 1 with arginine;

(11) substitution of the amino acid residue corresponding to the glutamic acid at position 27 of SEQ ID NO: 1 with glycine or arginine;

(12) substitution of the amino acid residue corresponding to the lysine at position 29 of SEQ ID NO: 1 with proline;

(13) substitution of the amino acid residue corresponding to the threonine at position 31 of SEQ ID NO: 1 with leucine;

(14) substitution of the amino acid residue corresponding to the threonine at position 36 of SEQ ID NO: 1 with alanine;

(15) substitution of the amino acid residue corresponding to the alanine at position 41 of SEQ ID NO: 1 with threonine;

(16) substitution of the amino acid residue corresponding to the asparagine at position 44 of SEQ ID NO: 1 with serine or glycine;

(17) substitution of the amino acid residue corresponding to the glutamic acid at position 49 of SEQ ID NO: 1 with threonine or isoleucine;

(18) substitution of the amino acid residue corresponding to the asparagine at position 50 of SEQ ID NO: 1 with any of serine, lysine, and aspartic acid;

(19) substitution of the amino acid residue corresponding to the glycine at position 51 of SEQ ID NO: 1 with valine;

(20) substitution of the amino acid residue corresponding to the glutamic acid at position 52 of SEQ ID NO: 1 with any of valine, glycine, and aspartic acid;

(21) substitution of the amino acid residue corresponding to the tyrosine at position 53 of SEQ ID NO: 1 with phenylalanine;

(22) substitution of the amino acid residue corresponding to the threonine at position 54 of SEQ ID NO: 1 with isoleucine or methionine;

(23) substitution of the amino acid residue corresponding to the asparagine at position 62 of SEQ ID NO: 1 with any of histidine, arginine, leucine, methionine, and tryptophan;

(24) substitution of the amino acid residue corresponding to the asparagine at position 65 of SEQ ID NO: 1 with tyrosine;

(25) substitution of the amino acid residue corresponding to the alanine at position 69 of SEQ ID NO: 1 with threonine;

(26) substitution of the amino acid residue corresponding to the threonine at position 2 of SEQ ID NO: 1 with serine or proline;

(27) substitution of the amino acid residue corresponding to the proline at position 3 of SEQ ID NO: 1 with arginine;

(28) substitution of the amino acid residue corresponding to the glutamic acid at position 5 of SEQ ID NO: 1 with lysine or arginine;

(29) substitution of the amino acid residue corresponding to the glutamic acid at position 27 of SEQ ID NO: 1 with any of valine, lysine, and isoleucine;

(30) substitution of the amino acid residue corresponding to the phenylalanine at position 32 of SEQ ID NO: 1 with leucine;

(31) substitution of the amino acid residue corresponding to the lysine at position 38 of SEQ ID NO: 1 with alanine;

(32) substitution of the amino acid residue corresponding to the asparagine at position 44 of SEQ ID NO: 1 with isoleucine;

(33) substitution of the amino acid residue corresponding to the alanine at position 47 of SEQ ID NO: 1 with threonine or arginine;

(34) substitution of the amino acid residue corresponding to the glutamic acid at position 52 of SEQ ID NO: 1 with asparagine;

(35) substitution of the amino acid residue corresponding to the threonine at position 2 of SEQ ID NO: 1 with alanine;

(36) substitution of the amino acid residue corresponding to the glutamic acid at position 5 of SEQ ID NO: 1 with aspartic acid;

(37) substitution of the amino acid residue corresponding to the proline at position 6 of SEQ ID NO: 1 with leucine or threonine;
(38) substitution of the amino acid residue corresponding to the lysine at position 7 of SEQ ID NO: 1 with proline;
(39) substitution of the amino acid residue corresponding to the valine at position 14 of SEQ ID NO: 1 with alanine;
(40) substitution of the amino acid residue corresponding to the isoleucine at position 23 of SEQ ID NO: 1 with arginine or valine;
(41) substitution of the amino acid residue corresponding to the lysine at position 29 of SEQ ID NO: 1 with phenylalanine;
(42) substitution of the amino acid residue corresponding to the threonine at position 31 of SEQ ID NO: 1 with methionine;
(43) substitution of the amino acid residue corresponding to the glutamic acid at position 33 of SEQ ID NO:1 with any of aspartic acid, glycine, and valine;
(44) substitution of the amino acid residue corresponding to the alanine at position 35 of SEQ ID NO: 1 with threonine;
(45) substitution of the amino acid residue corresponding to the threonine at position 36 of SEQ ID NO: 1 with serine;
(46) substitution of the amino acid residue corresponding to the alanine at position 37 of SEQ ID NO: 1 with threonine;
(47) substitution of the amino acid residue corresponding to the alanine at position 41 of SEQ ID NO: 1 with isoleucine or tyrosine;
(48) substitution of the amino acid residue corresponding to the asparagine at position 44 of SEQ ID NO: 1 with histidine or arginine;
(49) substitution of the amino acid residue corresponding to the glutamic acid at position 52 of SEQ ID NO: 1 with leucine or tyrosine;
(50) substitution of the amino acid residue corresponding to the glycine at position 60 of SEQ ID NO: 1 with arginine;
(51) substitution of the amino acid residue corresponding to the isoleucine at position 64 of SEQ ID NO: 1 with leucine;
(52) substitution of the amino acid residue corresponding to the isoleucine at position 66 of SEQ ID NO: 1 with valine; and
(53) substitution of the amino acid residue corresponding to the alanine at position 69 of SEQ ID NO: 1 with leucine or valine.

2. The protein according to claim 1, which is a protein of any of the following (a) to (c):
(a) a protein comprising an amino acid sequence which is the same as the amino acid sequence of SEQ ID NO:1 or 18 except that the amino acid sequence of the protein has one or more amino acid substitutions selected from at least the following (1) to (53), the protein having immunoglobulin-binding activity:
(1) substitution of the amino acid residue corresponding to the asparagine at position 50 of SEQ ID NO: 1 with tyrosine;
(2) substitution of the amino acid residue corresponding to the glutamic acid at position 1 of SEQ ID NO: 1 with glycine or valine;
(3) substitution of the amino acid residue corresponding to the proline at position 3 of SEQ ID NO: 1 with serine;
(4) substitution of the amino acid residue corresponding to the glutamic acid at position 4 of SEQ ID NO: 1 with lysine or glycine;
(5) substitution of the amino acid residue corresponding to the glutamic acid at position 5 of SEQ ID NO: 1 with valine;
(6) substitution of the amino acid residue corresponding to the lysine at position 7 of SEQ ID NO: 1 with alanine;
(7) substitution of the amino acid residue corresponding to the glutamic acid at position 8 of SEQ ID NO: 1 with glycine;
(8) substitution of the amino acid residue corresponding to the glutamic acid at position 9 of SEQ ID NO: 1 with valine;
(9) substitution of the amino acid residue corresponding to the isoleucine at position 17 of SEQ ID NO: 1 with phenylalanine;
(10) substitution of the amino acid residue corresponding to the glycine at position 21 of SEQ ID NO: 1 with arginine;
(11) substitution of the amino acid residue corresponding to the glutamic acid at position 27 of SEQ ID NO: 1 with glycine or arginine;
(12) substitution of the amino acid residue corresponding to the lysine at position 29 of SEQ ID NO: 1 with proline;
(13) substitution of the amino acid residue corresponding to the threonine at position 31 of SEQ ID NO: 1 with leucine;
(14) substitution of the amino acid residue corresponding to the threonine at position 36 of SEQ ID NO: 1 with alanine;
(15) substitution of the amino acid residue corresponding to the alanine at position 41 of SEQ ID NO: 1 with threonine;
(16) substitution of the amino acid residue corresponding to the asparagine at position 44 of SEQ ID NO: 1 with serine or glycine;
(17) substitution of the amino acid residue corresponding to the glutamic acid at position 49 of SEQ ID NO: 1 with threonine or isoleucine;
(18) substitution of the amino acid residue corresponding to the asparagine at position 50 of SEQ ID NO: 1 with any of serine, lysine, and aspartic acid;
(19) substitution of the amino acid residue corresponding to the glycine at position 51 of SEQ ID NO: 1 with valine;
(20) substitution of the amino acid residue corresponding to the glutamic acid at position 52 of SEQ ID NO: 1 with any of valine, glycine, and aspartic acid;
(21) substitution of the amino acid residue corresponding to the tyrosine at position 53 of SEQ ID NO: 1 with phenylalanine;
(22) substitution of the amino acid residue corresponding to the threonine at position 54 of SEQ ID NO: 1 with isoleucine or methionine;
(23) substitution of the amino acid residue corresponding to the asparagine at position 62 of SEQ ID NO: 1 with any of histidine, arginine, leucine, methionine, and tryptophan;
(24) substitution of the amino acid residue corresponding to the asparagine at position 65 of SEQ ID NO: 1 with tyrosine;

(25) substitution of the amino acid residue corresponding to the alanine at position 69 of SEQ ID NO: 1 with threonine;

(26) substitution of the amino acid residue corresponding to the threonine at position 2 of SEQ ID NO: 1 with serine or proline;

(27) substitution of the amino acid residue corresponding to the proline at position 3 of SEQ ID NO: 1 with arginine;

(28) substitution of the amino acid residue corresponding to the glutamic acid at position 5 of SEQ ID NO: 1 with lysine or arginine;

(29) substitution of the amino acid residue corresponding to the glutamic acid at position 27 of SEQ ID NO: 1 with any of valine, lysine, and isoleucine;

(30) substitution of the amino acid residue corresponding to the phenylalanine at position 32 of SEQ ID NO: 1 with leucine;

(31) substitution of the amino acid residue corresponding to the lysine at position 38 of SEQ ID NO: 1 with alanine;

(32) substitution of the amino acid residue corresponding to the asparagine at position 44 of SEQ ID NO: 1 with isoleucine;

(33) substitution of the amino acid residue corresponding to the alanine at position 47 of SEQ ID NO: 1 with threonine or arginine;

(34) substitution of the amino acid residue corresponding to the glutamic acid at position 52 of SEQ ID NO: 1 with asparagine;

(35) substitution of the amino acid residue corresponding to the threonine at position 2 of SEQ ID NO: 1 with alanine;

(36) substitution of the amino acid residue corresponding to the glutamic acid at position 5 of SEQ ID NO: 1 with aspartic acid;

(37) substitution of the amino acid residue corresponding to the proline at position 6 of SEQ ID NO: 1 with leucine or threonine;

(38) substitution of the amino acid residue corresponding to the lysine at position 7 of SEQ ID NO: 1 with proline;

(39) substitution of the amino acid residue corresponding to the valine at position 14 of SEQ ID NO: 1 with alanine;

(40) substitution of the amino acid residue corresponding to the isoleucine at position 23 of SEQ ID NO: 1 with arginine or valine;

(41) substitution of the amino acid residue corresponding to the lysine at position 29 of SEQ ID NO: 1 with phenylalanine;

(42) substitution of the amino acid residue corresponding to the threonine at position 31 of SEQ ID NO: 1 with methionine;

(43) substitution of the amino acid residue corresponding to the glutamic acid at position 33 of SEQ ID NO: 1 with any of aspartic acid, glycine, and valine;

(44) substitution of the amino acid residue corresponding to the alanine at position 35 of SEQ ID NO: 1 with threonine;

(45) substitution of the amino acid residue corresponding to the threonine at position 36 of SEQ ID NO: 1 with serine;

(46) substitution of the amino acid residue corresponding to the alanine at position 37 of SEQ ID NO: 1 with threonine;

(47) substitution of the amino acid residue corresponding to the alanine at position 41 of SEQ ID NO: 1 with isoleucine or tyrosine;

(48) substitution of the amino acid residue corresponding to the asparagine at position 44 of SEQ ID NO: 1 with histidine or arginine;

(49) substitution of the amino acid residue corresponding to the glutamic acid at position 52 of SEQ ID NO: 1 with leucine or tyrosine;

(50) substitution of the amino acid residue corresponding to the glycine at position 60 of SEQ ID NO: 1 with arginine;

(51) substitution of the amino acid residue corresponding to the isoleucine at position 64 of SEQ ID NO: 1 with leucine;

(52) substitution of the amino acid residue corresponding to the isoleucine at position 66 of SEQ ID NO: 1 with valine; and

(53) substitution of the amino acid residue corresponding to the alanine at position 69 of SEQ ID NO: 1 with leucine or valine;

(b) a protein comprising an amino acid sequence which is the same as the amino acid sequence of SEQ ID NO:1 or 18 except that the amino acid sequence of the protein has one or more amino acid substitutions selected from at least (1) to (53), and also has substitution, deletion, insertion, and/or addition of one or several amino acid residues at one or several positions other than (1) to (53), the protein having immunoglobulin-binding activity; and (c) a protein comprising an amino acid sequence having a homology of not less than 70% to the amino acid sequence of SEQ ID NO:1 or 18 or a partial sequence thereof, wherein the amino acid sequence of the protein has one or more amino acid substitutions selected from at least (1) to (53), the protein having immunoglobulin-binding activity.

3. The protein according to claim 1, which is a protein of any of the following (d) to (f):

(d) a protein comprising an amino acid sequence which is the same as the amino acid sequence of SEQ ID NO:1 or 18 except that the amino acid sequence of the protein has at least the following amino acid substitution (1), the protein having immunoglobulin-binding activity:

(1) substitution of the amino acid residue corresponding to the asparagine at position 50 of SEQ ID NO: 1 with tyrosine;

(e) a protein comprising an amino acid sequence which is the same as the amino acid sequence of SEQ ID NO:1 or 18 except that the amino acid sequence of the protein has at least the amino acid substitution (1), and also has substitution, deletion, insertion, and/or addition of one or several amino acid residues at one or several positions other than the above amino acid substitution, the protein having immunoglobulin-binding activity; and (f) a protein comprising an amino acid sequence having a homology of not less than 70% to the amino acid sequence of SEQ ID NO:1 or 18 or a partial sequence thereof, wherein the amino acid sequence of the protein has at least the amino acid substitution (1), the protein having immunoglobulin-binding activity.

4. The protein according to claim 1, further comprising one or more amino acid substitutions selected from at least the following (54) to (64):

(54) substitution of the amino acid residue corresponding to the lysine at position 7 of SEQ ID NO: 1 with glutamine;

(55) substitution of the amino acid residue corresponding to the lysine at position 13 of SEQ ID NO: 1 with valine;

(56) substitution of the amino acid residue corresponding to the lysine at position 29 of SEQ ID NO: 1 with valine or isoleucine;

(57) substitution of the amino acid residue corresponding to the proline at position 6 of SEQ ID NO: 1 with alanine;

(58) substitution of the amino acid residue corresponding to the glutamic acid at position 8 of SEQ ID NO: 1 with arginine;

(59) substitution of the amino acid residue corresponding to the asparagine at position 15 of SEQ ID NO: 1 with valine;

(60) substitution of the amino acid residue corresponding to the isoleucine at position 23 of SEQ ID NO: 1 with phenylalanine or leucine;

(61) substitution of the amino acid residue corresponding to the glutamic acid at position 34 of SEQ ID NO: 1 with any of aspartic acid, phenylalanine, leucine, and valine;

(62) substitution of the amino acid residue corresponding to the lysine at position 38 of SEQ ID NO: 1 with leucine;

(63) substitution of the amino acid residue corresponding to the asparagine at position 50 of SEQ ID NO: 1 with methionine; and

(64) substitution of the amino acid residue corresponding to the tyrosine at position 53 of SEQ ID NO: 1 with serine.

5. The protein according to claim 1, wherein one or more lysine residues selected from at least the following (I) to (VII) are substituted with a basic amino acid(s) other than lysine, and/or with an amino acid residue(s) containing a hydroxy group:

(I) the lysine residue corresponding to position 7 of SEQ ID NO:1;

(II) the lysine residue corresponding to position 13 of SEQ ID NO:1;

(III) the lysine residue corresponding to position 22 of SEQ ID NO:1;

(IV) the lysine residue corresponding to position 29 of SEQ ID NO:1;

(V) the lysine residue corresponding to position 38 of SEQ ID NO:1;

(VI) the lysine residue corresponding to position 48 of SEQ ID NO:1; and (VII) the lysine residue corresponding to position 67 of SEQ ID NO:1.

6. The protein according to claim 1, further comprising one or more amino acid substitutions selected from substitution of the amino acid residue corresponding to the glutamic acid at position 49 of SEQ ID NO:1 with aspartic acid, substitution of the amino acid residue corresponding to the proline at position 6 of SEQ ID NO:1 with serine, substitution of the amino acid residue corresponding to the asparagine at position 44 of SEQ ID NO: 1 with aspartic acid, substitution of the amino acid residue corresponding to the glutamic acid at position 49 of SEQ ID NO:1 with valine, substitution of the amino acid residue corresponding to the asparagine at position 62 of SEQ ID NO: 1 with tyrosine, substitution of the amino acid residue corresponding to the asparagine at position 23 of SEQ ID NO:1 with aspartic acid, and substitution of the amino acid residue corresponding to the asparagine at position 44 of SEQ ID NO: 1 with aspartic acid.

7. The protein according to claim 1, wherein the protein comprises at least any of the following amino acid substitutions (W), (X), (Y), (Z), (AA), (AB), (AC), (AD), and (AE):

(W) substitution of the amino acid residue corresponding to the lysine at position 7 of SEQ ID NO: 1 with alanine, substitution of the amino acid residue corresponding to the lysine at each of positions 13, 38, 48, and 67 of SEQ ID NO:1 with arginine, substitution of the amino acid residue corresponding to the lysine at position 22 of SEQ ID NO:1 with glutamine, substitution of the amino acid residue corresponding to the lysine at position 29 of SEQ ID NO:1 with isoleucine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, and substitution of the amino acid residue corresponding to the glutamic acid at position 52 of SEQ ID NO:1 with glycine;

(X) substitution of the amino acid residue corresponding to the lysine at position 7 of SEQ ID NO: 1 with alanine, substitution of the amino acid residue corresponding to the lysine at each of positions 13, 22, 38, 48, and 67 of SEQ ID NO:1 with arginine, substitution of the amino acid residue corresponding to the lysine at position 29 of SEQ ID NO:1 with isoleucine, substitution of the amino acid residue corresponding to the glutamic acid at position 49 of SEQ ID NO: 1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO: 1 with glycine, and substitution of the amino acid residue corresponding to the tyrosine at position 53 of SEQ ID NO:1 with phenylalanine;

(Y) substitution of the amino acid residue corresponding to the glutamic acid at position 4 of SEQ ID NO:1 with glycine, substitution of the amino acid residue corresponding to the lysine at position 7 of SEQ ID NO:1 with alanine, substitution of the amino acid residue corresponding to the lysine at each of positions 13, 22, 38, 48, and 67 of SEQ ID NO: 1 with arginine, substitution of the amino acid residue corresponding to the lysine at position 29 of SEQ ID NO:1 with isoleucine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with aspartic acid, and substitution of the amino acid residue corresponding to the tyrosine at position 53 of SEQ ID NO: 1 with phenylalanine;

(Z) substitution of the amino acid residue corresponding to the glutamic acid at position 4 of SEQ ID NO:1 with glycine, substitution of the amino acid residue corresponding to the lysine at position 7 of SEQ ID NO:1 with alanine, substitution of the amino acid residue corresponding to the lysine at each of positions 13, 22, 38, 48, and 67 of SEQ ID NO:1 with arginine, substitution of the amino acid residue corresponding to the glutamic acid at position 27 of SEQ ID NO: 1 with arginine, substitution of the amino acid residue corresponding to the lysine at position 29 of SEQ ID NO: 1 with isoleucine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO: 1 with aspartic acid, and substitution of the amino acid residue corresponding to the tyrosine at position 53 of SEQ ID NO: 1 with phenylalanine;

(AA) substitution of the amino acid residue corresponding to the glutamic acid at position 4 of SEQ ID NO:1 with glycine, substitution of the amino acid residue corresponding to the proline at position 6 of SEQ ID NO:1 with serine, substitution of the amino acid residue corresponding to the lysine at position 7 of SEQ ID NO:1 with alanine, substitution of the amino acid residue corresponding to the lysine at each of positions 13, 22, 48, and 67 of SEQ ID NO:1 with arginine, substitution of the amino acid residue corresponding to the lysine at position 29 of SEQ ID NO: 1 with isoleucine, substitution of the amino acid residue corresponding to the lysine at position 38 of SEQ ID NO:1 with glutamic acid, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with aspartic acid, and substitution of the amino acid residue corresponding to the tyrosine at position 53 of SEQ ID NO:1 with phenylalanine;

(AB) substitution of the amino acid residue corresponding to the glutamic acid at position 4 of SEQ ID NO:1 with glycine, substitution of the amino acid residue corresponding to the proline at position 6 of SEQ ID NO: 1 with serine, substitution of the amino acid residue corresponding to the lysine at position 7 of SEQ ID NO:1 with alanine, substitution of the amino acid residue corresponding to the lysine at each of positions 13, 22, 48, and 67 of SEQ ID NO:1 with arginine, substitution of the amino acid residue corresponding to the lysine at position 29 of SEQ ID NO: 1 with isoleucine, substitution of the amino acid residue corresponding to the lysine at position 38 of SEQ ID NO:1 with glutamic acid, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the glutamic acid at position 52 of SEQ ID NO:1 with valine, substitution of the amino acid residue corresponding to the tyrosine at position 53 of SEQ ID NO:1 with phenylalanine, and substitution of the amino acid residue corresponding to the alanine at position 69 of SEQ ID NO: 1 with valine;

(AC) substitution of the amino acid residue corresponding to the glutamic acid at position 4 of SEQ ID NO:1 with glycine, substitution of the amino acid residue corresponding to the proline at position 6 of SEQ ID NO: 1 with serine, substitution of the amino acid residue corresponding to the lysine at position 7 of SEQ ID NO:1 with alanine, substitution of the amino acid residue corresponding to the lysine at each of positions 13, 22, 48, and 67 of SEQ ID NO:1 with arginine, substitution of the amino acid residue corresponding to the lysine at position 29 of SEQ ID NO: 1 with isoleucine, substitution of the amino acid residue corresponding to the lysine at position 38 of SEQ ID NO:1 with glutamic acid, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the tyrosine at position 53 of SEQ ID NO:1 with phenylalanine, and substitution of the amino acid residue corresponding to the alanine at position 69 of SEQ ID NO:1 with valine;

(AD) substitution of the amino acid residue corresponding to the glutamic acid at position 4 of SEQ ID NO:1 with glycine, substitution of the amino acid residue corresponding to the proline at position 6 of SEQ ID NO:1 with serine, substitution of the amino acid residue corresponding to the lysine at position 7 of SEQ ID NO:1 with alanine, substitution of the amino acid residue corresponding to the lysine at each of positions 13, 22, 48, and 67 of SEQ ID NO:1 with arginine, substitution of the amino acid residue corresponding to the isoleucine at position 23 of SEQ ID NO:1 with arginine, substitution of the amino acid residue corresponding to the lysine at position 29 of SEQ ID NO:1 with isoleucine, substitution of the amino acid residue corresponding to the lysine at position 38 of SEQ ID NO: 1 with glutamic acid, substitution of the amino acid residue corresponding to the asparagine at position 44 of SEQ ID NO:1 with arginine, substitution of the amino acid residue corresponding to the glutamic acid at position 49 of SEQ ID NO:1 with aspartic acid, substitution of the amino acid residue corresponding to the asparagine at each of positions 50 and 62 of SEQ ID NO:1 with tyrosine, substitution of the amino acid residue corresponding to the tyrosine at position 53 of SEQ ID NO:1 with phenylalanine, and substitution of the amino acid residue corresponding to the alanine at position 69 of SEQ ID NO: 1 with valine; and (AE) substitution of the amino acid residue corresponding to the glutamic acid at position 4 of SEQ ID NO:1 with glycine, substitution of the amino acid residue corresponding to the proline at position 6 of SEQ ID NO: 1 with serine, substitution of the amino acid residue corresponding to the lysine at position 7 of SEQ ID NO:1 with alanine, substitution of the amino acid residue corresponding to the lysine at each of positions 13, 22, and 67 of SEQ ID NO:1 with arginine, substitution of the amino acid residue corresponding to the isoleucine at position 23 of SEQ ID NO: 1 with arginine, substitution of the amino acid residue corresponding to the lysine at position 29 of SEQ ID NO:1 with isoleucine, substitution of the amino acid residue corresponding to the lysine at position 38 of SEQ ID NO:1 with glutamic acid, substitution of the amino acid residue corresponding to the asparagine at position 44 of SEQ ID NO: 1 with arginine, substitution of the amino acid residue corresponding to the lysine at position 48 of SEQ ID NO:1 with histidine, substitution of the amino acid residue corresponding to the glutamic acid at position 49 of SEQ ID NO: 1 with aspartic acid, substitution of the amino acid residue corresponding to the asparagine at each of positions 50 and 62 of SEQ ID NO:1 with tyrosine, substitution of the amino acid residue corresponding to the tyrosine at position 53 of SEQ ID NO:1 with phenylalanine, substitution of the amino acid residue corresponding to the isoleucine at position 64 of SEQ ID NO: 1 with leucine, and substitution of the amino acid residue corresponding to the alanine at position 69 of SEQ ID NO: 1 with valine.

8. The protein according to claim 1, wherein the protein comprises the amino acid sequence of any of SEQ ID NOs: 179, 186, 199, 224, 240, 271, 275, 408, and 413.

9. A method of producing a protein having immunoglobulin-binding activity, the method comprising:

culturing a recombinant host containing a polynucleotide encoding the protein according to claim 1, or a recombinant host containing an expression vector containing the polynucleotide, to allow expression of the protein; and recovering the expressed protein.

10. The production method according to claim 9, wherein the host is *Escherichia coli*.

11. A column packed with an immunoglobulin adsorbent comprising:

an insoluble support; and a protein according to claim 1 immobilized on the insoluble support.

12. A method of separating immunoglobulin contained in a solution, the method comprising:

applying a solution containing immunoglobulin to the column according to claim 11, to allow adsorption of the immunoglobulin to the immunoglobulin adsorbent packed in the column; and eluting the immunoglobulin that has adsorbed to the immunoglobulin adsorbent.

* * * * *

SEQUENCE LISTING

```
Sequence total quantity: 438
SEQ ID NO: 1            moltype = AA  length = 70
FEATURE                 Location/Qualifiers
source                  1..70
                        mol_type = protein
                        organism = Finegoldia magna
SEQUENCE: 1
ETPEEPKEEV TIKVNLIFAD GKIQTAEFKG TFEEATAKAY AYANLLAKEN GEYTADLEDG  60
GNTINIKFAG                                                         70

SEQ ID NO: 2            moltype = DNA  length = 210
FEATURE                 Location/Qualifiers
source                  1..210
                        mol_type = genomic DNA
                        organism = Finegoldia magna
SEQUENCE: 2
gaaactcccg aagaaccaaa agaagaagtt acgattaagg ttaacttaat cttcgccgac  60
ggtaagattc agacagctga atttaaggga acattcgaag aagcgaccgc gaaagcatac  120
gcgtacgcca acctgctggc gaaagaaaac ggtgagtata ccgccgattt agaagatggc  180
ggcaatacga tcaatatcaa gtttgcgggt                                   210

SEQ ID NO: 3            moltype = DNA  length = 20
FEATURE                 Location/Qualifiers
misc_feature            1..20
                        note = PCR forward primer
source                  1..20
                        mol_type = other DNA
                        organism = synthetic construct
SEQUENCE: 3
taatacgact cactataggg                                              20

SEQ ID NO: 4            moltype = DNA  length = 19
FEATURE                 Location/Qualifiers
misc_feature            1..19
                        note = PCR reverse primer
source                  1..19
                        mol_type = other DNA
                        organism = synthetic construct
SEQUENCE: 4
tatgctagtt attgctcag                                               19

SEQ ID NO: 5            moltype = AA  length = 70
FEATURE                 Location/Qualifiers
REGION                  1..70
                        note = FpL_C3 N62Y
source                  1..70
                        mol_type = protein
```

```
                        organism = synthetic construct
SEQUENCE: 5
ETPEEPKEEV TIKVNLIFAD GKIQTAEFKG TFEEATAKAY AYANLLAKEN GEYTADLEDG  60
GYTINIKFAG                                                        70

SEQ ID NO: 6            moltype = AA  length = 70
FEATURE                 Location/Qualifiers
REGION                  1..70
                        note = FpL_C3 I17F N50S
source                  1..70
                        mol_type = protein
                        organism = synthetic construct
SEQUENCE: 6
ETPEEPKEEV TIKVNLFFAD GKIQTAEFKG TFEEATAKAY AYANLLAKES GEYTADLEDG  60
GNTINIKFAG                                                        70

SEQ ID NO: 7            moltype = AA  length = 70
FEATURE                 Location/Qualifiers
REGION                  1..70
                        note = FpL_C3 K22R K29R N44S
source                  1..70
                        mol_type = protein
                        organism = synthetic construct
SEQUENCE: 7
ETPEEPKEEV TIKVNLIFAD GRIQTAEFRG TFEEATAKAY AYASLLAKEN GEYTADLEDG  60
GNTINIKFAG                                                        70

SEQ ID NO: 8            moltype = AA  length = 70
FEATURE                 Location/Qualifiers
REGION                  1..70
                        note = FpL_C3 E8G E52V N62Y
source                  1..70
                        mol_type = protein
                        organism = synthetic construct
SEQUENCE: 8
ETPEEPKGEV TIKVNLIFAD GKIQTAEFKG TFEEATAKAY AYANLLAKEN GVYTADLEDG  60
GYTINIKFAG                                                        70

SEQ ID NO: 9            moltype = AA  length = 70
FEATURE                 Location/Qualifiers
REGION                  1..70
                        note = FpL_C3 E49V
source                  1..70
                        mol_type = protein
                        organism = synthetic construct
SEQUENCE: 9
ETPEEPKEEV TIKVNLIFAD GKIQTAEFKG TFEEATAKAY AYANLLAKVN GEYTADLEDG  60
GNTINIKFAG                                                        70

SEQ ID NO: 10           moltype = AA  length = 70
FEATURE                 Location/Qualifiers
REGION                  1..70
                        note = FpL_C3 K22R
source                  1..70
                        mol_type = protein
                        organism = synthetic construct
SEQUENCE: 10
ETPEEPKEEV TIKVNLIFAD GRIQTAEFKG TFEEATAKAY AYANLLAKEN GEYTADLEDG  60
GNTINIKFAG                                                        70

SEQ ID NO: 11           moltype = AA  length = 70
FEATURE                 Location/Qualifiers
REGION                  1..70
                        note = FpL_C3 N50Y E52G (FpL_C3 2a)
source                  1..70
                        mol_type = protein
                        organism = synthetic construct
SEQUENCE: 11
ETPEEPKEEV TIKVNLIFAD GKIQTAEFKG TFEEATAKAY AYANLLAKEY GGYTADLEDG  60
GNTINIKFAG                                                        70

SEQ ID NO: 12           moltype = AA  length = 70
FEATURE                 Location/Qualifiers
REGION                  1..70
                        note = FpL_C3 E27G A41T N50K N65Y
source                  1..70
                        mol_type = protein
                        organism = synthetic construct
SEQUENCE: 12
```

```
ETPEEPKEEV TIKVNLIFAD GKIQTAGFKG TFEEATAKAY TYANLLAKEK GEYTADLEDG  60
GNTIYIKFAG                                                        70

SEQ ID NO: 13          moltype = AA  length = 70
FEATURE                Location/Qualifiers
REGION                 1..70
                       note = FpL_C3 N50S
source                 1..70
                       mol_type = protein
                       organism = synthetic construct
SEQUENCE: 13
ETPEEPKEEV TIKVNLIFAD GKIQTAEFKG TFEEATAKAY AYANLLAKES GEYTADLEDG  60
GNTINIKFAG                                                        70

SEQ ID NO: 14          moltype = AA  length = 70
FEATURE                Location/Qualifiers
REGION                 1..70
                       note = FpL_C3 E5V
source                 1..70
                       mol_type = protein
                       organism = synthetic construct
SEQUENCE: 14
ETPEVPKEEV TIKVNLIFAD GKIQTAEFKG TFEEATAKAY AYANLLAKEN GEYTADLEDG  60
GNTINIKFAG                                                        70

SEQ ID NO: 15          moltype = AA  length = 70
FEATURE                Location/Qualifiers
REGION                 1..70
                       note = FpL_C3 P3S N50D T54I
source                 1..70
                       mol_type = protein
                       organism = synthetic construct
SEQUENCE: 15
ETSEEPKEEV TIKVNLIFAD GKIQTAEFKG TFEEATAKAY AYANLLAKED GEYIADLEDG  60
GNTINIKFAG                                                        70

SEQ ID NO: 16          moltype = AA  length = 70
FEATURE                Location/Qualifiers
REGION                 1..70
                       note = FpL_C3 E52G
source                 1..70
                       mol_type = protein
                       organism = synthetic construct
SEQUENCE: 16
ETPEEPKEEV TIKVNLIFAD GKIQTAEFKG TFEEATAKAY AYANLLAKEN GGYTADLEDG  60
GNTINIKFAG                                                        70

SEQ ID NO: 17          moltype = AA  length = 70
FEATURE                Location/Qualifiers
REGION                 1..70
                       note = FpL_C3 K38R
source                 1..70
                       mol_type = protein
                       organism = synthetic construct
SEQUENCE: 17
ETPEEPKEEV TIKVNLIFAD GKIQTAEFKG TFEEATARAY AYANLLAKEN GEYTADLEDG  60
GNTINIKFAG                                                        70

SEQ ID NO: 18          moltype = AA  length = 70
FEATURE                Location/Qualifiers
source                 1..70
                       mol_type = protein
                       organism = Finegoldia magna
SEQUENCE: 18
ETPEEPKEEV TIKVNLIFAD GKTQTAEFKG TFEEATAEAY RYADLLAKVN GEYTADLEDG  60
GYTINIKFAG                                                        70

SEQ ID NO: 19          moltype = DNA  length = 210
FEATURE                Location/Qualifiers
source                 1..210
                       mol_type = genomic DNA
                       organism = Finegoldia magna
SEQUENCE: 19
gaaactcccg aagaaccaaa agaagaagtt acgattaagg ttaacttaat cttcgccgac  60
ggtaagacac agacagctga atttaaggga acattcgaag aagcgaccgc ggaagcatac  120
cgttacgccg atctgctggc gaaagtgaac ggtgagtata ccgccgattt agaagatggc  180
ggctacacga tcaatatcaa gtttgcgggt                                  210

SEQ ID NO: 20          moltype = AA  length = 70
```

```
FEATURE                 Location/Qualifiers
REGION                  1..70
                        note = FpL_C4 E1G
source                  1..70
                        mol_type = protein
                        organism = synthetic construct
SEQUENCE: 20
GTPEEPKEEV TIKVNLIFAD GKTQTAEFKG TFEEATAEAY RYADLLAKVN GEYTADLEDG  60
GYTINIKFAG                                                        70

SEQ ID NO: 21           moltype = AA  length = 70
FEATURE                 Location/Qualifiers
REGION                  1..70
                        note = FpL_C4 N50D
source                  1..70
                        mol_type = protein
                        organism = synthetic construct
SEQUENCE: 21
ETPEEPKEEV TIKVNLIFAD GKTQTAEFKG TFEEATAEAY RYADLLAKVD GEYTADLEDG  60
GYTINIKFAG                                                        70

SEQ ID NO: 22           moltype = AA  length = 70
FEATURE                 Location/Qualifiers
REGION                  1..70
                        note = FpL_C4 K22R
source                  1..70
                        mol_type = protein
                        organism = synthetic construct
SEQUENCE: 22
ETPEEPKEEV TIKVNLIFAD GRTQTAEFKG TFEEATAEAY RYADLLAKVN GEYTADLEDG  60
GYTINIKFAG                                                        70

SEQ ID NO: 23           moltype = AA  length = 70
FEATURE                 Location/Qualifiers
REGION                  1..70
                        note = FpL_C3 3a
source                  1..70
                        mol_type = protein
                        organism = synthetic construct
SEQUENCE: 23
ETPEEPKEEV TIKVNLIFAD GKIQTAEFKG TFEEATAKAY AYANLLAKEY GGYTADLEDG  60
GYTINIKFAG                                                        70

SEQ ID NO: 24           moltype = DNA  length = 210
FEATURE                 Location/Qualifiers
misc_feature            1..210
                        note = FpL_C3 2a DNA
source                  1..210
                        mol_type = other DNA
                        organism = synthetic construct
SEQUENCE: 24
gaaactcccg aagaaccaaa agaagaagtt acgattaagg ttaacttaat cttcgccgac  60
ggtaagattc agacagctga atttaaggga acattcgaag aagcgaccgc gaaagcatac  120
gcgtacgcca acctgctggc gaaagaatac ggtgggtata ccgccgattt agaagatggc  180
ggcaatacga tcaatatcaa gtttgcgggt                                   210

SEQ ID NO: 25           moltype = DNA  length = 27
FEATURE                 Location/Qualifiers
misc_feature            1..27
                        note = PCR forward primer
source                  1..27
                        mol_type = other DNA
                        organism = synthetic construct
SEQUENCE: 25
ggcggctata cgatcaatat caagttt                                     27

SEQ ID NO: 26           moltype = DNA  length = 27
FEATURE                 Location/Qualifiers
misc_feature            1..27
                        note = PCR reverse primer
source                  1..27
                        mol_type = other DNA
                        organism = synthetic construct
SEQUENCE: 26
gatcgtatag ccgccatctt ctaaatc                                     27

SEQ ID NO: 27           moltype = AA  length = 70
FEATURE                 Location/Qualifiers
REGION                  1..70
```

```
                        note = FpL_C3 3b
source                  1..70
                        mol_type = protein
                        organism = synthetic construct
SEQUENCE: 27
ETPEEPKEEV TIKVNLIFAD GKIQTAEFKG TFEEATAKAY AYANLLAKVY GGYTADLEDG  60
GNTINIKFAG                                                         70

SEQ ID NO: 28           moltype = DNA  length = 27
FEATURE                 Location/Qualifiers
misc_feature            1..27
                        note = PCR forward primer
source                  1..27
                        mol_type = other DNA
                        organism = synthetic construct
SEQUENCE: 28
gcgaaagtat acggtgggta taccgcc                                      27

SEQ ID NO: 29           moltype = DNA  length = 27
FEATURE                 Location/Qualifiers
misc_feature            1..27
                        note = PCR reverse primer
source                  1..27
                        mol_type = other DNA
                        organism = synthetic construct
SEQUENCE: 29
accgtatact ttcgccagca ggttggc                                      27

SEQ ID NO: 30           moltype = AA  length = 70
FEATURE                 Location/Qualifiers
REGION                  1..70
                        note = FpL_C3 3c
source                  1..70
                        mol_type = protein
                        organism = synthetic construct
SEQUENCE: 30
ETPEEPKEEV TIKVNLIFAD GKIQTAEFKG TFEEATAKAY AYASLLAKEY GGYTADLEDG  60
GNTINIKFAG                                                         70

SEQ ID NO: 31           moltype = DNA  length = 27
FEATURE                 Location/Qualifiers
misc_feature            1..27
                        note = PCR forward primer
source                  1..27
                        mol_type = other DNA
                        organism = synthetic construct
SEQUENCE: 31
tacgccagcc tgctggcgaa agaatac                                      27

SEQ ID NO: 32           moltype = DNA  length = 27
FEATURE                 Location/Qualifiers
misc_feature            1..27
                        note = PCR reverse primer
source                  1..27
                        mol_type = other DNA
                        organism = synthetic construct
SEQUENCE: 32
cagcaggctg gcgtacgcgt atgcttt                                      27

SEQ ID NO: 33           moltype = AA  length = 70
FEATURE                 Location/Qualifiers
REGION                  1..70
                        note = FpL_C3 3d
source                  1..70
                        mol_type = protein
                        organism = synthetic construct
SEQUENCE: 33
ETPEEPKEEV TIKVNLIFAD GKIQTAEFKG TFEEATAKAY AYADLLAKEY GGYTADLEDG  60
GNTINIKFAG                                                         70

SEQ ID NO: 34           moltype = DNA  length = 27
FEATURE                 Location/Qualifiers
misc_feature            1..27
                        note = PCR forward primer
source                  1..27
                        mol_type = other DNA
                        organism = synthetic construct
SEQUENCE: 34
tacgccgatc tgctggcgaa agaatac                                      27
```

```
SEQ ID NO: 35          moltype = DNA  length = 27
FEATURE                Location/Qualifiers
misc_feature           1..27
                       note = PCR reverse primer
source                 1..27
                       mol_type = other DNA
                       organism = synthetic construct
SEQUENCE: 35
cagcagatcg gcgtacgcgt atgcttt                                      27

SEQ ID NO: 36          moltype = AA  length = 70
FEATURE                Location/Qualifiers
REGION                 1..70
                       note = FpL_C3 3e
source                 1..70
                       mol_type = protein
                       organism = synthetic construct
SEQUENCE: 36
ETPEEPKEEV TIKVNLIFAD GKIQTAEFKG TFEEATAKAY AYANLLAKVY GEYTADLEDG  60
GYTINIKFAG                                                         70

SEQ ID NO: 37          moltype = DNA  length = 210
FEATURE                Location/Qualifiers
misc_feature           1..210
                       note = FpL_C3 3e DNA
source                 1..210
                       mol_type = other DNA
                       organism = synthetic construct
SEQUENCE: 37
gaaaccccgg aagaaccaaa ggaggaagtc accatcaagg ttaatttgat tttcgccgac  60
ggtaaaatcc agacggcaga attcaaagga actttcgaag aagcgacagc taaagcgtac  120
gcatacgcaa acctgttagc aaaagtttac ggagaatata cggccgatct ggaggatggc  180
ggctatacca ttaacatcaa gtttgccggg                                   210

SEQ ID NO: 38          moltype = AA  length = 70
FEATURE                Location/Qualifiers
REGION                 1..70
                       note = FpL_C3 4a
source                 1..70
                       mol_type = protein
                       organism = synthetic construct
SEQUENCE: 38
ETPEEPKEEV TIKVNLIFAD GKIQTAEFKG TFEEATAKAY AYASLLAKVY GEYTADLEDG  60
GYTINIKFAG                                                         70

SEQ ID NO: 39          moltype = DNA  length = 210
FEATURE                Location/Qualifiers
misc_feature           1..210
                       note = FpL_C3 4a DNA
source                 1..210
                       mol_type = other DNA
                       organism = synthetic construct
SEQUENCE: 39
gaaaccccgg aagaaccaaa ggaggaagtc accatcaagg ttaatttgat tttcgccgac  60
ggtaaaatcc agacggcaga attcaaagga actttcgaag aagcgacagc taaagcgtac  120
gcatacgcaa gcctgttagc aaaagtttac ggagaatata cggccgatct ggaggatggc  180
ggctatacca ttaacatcaa gtttgccggg                                   210

SEQ ID NO: 40          moltype = AA  length = 70
FEATURE                Location/Qualifiers
REGION                 1..70
                       note = FpL_C3 4b
source                 1..70
                       mol_type = protein
                       organism = synthetic construct
SEQUENCE: 40
ETPEEPKEEV TIKVNLIFAD GKIQTAEFKG TFEEATAKAY AYADLLAKVY GEYTADLEDG  60
GYTINIKFAG                                                         70

SEQ ID NO: 41          moltype = DNA  length = 210
FEATURE                Location/Qualifiers
misc_feature           1..210
                       note = FpL_C3 4b DNA
source                 1..210
                       mol_type = other DNA
                       organism = synthetic construct
SEQUENCE: 41
gaaaccccgg aagaaccaaa ggaggaagtc accatcaagg ttaatttgat tttcgccgac  60
```

```
ggtaaaatcc agacggcaga attcaaagga actttcgaag aagcgacagc taaagcgtac  120
gcatacgcag atctgttagc aaaagtttac ggagaatata cggccgatct ggaggatggc  180
ggctatacca ttaacatcaa gtttgccggg                                   210

SEQ ID NO: 42          moltype = AA  length = 70
FEATURE                Location/Qualifiers
REGION                 1..70
                       note = FpL_C3 4c
source                 1..70
                       mol_type = protein
                       organism = synthetic construct
SEQUENCE: 42
ETPEEPKEEV TIKVNLIFAD GKIQTAEFKG TFEEATAKAY AYANLLAKVY GGYTADLEDG  60
GYTINIKFAG                                                         70

SEQ ID NO: 43          moltype = DNA  length = 210
FEATURE                Location/Qualifiers
misc_feature           1..210
                       note = FpL_C3 4c DNA
source                 1..210
                       mol_type = other DNA
                       organism = synthetic construct
SEQUENCE: 43
gaaaccccgg aagaaccaaa ggaggaagtc accatcaagg ttaatttgat tttcgccgac  60
ggtaaaatcc agacggcaga attcaaagga actttcgaag aagcgacagc taaagcgtac  120
gcatacgcaa acctgttagc aaaagtttac ggaggctata cggccgatct ggaggatggc  180
ggctatacca ttaacatcaa gtttgccggg                                   210

SEQ ID NO: 44          moltype = AA  length = 70
FEATURE                Location/Qualifiers
REGION                 1..70
                       note = FpL_C3 4d
source                 1..70
                       mol_type = protein
                       organism = synthetic construct
SEQUENCE: 44
ETPEEPKEEV TIKVNLIFAD GKIQTAEFKG TFEEATAKAY AYASLLAKEY GGYTADLEDG  60
GYTINIKFAG                                                         70

SEQ ID NO: 45          moltype = DNA  length = 210
FEATURE                Location/Qualifiers
misc_feature           1..210
                       note = FpL_C3 4d DNA
source                 1..210
                       mol_type = other DNA
                       organism = synthetic construct
SEQUENCE: 45
gaaaccccgg aagaaccaaa ggaggaagtc accatcaagg ttaatttgat tttcgccgac  60
ggtaaaatcc agacggcaga attcaaagga actttcgaag aagcgacagc taaagcgtac  120
gcatacgcaa gcctgttagc aaaagaatac ggaggctata cggccgatct ggaggatggc  180
ggctatacca ttaacatcaa gtttgccggg                                   210

SEQ ID NO: 46          moltype = AA  length = 70
FEATURE                Location/Qualifiers
REGION                 1..70
                       note = FpL_C3 4e
source                 1..70
                       mol_type = protein
                       organism = synthetic construct
SEQUENCE: 46
ETPEEPKEEV TIKVNLIFAD GKIQTAEFKG TFEEATAKAY AYADLLAKVY GEYTADLEDG  60
GYTINIKFAG                                                         70

SEQ ID NO: 47          moltype = DNA  length = 210
FEATURE                Location/Qualifiers
misc_feature           1..210
                       note = FpL_C3 4e DNA
source                 1..210
                       mol_type = other DNA
                       organism = synthetic construct
SEQUENCE: 47
gaaaccccgg aagaaccaaa ggaggaagtc accatcaagg ttaatttgat tttcgccgac  60
ggtaaaatcc agacggcaga attcaaagga actttcgaag aagcgacagc taaagcgtac  120
gcatacgcag atctgttagc aaaagaatac ggaggctata cggccgatct ggaggatggc  180
ggctatacca ttaacatcaa gtttgccggg                                   210

SEQ ID NO: 48          moltype = AA  length = 70
FEATURE                Location/Qualifiers
REGION                 1..70
```

```
                         note = FpL_C3 5a
source                   1..70
                         mol_type = protein
                         organism = synthetic construct
SEQUENCE: 48
ETPEEPKEEV TIKVNLIFAD GKIQTAEFKG TFEEATAKAY AYASLLAKVY GGYTADLEDG  60
GYTINIKFAG                                                         70

SEQ ID NO: 49            moltype = DNA  length = 210
FEATURE                  Location/Qualifiers
misc_feature             1..210
                         note = FpL_C3 5a DNA
source                   1..210
                         mol_type = other DNA
                         organism = synthetic construct
SEQUENCE: 49
gaaaccccgg aagaaccaaa ggaggaagtc accatcaagg ttaatttgat tttcgccgac  60
ggtaaaatcc agacggcaga attcaaagga actttcgaag aagcgacagc taaagcgtac  120
gcatacgcaa gcctgttagc aaaagtgtac ggaggctata cggccgatct ggaggatggc  180
ggctatacca ttaacatcaa gtttgccggg                                   210

SEQ ID NO: 50            moltype = AA  length = 70
FEATURE                  Location/Qualifiers
REGION                   1..70
                         note = FpL_C3 5b
source                   1..70
                         mol_type = protein
                         organism = synthetic construct
SEQUENCE: 50
ETPEEPKEEV TIKVNLIFAD GKIQTAEFKG TFEEATAKAY AYADLLAKVY GGYTADLEDG  60
GYTINIKFAG                                                         70

SEQ ID NO: 51            moltype = DNA  length = 210
FEATURE                  Location/Qualifiers
misc_feature             1..210
                         note = FpL_C3 5b DNA
source                   1..210
                         mol_type = other DNA
                         organism = synthetic construct
SEQUENCE: 51
gaaaccccgg aagaaccaaa ggaggaagtc accatcaagg ttaatttgat tttcgccgac  60
ggtaaaatcc agacggcaga attcaaagga actttcgaag aagcgacagc taaagcgtac  120
gcatacgcag atctgttagc aaaagtgtac ggaggctata cggccgatct ggaggatggc  180
ggctatacca ttaacatcaa gtttgccggg                                   210

SEQ ID NO: 52            moltype = DNA  length = 80
FEATURE                  Location/Qualifiers
misc_feature             1..80
                         note = Oligonucleotide
source                   1..80
                         mol_type = other DNA
                         organism = synthetic construct
SEQUENCE: 52
ctcgctgccc agccggcgat ggccatggaa actcccgaag aaccaaaaga agaagttacg  60
attaaggtta acttaatctt                                              80

SEQ ID NO: 53            moltype = DNA  length = 80
FEATURE                  Location/Qualifiers
misc_feature             1..80
                         note = Oligonucleotide
source                   1..80
                         mol_type = other DNA
                         organism = synthetic construct
SEQUENCE: 53
aagattaagt taaccttaat cgtaacttct tcttttggtt cttcgggagt ttccatggcc  60
atcgccggct gggcagcgag                                              80

SEQ ID NO: 54            moltype = DNA  length = 75
FEATURE                  Location/Qualifiers
misc_feature             1..75
                         note = Oligonucleotide
source                   1..75
                         mol_type = other DNA
                         organism = synthetic construct
SEQUENCE: 54
tacgattaag gttaacttaa tcttcgccga cggtaagatt cagacagctg aatttaaggg  60
aacattcgaa gaagc                                                   75

SEQ ID NO: 55            moltype = DNA  length = 75
```

```
FEATURE                Location/Qualifiers
misc_feature           1..75
                       note = Oligonucleotide
source                 1..75
                       mol_type = other DNA
                       organism = synthetic construct
SEQUENCE: 55
gcttcttcga atgttccctt aaattcagct gtctgaatct taccgtcggc gaagattaag  60
ttaaccttaa tcgta                                                   75

SEQ ID NO: 56          moltype = DNA  length = 77
FEATURE                Location/Qualifiers
misc_feature           1..77
                       note = Oligonucleotide
source                 1..77
                       mol_type = other DNA
                       organism = synthetic construct
SEQUENCE: 56
aatttaaggg aacattcgaa gaagcgaccg cgaaagcata cgcgtacgcc rrtctgctgg  60
cgaaagwawr tggtgda                                                 77

SEQ ID NO: 57          moltype = DNA  length = 77
FEATURE                Location/Qualifiers
misc_feature           1..77
                       note = Oligonucleotide
source                 1..77
                       mol_type = other DNA
                       organism = synthetic construct
SEQUENCE: 57
thcaccaywt wctttcgcca gcagayyggc gtacgcgtat gctttcgcgg tcgcttcttc  60
gaatgttccc ttaaatt                                                 77

SEQ ID NO: 58          moltype = DNA  length = 76
FEATURE                Location/Qualifiers
misc_feature           1..76
                       note = Oligonucleotide
source                 1..76
                       mol_type = other DNA
                       organism = synthetic construct
SEQUENCE: 58
rrtctgctgg cgaaagwawr tggtgdatat accgccgatt tagaagatgg cggcwatacg  60
atcaatatca agtttg                                                  76

SEQ ID NO: 59          moltype = DNA  length = 76
FEATURE                Location/Qualifiers
misc_feature           1..76
                       note = Oligonucleotide
source                 1..76
                       mol_type = other DNA
                       organism = synthetic construct
SEQUENCE: 59
caaacttgat attgatcgta twgccgccat cttctaaatc ggcggtatat hcaccaywtw  60
ctttcgccag cagayy                                                  76

SEQ ID NO: 60          moltype = DNA  length = 80
FEATURE                Location/Qualifiers
misc_feature           1..80
                       note = Oligonucleotide
source                 1..80
                       mol_type = other DNA
                       organism = synthetic construct
SEQUENCE: 60
atggcggcwa tacgatcaat atcaagtttg cgggtcatca ccaccatcac cactaagctt  60
gcggccgcac tcgagcacca                                              80

SEQ ID NO: 61          moltype = DNA  length = 80
FEATURE                Location/Qualifiers
misc_feature           1..80
                       note = Oligonucleotide
source                 1..80
                       mol_type = other DNA
                       organism = synthetic construct
SEQUENCE: 61
tggtgctcga gtgcggccgc aagcttagtg gtgatggtgg tgatgacccg caaacttgat  60
attgatcgta twgccgccat                                              80

SEQ ID NO: 62          moltype = AA  length = 70
FEATURE                Location/Qualifiers
REGION                 1..70
```

```
                      note = FpL_C3 4f
source                1..70
                      mol_type = protein
                      organism = synthetic construct
SEQUENCE: 62
ETPEEPKEEV TIKVNLIFAD GKIQTAEFKG TFEEATAKAY AYADLLAKEY GVYTADLEDG  60
GYTINIKFAG                                                         70

SEQ ID NO: 63         moltype = AA  length = 70
FEATURE               Location/Qualifiers
REGION                1..70
                      note = FpL_C3 5c
source                1..70
                      mol_type = protein
                      organism = synthetic construct
SEQUENCE: 63
ETPEEPKEEV TIKVNLIFAD GKIQTAEFKG TFEEATAKAY AYAGLLAKVY GVYTADLEDG  60
GYTINIKFAG                                                         70

SEQ ID NO: 64         moltype = AA  length = 70
FEATURE               Location/Qualifiers
REGION                1..70
                      note = FpL_C3 5d
source                1..70
                      mol_type = protein
                      organism = synthetic construct
SEQUENCE: 64
ETPEEPKEEV TIKVNLIFAD GKIQTAEFKG TFEEATAKAY AYAGLLAKVS GVYTADLEDG  60
GYTINIKFAG                                                         70

SEQ ID NO: 65         moltype = DNA  length = 27
FEATURE               Location/Qualifiers
misc_feature          1..27
                      note = G21X forward primer 1
misc_difference       7
                      note = a, c, g, or t
misc_difference       8
                      note = a, g, or t
source                1..27
                      mol_type = other DNA
                      organism = synthetic construct
SEQUENCE: 65
gccgacndta agattcagac agctgaa                                      27

SEQ ID NO: 66         moltype = DNA  length = 27
FEATURE               Location/Qualifiers
misc_feature          1..27
                      note = G21X forward primer 2
source                1..27
                      mol_type = other DNA
                      organism = synthetic construct
SEQUENCE: 66
gccgacvhga agattcagac agctgaa                                      27

SEQ ID NO: 67         moltype = DNA  length = 27
FEATURE               Location/Qualifiers
misc_feature          1..27
                      note = G21X forward primer 3
source                1..27
                      mol_type = other DNA
                      organism = synthetic construct
SEQUENCE: 67
gccgactgga agattcagac agctgaa                                      27

SEQ ID NO: 68         moltype = DNA  length = 27
FEATURE               Location/Qualifiers
misc_feature          1..27
                      note = G21X reverse primer 1
misc_difference       8
                      note = a, c, or t
misc_difference       9
                      note = a, c, g, or t
source                1..27
                      mol_type = other DNA
                      organism = synthetic construct
SEQUENCE: 68
aatcttahng tcggcgaaga ttaagtt                                      27

SEQ ID NO: 69         moltype = DNA  length = 27
```

```
FEATURE                 Location/Qualifiers
misc_feature            1..27
                        note = G21X reverse primer 2
source                  1..27
                        mol_type = other DNA
                        organism = synthetic construct
SEQUENCE: 69
aatcttcdbg tcggcgaaga ttaagtt                                        27

SEQ ID NO: 70           moltype = DNA  length = 27
FEATURE                 Location/Qualifiers
misc_feature            1..27
                        note = G21X reverse primer 3
source                  1..27
                        mol_type = other DNA
                        organism = synthetic construct
SEQUENCE: 70
aatcttccag tcggcgaaga ttaagtt                                        27

SEQ ID NO: 71           moltype = DNA  length = 27
FEATURE                 Location/Qualifiers
misc_feature            1..27
                        note = K22X forward primer 1
misc_difference         7
                        note = a, c, g, or t
misc_difference         8
                        note = a, g, or t
source                  1..27
                        mol_type = other DNA
                        organism = synthetic construct
SEQUENCE: 71
gacggtndta ttcagacagc tgaattt                                        27

SEQ ID NO: 72           moltype = DNA  length = 27
FEATURE                 Location/Qualifiers
misc_feature            1..27
                        note = K22X forward primer 2
source                  1..27
                        mol_type = other DNA
                        organism = synthetic construct
SEQUENCE: 72
gacggtvhga ttcagacagc tgaattt                                        27

SEQ ID NO: 73           moltype = DNA  length = 27
FEATURE                 Location/Qualifiers
misc_feature            1..27
                        note = K22X forward primer 3
source                  1..27
                        mol_type = other DNA
                        organism = synthetic construct
SEQUENCE: 73
gacggttgga ttcagacagc tgaattt                                        27

SEQ ID NO: 74           moltype = DNA  length = 27
FEATURE                 Location/Qualifiers
misc_feature            1..27
                        note = K22X reverse primer 1
misc_difference         8
                        note = a, c, or t
misc_difference         9
                        note = a, c, g, or t
source                  1..27
                        mol_type = other DNA
                        organism = synthetic construct
SEQUENCE: 74
ctgaatahna ccgtcggcga agattaa                                        27

SEQ ID NO: 75           moltype = DNA  length = 27
FEATURE                 Location/Qualifiers
misc_feature            1..27
                        note = K22X reverse primer 2
source                  1..27
                        mol_type = other DNA
                        organism = synthetic construct
SEQUENCE: 75
ctgaatcdba ccgtcggcga agattaa                                        27

SEQ ID NO: 76           moltype = DNA  length = 27
FEATURE                 Location/Qualifiers
```

```
misc_feature            1..27
                        note = K22X reverse primer 3
source                  1..27
                        mol_type = other DNA
                        organism = synthetic construct
SEQUENCE: 76
ctgaatccaa ccgtcggcga agattaa                                      27

SEQ ID NO: 77           moltype = DNA  length = 27
FEATURE                 Location/Qualifiers
misc_feature            1..27
                        note = T31X forward primer 1
misc_difference         7
                        note = a, c, g, or t
misc_difference         8
                        note = a, g, or t
source                  1..27
                        mol_type = other DNA
                        organism = synthetic construct
SEQUENCE: 77
aagggandtt tcgaagaagc gaccgcg                                      27

SEQ ID NO: 78           moltype = DNA  length = 27
FEATURE                 Location/Qualifiers
misc_feature            1..27
                        note = T31X forward primer 2
source                  1..27
                        mol_type = other DNA
                        organism = synthetic construct
SEQUENCE: 78
aagggavhgt tcgaagaagc gaccgcg                                      27

SEQ ID NO: 79           moltype = DNA  length = 27
FEATURE                 Location/Qualifiers
misc_feature            1..27
                        note = T31X forward primer 3
source                  1..27
                        mol_type = other DNA
                        organism = synthetic construct
SEQUENCE: 79
aagggatggt tcgaagaagc gaccgcg                                      27

SEQ ID NO: 80           moltype = DNA  length = 27
FEATURE                 Location/Qualifiers
misc_feature            1..27
                        note = T31X reverse primer 1
misc_difference         8
                        note = a, c, or t
misc_difference         9
                        note = a, c, g, or t
source                  1..27
                        mol_type = other DNA
                        organism = synthetic construct
SEQUENCE: 80
ttcgaaahnt cccttaaatt cagctgt                                      27

SEQ ID NO: 81           moltype = DNA  length = 27
FEATURE                 Location/Qualifiers
misc_feature            1..27
                        note = T31X reverse primer 2
source                  1..27
                        mol_type = other DNA
                        organism = synthetic construct
SEQUENCE: 81
ttcgaacdbt cccttaaatt cagctgt                                      27

SEQ ID NO: 82           moltype = DNA  length = 27
FEATURE                 Location/Qualifiers
misc_feature            1..27
                        note = T31X reverse primer 3
source                  1..27
                        mol_type = other DNA
                        organism = synthetic construct
SEQUENCE: 82
ttcgaaccat cccttaaatt cagctgt                                      27

SEQ ID NO: 83           moltype = DNA  length = 27
FEATURE                 Location/Qualifiers
misc_feature            1..27
```

```
                        note = E49X forward primer 1
misc_difference         7
                        note = a, c, g, or t
misc_difference         8
                        note = a, g, or t
source                  1..27
                        mol_type = other DNA
                        organism = synthetic construct
SEQUENCE: 83
gcgaaandta acggtgagta taccgcc                                       27

SEQ ID NO: 84           moltype = DNA  length = 27
FEATURE                 Location/Qualifiers
misc_feature            1..27
                        note = E49X forward primer 2
source                  1..27
                        mol_type = other DNA
                        organism = synthetic construct
SEQUENCE: 84
gcgaaavhga acggtgagta taccgcc                                       27

SEQ ID NO: 85           moltype = DNA  length = 27
FEATURE                 Location/Qualifiers
misc_feature            1..27
                        note = E49X forward primer 3
source                  1..27
                        mol_type = other DNA
                        organism = synthetic construct
SEQUENCE: 85
gcgaaatgga acggtgagta taccgcc                                       27

SEQ ID NO: 86           moltype = DNA  length = 27
FEATURE                 Location/Qualifiers
misc_feature            1..27
                        note = E49X reverse primer 1
misc_difference         8
                        note = a, c, or t
misc_difference         9
                        note = a, c, g, or t
source                  1..27
                        mol_type = other DNA
                        organism = synthetic construct
SEQUENCE: 86
accgttahnt ttcgccagca ggttggc                                       27

SEQ ID NO: 87           moltype = DNA  length = 27
FEATURE                 Location/Qualifiers
misc_feature            1..27
                        note = E49X reverse primer 2
source                  1..27
                        mol_type = other DNA
                        organism = synthetic construct
SEQUENCE: 87
accgttcdbt ttcgccagca ggttggc                                       27

SEQ ID NO: 88           moltype = DNA  length = 27
FEATURE                 Location/Qualifiers
misc_feature            1..27
                        note = E49X reverse primer 3
source                  1..27
                        mol_type = other DNA
                        organism = synthetic construct
SEQUENCE: 88
accgttccat ttcgccagca ggttggc                                       27

SEQ ID NO: 89           moltype = DNA  length = 27
FEATURE                 Location/Qualifiers
misc_feature            1..27
                        note = G51X forward primer 1
misc_difference         7
                        note = a, c, g, or t
misc_difference         8
                        note = a, g, or t
source                  1..27
                        mol_type = other DNA
                        organism = synthetic construct
SEQUENCE: 89
gaaaacndtg agtataccgc cgattta                                       27
```

```
SEQ ID NO: 90          moltype = DNA  length = 27
FEATURE                Location/Qualifiers
misc_feature           1..27
                       note = G51X forward primer 2
source                 1..27
                       mol_type = other DNA
                       organism = synthetic construct
SEQUENCE: 90
gaaaacvhgg agtataccgc cgattta                                      27

SEQ ID NO: 91          moltype = DNA  length = 27
FEATURE                Location/Qualifiers
misc_feature           1..27
                       note = G51X forward primer 3
source                 1..27
                       mol_type = other DNA
                       organism = synthetic construct
SEQUENCE: 91
gaaaactggg agtataccgc cgattta                                      27

SEQ ID NO: 92          moltype = DNA  length = 27
FEATURE                Location/Qualifiers
misc_feature           1..27
                       note = G51X reverse primer 1
misc_difference        8
                       note = a, c, or t
misc_difference        9
                       note = a, c, g, or t
source                 1..27
                       mol_type = other DNA
                       organism = synthetic construct
SEQUENCE: 92
atactcahng ttttctttcg ccagcag                                      27

SEQ ID NO: 93          moltype = DNA  length = 27
FEATURE                Location/Qualifiers
misc_feature           1..27
                       note = G51X reverse primer 2
source                 1..27
                       mol_type = other DNA
                       organism = synthetic construct
SEQUENCE: 93
atactccdbg ttttctttcg ccagcag                                      27

SEQ ID NO: 94          moltype = DNA  length = 27
FEATURE                Location/Qualifiers
misc_feature           1..27
                       note = G51X reverse primer 3
source                 1..27
                       mol_type = other DNA
                       organism = synthetic construct
SEQUENCE: 94
atactcccag ttttctttcg ccagcag                                      27

SEQ ID NO: 95          moltype = DNA  length = 27
FEATURE                Location/Qualifiers
misc_feature           1..27
                       note = N62X forward primer 1
misc_difference        7
                       note = a, c, g, or t
misc_difference        8
                       note = a, g, or t
source                 1..27
                       mol_type = other DNA
                       organism = synthetic construct
SEQUENCE: 95
ggcggcndta cgatcaatat caagttt                                      27

SEQ ID NO: 96          moltype = DNA  length = 27
FEATURE                Location/Qualifiers
misc_feature           1..27
                       note = N62X forward primer 2
source                 1..27
                       mol_type = other DNA
                       organism = synthetic construct
SEQUENCE: 96
ggcggcvhga cgatcaatat caagttt                                      27

SEQ ID NO: 97          moltype = DNA  length = 27
```

```
FEATURE                Location/Qualifiers
misc_feature           1..27
                       note = N62X forward primer 3
source                 1..27
                       mol_type = other DNA
                       organism = synthetic construct
SEQUENCE: 97
ggcggctgga cgatcaatat caagttt                                      27

SEQ ID NO: 98          moltype = DNA  length = 27
FEATURE                Location/Qualifiers
misc_feature           1..27
                       note = N62X reverse primer 1
misc_difference        8
                       note = a, c, or t
misc_difference        9
                       note = a, c, g, or t
source                 1..27
                       mol_type = other DNA
                       organism = synthetic construct
SEQUENCE: 98
gatcgtahng ccgccatctt ctaaatc                                      27

SEQ ID NO: 99          moltype = DNA  length = 27
FEATURE                Location/Qualifiers
misc_feature           1..27
                       note = N62X reverse primer 2
source                 1..27
                       mol_type = other DNA
                       organism = synthetic construct
SEQUENCE: 99
gatcgtcdbg ccgccatctt ctaaatc                                      27

SEQ ID NO: 100         moltype = DNA  length = 27
FEATURE                Location/Qualifiers
misc_feature           1..27
                       note = N62X reverse primer 3
source                 1..27
                       mol_type = other DNA
                       organism = synthetic construct
SEQUENCE: 100
gatcgtccag ccgccatctt ctaaatc                                      27

SEQ ID NO: 101         moltype = AA  length = 70
FEATURE                Location/Qualifiers
REGION                 1..70
                       note = FpL_C3 G21R
source                 1..70
                       mol_type = protein
                       organism = synthetic construct
SEQUENCE: 101
ETPEEPKEEV TIKVNLIFAD RKIQTAEFKG TFEEATAKAY AYANLLAKEN GEYTADLEDG  60
GNTINIKFAG                                                         70

SEQ ID NO: 102         moltype = AA  length = 70
FEATURE                Location/Qualifiers
REGION                 1..70
                       note = FpL_C3 K22T
source                 1..70
                       mol_type = protein
                       organism = synthetic construct
SEQUENCE: 102
ETPEEPKEEV TIKVNLIFAD GTIQTAEFKG TFEEATAKAY AYANLLAKEN GEYTADLEDG  60
GNTINIKFAG                                                         70

SEQ ID NO: 103         moltype = AA  length = 70
FEATURE                Location/Qualifiers
REGION                 1..70
                       note = FpL_C3 T31L
source                 1..70
                       mol_type = protein
                       organism = synthetic construct
SEQUENCE: 103
ETPEEPKEEV TIKVNLIFAD GKIQTAEFKG LFEEATAKAY AYANLLAKEN GEYTADLEDG  60
GNTINIKFAG                                                         70

SEQ ID NO: 104         moltype = AA  length = 70
FEATURE                Location/Qualifiers
REGION                 1..70
```

```
                        note = FpL_C3 E49T
source                  1..70
                        mol_type = protein
                        organism = synthetic construct
SEQUENCE: 104
ETPEEPKEEV TIKVNLIFAD GKIQTAEFKG TFEEATAKAY AYANLLAKTN GEYTADLEDG  60
GNTINIKFAG                                                         70

SEQ ID NO: 105          moltype = AA  length = 70
FEATURE                 Location/Qualifiers
REGION                  1..70
                        note = FpL_C3 E49I
source                  1..70
                        mol_type = protein
                        organism = synthetic construct
SEQUENCE: 105
ETPEEPKEEV TIKVNLIFAD GKIQTAEFKG TFEEATAKAY AYANLLAKIN GEYTADLEDG  60
GNTINIKFAG                                                         70

SEQ ID NO: 106          moltype = AA  length = 70
FEATURE                 Location/Qualifiers
REGION                  1..70
                        note = FpL_C3 G51V
source                  1..70
                        mol_type = protein
                        organism = synthetic construct
SEQUENCE: 106
ETPEEPKEEV TIKVNLIFAD GKIQTAEFKG TFEEATAKAY AYANLLAKEN VEYTADLEDG  60
GNTINIKFAG                                                         70

SEQ ID NO: 107          moltype = AA  length = 70
FEATURE                 Location/Qualifiers
REGION                  1..70
                        note = FpL_C3 N62H
source                  1..70
                        mol_type = protein
                        organism = synthetic construct
SEQUENCE: 107
ETPEEPKEEV TIKVNLIFAD GKIQTAEFKG TFEEATAKAY AYANLLAKEN GEYTADLEDG  60
GHTINIKFAG                                                         70

SEQ ID NO: 108          moltype = AA  length = 70
FEATURE                 Location/Qualifiers
REGION                  1..70
                        note = FpL_C3 N62R
source                  1..70
                        mol_type = protein
                        organism = synthetic construct
SEQUENCE: 108
ETPEEPKEEV TIKVNLIFAD GKIQTAEFKG TFEEATAKAY AYANLLAKEN GEYTADLEDG  60
GRTINIKFAG                                                         70

SEQ ID NO: 109          moltype = AA  length = 70
FEATURE                 Location/Qualifiers
REGION                  1..70
                        note = FpL_C3 N62L
source                  1..70
                        mol_type = protein
                        organism = synthetic construct
SEQUENCE: 109
ETPEEPKEEV TIKVNLIFAD GKIQTAEFKG TFEEATAKAY AYANLLAKEN GEYTADLEDG  60
GLTINIKFAG                                                         70

SEQ ID NO: 110          moltype = AA  length = 70
FEATURE                 Location/Qualifiers
REGION                  1..70
                        note = FpL_C3 N62M
source                  1..70
                        mol_type = protein
                        organism = synthetic construct
SEQUENCE: 110
ETPEEPKEEV TIKVNLIFAD GKIQTAEFKG TFEEATAKAY AYANLLAKEN GEYTADLEDG  60
GMTINIKFAG                                                         70

SEQ ID NO: 111          moltype = AA  length = 70
FEATURE                 Location/Qualifiers
REGION                  1..70
                        note = FpL_C3 N62W
source                  1..70
```

```
                        mol_type = protein
                        organism = synthetic construct
SEQUENCE: 111
ETPEEPKEEV TIKVNLIFAD GKIQTAEFKG TFEEATAKAY AYANLLAKEN GEYTADLEDG  60
GWTINIKFAG                                                         70

SEQ ID NO: 112          moltype = AA  length = 69
FEATURE                 Location/Qualifiers
source                  1..69
                        mol_type = protein
                        organism = Finegoldia magna
SEQUENCE: 112
ETPEPEEEVT IKANLIFADG STQNAEFKGT FAKAVSDAYA YADALKKDNG EYTVDVADKG  60
LTLNIKFAG                                                          69

SEQ ID NO: 113          moltype = AA  length = 70
FEATURE                 Location/Qualifiers
source                  1..70
                        mol_type = protein
                        organism = Finegoldia magna
SEQUENCE: 113
EKPEEPKEEV TIKVNLIFAD GKTQTAEFKG TFEEATAKAY AYADLLAKEN GEYTADLEDG  60
GNTINIKFAG                                                         70

SEQ ID NO: 114          moltype = AA  length = 69
FEATURE                 Location/Qualifiers
REGION                  1..69
                        note = FpL_C1KR
source                  1..69
                        mol_type = protein
                        organism = synthetic construct
SEQUENCE: 114
ETPEPEEEVT IRANLIFADG STQNAEFRGT FARAVSDAYA YADALRRDNG EYTVDVADRG  60
LTLNIRFAG                                                          69

SEQ ID NO: 115          moltype = AA  length = 70
FEATURE                 Location/Qualifiers
REGION                  1..70
                        note = FpL_C2KR
source                  1..70
                        mol_type = protein
                        organism = synthetic construct
SEQUENCE: 115
ERPEEPREEV TIRVNLIFAD GRTQTAEFRG TFEEATARAY AYADLLAREN GEYTADLEDG  60
GNTINIRFAG                                                         70

SEQ ID NO: 116          moltype = AA  length = 70
FEATURE                 Location/Qualifiers
REGION                  1..70
                        note = FpL_C3KR
source                  1..70
                        mol_type = protein
                        organism = synthetic construct
SEQUENCE: 116
ETPEEPREEV TIRVNLIFAD GRIQTAEFRG TFEEATARAY AYANLLAREN GEYTADLEDG  60
GNTINIRFAG                                                         70

SEQ ID NO: 117          moltype = AA  length = 70
FEATURE                 Location/Qualifiers
REGION                  1..70
                        note = FpL_C4KR
source                  1..70
                        mol_type = protein
                        organism = synthetic construct
SEQUENCE: 117
ETPEEPREEV TIRVNLIFAD GRTQTAEFRG TFEEATAEAY RYADLLARVN GEYTADLEDG  60
GYTINIRFAG                                                         70

SEQ ID NO: 118          moltype = DNA  length = 207
FEATURE                 Location/Qualifiers
misc_feature            1..207
                        note = FpL_C1 DNA
source                  1..207
                        mol_type = other DNA
                        organism = synthetic construct
SEQUENCE: 118
gaaactcccg aaccagagga agaagttacg attaaggcta acttaatctt cgccgacggt  60
tcgacacaga atgctgaatt taagggaaca ttcgcgaaag cggtgtcaga tgcatacgcg  120
tacgccgatg cgttgaagaa agataacggt gagtataccg ttgacgtagc ggataaaggc  180
```

```
ctgaccttaa atatcaagtt tgcgggt                                    207

SEQ ID NO: 119         moltype = DNA  length = 210
FEATURE                Location/Qualifiers
misc_feature           1..210
                       note = FpL_C2 DNA
source                 1..210
                       mol_type = other DNA
                       organism = synthetic construct
SEQUENCE: 119
gaaaagcccg aagaaccaaa agaagaagtt acgattaagg ttaacttaat cttcgccgac  60
ggtaagacac agacagctga atttaaggga acattcgaag aagcgaccgc gaaagcatac  120
gcgtacgccg atctgctggc gaaagaaaac ggtgagtata ccgccgattt agaagatggc  180
ggcaatacga tcaatatcaa gtttgcgggt                                 210

SEQ ID NO: 120         moltype = DNA  length = 207
FEATURE                Location/Qualifiers
misc_feature           1..207
                       note = FpL_C1KR DNA
source                 1..207
                       mol_type = other DNA
                       organism = synthetic construct
SEQUENCE: 120
gaaacgccgg aaccagaaga ggaggttaca attcgcgcga acttaatttt cgcggacggt  60
tcgactcaga acgccgaatt ccgcggtacc tttgctcgcg cagtaagcga tgcgtatgcg  120
tacgcagacg ccctgcgccg tgataatggc gaatataccg tggatgtcgc tgatcgtggc  180
ctgaccttga atatccgttt tgccggg                                    207

SEQ ID NO: 121         moltype = DNA  length = 210
FEATURE                Location/Qualifiers
misc_feature           1..210
                       note = FpL_C2KR DNA
source                 1..210
                       mol_type = other DNA
                       organism = synthetic construct
SEQUENCE: 121
gaacgcccag aagagccgcg cgaagaagtt acgatccgtg tgaacttaat tttcgcagac  60
ggccgtacgc agaccgcgga gtttcgtggt acatttgaag aggctaccgc gcgcgcctat  120
gcatatgccg atctgttggc tcgcgaaaac ggggaataca ctgcagatct ggaggatggt  180
gggaacacca tcaacattcg tttcgcgggc                                 210

SEQ ID NO: 122         moltype = DNA  length = 210
FEATURE                Location/Qualifiers
misc_feature           1..210
                       note = FpL_C3KR DNA
source                 1..210
                       mol_type = other DNA
                       organism = synthetic construct
SEQUENCE: 122
gaaaccccag aagaaccgcg cgaggaggtg accattcgtg ttaacttaat ctttgcagac  60
ggtcgcatcc agacagcgga attccgcggg actttcgaag aagcgacagc acgtgcctat  120
gcttatgcga atttgctggc ccgtgaaaac ggagaatata ccgccgatct ggaagatggt  180
ggcaatacga tcaacattcg ttttgcaggc                                 210

SEQ ID NO: 123         moltype = DNA  length = 210
FEATURE                Location/Qualifiers
misc_feature           1..210
                       note = FpL_C4KR DNA
source                 1..210
                       mol_type = other DNA
                       organism = synthetic construct
SEQUENCE: 123
gaaacaccag aagagccacg tgaagaagtt accattcgcg tgaatctgat ctttgccgac  60
ggccgtaccc agaccgctga attccgcggt acattcgaag aagccacagc tgaggcctac  120
cgctacgcag atttgctggc gcgcgtcaac ggtgaatata cggcggacct ggaagatggc  180
gggtatacca tcaacatccg ctttgcggga                                 210

SEQ ID NO: 124         moltype = DNA  length = 27
FEATURE                Location/Qualifiers
misc_feature           1..27
                       note = K7X forward primer 1
misc_difference        7
                       note = a, c, g, or t
misc_difference        8
                       note = a, g, or t
source                 1..27
                       mol_type = other DNA
                       organism = synthetic construct
SEQUENCE: 124
```

```
gagccandtg aagaagttac cattcgc                                   27

SEQ ID NO: 125          moltype = DNA  length = 27
FEATURE                 Location/Qualifiers
misc_feature            1..27
                        note = K7X forward primer 2
source                  1..27
                        mol_type = other DNA
                        organism = synthetic construct
SEQUENCE: 125
gagccavhgg aagaagttac cattcgc                                   27

SEQ ID NO: 126          moltype = DNA  length = 27
FEATURE                 Location/Qualifiers
misc_feature            1..27
                        note = K7X forward primer 3
source                  1..27
                        mol_type = other DNA
                        organism = synthetic construct
SEQUENCE: 126
gagccatggg aagaagttac cattcgc                                   27

SEQ ID NO: 127          moltype = DNA  length = 27
FEATURE                 Location/Qualifiers
misc_feature            1..27
                        note = K7X reverse primer 1
misc_difference         8
                        note = a, c, or t
misc_difference         9
                        note = a, c, g, or t
source                  1..27
                        mol_type = other DNA
                        organism = synthetic construct
SEQUENCE: 127
ttcttcahnt ggctcttctg gtgtttc                                   27

SEQ ID NO: 128          moltype = DNA  length = 27
FEATURE                 Location/Qualifiers
misc_feature            1..27
                        note = K7X reverse primer 2
source                  1..27
                        mol_type = other DNA
                        organism = synthetic construct
SEQUENCE: 128
ttcttccdbt ggctcttctg gtgtttc                                   27

SEQ ID NO: 129          moltype = DNA  length = 27
FEATURE                 Location/Qualifiers
misc_feature            1..27
                        note = K7X reverse primer 3
source                  1..27
                        mol_type = other DNA
                        organism = synthetic construct
SEQUENCE: 129
ttcttcccat ggctcttctg gtgtttc                                   27

SEQ ID NO: 130          moltype = DNA  length = 27
FEATURE                 Location/Qualifiers
misc_feature            1..27
                        note = K29X forward primer 1
misc_difference         7
                        note = a, c, g, or t
misc_difference         8
                        note = a, g, or t
source                  1..27
                        mol_type = other DNA
                        organism = synthetic construct
SEQUENCE: 130
gaattcndtg gtacattcga agaagcc                                   27

SEQ ID NO: 131          moltype = DNA  length = 27
FEATURE                 Location/Qualifiers
misc_feature            1..27
                        note = K29X forward primer 2
source                  1..27
                        mol_type = other DNA
                        organism = synthetic construct
SEQUENCE: 131
gaattcvhgg gtacattcga agaagcc                                   27
```

```
SEQ ID NO: 132         moltype = DNA  length = 27
FEATURE                Location/Qualifiers
misc_feature           1..27
                       note = K29X forward primer 3
source                 1..27
                       mol_type = other DNA
                       organism = synthetic construct
SEQUENCE: 132
gaattctggg gtacattcga agaagcc                                      27

SEQ ID NO: 133         moltype = DNA  length = 27
FEATURE                Location/Qualifiers
misc_feature           1..27
                       note = K29X reverse primer 1
misc_difference        8
                       note = a, c, or t
misc_difference        9
                       note = a, c, g, or t
source                 1..27
                       mol_type = other DNA
                       organism = synthetic construct
SEQUENCE: 133
tgtaccahng aattcagcgg tctgggt                                      27

SEQ ID NO: 134         moltype = DNA  length = 27
FEATURE                Location/Qualifiers
misc_feature           1..27
                       note = K29X reverse primer 2
source                 1..27
                       mol_type = other DNA
                       organism = synthetic construct
SEQUENCE: 134
tgtacccdbg aattcagcgg tctgggt                                      27

SEQ ID NO: 135         moltype = DNA  length = 27
FEATURE                Location/Qualifiers
misc_feature           1..27
                       note = K29X reverse primer 3
source                 1..27
                       mol_type = other DNA
                       organism = synthetic construct
SEQUENCE: 135
tgtaccccag aattcagcgg tctgggt                                      27

SEQ ID NO: 136         moltype = AA  length = 70
FEATURE                Location/Qualifiers
REGION                 1..70
                       note = FpL_C4KR K7A
source                 1..70
                       mol_type = protein
                       organism = synthetic construct
SEQUENCE: 136
ETPEEPAEEV TIRVNLIFAD GRTQTAEFRG TFEEATAEAY RYADLLARVN GEYTADLEDG  60
GYTINIRFAG                                                         70

SEQ ID NO: 137         moltype = AA  length = 70
FEATURE                Location/Qualifiers
REGION                 1..70
                       note = FpL_C4KR K29P
source                 1..70
                       mol_type = protein
                       organism = synthetic construct
SEQUENCE: 137
ETPEEPREEV TIRVNLIFAD GRTQTAEFPG TFEEATAEAY RYADLLARVN GEYTADLEDG  60
GYTINIRFAG                                                         70

SEQ ID NO: 138         moltype = AA  length = 70
FEATURE                Location/Qualifiers
REGION                 1..70
                       note = FpL_C3KR 1a
source                 1..70
                       mol_type = protein
                       organism = synthetic construct
SEQUENCE: 138
ETPEEPREEV TIRVNLIFAD RRIQTAEFRG TFEEATARAY AYANLLAREN GEYTADLEDG  60
GNTINIRFAG                                                         70

SEQ ID NO: 139         moltype = AA  length = 70
```

```
FEATURE                 Location/Qualifiers
REGION                  1..70
                        note = FpL_C3KR 1b
source                  1..70
                        mol_type = protein
                        organism = synthetic construct
SEQUENCE: 139
ETPEEPREEV TIRVNLIFAD GRIQTAEFRG TFEEATARAY AYANLLAREN VEYTADLEDG  60
GNTINIRFAG                                                         70

SEQ ID NO: 140          moltype = AA  length = 70
FEATURE                 Location/Qualifiers
REGION                  1..70
                        note = FpL_C3KR 1c
source                  1..70
                        mol_type = protein
                        organism = synthetic construct
SEQUENCE: 140
ETPEEPREEV TIRVNLIFAD GRIQTAEFRG TFEEATARAY AYANLLAREN GEYTADLEDG  60
GYTINIRFAG                                                         70

SEQ ID NO: 141          moltype = AA  length = 70
FEATURE                 Location/Qualifiers
REGION                  1..70
                        note = FpL_C3KR 3a
source                  1..70
                        mol_type = protein
                        organism = synthetic construct
SEQUENCE: 141
ETPEEPREEV TIRVNLIFAD GRIQTAEFRG TFEEATARAY AYANLLAREY GGYTADLEDG  60
GYTINIRFAG                                                         70

SEQ ID NO: 142          moltype = AA  length = 70
FEATURE                 Location/Qualifiers
REGION                  1..70
                        note = FpL_C3KX
source                  1..70
                        mol_type = protein
                        organism = synthetic construct
SEQUENCE: 142
ETPEEPAEEV TIRVNLIFAD GQIQTAEFIG TFEEATARAY AYANLLAREN GEYTADLEDG  60
GNTINIRFAG                                                         70

SEQ ID NO: 143          moltype = AA  length = 70
FEATURE                 Location/Qualifiers
REGION                  1..70
                        note = FpL_C3KX 1a
source                  1..70
                        mol_type = protein
                        organism = synthetic construct
SEQUENCE: 143
ETPEEPAEEV TIRVNLIFAD RQIQTAEFIG TFEEATARAY AYANLLAREN GEYTADLEDG  60
GNTINIRFAG                                                         70

SEQ ID NO: 144          moltype = AA  length = 70
FEATURE                 Location/Qualifiers
REGION                  1..70
                        note = FpL_C3KX 3a
source                  1..70
                        mol_type = protein
                        organism = synthetic construct
SEQUENCE: 144
ETPEEPAEEV TIRVNLIFAD GQIQTAEFIG TFEEATARAY AYANLLAREY GGYTADLEDG  60
GYTINIRFAG                                                         70

SEQ ID NO: 145          moltype = AA  length = 70
FEATURE                 Location/Qualifiers
REGION                  1..70
                        note = FpL_C3KX 4g
source                  1..70
                        mol_type = protein
                        organism = synthetic construct
SEQUENCE: 145
ETPEEPAEEV TIRVNLIFAD RQIQTAEFIG TFEEATARAY AYANLLAREY GGYTADLEDG  60
GYTINIRFAG                                                         70

SEQ ID NO: 146          moltype = DNA  length = 27
FEATURE                 Location/Qualifiers
misc_feature            1..27
```

```
                        note = PCR forward primer
source                  1..27
                        mol_type = other DNA
                        organism = synthetic construct
SEQUENCE: 146
gcagaccgtc gcatccagac agcggaa                                         27

SEQ ID NO: 147          moltype = DNA  length = 27
FEATURE                 Location/Qualifiers
misc_feature            1..27
                        note = PCR reverse primer
source                  1..27
                        mol_type = other DNA
                        organism = synthetic construct
SEQUENCE: 147
gatgcgacgg tctgcaaaga ttaagtt                                         27

SEQ ID NO: 148          moltype = DNA  length = 27
FEATURE                 Location/Qualifiers
misc_feature            1..27
                        note = PCR forward primer
source                  1..27
                        mol_type = other DNA
                        organism = synthetic construct
SEQUENCE: 148
gaaaacgtgg aatatacggc ggatctg                                         27

SEQ ID NO: 149          moltype = DNA  length = 27
FEATURE                 Location/Qualifiers
misc_feature            1..27
                        note = PCR reverse primer
source                  1..27
                        mol_type = other DNA
                        organism = synthetic construct
SEQUENCE: 149
atattccacg ttttcacggg ccagcaa                                         27

SEQ ID NO: 150          moltype = DNA  length = 210
FEATURE                 Location/Qualifiers
misc_feature            1..210
                        note = FpL_C3KR 1c DNA
source                  1..210
                        mol_type = other DNA
                        organism = synthetic construct
SEQUENCE: 150
gaaacaccag aagagccacg tgaagaagtt accattcgcg tgaatctgat ctttgccgac  60
ggccgtatcc agaccgctga attccgcggt acattcgaag aagccacagc tcgtgcctat  120
gcttatgcga atttgctggc ccgtgaaaac ggagaatata cggcggacct ggaagatggc  180
gggtatacca tcaacatccg ctttgcggga                                   210

SEQ ID NO: 151          moltype = DNA  length = 24
FEATURE                 Location/Qualifiers
misc_feature            1..24
                        note = PCR forward primer
source                  1..24
                        mol_type = other DNA
                        organism = synthetic construct
SEQUENCE: 151
tatacggcgg acctggaaga tggc                                            24

SEQ ID NO: 152          moltype = DNA  length = 24
FEATURE                 Location/Qualifiers
misc_feature            1..24
                        note = PCR reverse primer
source                  1..24
                        mol_type = other DNA
                        organism = synthetic construct
SEQUENCE: 152
gtcggcaaag atcagattca cgcg                                            24

SEQ ID NO: 153          moltype = DNA  length = 66
FEATURE                 Location/Qualifiers
misc_feature            1..66
                        note = Oligonucleotide
source                  1..66
                        mol_type = other DNA
                        organism = synthetic construct
SEQUENCE: 153
ctgatctttg ccgacggccg tatccagacc gctgaattcc gcggtacatt cgaagaagcc  60
```

```
acagct                                                             66

SEQ ID NO: 154          moltype = DNA  length = 66
FEATURE                 Location/Qualifiers
misc_feature            1..66
                        note = Oligonucleotide
source                  1..66
                        mol_type = other DNA
                        organism = synthetic construct
SEQUENCE: 154
agctgtggct tcttcgaatg taccgcggaa ttcagcggtc tggatacggc cgtcggcaaa  60
gatcag                                                             66

SEQ ID NO: 155          moltype = DNA  length = 75
FEATURE                 Location/Qualifiers
misc_feature            1..75
                        note = Oligonucleotide
source                  1..75
                        mol_type = other DNA
                        organism = synthetic construct
SEQUENCE: 155
gaagaagcca cagctcgtgc ctatgcttat gcgaatttgc tggcccgtga aaacggagaa  60
tatacggcgg acctg                                                   75

SEQ ID NO: 156          moltype = DNA  length = 75
FEATURE                 Location/Qualifiers
misc_feature            1..75
                        note = Oligonucleotide
source                  1..75
                        mol_type = other DNA
                        organism = synthetic construct
SEQUENCE: 156
caggtccgcc gtatattctc cgttttcacg ggccagcaaa ttcgcataag cataggcacg  60
agctgtggct tcttc                                                   75

SEQ ID NO: 157          moltype = DNA  length = 210
FEATURE                 Location/Qualifiers
misc_feature            1..210
                        note = FpL_C3KR 3a DNA
source                  1..210
                        mol_type = other DNA
                        organism = synthetic construct
SEQUENCE: 157
gaaacaccag aagagccacg tgaagaagtt accattcgcg tgaatctgat ctttgccgac  60
ggccgtatcc agaccgctga attccgcggt acattcgaag aagccacagc tcgtgcctat  120
gcttatgcga atttgctggc ccgtgaatat ggaggctata cggcggacct ggaagatggc  180
gggtatacca tcaacatccg ctttgcggga                                   210

SEQ ID NO: 158          moltype = DNA  length = 75
FEATURE                 Location/Qualifiers
misc_feature            1..75
                        note = Oligonucleotide
source                  1..75
                        mol_type = other DNA
                        organism = synthetic construct
SEQUENCE: 158
gaagaagcca cagctcgtgc ctatgcttat gcgaatttgc tggcccgtga atatggaggc  60
tatacggcgg acctg                                                   75

SEQ ID NO: 159          moltype = DNA  length = 75
FEATURE                 Location/Qualifiers
misc_feature            1..75
                        note = Oligonucleotide
source                  1..75
                        mol_type = other DNA
                        organism = synthetic construct
SEQUENCE: 159
caggtccgcc gtatagcctc catattcacg ggccagcaaa ttcgcataag cataggcacg  60
agctgtggct tcttc                                                   75

SEQ ID NO: 160          moltype = DNA  length = 210
FEATURE                 Location/Qualifiers
misc_feature            1..210
                        note = FpL_C4KR R7A DNA
source                  1..210
                        mol_type = other DNA
                        organism = synthetic construct
SEQUENCE: 160
gaaacaccag aagagccagc ggaagaagtt accattcgcg tgaatctgat ctttgccgac  60
```

```
ggccgtaccc agaccgctga attccgcggt acattcgaag aagccacagc tgaggcctac  120
cgctacgcag atttgctggc gcgcgtcaac ggtgaatata cggcggacct ggaagatggc  180
gggtatacca tcaacatccg ctttgcggga                                     210

SEQ ID NO: 161          moltype = DNA  length = 210
FEATURE                 Location/Qualifiers
misc_feature            1..210
                        note = FpL_C3KX DNA
source                  1..210
                        mol_type = other DNA
                        organism = synthetic construct
SEQUENCE: 161
gaaacaccag aagagccagc ggaagaagtt accattcgcg tgaatctgat ctttgccgac  60
ggccagatcc agaccgctga attcattggt acattcgaag aagccacagc tcgtgcctat  120
gcttatgcga atttgctggc ccgtgaaaac ggagaatata cggcggacct ggaagatggc  180
gggaatacca tcaacatccg ctttgcggga                                     210

SEQ ID NO: 162          moltype = DNA  length = 36
FEATURE                 Location/Qualifiers
misc_feature            1..36
                        note = PCR forward primer
source                  1..36
                        mol_type = other DNA
                        organism = synthetic construct
SEQUENCE: 162
tatacggcgg acctggaaga tggcgggaat accatc                              36

SEQ ID NO: 163          moltype = DNA  length = 66
FEATURE                 Location/Qualifiers
misc_feature            1..66
                        note = Oligonucleotide
source                  1..66
                        mol_type = other DNA
                        organism = synthetic construct
SEQUENCE: 163
ctgatctttg ccgacggcca gatccagacc gctgaattca ttggtacatt cgaagaagcc  60
acagct                                                               66

SEQ ID NO: 164          moltype = DNA  length = 66
FEATURE                 Location/Qualifiers
misc_feature            1..66
                        note = Oligonucleotide
source                  1..66
                        mol_type = other DNA
                        organism = synthetic construct
SEQUENCE: 164
agctgtggct tcttcgaatg taccaatgaa ttcagcggtc tggatctggc cgtcggcaaa  60
gatcag                                                               66

SEQ ID NO: 165          moltype = DNA  length = 210
FEATURE                 Location/Qualifiers
misc_feature            1..210
                        note = FpL_C3KX 1a DNA
source                  1..210
                        mol_type = other DNA
                        organism = synthetic construct
SEQUENCE: 165
gaaacaccag aagagccagc ggaagaagtt accattcgcg tgaatctgat ctttgccgac  60
cgccagatcc agaccgctga attcattggt acattcgaag aagccacagc tcgtgcctat  120
gcttatgcga atttgctggc ccgtgaaaac ggagaatata cggcggacct ggaagatggc  180
gggaatacca tcaacatccg ctttgcggga                                     210

SEQ ID NO: 166          moltype = DNA  length = 66
FEATURE                 Location/Qualifiers
misc_feature            1..66
                        note = Oligonucleotide
source                  1..66
                        mol_type = other DNA
                        organism = synthetic construct
SEQUENCE: 166
ctgatctttg ccgaccgcca gatccagacc gctgaattca ttggtacatt cgaagaagcc  60
acagct                                                               66

SEQ ID NO: 167          moltype = DNA  length = 66
FEATURE                 Location/Qualifiers
misc_feature            1..66
                        note = Oligonucleotide
source                  1..66
                        mol_type = other DNA
```

```
                        organism = synthetic construct
SEQUENCE: 167
agctgtggct tcttcgaatg taccaatgaa ttcagcggtc tggatctggc ggtcggcaaa  60
gatcag                                                             66

SEQ ID NO: 168          moltype = DNA  length = 210
FEATURE                 Location/Qualifiers
misc_feature            1..210
                        note = FpL_C3KX 3a DNA
source                  1..210
                        mol_type = other DNA
                        organism = synthetic construct
SEQUENCE: 168
gaaacaccag aagagccagc ggaagaagtt accattcgcg tgaatctgat ctttgccgac  60
ggtcagattc agaccgctga attcattggt acattcgaag aagccacagc tcgtgcctat  120
gcttatgcga atttgctggc ccgtgaatat ggtggctata cggcggacct ggaagatggc  180
gggtatacca tcaacatccg ctttgcggga                                   210

SEQ ID NO: 169          moltype = DNA  length = 66
FEATURE                 Location/Qualifiers
misc_feature            1..66
                        note = Oligonucleotide
source                  1..66
                        mol_type = other DNA
                        organism = synthetic construct
SEQUENCE: 169
ctgatctttg ccgacggtca gattcagacc gctgaattca ttggtacatt cgaagaagcc  60
acagct                                                             66

SEQ ID NO: 170          moltype = DNA  length = 66
FEATURE                 Location/Qualifiers
misc_feature            1..66
                        note = Oligonucleotide
source                  1..66
                        mol_type = other DNA
                        organism = synthetic construct
SEQUENCE: 170
agctgtggct tcttcgaatg taccaatgaa ttcagcggtc tgaatctgac cgtcggcaaa  60
gatcag                                                             66

SEQ ID NO: 171          moltype = DNA  length = 210
FEATURE                 Location/Qualifiers
misc_feature            1..210
                        note = FpL_C3KX 4g DNA
source                  1..210
                        mol_type = other DNA
                        organism = synthetic construct
SEQUENCE: 171
gaaacaccag aagagccagc ggaagaagtt accattcgcg tgaatctgat ctttgccgac  60
cgtcagattc agaccgctga attcattggt acattcgaag aagccacagc tcgtgcctat  120
gcttatgcga atttgctggc ccgtgaatat ggtggctata cggcggacct ggaagatggc  180
gggtatacca tcaacatccg ctttgcggga                                   210

SEQ ID NO: 172          moltype = AA  length = 70
FEATURE                 Location/Qualifiers
REGION                  1..70
                        note = FpL_C3KX 3a E1G
source                  1..70
                        mol_type = protein
                        organism = synthetic construct
SEQUENCE: 172
GTPEEPAEEV TIRVNLIFAD GQIQTAEFIG TFEEATARAY AYANLLAREY GGYTADLEDG  60
GYTINIRFAG                                                         70

SEQ ID NO: 173          moltype = AA  length = 70
FEATURE                 Location/Qualifiers
REGION                  1..70
                        note = FpL_C3KX 3a E1V
source                  1..70
                        mol_type = protein
                        organism = synthetic construct
SEQUENCE: 173
VTPEEPAEEV TIRVNLIFAD GQIQTAEFIG TFEEATARAY AYANLLAREY GGYTADLEDG  60
GYTINIRFAG                                                         70

SEQ ID NO: 174          moltype = AA  length = 70
FEATURE                 Location/Qualifiers
REGION                  1..70
                        note = FpL_C3KX 3a K22R
```

```
source                  1..70
                        mol_type = protein
                        organism = synthetic construct
SEQUENCE: 174
ETPEEPAEEV TIRVNLIFAD GRIQTAEFIG TFEEATARAY AYANLLAREY GGYTADLEDG  60
GYTINIRFAG                                                        70

SEQ ID NO: 175          moltype = AA  length = 70
FEATURE                 Location/Qualifiers
REGION                  1..70
                        note = FpL_C3KX 3a E4K
source                  1..70
                        mol_type = protein
                        organism = synthetic construct
SEQUENCE: 175
ETPKEPAEEV TIRVNLIFAD GQIQTAEFIG TFEEATARAY AYANLLAREY GGYTADLEDG  60
GYTINIRFAG                                                        70

SEQ ID NO: 176          moltype = AA  length = 70
FEATURE                 Location/Qualifiers
REGION                  1..70
                        note = FpL_C3KX 3a K22T
source                  1..70
                        mol_type = protein
                        organism = synthetic construct
SEQUENCE: 176
ETPEEPAEEV TIRVNLIFAD GTIQTAEFIG TFEEATARAY AYANLLAREY GGYTADLEDG  60
GYTINIRFAG                                                        70

SEQ ID NO: 177          moltype = AA  length = 70
FEATURE                 Location/Qualifiers
REGION                  1..70
                        note = FpL_C3KX 3a E27R
source                  1..70
                        mol_type = protein
                        organism = synthetic construct
SEQUENCE: 177
ETPEEPAEEV TIRVNLIFAD GQIQTARFIG TFEEATARAY AYANLLAREY GGYTADLEDG  60
GYTINIRFAG                                                        70

SEQ ID NO: 178          moltype = AA  length = 70
FEATURE                 Location/Qualifiers
REGION                  1..70
                        note = FpL_C3KX 3a T36A
source                  1..70
                        mol_type = protein
                        organism = synthetic construct
SEQUENCE: 178
ETPEEPAEEV TIRVNLIFAD GQIQTAEFIG TFEEAAARAY AYANLLAREY GGYTADLEDG  60
GYTINIRFAG                                                        70

SEQ ID NO: 179          moltype = AA  length = 70
FEATURE                 Location/Qualifiers
REGION                  1..70
                        note = FpL_C3KX 4h
source                  1..70
                        mol_type = protein
                        organism = synthetic construct
SEQUENCE: 179
ETPEEPAEEV TIRVNLIFAD GQIQTAEFIG TFEEATARAY AYANLLARDY GGYTADLEDG  60
GYTINIRFAG                                                        70

SEQ ID NO: 180          moltype = DNA  length = 210
FEATURE                 Location/Qualifiers
misc_feature            1..210
                        note = FpL_C3KX 4h DNA
source                  1..210
                        mol_type = other DNA
                        organism = synthetic construct
SEQUENCE: 180
gaaacaccag aagagccagc ggaagaagtt accattcgcg tgaatctgat ctttgccgac  60
ggtcagattc agaccgctga attcattggt acattcgaag aagccacagc tcgtgcctat  120
gcttatgcga atttgctggc ccgtgattat ggtggctata cggcggacct ggaagatggc  180
gggtatacca tcaacatccg ctttgcggga                                  210

SEQ ID NO: 181          moltype = AA  length = 70
FEATURE                 Location/Qualifiers
REGION                  1..70
                        note = FpL_C3KX 4h_E9V
```

```
source                  1..70
                        mol_type = protein
                        organism = synthetic construct
SEQUENCE: 181
ETPEEPAEVV TIRVNLIFAD GQIQTAEFIG TFEEATARAY AYANLLARDY GGYTADLEDG  60
GYTINIRFAG                                                         70

SEQ ID NO: 182          moltype = AA  length = 70
FEATURE                 Location/Qualifiers
REGION                  1..70
                        note = FpL_C3KX 4i
source                  1..70
                        mol_type = protein
                        organism = synthetic construct
SEQUENCE: 182
ETPEEPAEEV TIRVNLIFAD GRIQTAEFIG TFEEATARAY AYANLLARDY GGYTADLEDG  60
GYTINIRFAG                                                         70

SEQ ID NO: 183          moltype = AA  length = 70
FEATURE                 Location/Qualifiers
REGION                  1..70
                        note = FpL_C3KX 4h Y53F
source                  1..70
                        mol_type = protein
                        organism = synthetic construct
SEQUENCE: 183
ETPEEPAEEV TIRVNLIFAD GQIQTAEFIG TFEEATARAY AYANLLARDY GGFTADLEDG  60
GYTINIRFAG                                                         70

SEQ ID NO: 184          moltype = AA  length = 70
FEATURE                 Location/Qualifiers
REGION                  1..70
                        note = FpL_C3KX 4h T54M
source                  1..70
                        mol_type = protein
                        organism = synthetic construct
SEQUENCE: 184
ETPEEPAEEV TIRVNLIFAD GQIQTAEFIG TFEEATARAY AYANLLARDY GGYMADLEDG  60
GYTINIRFAG                                                         70

SEQ ID NO: 185          moltype = AA  length = 70
FEATURE                 Location/Qualifiers
REGION                  1..70
                        note = FpL_C3KX 4h A69T
source                  1..70
                        mol_type = protein
                        organism = synthetic construct
SEQUENCE: 185
ETPEEPAEEV TIRVNLIFAD GQIQTAEFIG TFEEATARAY AYANLLARDY GGYTADLEDG  60
GYTINIRFTG                                                         70

SEQ ID NO: 186          moltype = AA  length = 70
FEATURE                 Location/Qualifiers
REGION                  1..70
                        note = FpL_C3KX 5e
source                  1..70
                        mol_type = protein
                        organism = synthetic construct
SEQUENCE: 186
ETPEEPAEEV TIRVNLIFAD GRIQTAEFIG TFEEATARAY AYANLLARDY GGFTADLEDG  60
GYTINIRFAG                                                         70

SEQ ID NO: 187          moltype = AA  length = 70
FEATURE                 Location/Qualifiers
REGION                  1..70
                        note = FpL_C3KX 5f
source                  1..70
                        mol_type = protein
                        organism = synthetic construct
SEQUENCE: 187
ETPEEPAEEV TIRVNLIFAD GRIQTAEFIG TFEEATARAY AYANLLARDY GGYMADLEDG  60
GYTINIRFAG                                                         70

SEQ ID NO: 188          moltype = DNA  length = 210
FEATURE                 Location/Qualifiers
misc_feature            1..210
                        note = FpL_C3KX 4i DNA
source                  1..210
                        mol_type = other DNA
```

```
                         organism = synthetic construct
SEQUENCE: 188
gaaacaccag aagagccagc ggaagaagtt accattcgcg tgaatctgat ctttgccgac  60
ggtcggattc agaccgctga attcattggt acattcgaag aagccacagc tcgtgcctat  120
gcttatgcga atttgctggc ccgtgattat ggtggctata cggcggacct ggaagatggc  180
gggtatacca tcaacatccg ctttgcggga                                    210

SEQ ID NO: 189           moltype = DNA  length = 27
FEATURE                  Location/Qualifiers
misc_feature             1..27
                         note = PCR forward primer
source                   1..27
                         mol_type = other DNA
                         organism = synthetic construct
SEQUENCE: 189
ggtggcttta cggcggacct ggaagat                                       27

SEQ ID NO: 190           moltype = DNA  length = 27
FEATURE                  Location/Qualifiers
misc_feature             1..27
                         note = PCR reverse primer
source                   1..27
                         mol_type = other DNA
                         organism = synthetic construct
SEQUENCE: 190
cgccgtaaag ccaccataat cacgggc                                       27

SEQ ID NO: 191           moltype = DNA  length = 27
FEATURE                  Location/Qualifiers
misc_feature             1..27
                         note = PCR forward primer
source                   1..27
                         mol_type = other DNA
                         organism = synthetic construct
SEQUENCE: 191
ggctatatgg cggacctgga agatggc                                       27

SEQ ID NO: 192           moltype = DNA  length = 27
FEATURE                  Location/Qualifiers
misc_feature             1..27
                         note = PCR reverse primer
source                   1..27
                         mol_type = other DNA
                         organism = synthetic construct
SEQUENCE: 192
gtccgccata tagccaccat aatcacg                                       27

SEQ ID NO: 193           moltype = DNA  length = 210
FEATURE                  Location/Qualifiers
misc_feature             1..210
                         note = FpL_C3KX 5e DNA
source                   1..210
                         mol_type = other DNA
                         organism = synthetic construct
SEQUENCE: 193
gaaacaccag aagagccagc ggaagaagtt accattcgcg tgaatctgat ctttgccgac  60
ggtcggattc agaccgctga attcattggt acattcgaag aagccacagc tcgtgcctat  120
gcttatgcga atttgctggc ccgtgattat ggtggcttta cggcggacct ggaagatggc  180
gggtatacca tcaacatccg ctttgcggga                                    210

SEQ ID NO: 194           moltype = AA  length = 70
FEATURE                  Location/Qualifiers
REGION                   1..70
                         note = FpL_C3KX 5e E1V
source                   1..70
                         mol_type = protein
                         organism = synthetic construct
SEQUENCE: 194
VTPEEPAEEV TIRVNLIFAD GRIQTAEFIG TFEEATARAY AYANLLARDY GGFTADLEDG  60
GYTINIRFAG                                                          70

SEQ ID NO: 195           moltype = AA  length = 70
FEATURE                  Location/Qualifiers
REGION                   1..70
                         note = FpL_C3KX 5e E4G
source                   1..70
                         mol_type = protein
                         organism = synthetic construct
SEQUENCE: 195
```

```
ETPGEPAEEV TIRVNLIFAD GRIQTAEFIG TFEEATARAY AYANLLARDY GGFTADLEDG  60
GYTINIRFAG                                                         70

SEQ ID NO: 196         moltype = AA  length = 70
FEATURE                Location/Qualifiers
REGION                 1..70
                       note = FpL_C3KX 5e K7S
source                 1..70
                       mol_type = protein
                       organism = synthetic construct
SEQUENCE: 196
ETPEEPSEEV TIRVNLIFAD GRIQTAEFIG TFEEATARAY AYANLLARDY GGFTADLEDG  60
GYTINIRFAG                                                         70

SEQ ID NO: 197         moltype = AA  length = 70
FEATURE                Location/Qualifiers
REGION                 1..70
                       note = FpL_C3KX 5e G21R
source                 1..70
                       mol_type = protein
                       organism = synthetic construct
SEQUENCE: 197
ETPEEPAEEV TIRVNLIFAD RRIQTAEFIG TFEEATARAY AYANLLARDY GGFTADLEDG  60
GYTINIRFAG                                                         70

SEQ ID NO: 198         moltype = AA  length = 70
FEATURE                Location/Qualifiers
REGION                 1..70
                       note = FpL_C3KX 5e G52D
source                 1..70
                       mol_type = protein
                       organism = synthetic construct
SEQUENCE: 198
ETPEEPAEEV TIRVNLIFAD GRIQTAEFIG TFEEATARAY AYANLLARDY GDFTADLEDG  60
GYTINIRFAG                                                         70

SEQ ID NO: 199         moltype = AA  length = 70
FEATURE                Location/Qualifiers
REGION                 1..70
                       note = FpL_C3KX 6a
source                 1..70
                       mol_type = protein
                       organism = synthetic construct
SEQUENCE: 199
ETPGEPAEEV TIRVNLIFAD GRIQTAEFIG TFEEATARAY AYANLLARDY GDFTADLEDG  60
GYTINIRFAG                                                         70

SEQ ID NO: 200         moltype = AA  length = 70
FEATURE                Location/Qualifiers
REGION                 1..70
                       note = FpL_C3KX 5g
source                 1..70
                       mol_type = protein
                       organism = synthetic construct
SEQUENCE: 200
ETPEEPSEEV TIRVNLIFAD GRIQTAEFIG TFEEATARAY AYANLLARDY GDFTADLEDG  60
GYTINIRFAG                                                         70

SEQ ID NO: 201         moltype = AA  length = 70
FEATURE                Location/Qualifiers
REGION                 1..70
                       note = FpL_C3KX 6b
source                 1..70
                       mol_type = protein
                       organism = synthetic construct
SEQUENCE: 201
ETPGEPSEEV TIRVNLIFAD GRIQTAEFIG TFEEATARAY AYANLLARDY GGFTADLEDG  60
GYTINIRFAG                                                         70

SEQ ID NO: 202         moltype = DNA  length = 210
FEATURE                Location/Qualifiers
misc_feature           1..210
                       note = FpL_C3KX 5e G52D DNA
source                 1..210
                       mol_type = other DNA
                       organism = synthetic construct
SEQUENCE: 202
gaaacaccag aagagccagc ggaagaagtt accattcgcg tgaatctgat ctttgccgac  60
ggtcggattc agaccgctga attcattggt acattcgaag aagccacagc tcgtgcctat  120
```

```
gcttatgcga atttgctggc ccgtgattat ggtgacttta cggcggacct ggaagatggc  180
gggtatacca tcaacatccg ctttgcggga                                   210

SEQ ID NO: 203         moltype = DNA  length = 27
FEATURE                Location/Qualifiers
misc_feature           1..27
                       note = PCR forward primer
source                 1..27
                       mol_type = other DNA
                       organism = synthetic construct
SEQUENCE: 203
acaccaggag agccagcgga agaagtt                                      27

SEQ ID NO: 204         moltype = DNA  length = 27
FEATURE                Location/Qualifiers
misc_feature           1..27
                       note = PCR reverse primer
source                 1..27
                       mol_type = other DNA
                       organism = synthetic construct
SEQUENCE: 204
tggctctcct ggtgtttcca tggtata                                      27

SEQ ID NO: 205         moltype = DNA  length = 27
FEATURE                Location/Qualifiers
misc_feature           1..27
                       note = PCR forward primer
source                 1..27
                       mol_type = other DNA
                       organism = synthetic construct
SEQUENCE: 205
gagccatcgg aagaagttac cattcgc                                      27

SEQ ID NO: 206         moltype = DNA  length = 27
FEATURE                Location/Qualifiers
misc_feature           1..27
                       note = PCR reverse primer
source                 1..27
                       mol_type = other DNA
                       organism = synthetic construct
SEQUENCE: 206
ttcttccgat ggctcttctg gtgtttc                                      27

SEQ ID NO: 207         moltype = DNA  length = 210
FEATURE                Location/Qualifiers
misc_feature           1..210
                       note = FpL_C3KX 5e E4G DNA
source                 1..210
                       mol_type = other DNA
                       organism = synthetic construct
SEQUENCE: 207
gaaacaccag gagagccagc ggaagaagtt accattcgcg tgaatctgat ctttgccgac  60
ggtcggattc agaccgctga attcattggt acattcgaag aagccacagc tcgtgcctat  120
gcttatgcga atttgctggc ccgtgattat ggtggcttta cggcggacct ggaagatggc  180
gggtatacca tcaacatccg ctttgcggga                                   210

SEQ ID NO: 208         moltype = DNA  length = 27
FEATURE                Location/Qualifiers
misc_feature           1..27
                       note = PCR reverse primer
source                 1..27
                       mol_type = other DNA
                       organism = synthetic construct
SEQUENCE: 208
ttcttccgat ggctctcctg gtgtttc                                      27

SEQ ID NO: 209         moltype = AA  length = 719
FEATURE                Location/Qualifiers
source                 1..719
                       mol_type = protein
                       organism = Finegoldia magna
SEQUENCE: 209
MAALAGAIVV TGGVGSYAAD EPIDLEKLEE KRDKENVGNL PKFDNEVKDG SENPMAKYPD  60
FDDEASTRFE TENNEFEEKK VVSDNFFDQS EHPFVENKEE TPETPETDSE EEVTIKANLI  120
FANGSTQTAE FKGTFEKATS EAYAYADTLK KDNGEYTVDV ADKGYTLNIK FAGKEKTPEE  180
PKEEVTIKAN LIYADGKTQT AEFKGTFEEA TAEAYRYADA LKKDNGEYTV DVADKGYTLN  240
IKFAGKEKTP EEPKEEVTIK ANLIYADGKT QTAEFKGTFE EATAEAYRYA DLLAKENGKY  300
TVDVADKGYT LNIKFAGKEK TPEEPKEEVT IKANLIYADG KTQTAEFKGT FAEATAEAYR  360
YADLLAKENG KYTADLEDGG YTINIRFAGK KVDEKPEEKE QVTIKENIYF EDGTVQTATF  420
```

```
KGTFAEATAE AYRYADLLSK EHGKYTADLE DGGYTINIRF AGKEEPEETP EKPEVQDGYA  480
SYEEAEAAAK EALKNDDVNK SYTIRQGADG RYYYVLSPVE AEEEKPEAQN GYATYEEAEA  540
AAKKALENDP INKSYSIRQG ADGRYYYVLS PVEAETPEKP VEPSEPSTPD VPSNPSNPST  600
PDVPSTPDVP SNPSTPEVPS NPSTPGNEEK PGNEQKPGNE QKPGNEQKPG NEQKPGNEQK  660
PDQPSKPEKE ENGKGGVDSP KKKEKAALPK AGSEAEILTL AAASLSSVAG AFISLKKRK   719

SEQ ID NO: 210         moltype = AA  length = 992
FEATURE                Location/Qualifiers
source                 1..992
                       mol_type = protein
                       organism = Finegoldia magna
SEQUENCE: 210
MKINKKLLMA ALAGAIVVGG GANAYAAEED NTDNNLSMDE ISDAYFDYHG DVSDSVDPVE  60
EEIDEALAKA LAEAKETAKK HIDSLNHLSE TAKKLAKNDI DSATTINAIN DIVARADVME  120
RKTAEKEEAE KLAAAKETAK KHIDELKHLA DKTKELAKRD IDSATTINAI NDIVARADVM  180
ERKTAEKEEA EKLAAAKETA KKHIDELKHL ADKTKELAKR DIDSATTIDA INDIVARADV  240
MERKLSEKET PEPEEEVTIK ANLIFADGST QNAEFKGTFA KAVSDAYAYA DALKKDNGEY  300
TVDVADKGLT LNIKFAGKKE KPEEPKEEVT IKVNLIFADG KTQTAEFKGT FEEATAKAYA  360
YADLLAKENG EYTADLEDGG NTINIKFAGK ETPETPEEPK EEVTIKVNLI FADGKIQTAE  420
FKGTFEEATA KAYAYANLLA KENGEYTADL EDGGNTINIK FAGKETPETP EEPKEEVTIK  480
VNLIFADGKT QTAEFKGTFE EATAEAYRYA DLLAKVNGEY TADLEDGGYT INIKFAGKEQ  540
PGENPGITID EWLLKNAKEE AIKELKEAGI TSDLYFSLIN KAKTVEGVEA LKNEILKAHA  600
GEETPELKDG YATYEEAEAA AKEALKNDDV NNAYEIVQGA DGRYYYVLKI EVADEEEPGE  660
DTPEVQEGYA TYEEAEAAAK EALKEDKVNN AYEVVQGADG RYYYVLKIED KEDEQPGEEP  720
GENPGITIDE WLLKNAKEDA IKELKEAGIS SDIYFDAINK AKTVEGVEAL KNEILKAHAE  780
KPGENPGITI DEWLLKNAKE AAIKELKEAG ITAEYLFNLI NKAKTVEGVE SLKNEILKAH  840
AEKPGENPGI TIDEWLLKNA KEDAIKELKE AGITSDIYFD AINKAKTIEG VEALKNEILK  900
AHKKDEEPGK KPGEDKKPED KKPGEDKKPE DKKPGEDKKP EDKKPGKTDK DSPNKKKKAK  960
LPKAGSEAEI LTLAAAALST AAGAYVSLKK RK                                992

SEQ ID NO: 211         moltype = DNA  length = 210
FEATURE                Location/Qualifiers
misc_feature           1..210
                       note = FpL_C3KX 6a DNA
source                 1..210
                       mol_type = other DNA
                       organism = synthetic construct
SEQUENCE: 211
gaaacaccag gagagccagc ggaagaagtt accattcgcg tgaatctgat ctttgccgac  60
ggtcggattc agaccgctga attcattggt acattcgaag aagccacagc tcgtgcctat  120
gcttatgcga atttgctggc ccgtgattat ggtgacttta cggcggacct ggaagatggc  180
gggtatacca tcaacatccg ctttgcggga                                   210

SEQ ID NO: 212         moltype = AA  length = 70
FEATURE                Location/Qualifiers
REGION                 1..70
                       note = FpL_C3KX 6a K38A
source                 1..70
                       mol_type = protein
                       organism = synthetic construct
SEQUENCE: 212
ETPGEPAEEV TIRVNLIFAD GRIQTAEFIG TFEEATAAAY AYANLLARDY GDFTADLEDG  60
GYTINIRFAG                                                         70

SEQ ID NO: 213         moltype = AA  length = 70
FEATURE                Location/Qualifiers
REGION                 1..70
                       note = FpL_C3KX 6a F32L A47T
source                 1..70
                       mol_type = protein
                       organism = synthetic construct
SEQUENCE: 213
ETPGEPAEEV TIRVNLIFAD GRIQTAEFIG TLEEATARAY AYANLLTRDY GDFTADLEDG  60
GYTINIRFAG                                                         70

SEQ ID NO: 214         moltype = AA  length = 70
FEATURE                Location/Qualifiers
REGION                 1..70
                       note = FpL_C3KX 6a T2S
source                 1..70
                       mol_type = protein
                       organism = synthetic construct
SEQUENCE: 214
ESPGEPAEEV TIRVNLIFAD GRIQTAEFIG TFEEATARAY AYANLLARDY GDFTADLEDG  60
GYTINIRFAG                                                         70

SEQ ID NO: 215         moltype = AA  length = 70
FEATURE                Location/Qualifiers
REGION                 1..70
```

```
                        note = FpL_C3KX 6a E27K
source                  1..70
                        mol_type = protein
                        organism = synthetic construct
SEQUENCE: 215
ETPGEPAEEV TIRVNLIFAD GRIQTAKFIG TFEEATARAY AYANLLARDY GDFTADLEDG  60
GYTINIRFAG                                                         70

SEQ ID NO: 216          moltype = AA  length = 70
FEATURE                 Location/Qualifiers
REGION                  1..70
                        note = FpL_C3KX 6a T2P P3R E9V D52N
source                  1..70
                        mol_type = protein
                        organism = synthetic construct
SEQUENCE: 216
EPRGEPAEVV TIRVNLIFAD GRIQTAEFIG TFEEATARAY AYANLLARNY GNFTADLEDG  60
GYTINIRFAG                                                         70

SEQ ID NO: 217          moltype = AA  length = 70
FEATURE                 Location/Qualifiers
REGION                  1..70
                        note = FpL_C3KX 6a E27I
source                  1..70
                        mol_type = protein
                        organism = synthetic construct
SEQUENCE: 217
ETPGEPAEEV TIRVNLIFAD GRIQTAIFIG TFEEATARAY AYANLLARDY GDFTADLEDG  60
GYTINIRFAG                                                         70

SEQ ID NO: 218          moltype = AA  length = 70
FEATURE                 Location/Qualifiers
REGION                  1..70
                        note = FpL_C3KX 6a N44I
source                  1..70
                        mol_type = protein
                        organism = synthetic construct
SEQUENCE: 218
ETPGEPAEEV TIRVNLIFAD GRIQTAEFIG TFEEATARAY AYAILLARDY GDFTADLEDG  60
GYTINIRFAG                                                         70

SEQ ID NO: 219          moltype = AA  length = 70
FEATURE                 Location/Qualifiers
REGION                  1..70
                        note = FpL_C3KX 6a E5K N44I
source                  1..70
                        mol_type = protein
                        organism = synthetic construct
SEQUENCE: 219
ETPGKPAEEV TIRVNLIFAD GRIQTAEFIG TFEEATARAY AYAILLARDY GDFTADLEDG  60
GYTINIRFAG                                                         70

SEQ ID NO: 220          moltype = AA  length = 70
FEATURE                 Location/Qualifiers
REGION                  1..70
                        note = FpL_C3KX 6a P3R
source                  1..70
                        mol_type = protein
                        organism = synthetic construct
SEQUENCE: 220
ETRGEPAEEV TIRVNLIFAD GRIQTAEFIG TFEEATARAY AYANLLARDY GDFTADLEDG  60
GYTINIRFAG                                                         70

SEQ ID NO: 221          moltype = AA  length = 70
FEATURE                 Location/Qualifiers
REGION                  1..70
                        note = FpL_C3KX 6a E5K
source                  1..70
                        mol_type = protein
                        organism = synthetic construct
SEQUENCE: 221
ETPGKPAEEV TIRVNLIFAD GRIQTAEFIG TFEEATARAY AYANLLARDY GDFTADLEDG  60
GYTINIRFAG                                                         70

SEQ ID NO: 222          moltype = AA  length = 70
FEATURE                 Location/Qualifiers
REGION                  1..70
                        note = FpL_C3KX 6a E27V
source                  1..70
```

```
                        mol_type = protein
                        organism = synthetic construct
SEQUENCE: 222
ETPGEPAEEV TIRVNLIFAD GRIQTAVFIG TFEEATARAY AYANLLARDY GDFTADLEDG  60
GYTINIRFAG                                                         70

SEQ ID NO: 223          moltype = AA  length = 70
FEATURE                 Location/Qualifiers
REGION                  1..70
                        note = FpL_C3KX 7a
source                  1..70
                        mol_type = protein
                        organism = synthetic construct
SEQUENCE: 223
ETPGRPAEEV TIRVNLIFAD GRIQTAEFIG TFEEATARAY AYANLLARDY GDFTADLEDG  60
GYTINIRFAG                                                         70

SEQ ID NO: 224          moltype = AA  length = 70
FEATURE                 Location/Qualifiers
REGION                  1..70
                        note = FpL_C3KX 7b
source                  1..70
                        mol_type = protein
                        organism = synthetic construct
SEQUENCE: 224
ETPGEPAEEV TIRVNLIFAD GRIQTARFIG TFEEATARAY AYANLLARDY GDFTADLEDG  60
GYTINIRFAG                                                         70

SEQ ID NO: 225          moltype = AA  length = 70
FEATURE                 Location/Qualifiers
REGION                  1..70
                        note = FpL_C3KX 7c
source                  1..70
                        mol_type = protein
                        organism = synthetic construct
SEQUENCE: 225
ETPGEPAEEV TIRVNLIFAD GRIQTAEFIG TFEEATARAY AYANLLRRDY GDFTADLEDG  60
GYTINIRFAG                                                         70

SEQ ID NO: 226          moltype = DNA  length = 33
FEATURE                 Location/Qualifiers
misc_feature            1..33
                        note = PCR forward primer
source                  1..33
                        mol_type = other DNA
                        organism = synthetic construct
SEQUENCE: 226
gaaacacgag gaagaccagc ggaagaagtt acc                               33

SEQ ID NO: 227          moltype = DNA  length = 33
FEATURE                 Location/Qualifiers
misc_feature            1..33
                        note = PCR reverse primer
source                  1..33
                        mol_type = other DNA
                        organism = synthetic construct
SEQUENCE: 227
cgctggtctt cctggtgttt ccatggccat cgc                               33

SEQ ID NO: 228          moltype = DNA  length = 27
FEATURE                 Location/Qualifiers
misc_feature            1..27
                        note = PCR forward primer
source                  1..27
                        mol_type = other DNA
                        organism = synthetic construct
SEQUENCE: 228
accgctagat tcattggtac attcgaa                                      27

SEQ ID NO: 229          moltype = DNA  length = 27
FEATURE                 Location/Qualifiers
misc_feature            1..27
                        note = PCR reverse primer
source                  1..27
                        mol_type = other DNA
                        organism = synthetic construct
SEQUENCE: 229
aatgaatcta gcggtctgaa tccgacc                                      27
```

```
SEQ ID NO: 230         moltype = DNA  length = 27
FEATURE                Location/Qualifiers
misc_feature           1..27
                       note = PCR forward primer
source                 1..27
                       mol_type = other DNA
                       organism = synthetic construct
SEQUENCE: 230
ttgctgaggc gtgattatgg tgacttt                                      27

SEQ ID NO: 231         moltype = DNA  length = 27
FEATURE                Location/Qualifiers
misc_feature           1..27
                       note = PCR reverse primer
source                 1..27
                       mol_type = other DNA
                       organism = synthetic construct
SEQUENCE: 231
atcacgcctc agcaaattcg cataagc                                      27

SEQ ID NO: 232         moltype = DNA  length = 18
FEATURE                Location/Qualifiers
misc_feature           1..18
                       note = 6His DNA
source                 1..18
                       mol_type = other DNA
                       organism = synthetic construct
SEQUENCE: 232
catcaccacc atcaccac                                                18

SEQ ID NO: 233         moltype = DNA  length = 210
FEATURE                Location/Qualifiers
misc_feature           1..210
                       note = FpL_C3KX 5e_DNA
source                 1..210
                       mol_type = other DNA
                       organism = synthetic construct
SEQUENCE: 233
gaaacaccag aagagccagc ggaagaagtt accattcgcg tgaatctgat ctttgccgac  60
ggtcggattc agaccgctga attcattggt acattcgaag aagccacagc tcgtgcctat  120
gcttatgcga atttgctggc ccgtgattat ggtggcttta cggcggacct ggaagatggc  180
gggtatacga tcaatatccg ttttgcgggc                                   210

SEQ ID NO: 234         moltype = DNA  length = 30
FEATURE                Location/Qualifiers
misc_feature           1..30
                       note = PCR forward primer
source                 1..30
                       mol_type = other DNA
                       organism = synthetic construct
SEQUENCE: 234
ccagaagaga gcgcggaaga agttaccatt                                   30

SEQ ID NO: 235         moltype = DNA  length = 30
FEATURE                Location/Qualifiers
misc_feature           1..30
                       note = PCR reverse primer
source                 1..30
                       mol_type = other DNA
                       organism = synthetic construct
SEQUENCE: 235
ttcttccgcg ctctcttctg gtgtttccat                                   30

SEQ ID NO: 236         moltype = AA  length = 70
FEATURE                Location/Qualifiers
REGION                 1..70
                       note = FpL_C3KX5e_P6S
source                 1..70
                       mol_type = protein
                       organism = synthetic construct
SEQUENCE: 236
ETPEESAEEV TIRVNLIFAD GRIQTAEFIG TFEEATARAY AYANLLARDY GGFTADLEDG  60
GYTINIRFAG                                                         70

SEQ ID NO: 237         moltype = DNA  length = 27
FEATURE                Location/Qualifiers
misc_feature           1..27
                       note = PCR forward primer
source                 1..27
```

```
                         mol_type = other DNA
                         organism = synthetic construct
SEQUENCE: 237
acagcagaag cctatgctta tgcgaat                                       27

SEQ ID NO: 238           moltype = DNA  length = 27
FEATURE                  Location/Qualifiers
misc_feature             1..27
                         note = PCR reverse primer
source                   1..27
                         mol_type = other DNA
                         organism = synthetic construct
SEQUENCE: 238
ataggcttct gctgtcgctt cttcgaa                                       27

SEQ ID NO: 239           moltype = AA  length = 70
FEATURE                  Location/Qualifiers
REGION                   1..70
                         note = FpL_C3KR_K38E
source                   1..70
                         mol_type = protein
                         organism = synthetic construct
SEQUENCE: 239
ETPEEPREEV TIRVNLIFAD GRIQTAEFRG TFEEATAEAY AYANLLAREN GEYTADLEDG  60
GNTINIRFAG                                                          70

SEQ ID NO: 240           moltype = AA  length = 70
FEATURE                  Location/Qualifiers
REGION                   1..70
                         note = FpL_C3KX 7d
source                   1..70
                         mol_type = protein
                         organism = synthetic construct
SEQUENCE: 240
ETPGESAEEV TIRVNLIFAD GRIQTAEFIG TFEEATAEAY AYANLLARDY GDFTADLEDG  60
GYTINIRFAG                                                          70

SEQ ID NO: 241           moltype = DNA  length = 210
FEATURE                  Location/Qualifiers
misc_feature             1..210
                         note = FpL_C3KX 7d_DNA
source                   1..210
                         mol_type = other DNA
                         organism = synthetic construct
SEQUENCE: 241
gaaacaccag gagagtcagc ggaagaagtt accattcgcg tgaatctgat ctttgccgac  60
ggtcggattc agaccgctga attcattggt acattcgaag aagccacagc tgaagcctat  120
gcttatgcga atttgctggc ccgtgattat ggtgacttta cggcggacct ggaagatggc  180
gggtatacca tcaacatccg ctttgcggga                                    210

SEQ ID NO: 242           moltype = AA  length = 70
FEATURE                  Location/Qualifiers
REGION                   1..70
                         note = FpL_C3KX 7d_A69V
source                   1..70
                         mol_type = protein
                         organism = synthetic construct
SEQUENCE: 242
ETPGESAEEV TIRVNLIFAD GRIQTAEFIG TFEEATAEAY AYANLLARDY GDFTADLEDG  60
GYTINIRFVG                                                          70

SEQ ID NO: 243           moltype = AA  length = 70
FEATURE                  Location/Qualifiers
REGION                   1..70
                         note = FpL_C3KX 7d_I29F
source                   1..70
                         mol_type = protein
                         organism = synthetic construct
SEQUENCE: 243
ETPGESAEEV TIRVNLIFAD GRIQTAEFFG TFEEATAEAY AYANLLARDY GDFTADLEDG  60
GYTINIRFAG                                                          70

SEQ ID NO: 244           moltype = AA  length = 70
FEATURE                  Location/Qualifiers
REGION                   1..70
                         note = FpL_C3KX 7d_E8G,E33V
source                   1..70
                         mol_type = protein
                         organism = synthetic construct
```

```
SEQUENCE: 244
ETPGESAGEV TIRVNLIFAD GRIQTAEFIG TFVEATAEAY AYANLLARDY GDFTADLEDG  60
GYTINIRFAG                                                          70

SEQ ID NO: 245         moltype = DNA  length = 27
FEATURE                Location/Qualifiers
misc_feature           1..27
                       note = I23X forward primer 1
misc_difference        7
                       note = a, c, g, or t
source                 1..27
                       mol_type = other DNA
                       organism = synthetic construct
SEQUENCE: 245
ggtcggndtc agaccgctga attcatt                                       27

SEQ ID NO: 246         moltype = DNA  length = 27
FEATURE                Location/Qualifiers
misc_feature           1..27
                       note = I23X forward primer 2
source                 1..27
                       mol_type = other DNA
                       organism = synthetic construct
SEQUENCE: 246
ggtcggvhgc agaccgctga attcatt                                       27

SEQ ID NO: 247         moltype = DNA  length = 27
FEATURE                Location/Qualifiers
misc_feature           1..27
                       note = I23X forward primer 3
source                 1..27
                       mol_type = other DNA
                       organism = synthetic construct
SEQUENCE: 247
ggtcggtggc agaccgctga attcatt                                       27

SEQ ID NO: 248         moltype = DNA  length = 27
FEATURE                Location/Qualifiers
misc_feature           1..27
                       note = I23X reverse primer 1
misc_difference        9
                       note = a, c, g, or t
source                 1..27
                       mol_type = other DNA
                       organism = synthetic construct
SEQUENCE: 248
accgtcahnc cgaccgtcgg caaagat                                       27

SEQ ID NO: 249         moltype = DNA  length = 27
FEATURE                Location/Qualifiers
misc_feature           1..27
                       note = I23X reverse primer 2
source                 1..27
                       mol_type = other DNA
                       organism = synthetic construct
SEQUENCE: 249
accgtccdbc cgaccgtcgg caaagat                                       27

SEQ ID NO: 250         moltype = DNA  length = 27
FEATURE                Location/Qualifiers
misc_feature           1..27
                       note = A41X forward primer 1
source                 1..27
                       mol_type = other DNA
                       organism = synthetic construct
SEQUENCE: 250
accgtcccac cgaccgtcgg caaagat                                       27

SEQ ID NO: 251         moltype = AA  length = 70
FEATURE                Location/Qualifiers
REGION                 1..70
                       note = FpL_C3KX 7d_I23R
source                 1..70
                       mol_type = protein
                       organism = synthetic construct
SEQUENCE: 251
ETPGESAEEV TIRVNLIFAD GRRQTAEFIG TFEEATAEAY AYANLLARDY GDFTADLEDG  60
GYTINIRFAG                                                          70
```

```
SEQ ID NO: 252          moltype = DNA  length = 27
FEATURE                 Location/Qualifiers
misc_feature            1..27
                        note = A41X forward primer 1
misc_difference         7
                        note = a, c, g, or t
source                  1..27
                        mol_type = other DNA
                        organism = synthetic construct
SEQUENCE: 252
gcctatndtt atgcgaattt gctggcc                                    27

SEQ ID NO: 253          moltype = DNA  length = 27
FEATURE                 Location/Qualifiers
misc_feature            1..27
                        note = A41X forward primer 2
source                  1..27
                        mol_type = other DNA
                        organism = synthetic construct
SEQUENCE: 253
gcctatvhgt atgcgaattt gctggcc                                    27

SEQ ID NO: 254          moltype = DNA  length = 27
FEATURE                 Location/Qualifiers
misc_feature            1..27
                        note = A41X forward primer 3
source                  1..27
                        mol_type = other DNA
                        organism = synthetic construct
SEQUENCE: 254
gcctattggt atgcgaattt gctggcc                                    27

SEQ ID NO: 255          moltype = DNA  length = 27
FEATURE                 Location/Qualifiers
misc_feature            1..27
                        note = A41X reverse primer 1
misc_difference         9
                        note = a, c, g, or t
source                  1..27
                        mol_type = other DNA
                        organism = synthetic construct
SEQUENCE: 255
ggcttcahna taggcttcag ctgtggc                                    27

SEQ ID NO: 256          moltype = DNA  length = 27
FEATURE                 Location/Qualifiers
misc_feature            1..27
                        note = A41X reverse primer 2
source                  1..27
                        mol_type = other DNA
                        organism = synthetic construct
SEQUENCE: 256
ggcttccdba taggcttcag ctgtggc                                    27

SEQ ID NO: 257          moltype = DNA  length = 27
FEATURE                 Location/Qualifiers
misc_feature            1..27
                        note = A41X reverse primer 3
source                  1..27
                        mol_type = other DNA
                        organism = synthetic construct
SEQUENCE: 257
ggcttcccaa taggcttcag ctgtggc                                    27

SEQ ID NO: 258          moltype = AA  length = 70
FEATURE                 Location/Qualifiers
REGION                  1..70
                        note = FpL_C3KX 7d_A41I
source                  1..70
                        mol_type = protein
                        organism = synthetic construct
SEQUENCE: 258
ETPGESAEEV TIRVNLIFAD GRIQTAEFIG TFEEATAEAY IYANLLARDY GDFTADLEDG  60
GYTINIRFAG                                                       70

SEQ ID NO: 259          moltype = AA  length = 70
FEATURE                 Location/Qualifiers
REGION                  1..70
                        note = FpL_C3KX 7d_A41Y
```

```
source                  1..70
                        mol_type = protein
                        organism = synthetic construct
SEQUENCE: 259
ETPGESAEEV TIRVNLIFAD GRIQTAEFIG TFEEATAEAY YYANLLARDY GDFTADLEDG  60
GYTINIRFAG                                                         70

SEQ ID NO: 260          moltype = DNA  length = 27
FEATURE                 Location/Qualifiers
misc_feature            1..27
                        note = E52X forward primer 1
misc_difference         7
                        note = a, c, g, or t
source                  1..27
                        mol_type = other DNA
                        organism = synthetic construct
SEQUENCE: 260
tatggtndtt ttacggcgga cctggaa                                      27

SEQ ID NO: 261          moltype = DNA  length = 27
FEATURE                 Location/Qualifiers
misc_feature            1..27
                        note = E52X forward primer 2
source                  1..27
                        mol_type = other DNA
                        organism = synthetic construct
SEQUENCE: 261
tatggtvhgt ttacggcgga cctggaa                                      27

SEQ ID NO: 262          moltype = DNA  length = 27
FEATURE                 Location/Qualifiers
misc_feature            1..27
                        note = E52X forward primer 3
source                  1..27
                        mol_type = other DNA
                        organism = synthetic construct
SEQUENCE: 262
tatggttggt ttacggcgga cctggaa                                      27

SEQ ID NO: 263          moltype = DNA  length = 27
FEATURE                 Location/Qualifiers
misc_feature            1..27
                        note = E52X reverse primer 1
misc_difference         9
                        note = a, c, g, or t
source                  1..27
                        mol_type = other DNA
                        organism = synthetic construct
SEQUENCE: 263
ataatcahna ccataatcac gggccag                                      27

SEQ ID NO: 264          moltype = DNA  length = 27
FEATURE                 Location/Qualifiers
misc_feature            1..27
                        note = E52X reverse primer 2
source                  1..27
                        mol_type = other DNA
                        organism = synthetic construct
SEQUENCE: 264
ataatccdba ccataatcac gggccag                                      27

SEQ ID NO: 265          moltype = DNA  length = 27
FEATURE                 Location/Qualifiers
misc_feature            1..27
                        note = E52X reverse primer 3
source                  1..27
                        mol_type = other DNA
                        organism = synthetic construct
SEQUENCE: 265
ataatcccaa ccataatcac gggccag                                      27

SEQ ID NO: 266          moltype = AA  length = 70
FEATURE                 Location/Qualifiers
REGION                  1..70
                        note = FpL_C3KX 7d_E52L
source                  1..70
                        mol_type = protein
                        organism = synthetic construct
SEQUENCE: 266
```

```
ETPGESAEEV TIRVNLIFAD GRIQTAEFIG TFEEATAEAY AYANLLARDY GLFTADLEDG  60
GYTINIRFAG                                                         70

SEQ ID NO: 267         moltype = AA  length = 70
FEATURE                Location/Qualifiers
REGION                 1..70
                       note = FpL_C3KX 7d_E52V
source                 1..70
                       mol_type = protein
                       organism = synthetic construct
SEQUENCE: 267
ETPGESAEEV TIRVNLIFAD GRIQTAEFIG TFEEATAEAY AYANLLARDY GVFTADLEDG  60
GYTINIRFAG                                                         70

SEQ ID NO: 268         moltype = DNA  length = 210
FEATURE                Location/Qualifiers
misc_feature           1..210
                       note = FpL_C3KX 7d_A69V_DNA
source                 1..210
                       mol_type = other DNA
                       organism = synthetic construct
SEQUENCE: 268
gaaacaccag gagagtcagc ggaagaagtt accattcgcg tgaatctgat ctttgccgac  60
ggtcggattc agaccgccga attcattggt acattcgaag aagccacagc tgaagcctat  120
gcttatgcga atttgctggc ccgtgattat ggtgacttta cggcggacct ggaagatggc  180
gggtatacca tcaacatccg ctttgtggga                                   210

SEQ ID NO: 269         moltype = DNA  length = 30
FEATURE                Location/Qualifiers
misc_feature           1..30
                       note = PCR forward primer
source                 1..30
                       mol_type = other DNA
                       organism = synthetic construct
SEQUENCE: 269
gattatggtg tgtttacggc ggacctggaa                                   30

SEQ ID NO: 270         moltype = DNA  length = 30
FEATURE                Location/Qualifiers
misc_feature           1..30
                       note = PCR reverse primer
source                 1..30
                       mol_type = other DNA
                       organism = synthetic construct
SEQUENCE: 270
cgccgtaaac acaccataat cacgggccag                                   30

SEQ ID NO: 271         moltype = AA  length = 70
FEATURE                Location/Qualifiers
REGION                 1..70
                       note = FpL_C3KX 8a
source                 1..70
                       mol_type = protein
                       organism = synthetic construct
SEQUENCE: 271
ETPGESAEEV TIRVNLIFAD GRIQTAEFIG TFEEATAEAY AYANLLARDY GVFTADLEDG  60
GYTINIRFVG                                                         70

SEQ ID NO: 272         moltype = DNA  length = 30
FEATURE                Location/Qualifiers
misc_feature           1..30
                       note = PCR forward primer
source                 1..30
                       mol_type = other DNA
                       organism = synthetic construct
SEQUENCE: 272
gattatggtc tgtttacggc ggacctggaa                                   30

SEQ ID NO: 273         moltype = DNA  length = 30
FEATURE                Location/Qualifiers
misc_feature           1..30
                       note = PCR reverse primer
source                 1..30
                       mol_type = other DNA
                       organism = synthetic construct
SEQUENCE: 273
cgccgtaaac agaccataat cacgggccag                                   30

SEQ ID NO: 274         moltype = AA  length = 70
```

```
FEATURE              Location/Qualifiers
REGION               1..70
                     note = FpL_C3KX 8b
source               1..70
                     mol_type = protein
                     organism = synthetic construct
SEQUENCE: 274
ETPGESAEEV TIRVNLIFAD GRIQTAEFIG TFEEATAEAY AYANLLARDY GLFTADLEDG  60
GYTINIRFVG                                                         70

SEQ ID NO: 275       moltype = AA  length = 70
FEATURE              Location/Qualifiers
REGION               1..70
                     note = FpL_C3KX 7e
source               1..70
                     mol_type = protein
                     organism = synthetic construct
SEQUENCE: 275
ETPGESAEEV TIRVNLIFAD GRIQTAEFIG TFEEATAEAY AYANLLARDY GEFTADLEDG  60
GYTINIRFVG                                                         70

SEQ ID NO: 276       moltype = DNA  length = 210
FEATURE              Location/Qualifiers
misc_feature         1..210
                     note = FpL_C3KX 7e_DNA
source               1..210
                     mol_type = other DNA
                     organism = synthetic construct
SEQUENCE: 276
gaaaccccgg gagaatcggc tgaagaggtc accattcgtg tgaacttaat cttcgctgat  60
ggtcgcatcc aaacggcaga gttcattggg acgtttgaag aagcaaccgc cgaagcgtac  120
gcgtacgcca acctcctcgc ccgcgattac ggtgaattta cagccgattt ggaagatggc  180
ggttatacga tcaatatccg cttcgtgggc                                   210

SEQ ID NO: 277       moltype = DNA  length = 30
FEATURE              Location/Qualifiers
misc_feature         1..30
                     note = PCR forward primer
source               1..30
                     mol_type = other DNA
                     organism = synthetic construct
SEQUENCE: 277
gattatggtg aatttacggc ggacctggaa                                   30

SEQ ID NO: 278       moltype = DNA  length = 30
FEATURE              Location/Qualifiers
misc_feature         1..30
                     note = PCR reverse primer
source               1..30
                     mol_type = other DNA
                     organism = synthetic construct
SEQUENCE: 278
cgccgtaaat tcaccataat cacgggccag                                   30

SEQ ID NO: 279       moltype = AA  length = 70
FEATURE              Location/Qualifiers
REGION               1..70
                     note = FpL_C3KX 7e_P3R
source               1..70
                     mol_type = protein
                     organism = synthetic construct
SEQUENCE: 279
ETRGESAEEV TIRVNLIFAD GRIQTAEFIG TFEEATAEAY AYANLLARDY GEFTADLEDG  60
GYTINIRFVG                                                         70

SEQ ID NO: 280       moltype = AA  length = 70
FEATURE              Location/Qualifiers
REGION               1..70
                     note = FpL_C3KX 7e_P3R,K38R
source               1..70
                     mol_type = protein
                     organism = synthetic construct
SEQUENCE: 280
ETRGESAEEV TIRVNLIFAD GRIQTAEFIG TFEEATARAY AYANLLARDY GEFTADLEDG  60
GYTINIRFVG                                                         70

SEQ ID NO: 281       moltype = AA  length = 70
FEATURE              Location/Qualifiers
REGION               1..70
```

```
                        note = FpL_C3KX 7e_P3R,I66V
source                  1..70
                        mol_type = protein
                        organism = synthetic construct
SEQUENCE: 281
ETRGESAEEV TIRVNLIFAD GRIQTAEFIG TFEEATAEAY AYANLLARDY GEFTADLEDG  60
GYTINVRFVG                                                         70

SEQ ID NO: 282          moltype = AA  length = 70
FEATURE                 Location/Qualifiers
REGION                  1..70
                        note = FpL_C3KX 7e_P3R,T31M
source                  1..70
                        mol_type = protein
                        organism = synthetic construct
SEQUENCE: 282
ETRGESAEEV TIRVNLIFAD GRIQTAEFIG MFEEATAEAY AYANLLARDY GEFTADLEDG  60
GYTINIRFVG                                                         70

SEQ ID NO: 283          moltype = AA  length = 70
FEATURE                 Location/Qualifiers
REGION                  1..70
                        note = FpL_C3KX 7e_P6L
source                  1..70
                        mol_type = protein
                        organism = synthetic construct
SEQUENCE: 283
ETPGELAEEV TIRVNLIFAD GRIQTAEFIG TFEEATAEAY AYANLLARDY GEFTADLEDG  60
GYTINIRFVG                                                         70

SEQ ID NO: 284          moltype = AA  length = 70
FEATURE                 Location/Qualifiers
REGION                  1..70
                        note = FpL_C3KX 7e_A35T
source                  1..70
                        mol_type = protein
                        organism = synthetic construct
SEQUENCE: 284
ETPGESAEEV TIRVNLIFAD GRIQTAEFIG TFEETTAEAY AYANLLARDY GEFTADLEDG  60
GYTINIRFVG                                                         70

SEQ ID NO: 285          moltype = AA  length = 70
FEATURE                 Location/Qualifiers
REGION                  1..70
                        note = FpL_C3KX 7e_E33G
source                  1..70
                        mol_type = protein
                        organism = synthetic construct
SEQUENCE: 285
ETPGESAEEV TIRVNLIFAD GRIQTAEFIG TFGEATAEAY AYANLLARDY GEFTADLEDG  60
GYTINIRFVG                                                         70

SEQ ID NO: 286          moltype = AA  length = 70
FEATURE                 Location/Qualifiers
REGION                  1..70
                        note = FpL_C3KX 7e_E5D,P6L
source                  1..70
                        mol_type = protein
                        organism = synthetic construct
SEQUENCE: 286
ETPGDLAEEV TIRVNLIFAD GRIQTAEFIG TFEEATAEAY AYANLLARDY GEFTADLEDG  60
GYTINIRFVG                                                         70

SEQ ID NO: 287          moltype = AA  length = 70
FEATURE                 Location/Qualifiers
REGION                  1..70
                        note = FpL_C3KX 7e_A69L
source                  1..70
                        mol_type = protein
                        organism = synthetic construct
SEQUENCE: 287
ETPGESAEEV TIRVNLIFAD GRIQTAEFIG TFEEATAEAY AYANLLARDY GEFTADLEDG  60
GYTINIRFLG                                                         70

SEQ ID NO: 288          moltype = AA  length = 70
FEATURE                 Location/Qualifiers
REGION                  1..70
                        note = FpL_C3KX 7e_A37T
source                  1..70
```

```
                        mol_type = protein
                        organism = synthetic construct
SEQUENCE: 288
ETPGESAEEV TIRVNLIFAD GRIQTAEFIG TFEEATTEAY AYANLLARDY GEFTADLEDG  60
GYTINIRFVG                                                         70

SEQ ID NO: 289          moltype = AA  length = 70
FEATURE                 Location/Qualifiers
REGION                  1..70
                        note = FpL_C3KX 7e_E33D,E52G
source                  1..70
                        mol_type = protein
                        organism = synthetic construct
SEQUENCE: 289
ETPGESAEEV TIRVNLIFAD GRIQTAEFIG TFDEATAEAY AYANLLARDY GGFTADLEDG  60
GYTINIRFVG                                                         70

SEQ ID NO: 290          moltype = AA  length = 70
FEATURE                 Location/Qualifiers
REGION                  1..70
                        note = FpL_C3KX 7e_T2A,K7P
source                  1..70
                        mol_type = protein
                        organism = synthetic construct
SEQUENCE: 290
EAPGESPEEV TIRVNLIFAD GRIQTAEFIG TFEEATAEAY AYANLLARDY GEFTADLEDG  60
GYTINIRFVG                                                         70

SEQ ID NO: 291          moltype = AA  length = 70
FEATURE                 Location/Qualifiers
REGION                  1..70
                        note = FpL_C3KX 7e_I23V
source                  1..70
                        mol_type = protein
                        organism = synthetic construct
SEQUENCE: 291
ETPGESAEEV TIRVNLIFAD GRVQTAEFIG TFEEATAEAY AYANLLARDY GEFTADLEDG  60
GYTINIRFVG                                                         70

SEQ ID NO: 292          moltype = AA  length = 70
FEATURE                 Location/Qualifiers
REGION                  1..70
                        note = FpL_C3KX 7e_P6T
source                  1..70
                        mol_type = protein
                        organism = synthetic construct
SEQUENCE: 292
ETPGETAEEV TIRVNLIFAD GRIQTAEFIG TFEEATAEAY AYANLLARDY GEFTADLEDG  60
GYTINIRFVG                                                         70

SEQ ID NO: 293          moltype = AA  length = 70
FEATURE                 Location/Qualifiers
REGION                  1..70
                        note = FpL_C3KX 7e_T36S
source                  1..70
                        mol_type = protein
                        organism = synthetic construct
SEQUENCE: 293
ETPGESAEEV TIRVNLIFAD GRIQTAEFIG TFEEASAEAY AYANLLARDY GEFTADLEDG  60
GYTINIRFVG                                                         70

SEQ ID NO: 294          moltype = DNA  length = 30
FEATURE                 Location/Qualifiers
misc_feature            1..30
                        note = PCR forward primer
source                  1..30
                        mol_type = other DNA
                        organism = synthetic construct
SEQUENCE: 294
accattcgtg cgaacttaat cttcgctgat                                   30

SEQ ID NO: 295          moltype = DNA  length = 30
FEATURE                 Location/Qualifiers
misc_feature            1..30
                        note = PCR reverse primer
source                  1..30
                        mol_type = other DNA
                        organism = synthetic construct
SEQUENCE: 295
```

```
gattaagttc gcacgaatgg tgacctcttc                                     30

SEQ ID NO: 296         moltype = AA  length = 70
FEATURE                Location/Qualifiers
REGION                 1..70
                       note = FpL_C3KX 7e_V14A
source                 1..70
                       mol_type = protein
                       organism = synthetic construct
SEQUENCE: 296
ETPGESAEEV TIRANLIFAD GRIQTAEFIG TFEEATAEAY AYANLLARDY GEFTADLEDG  60
GYTINIRFVG                                                          70

SEQ ID NO: 297         moltype = DNA  length = 30
FEATURE                Location/Qualifiers
misc_feature           1..30
                       note = PCR forward primer
source                 1..30
                       mol_type = other DNA
                       organism = synthetic construct
SEQUENCE: 297
ttcgctgatc gtcgcatcca aacggcagag                                     30

SEQ ID NO: 298         moltype = DNA  length = 30
FEATURE                Location/Qualifiers
misc_feature           1..30
                       note = PCR reverse primer
source                 1..30
                       mol_type = other DNA
                       organism = synthetic construct
SEQUENCE: 298
ttggatgcga cgatcagcga agattaagtt                                     30

SEQ ID NO: 299         moltype = AA  length = 70
FEATURE                Location/Qualifiers
REGION                 1..70
                       note = FpL_C3KX 7e_G21R
source                 1..70
                       mol_type = protein
                       organism = synthetic construct
SEQUENCE: 299
ETPGESAEEV TIRVNLIFAD RRIQTAEFIG TFEEATAEAY AYANLLARDY GEFTADLEDG  60
GYTINIRFVG                                                          70

SEQ ID NO: 300         moltype = DNA  length = 30
FEATURE                Location/Qualifiers
misc_feature           1..30
                       note = PCR forward primer
source                 1..30
                       mol_type = other DNA
                       organism = synthetic construct
SEQUENCE: 300
gatggtcgca cccaaacggc agagttcatt                                     30

SEQ ID NO: 301         moltype = DNA  length = 30
FEATURE                Location/Qualifiers
misc_feature           1..30
                       note = PCR reverse primer
source                 1..30
                       mol_type = other DNA
                       organism = synthetic construct
SEQUENCE: 301
tgccgtttgg gtgcgaccat cagcgaagat                                     30

SEQ ID NO: 302         moltype = AA  length = 70
FEATURE                Location/Qualifiers
REGION                 1..70
                       note = FpL_C3KX 7e_I23T
source                 1..70
                       mol_type = protein
                       organism = synthetic construct
SEQUENCE: 302
ETPGESAEEV TIRVNLIFAD GRTQTAEFIG TFEEATAEAY AYANLLARDY GEFTADLEDG  60
GYTINIRFVG                                                          70

SEQ ID NO: 303         moltype = DNA  length = 30
FEATURE                Location/Qualifiers
misc_feature           1..30
                       note = PCR forward primer
```

```
source                  1..30
                        mol_type = other DNA
                        organism = synthetic construct
SEQUENCE: 303
gaagcgtacc gttacgccaa cctcctcgcc                                    30

SEQ ID NO: 304          moltype = DNA  length = 30
FEATURE                 Location/Qualifiers
misc_feature            1..30
                        note = PCR reverse primer
source                  1..30
                        mol_type = other DNA
                        organism = synthetic construct
SEQUENCE: 304
gttggcgtaa cggtacgctt cggcggttgc                                    30

SEQ ID NO: 305          moltype = AA  length = 70
FEATURE                 Location/Qualifiers
REGION                  1..70
                        note = FpL_C3KX 7e_A41R
source                  1..70
                        mol_type = protein
                        organism = synthetic construct
SEQUENCE: 305
ETPGESAEEV TIRVNLIFAD GRIQTAEFIG TFEEATAEAY RYANLLARDY GEFTADLEDG  60
GYTINIRFVG                                                          70

SEQ ID NO: 306          moltype = DNA  length = 30
FEATURE                 Location/Qualifiers
misc_feature            1..30
                        note = PCR forward primer
source                  1..30
                        mol_type = other DNA
                        organism = synthetic construct
SEQUENCE: 306
gcgtacgccg atctcctcgc ccgcgattac                                    30

SEQ ID NO: 307          moltype = DNA  length = 30
FEATURE                 Location/Qualifiers
misc_feature            1..30
                        note = PCR reverse primer
source                  1..30
                        mol_type = other DNA
                        organism = synthetic construct
SEQUENCE: 307
ggcgaggaga tcggcgtacg cgtacgcttc                                    30

SEQ ID NO: 308          moltype = AA  length = 70
FEATURE                 Location/Qualifiers
REGION                  1..70
                        note = FpL_C3KX 7e_N44D
source                  1..70
                        mol_type = protein
                        organism = synthetic construct
SEQUENCE: 308
ETPGESAEEV TIRVNLIFAD GRIQTAEFIG TFEEATAEAY AYADLLARDY GEFTADLEDG  60
GYTINIRFVG                                                          70

SEQ ID NO: 309          moltype = DNA  length = 30
FEATURE                 Location/Qualifiers
misc_feature            1..30
                        note = PCR forward primer
source                  1..30
                        mol_type = other DNA
                        organism = synthetic construct
SEQUENCE: 309
gcgtacgccc gtctcctcgc ccgcgattac                                    30

SEQ ID NO: 310          moltype = DNA  length = 30
FEATURE                 Location/Qualifiers
misc_feature            1..30
                        note = PCR reverse primer
source                  1..30
                        mol_type = other DNA
                        organism = synthetic construct
SEQUENCE: 310
ggcgaggaga cgggcgtacg cgtacgcttc                                    30

SEQ ID NO: 311          moltype = AA  length = 70
```

```
FEATURE               Location/Qualifiers
REGION                1..70
                      note = FpL_C3KX 7e_N44R
source                1..70
                      mol_type = protein
                      organism = synthetic construct
SEQUENCE: 311
ETPGESAEEV TIRVNLIFAD GRIQTAEFIG TFEEATAEAY AYARLLARDY GEFTADLEDG  60
GYTINIRFVG                                                         70

SEQ ID NO: 312        moltype = DNA  length = 30
FEATURE               Location/Qualifiers
misc_feature          1..30
                      note = PCR forward primer
source                1..30
                      mol_type = other DNA
                      organism = synthetic construct
SEQUENCE: 312
gcgtacgccc atctcctcgc ccgcgattac                                   30

SEQ ID NO: 313        moltype = DNA  length = 30
FEATURE               Location/Qualifiers
misc_feature          1..30
                      note = PCR reverse primer
source                1..30
                      mol_type = other DNA
                      organism = synthetic construct
SEQUENCE: 313
ggcgaggaga tgggcgtacg cgtacgcttc                                   30

SEQ ID NO: 314        moltype = AA  length = 70
FEATURE               Location/Qualifiers
REGION                1..70
                      note = FpL_C3KX 7e_N44H
source                1..70
                      mol_type = protein
                      organism = synthetic construct
SEQUENCE: 314
ETPGESAEEV TIRVNLIFAD GRIQTAEFIG TFEEATAEAY AYAHLLARDY GEFTADLEDG  60
GYTINIRFVG                                                         70

SEQ ID NO: 315        moltype = DNA  length = 30
FEATURE               Location/Qualifiers
misc_feature          1..30
                      note = PCR forward primer
source                1..30
                      mol_type = other DNA
                      organism = synthetic construct
SEQUENCE: 315
gattacggtt attttacagc cgatttggaa                                   30

SEQ ID NO: 316        moltype = DNA  length = 30
FEATURE               Location/Qualifiers
misc_feature          1..30
                      note = PCR reverse primer
source                1..30
                      mol_type = other DNA
                      organism = synthetic construct
SEQUENCE: 316
ggctgtaaaa taaccgtaat cgcgggcgag                                   30

SEQ ID NO: 317        moltype = AA  length = 70
FEATURE               Location/Qualifiers
REGION                1..70
                      note = FpL_C3KX 7e_E52Y
source                1..70
                      mol_type = protein
                      organism = synthetic construct
SEQUENCE: 317
ETPGESAEEV TIRVNLIFAD GRIQTAEFIG TFEEATAEAY AYANLLARDY GYFTADLEDG  60
GYTINIRFVG                                                         70

SEQ ID NO: 318        moltype = DNA  length = 30
FEATURE               Location/Qualifiers
misc_feature          1..30
                      note = PCR forward primer
source                1..30
                      mol_type = other DNA
                      organism = synthetic construct
```

```
SEQUENCE: 318
ttggaagatc gtggttatac gatcaatatc                              30

SEQ ID NO: 319         moltype = DNA  length = 30
FEATURE                Location/Qualifiers
misc_feature           1..30
                       note = PCR reverse primer
source                 1..30
                       mol_type = other DNA
                       organism = synthetic construct
SEQUENCE: 319
cgtataacca cgatcttcca aatcggctgt                              30

SEQ ID NO: 320         moltype = AA  length = 70
FEATURE                Location/Qualifiers
REGION                 1..70
                       note = FpL_C3KX 7e_G60R
source                 1..70
                       mol_type = protein
                       organism = synthetic construct
SEQUENCE: 320
ETPGESAEEV TIRVNLIFAD GRIQTAEFIG TFEEATAEAY AYANLLARDY GEFTADLEDR  60
GYTINIRFVG                                                    70

SEQ ID NO: 321         moltype = DNA  length = 30
FEATURE                Location/Qualifiers
misc_feature           1..30
                       note = PCR forward primer
source                 1..30
                       mol_type = other DNA
                       organism = synthetic construct
SEQUENCE: 321
ggttatacgc tgaatatccg cttcgtgggc                              30

SEQ ID NO: 322         moltype = DNA  length = 30
FEATURE                Location/Qualifiers
misc_feature           1..30
                       note = PCR reverse primer
source                 1..30
                       mol_type = other DNA
                       organism = synthetic construct
SEQUENCE: 322
gcggatattc agcgtataac cgccatcttc                              30

SEQ ID NO: 323         moltype = AA  length = 70
FEATURE                Location/Qualifiers
REGION                 1..70
                       note = FpL_C3KX 7e_I64L
source                 1..70
                       mol_type = protein
                       organism = synthetic construct
SEQUENCE: 323
ETPGESAEEV TIRVNLIFAD GRIQTAEFIG TFEEATAEAY AYANLLARDY GEFTADLEDG  60
GYTLNIRFVG                                                    70

SEQ ID NO: 324         moltype = AA  length = 23
FEATURE                Location/Qualifiers
REGION                 1..23
                       note = Immobilization tag (IT)
source                 1..23
                       mol_type = protein
                       organism = synthetic construct
SEQUENCE: 324
ALPSKSKKIL KEAKKLNKAQ APK                                     23

SEQ ID NO: 325         moltype = AA  length = 6
FEATURE                Location/Qualifiers
REGION                 1..6
                       note = 6-Histidine tag (6H)
source                 1..6
                       mol_type = protein
                       organism = synthetic construct
SEQUENCE: 325
HHHHHH                                                        6

SEQ ID NO: 326         moltype = AA  length = 312
FEATURE                Location/Qualifiers
REGION                 1..312
                       note = (FpL_C3KX 7e)4-IT-6H3K
```

```
source                 1..312
                       mol_type = protein
                       organism = synthetic construct
SEQUENCE: 326
ETPGESAEEV TIRVNLIFAD GRIQTAEFIG TFEEATAEAY AYANLLARDY GEFTADLEDG  60
GYTINIRFVG ETPGESAEEV TIRVNLIFAD GRIQTAEFIG TFEEATAEAY AYANLLARDY  120
GEFTADLEDG GYTINIRFVG ETPGESAEEV TIRVNLIFAD GRIQTAEFIG TFEEATAEAY  180
AYANLLARDY GEFTADLEDG GYTINIRFVG ETPGESAEEV TIRVNLIFAD GRIQTAEFIG  240
TFEEATAEAY AYANLLARDY GEFTADLEDG GYTINIRFVG ALPSKSKKIL KEAKKLNKAQ  300
APKHHHHHHK KK                                                      312

SEQ ID NO: 327         moltype = DNA  length = 939
FEATURE                Location/Qualifiers
misc_feature           1..939
                       note = (FpL_C3KX 7e)4-IT-6H3K_DNA
source                 1..939
                       mol_type = other DNA
                       organism = synthetic construct
SEQUENCE: 327
gaaaccccgg gagaatcggc tgaagaggtc accattcgtg tgaacttaat cttcgctgat  60
ggtcgcatcc aaacggcaga gttcattggg acgtttgaag aagcaaccgc cgaagcgtac  120
gcgtacgcca acctcctcgc ccgcgattac ggtgaattta cagccgattt ggaagatggc  180
ggttatacga ttaatattcg tttcgttggg gaaaccccgg gagaatcggc tgaagaggtc  240
accattcgtg tgaacttaat cttcgctgat ggtcgcatcc aaacggcaga gttcattggg  300
acgtttgaag aagcaaccgc cgaagcgtac gcgtacgcca acctcctcgc ccgcgattac  360
ggtgaattta cagccgattt ggaagatggc ggttatacga tcaatatccg cttcgtgggc  420
gagaccccgg gcgaatcggc cgaggaggtc accattcgtg tgaacttaat cttcgctgat  480
ggtcgcatcc aaacggcaga gttcattggg acgtttgaag aagcaaccgc cgaagcgtac  540
gcgtacgcca acctcctcgc ccgcgattac ggtgaattta cagccgattt ggaagatggc  600
ggttatacta tcaatatccg cttcgtcggc gaaaccccgg gagaatcggc tgaagaggtc  660
accattcgtg tgaacttaat cttcgctgat ggtcgcatcc aaacggcaga gttcattggg  720
acgtttgaag aagcaaccgc cgaagcgtac gcgtacgcca acctcctcgc ccgcgattac  780
ggtgaattta cagccgattt ggaagatggc ggttatacga tcaatatccg cttcgtgggc  840
gcgctgccgt ctaaatcgaa gaaaattctg aaagaagcca agaaactgaa taaagctcag  900
gcgccgaaac atcaccacca tcaccacaag aagaaataa                         939

SEQ ID NO: 328         moltype = DNA  length = 69
FEATURE                Location/Qualifiers
misc_feature           1..69
                       note = Immobilization tag_DNA
source                 1..69
                       mol_type = other DNA
                       organism = synthetic construct
SEQUENCE: 328
gcgctgccgt ctaaatcgaa gaaaattctg aaagaagcca agaaactgaa taaagctcag  60
gcgccgaaa                                                          69

SEQ ID NO: 329         moltype = DNA  length = 51
FEATURE                Location/Qualifiers
misc_feature           1..51
                       note = PCR forward primer
source                 1..51
                       mol_type = other DNA
                       organism = synthetic construct
SEQUENCE: 329
ctcgctgccc agccggcgat ggccatggaa accccgggag aatcggctga a           51

SEQ ID NO: 330         moltype = DNA  length = 48
FEATURE                Location/Qualifiers
misc_feature           1..48
                       note = PCR reverse primer
source                 1..48
                       mol_type = other DNA
                       organism = synthetic construct
SEQUENCE: 330
cccaacgaaa cgaatattaa tcgtataacc gccatcttcc aaatcggc               48

SEQ ID NO: 331         moltype = DNA  length = 48
FEATURE                Location/Qualifiers
misc_feature           1..48
                       note = PCR forward primer
source                 1..48
                       mol_type = other DNA
                       organism = synthetic construct
SEQUENCE: 331
acgattaata ttcgtttcgt tggggaaacc ccgggagaat cggctgaa               48

SEQ ID NO: 332         moltype = DNA  length = 48
FEATURE                Location/Qualifiers
```

```
misc_feature          1..48
                      note = PCR reverse primer
source                1..48
                      mol_type = other DNA
                      organism = synthetic construct
SEQUENCE: 332
ctcggccgat tcgcccgggg tctcgcccac gaagcggata ttgatcgt                48

SEQ ID NO: 333        moltype = DNA  length = 48
FEATURE               Location/Qualifiers
misc_feature          1..48
                      note = PCR forward primer
source                1..48
                      mol_type = other DNA
                      organism = synthetic construct
SEQUENCE: 333
gagaccccgg gcgaatcggc cgaggaggtc accattcgtg tgaactta                48

SEQ ID NO: 334        moltype = DNA  length = 48
FEATURE               Location/Qualifiers
misc_feature          1..48
                      note = PCR reverse primer
source                1..48
                      mol_type = other DNA
                      organism = synthetic construct
SEQUENCE: 334
gccgacgaag cggatattga tagtataacc gccatcttcc aaatcggc                48

SEQ ID NO: 335        moltype = DNA  length = 48
FEATURE               Location/Qualifiers
misc_feature          1..48
                      note = PCR forward primer
source                1..48
                      mol_type = other DNA
                      organism = synthetic construct
SEQUENCE: 335
actatcaata tccgcttcgt cggcgaaacc ccgggagaat cggctgaa                48

SEQ ID NO: 336        moltype = DNA  length = 78
FEATURE               Location/Qualifiers
misc_feature          1..78
                      note = PCR reverse primer
source                1..78
                      mol_type = other DNA
                      organism = synthetic construct
SEQUENCE: 336
tttattcagt ttcttggctt ctttcagaat tttcttcgat ttagacggca gcgcgcccac  60
gaagcggata ttgatcgt                                                 78

SEQ ID NO: 337        moltype = DNA  length = 69
FEATURE               Location/Qualifiers
misc_feature          1..69
                      note = Oligonucleotide
source                1..69
                      mol_type = other DNA
                      organism = synthetic construct
SEQUENCE: 337
aaagaagcca agaaactgaa taaagctcag gcgccgaaac atcaccacca tcaccacaag  60
aagaaataa                                                           69

SEQ ID NO: 338        moltype = DNA  length = 69
FEATURE               Location/Qualifiers
misc_feature          1..69
                      note = Oligonucleotide
source                1..69
                      mol_type = other DNA
                      organism = synthetic construct
SEQUENCE: 338
ttatttcttc ttgtggtgat ggtggtgatg tttcggcgcc tgagctttat tcagtttctt  60
ggcttcttt                                                           69

SEQ ID NO: 339        moltype = DNA  length = 42
FEATURE               Location/Qualifiers
misc_feature          1..42
                      note = PCR forward primer
source                1..42
                      mol_type = other DNA
                      organism = synthetic construct
SEQUENCE: 339
```

```
caccatcacc acaagaagaa ataagcttgc ggccgcactc ga                    42

SEQ ID NO: 340         moltype = DNA  length = 27
FEATURE                Location/Qualifiers
misc_feature           1..27
                       note = PCR reverse primer
source                 1..27
                       mol_type = other DNA
                       organism = synthetic construct
SEQUENCE: 340
catggccatc gccggctggg cagcgag                                     27

SEQ ID NO: 341         moltype = AA  length = 70
FEATURE                Location/Qualifiers
REGION                 1..70
                       note = FpL_C3KX 6c
source                 1..70
                       mol_type = protein
                       organism = synthetic construct
SEQUENCE: 341
ETPGESAEEV TIRVNLIFAD GRIQTAEFIG TFEEATAEAY AYANLLARDN GEFTADLEDG  60
GYTINIRFVG                                                         70

SEQ ID NO: 342         moltype = DNA  length = 210
FEATURE                Location/Qualifiers
misc_feature           1..210
                       note = FpL_C3KX 6c_DNA
source                 1..210
                       mol_type = other DNA
                       organism = synthetic construct
SEQUENCE: 342
gaaaccccgg gagaatcggc tgaagaggtc accattcgtg tgaacttaat cttcgctgat  60
ggtcgcatcc aaacggcaga gttcattggg acgtttgaag aagcaaccgc cgaagcgtac  120
gcgtacgcca acctcctcgc ccgcgataac ggtgaattta cagccgattt ggaagatggc  180
ggttatacga tcaatatccg cttcgtgggc                                  210

SEQ ID NO: 343         moltype = AA  length = 312
FEATURE                Location/Qualifiers
REGION                 1..312
                       note = (FpL_C3KX 6c)4-IT-6H3K
source                 1..312
                       mol_type = protein
                       organism = synthetic construct
SEQUENCE: 343
ETPGESAEEV TIRVNLIFAD GRIQTAEFIG TFEEATAEAY AYANLLARDN GEFTADLEDG  60
GYTINIRFVG ETPGESAEEV TIRVNLIFAD GRIQTAEFIG TFEEATAEAY AYANLLARDN  120
GEFTADLEDG GYTINIRFVG ETPGESAEEV TIRVNLIFAD GRIQTAEFIG TFEEATAEAY  180
AYANLLARDN GEFTADLEDG GYTINIRFVG ETPGESAEEV TIRVNLIFAD GRIQTAEFIG  240
TFEEATAEAY AYANLLARDN GEFTADLEDG GYTINIRFVG ALPSKSKKIL KEAKKLNKAQ  300
APKHHHHHHK KK                                                      312

SEQ ID NO: 344         moltype = DNA  length = 939
FEATURE                Location/Qualifiers
misc_feature           1..939
                       note = (FpL_C3KX 6c)4-IT-6H3K_DNA
source                 1..939
                       mol_type = other DNA
                       organism = synthetic construct
SEQUENCE: 344
gaaaccccgg gagaatcggc tgaagaggtc accattcgtg tgaacttaat cttcgctgat  60
ggtcgcatcc aaacggcaga gttcattggg acgtttgaag aagcaaccgc cgaagcgtac  120
gcgtacgcca acctcctcgc ccgcgataac ggtgaattta cagccgattt ggaagatggc  180
ggttatacga ttaatattcg tttcgttggg gaaaccccgg gagaatcggc tgaagaggtc  240
accattcgtg tgaacttaat cttcgctgat ggtcgcatcc aaacggcaga gttcattggg  300
acgtttgaag aagcaaccgc cgaagcgtac gcgtacgcca acctcctcgc ccgcgataac  360
ggtgaattta cagccgattt ggaagatggc ggttatacga tcaatatccg cttcgtgggc  420
gagaccccgg gcgaatcggc cgaggaggtc accattcgtg tgaacttaat cttcgctgat  480
ggtcgcatcc aaacggcaga gttcattggg acgtttgaag aagcaaccgc cgaagcgtac  540
gcgtacgcca acctcctcgc ccgcgataac ggtgaattta cagccgattt ggaagatggc  600
ggttatacta tcaatatccg cttcgtcggc gaaaccccgg gagaatcggc tgaagaggtc  660
accattcgtg tgaacttaat cttcgctgat ggtcgcatcc aaacggcaga gttcattggg  720
acgtttgaag aagcaaccgc cgaagcgtac gcgtacgcca acctcctcgc ccgcgataac  780
ggtgaattta cagccgattt ggaagatggc ggttatacga tcaatatccg cttcgtgggc  840
gcgctgccgt ctaaatcgaa gaaaattctg aaagaagcca agaaactgaa taaagctcag  900
gcgccgaaac atcaccacca tcaccacaag aagaaataa                         939

SEQ ID NO: 345         moltype = DNA  length = 27
FEATURE                Location/Qualifiers
misc_feature           1..27
```

```
                        note = K13X forward primer 1
misc_difference         7
                        note = a, c, g, or t
misc_difference         8
                        note = a, g, or t
source                  1..27
                        mol_type = other DNA
                        organism = synthetic construct
SEQUENCE: 345
accattndtg tgaatctgat ctttgcc                                    27

SEQ ID NO: 346          moltype = DNA  length = 27
FEATURE                 Location/Qualifiers
misc_feature            1..27
                        note = K13X forward primer 2
misc_difference         7
                        note = a, c, or g
misc_difference         8
                        note = a, c, or t
source                  1..27
                        mol_type = other DNA
                        organism = synthetic construct
SEQUENCE: 346
accattvhgg tgaatctgat ctttgcc                                    27

SEQ ID NO: 347          moltype = DNA  length = 27
FEATURE                 Location/Qualifiers
misc_feature            1..27
                        note = K13X forward primer 3
source                  1..27
                        mol_type = other DNA
                        organism = synthetic construct
SEQUENCE: 347
accatttggg tgaatctgat ctttgcc                                    27

SEQ ID NO: 348          moltype = DNA  length = 27
FEATURE                 Location/Qualifiers
misc_feature            1..27
                        note = K13X reverse primer 1
misc_difference         8
                        note = a, c, or t
misc_difference         9
                        note = a, c, g, or t
source                  1..27
                        mol_type = other DNA
                        organism = synthetic construct
SEQUENCE: 348
attcacahna atggtaactt cttcacg                                    27

SEQ ID NO: 349          moltype = DNA  length = 27
FEATURE                 Location/Qualifiers
misc_feature            1..27
                        note = K13X reverse primer 2
misc_difference         8
                        note = a, g, or t
misc_difference         9
                        note = c, g, or t
source                  1..27
                        mol_type = other DNA
                        organism = synthetic construct
SEQUENCE: 349
attcaccdba atggtaactt cttcacg                                    27

SEQ ID NO: 350          moltype = DNA  length = 27
FEATURE                 Location/Qualifiers
misc_feature            1..27
                        note = K13X reverse primer 3
source                  1..27
                        mol_type = other DNA
                        organism = synthetic construct
SEQUENCE: 350
attcacccaa atggtaactt cttcacg                                    27

SEQ ID NO: 351          moltype = DNA  length = 27
FEATURE                 Location/Qualifiers
misc_feature            1..27
                        note = K22X forward primer 1
misc_difference         7
                        note = a, c, g, or t
```

```
misc_difference        8
                       note = a, g, or t
source                 1..27
                       mol_type = other DNA
                       organism = synthetic construct
SEQUENCE: 351
gacggcndta cccagaccgc tgaattc                                    27

SEQ ID NO: 352         moltype = DNA  length = 27
FEATURE                Location/Qualifiers
misc_feature           1..27
                       note = K22X forward primer 2
misc_difference        7
                       note = a, c, or g
misc_difference        8
                       note = a, c, or t
source                 1..27
                       mol_type = other DNA
                       organism = synthetic construct
SEQUENCE: 352
gacggcvhga cccagaccgc tgaattc                                    27

SEQ ID NO: 353         moltype = DNA  length = 27
FEATURE                Location/Qualifiers
misc_feature           1..27
                       note = K22X forward primer 3
source                 1..27
                       mol_type = other DNA
                       organism = synthetic construct
SEQUENCE: 353
gacggctgga cccagaccgc tgaattc                                    27

SEQ ID NO: 354         moltype = DNA  length = 27
FEATURE                Location/Qualifiers
misc_feature           1..27
                       note = K22X reverse primer 1
misc_difference        8
                       note = a, c, or t
misc_difference        9
                       note = a, c, g, or t
source                 1..27
                       mol_type = other DNA
                       organism = synthetic construct
SEQUENCE: 354
ctgggtahng ccgtcggcaa agatcag                                    27

SEQ ID NO: 355         moltype = DNA  length = 27
FEATURE                Location/Qualifiers
misc_feature           1..27
                       note = K22X reverse primer 2
misc_difference        8
                       note = a, g, or t
misc_difference        9
                       note = c, g, or t
source                 1..27
                       mol_type = other DNA
                       organism = synthetic construct
SEQUENCE: 355
ctgggtcdbg ccgtcggcaa agatcag                                    27

SEQ ID NO: 356         moltype = DNA  length = 27
FEATURE                Location/Qualifiers
misc_feature           1..27
                       note = K22X reverse primer 3
source                 1..27
                       mol_type = other DNA
                       organism = synthetic construct
SEQUENCE: 356
ctgggtccag ccgtcggcaa agatcag                                    27

SEQ ID NO: 357         moltype = AA  length = 70
FEATURE                Location/Qualifiers
REGION                 1..70
                       note = FpL_C4KR_K7Q
source                 1..70
                       mol_type = protein
                       organism = synthetic construct
SEQUENCE: 357
ETPEEPQEEV TIRVNLIFAD GRTQTAEFRG TFEEATAEAY RYADLLARVN GEYTADLEDG  60
```

```
GYTINIRFAG                                                        70

SEQ ID NO: 358          moltype = AA  length = 70
FEATURE                 Location/Qualifiers
REGION                  1..70
                        note = FpL_C4KR_K13V
source                  1..70
                        mol_type = protein
                        organism = synthetic construct
SEQUENCE: 358
ETPEEPREEV TIVVNLIFAD GRTQTAEFRG TFEEATAEAY RYADLLARVN GEYTADLEDG  60
GYTINIRFAG                                                        70

SEQ ID NO: 359          moltype = AA  length = 70
FEATURE                 Location/Qualifiers
REGION                  1..70
                        note = FpL_C4K_K22T
source                  1..70
                        mol_type = protein
                        organism = synthetic construct
SEQUENCE: 359
ETPEEPREEV TIRVNLIFAD GTTQTAEFRG TFEEATAEAY RYADLLARVN GEYTADLEDG  60
GYTINIRFAG                                                        70

SEQ ID NO: 360          moltype = AA  length = 70
FEATURE                 Location/Qualifiers
REGION                  1..70
                        note = FpL_C4KR_K29P
source                  1..70
                        mol_type = protein
                        organism = synthetic construct
SEQUENCE: 360
ETPEEPREEV TIRVNLIFAD GRTQTAEFPG TFEEATAEAY RYADLLARVN GEYTADLEDG  60
GYTINIRFAG                                                        70

SEQ ID NO: 361          moltype = AA  length = 70
FEATURE                 Location/Qualifiers
REGION                  1..70
                        note = FpL_C4KR_K29V
source                  1..70
                        mol_type = protein
                        organism = synthetic construct
SEQUENCE: 361
ETPEEPREEV TIRVNLIFAD GRTQTAEFVG TFEEATAEAY RYADLLARVN GEYTADLEDG  60
GYTINIRFAG                                                        70

SEQ ID NO: 362          moltype = AA  length = 70
FEATURE                 Location/Qualifiers
REGION                  1..70
                        note = FpL_C4KR_K29I
source                  1..70
                        mol_type = protein
                        organism = synthetic construct
SEQUENCE: 362
ETPEEPREEV TIRVNLIFAD GRTQTAEFIG TFEEATAEAY RYADLLARVN GEYTADLEDG  60
GYTINIRFAG                                                        70

SEQ ID NO: 363          moltype = DNA  length = 30
FEATURE                 Location/Qualifiers
misc_feature            1..30
                        note = FpL_C3KX 7d_P6A forward primer
source                  1..30
                        mol_type = other DNA
                        organism = synthetic construct
SEQUENCE: 363
ccaggagagg cggcggaaga agttaccatt                                  30

SEQ ID NO: 364          moltype = DNA  length = 30
FEATURE                 Location/Qualifiers
misc_feature            1..30
                        note = FpL_C3KX 7d_P6A reverse primer
source                  1..30
                        mol_type = other DNA
                        organism = synthetic construct
SEQUENCE: 364
ttcttccgcc gcctctcctg gtgtttccat                                  30

SEQ ID NO: 365          moltype = AA  length = 70
FEATURE                 Location/Qualifiers
```

```
REGION                  1..70
                        note = FpL_C3KX 7d_P6A
source                  1..70
                        mol_type = protein
                        organism = synthetic construct
SEQUENCE: 365
ETPGEAAEEV TIRVNLIFAD GRIQTAEFIG TFEEATAEAY AYANLLARDY GDFTADLEDG  60
GYTINIRFAG                                                         70

SEQ ID NO: 366          moltype = DNA  length = 30
FEATURE                 Location/Qualifiers
misc_feature            1..30
                        note = FpL_C3KX 7d_E8G forward primer
source                  1..30
                        mol_type = other DNA
                        organism = synthetic construct
SEQUENCE: 366
gagtcagcgg gcgaagttac cattcgcgtg                                   30

SEQ ID NO: 367          moltype = DNA  length = 30
FEATURE                 Location/Qualifiers
misc_feature            1..30
                        note = FpL_C3KX 7d_E8G reverse primer
source                  1..30
                        mol_type = other DNA
                        organism = synthetic construct
SEQUENCE: 367
ggtaacttcg cccgctgact ctcctggtgt                                   30

SEQ ID NO: 368          moltype = AA  length = 70
FEATURE                 Location/Qualifiers
REGION                  1..70
                        note = FpL_C3KX 7d_E8G
source                  1..70
                        mol_type = protein
                        organism = synthetic construct
SEQUENCE: 368
ETPGESAGEV TIRVNLIFAD GRIQTAEFIG TFEEATAEAY AYANLLARDY GDFTADLEDG  60
GYTINIRFAG                                                         70

SEQ ID NO: 369          moltype = DNA  length = 30
FEATURE                 Location/Qualifiers
misc_feature            1..30
                        note = FpL_C3KX 7d_E8R forward primer
source                  1..30
                        mol_type = other DNA
                        organism = synthetic construct
SEQUENCE: 369
gagtcagcgc gtgaagttac cattcgcgtg                                   30

SEQ ID NO: 370          moltype = DNA  length = 30
FEATURE                 Location/Qualifiers
misc_feature            1..30
                        note = FpL_C3KX 7d_E8R reverse primer
source                  1..30
                        mol_type = other DNA
                        organism = synthetic construct
SEQUENCE: 370
ggtaacttca cgcgctgact ctcctggtgt                                   30

SEQ ID NO: 371          moltype = AA  length = 70
FEATURE                 Location/Qualifiers
REGION                  1..70
                        note = FpL_C3KX 7d_E8R
source                  1..70
                        mol_type = protein
                        organism = synthetic construct
SEQUENCE: 371
ETPGESAREV TIRVNLIFAD GRIQTAEFIG TFEEATAEAY AYANLLARDY GDFTADLEDG  60
GYTINIRFAG                                                         70

SEQ ID NO: 372          moltype = DNA  length = 27
FEATURE                 Location/Qualifiers
misc_feature            1..27
                        note = FpL_C3KX 7d_G21R forward primer
source                  1..27
                        mol_type = other DNA
                        organism = synthetic construct
SEQUENCE: 372
```

```
gccgaccgtc ggattcagac cgctgaa                                  27

SEQ ID NO: 373          moltype = DNA  length = 27
FEATURE                 Location/Qualifiers
misc_feature            1..27
                        note = FpL_C3KX 7d_G21R reverse primer
source                  1..27
                        mol_type = other DNA
                        organism = synthetic construct
SEQUENCE: 373
aatccgacgg tcggcaaaga tcagatt                                  27

SEQ ID NO: 374          moltype = AA  length = 70
FEATURE                 Location/Qualifiers
REGION                  1..70
                        note = FpL_C3KX 7d_G21R
source                  1..70
                        mol_type = protein
                        organism = synthetic construct
SEQUENCE: 374
ETPGESAEEV TIRVNLIFAD RRIQTAEFIG TFEEATAEAY AYANLLARDY GDFTADLEDG  60
GYTINIRFAG                                                     70

SEQ ID NO: 375          moltype = DNA  length = 30
FEATURE                 Location/Qualifiers
misc_feature            1..30
                        note = FpL_C3KX 7d_I23F forward primer
source                  1..30
                        mol_type = other DNA
                        organism = synthetic construct
SEQUENCE: 375
gacggtcggt ttcagaccgc tgaattcatt                               30

SEQ ID NO: 376          moltype = DNA  length = 30
FEATURE                 Location/Qualifiers
misc_feature            1..30
                        note = FpL_C3KX 7d_I23F reverse primer
source                  1..30
                        mol_type = other DNA
                        organism = synthetic construct
SEQUENCE: 376
agcggtctga aaccgaccgt cggcaaagat                               30

SEQ ID NO: 377          moltype = AA  length = 70
FEATURE                 Location/Qualifiers
REGION                  1..70
                        note = FpL_C3KX 7d_I23F
source                  1..70
                        mol_type = protein
                        organism = synthetic construct
SEQUENCE: 377
ETPGESAEEV TIRVNLIFAD GRFQTAEFIG TFEEATAEAY AYANLLARDY GDFTADLEDG  60
GYTINIRFAG                                                     70

SEQ ID NO: 378          moltype = DNA  length = 30
FEATURE                 Location/Qualifiers
misc_feature            1..30
                        note = FpL_C3KX 7d_I23L forward primer
source                  1..30
                        mol_type = other DNA
                        organism = synthetic construct
SEQUENCE: 378
gacggtcggc tgcagaccgc tgaattcatt                               30

SEQ ID NO: 379          moltype = DNA  length = 30
FEATURE                 Location/Qualifiers
misc_feature            1..30
                        note = FpL_C3KX 7d_I23L reverse primer
source                  1..30
                        mol_type = other DNA
                        organism = synthetic construct
SEQUENCE: 379
agcggtctgc agccgaccgt cggcaaagat                               30

SEQ ID NO: 380          moltype = AA  length = 70
FEATURE                 Location/Qualifiers
REGION                  1..70
                        note = FpL_C3KX 7d_I23L
source                  1..70
```

```
                        mol_type = protein
                        organism = synthetic construct
SEQUENCE: 380
ETPGESAEEV TIRVNLIFAD GRLQTAEFIG TFEEATAEAY AYANLLARDY GDFTADLEDG  60
GYTINIRFAG                                                         70

SEQ ID NO: 381          moltype = DNA  length = 30
FEATURE                 Location/Qualifiers
misc_feature            1..30
                        note = FpL_C3KX 7d_E33V forward primer
source                  1..30
                        mol_type = other DNA
                        organism = synthetic construct
SEQUENCE: 381
cgtacattcg tggaagccac agctgaagcc                                   30

SEQ ID NO: 382          moltype = DNA  length = 30
FEATURE                 Location/Qualifiers
misc_feature            1..30
                        note = FpL_C3KX 7d_E33V reverse primer
source                  1..30
                        mol_type = other DNA
                        organism = synthetic construct
SEQUENCE: 382
tgtggcttcc acgaatgtac caatgaattc                                   30

SEQ ID NO: 383          moltype = AA  length = 70
FEATURE                 Location/Qualifiers
REGION                  1..70
                        note = FpL_C3KX 7d_E33V
source                  1..70
                        mol_type = protein
                        organism = synthetic construct
SEQUENCE: 383
ETPGESAEEV TIRVNLIFAD GRIQTAEFIG TFVEATAEAY AYANLLARDY GDFTADLEDG  60
GYTINIRFAG                                                         70

SEQ ID NO: 384          moltype = DNA  length = 30
FEATURE                 Location/Qualifiers
misc_feature            1..30
                        note = FpL_C3KX 7d_K38H forward primer
source                  1..30
                        mol_type = other DNA
                        organism = synthetic construct
SEQUENCE: 384
gccacagctc atgcctatgc ttatgcgaat                                   30

SEQ ID NO: 385          moltype = DNA  length = 30
FEATURE                 Location/Qualifiers
misc_feature            1..30
                        note = FpL_C3KX 7d_K38H reverse primer
source                  1..30
                        mol_type = other DNA
                        organism = synthetic construct
SEQUENCE: 385
agcataggca tgagctgtgg cttcttcgaa                                   30

SEQ ID NO: 386          moltype = AA  length = 70
FEATURE                 Location/Qualifiers
REGION                  1..70
                        note = FpL_C3KX 7d_K38H
source                  1..70
                        mol_type = protein
                        organism = synthetic construct
SEQUENCE: 386
ETPGESAEEV TIRVNLIFAD GRIQTAEFIG TFEEATAHAY AYANLLARDY GDFTADLEDG  60
GYTINIRFAG                                                         70

SEQ ID NO: 387          moltype = DNA  length = 30
FEATURE                 Location/Qualifiers
misc_feature            1..30
                        note = FpL_C3KX 7d_K38L forward primer
source                  1..30
                        mol_type = other DNA
                        organism = synthetic construct
SEQUENCE: 387
gccacagctc tggcctatgc ttatgcgaat                                   30

SEQ ID NO: 388          moltype = DNA  length = 30
```

```
FEATURE                Location/Qualifiers
misc_feature           1..30
                       note = FpL_C3KX 7d_K38L reverse primer
source                 1..30
                       mol_type = other DNA
                       organism = synthetic construct
SEQUENCE: 388
agcataggcc agagctgtgg cttcttcgaa                                   30

SEQ ID NO: 389         moltype = AA  length = 70
FEATURE                Location/Qualifiers
REGION                 1..70
                       note = FpL_C3KX 7d_K38L
source                 1..70
                       mol_type = protein
                       organism = synthetic construct
SEQUENCE: 389
ETPGESAEEV TIRVNLIFAD GRIQTAEFIG TFEEATALAY AYANLLARDY GDFTADLEDG  60
GYTINIRFAG                                                         70

SEQ ID NO: 390         moltype = DNA  length = 30
FEATURE                Location/Qualifiers
misc_feature           1..30
                       note = FpL_C3KX 7d_N44H forward primer
source                 1..30
                       mol_type = other DNA
                       organism = synthetic construct
SEQUENCE: 390
gcttatgcgc atttgctggc ccgtgattat                                   30

SEQ ID NO: 391         moltype = DNA  length = 30
FEATURE                Location/Qualifiers
misc_feature           1..30
                       note = FpL_C3KX 7d_N44H reverse primer
source                 1..30
                       mol_type = other DNA
                       organism = synthetic construct
SEQUENCE: 391
ggccagcaaa tgcgcataag cataggcttc                                   30

SEQ ID NO: 392         moltype = AA  length = 70
FEATURE                Location/Qualifiers
REGION                 1..70
                       note = FpL_C3KX 7d_N44H
source                 1..70
                       mol_type = protein
                       organism = synthetic construct
SEQUENCE: 392
ETPGESAEEV TIRVNLIFAD GRIQTAEFIG TFEEATAEAY AYAHLLARDY GDFTADLEDG  60
GYTINIRFAG                                                         70

SEQ ID NO: 393         moltype = DNA  length = 30
FEATURE                Location/Qualifiers
misc_feature           1..30
                       note = FpL_C3KX 7d_N44R forward primer
source                 1..30
                       mol_type = other DNA
                       organism = synthetic construct
SEQUENCE: 393
gcttatgcgc gtttgctggc ccgtgattat                                   30

SEQ ID NO: 394         moltype = DNA  length = 30
FEATURE                Location/Qualifiers
misc_feature           1..30
                       note = FpL_C3KX 7d_N44R reverse primer
source                 1..30
                       mol_type = other DNA
                       organism = synthetic construct
SEQUENCE: 394
ggccagcaaa cgcgcataag cataggcttc                                   30

SEQ ID NO: 395         moltype = AA  length = 70
FEATURE                Location/Qualifiers
REGION                 1..70
                       note = FpL_C3KX 7d_N44R
source                 1..70
                       mol_type = protein
                       organism = synthetic construct
SEQUENCE: 395
```

```
ETPGESAEEV TIRVNLIFAD GRIQTAEFIG TFEEATAEAY AYARLLARDY GDFTADLEDG  60
GYTINIRFAG                                                        70

SEQ ID NO: 396         moltype = DNA  length = 30
FEATURE                Location/Qualifiers
misc_feature           1..30
                       note = FpL_C3KX 7d_R48H forward primer
source                 1..30
                       mol_type = other DNA
                       organism = synthetic construct
SEQUENCE: 396
ttgctggccc atgattatgg tgactttacg                                  30

SEQ ID NO: 397         moltype = DNA  length = 30
FEATURE                Location/Qualifiers
misc_feature           1..30
                       note = FpL_C3KX 7d_R48H reverse primer
source                 1..30
                       mol_type = other DNA
                       organism = synthetic construct
SEQUENCE: 397
aacataatca tgggccagca aattcgcata                                  30

SEQ ID NO: 398         moltype = AA  length = 70
FEATURE                Location/Qualifiers
REGION                 1..70
                       note = FpL_C3KX 7d_R48H
source                 1..70
                       mol_type = protein
                       organism = synthetic construct
SEQUENCE: 398
ETPGESAEEV TIRVNLIFAD GRIQTAEFIG TFEEATAEAY AYANLLAHDY GDFTADLEDG  60
GYTINIRFAG                                                        70

SEQ ID NO: 399         moltype = DNA  length = 30
FEATURE                Location/Qualifiers
misc_feature           1..30
                       note = FpL_C3KX 7d_N50M forward primer
source                 1..30
                       mol_type = other DNA
                       organism = synthetic construct
SEQUENCE: 399
gcccgtgata tgggtgactt tacggcggac                                  30

SEQ ID NO: 400         moltype = DNA  length = 30
FEATURE                Location/Qualifiers
misc_feature           1..30
                       note = FpL_C3KX 7d_N50M reverse primer
source                 1..30
                       mol_type = other DNA
                       organism = synthetic construct
SEQUENCE: 400
aaagtcaccc atatcacggg ccagcaaatt                                  30

SEQ ID NO: 401         moltype = AA  length = 70
FEATURE                Location/Qualifiers
REGION                 1..70
                       note = FpL_C3KX 7d_N50M
source                 1..70
                       mol_type = protein
                       organism = synthetic construct
SEQUENCE: 401
ETPGESAEEV TIRVNLIFAD GRIQTAEFIG TFEEATAEAY AYANLLARDM GDFTADLEDG  60
GYTINIRFAG                                                        70

SEQ ID NO: 402         moltype = DNA  length = 30
FEATURE                Location/Qualifiers
misc_feature           1..30
                       note = FpL_C3KX 7d_E52Y forward primer
source                 1..30
                       mol_type = other DNA
                       organism = synthetic construct
SEQUENCE: 402
gattatggtt attttacggc ggacctggaa                                  30

SEQ ID NO: 403         moltype = DNA  length = 30
FEATURE                Location/Qualifiers
misc_feature           1..30
                       note = FpL_C3KX 7d_E52Y reverse primer
```

```
source                  1..30
                        mol_type = other DNA
                        organism = synthetic construct
SEQUENCE: 403
cgccgtaaaa taaccataat cacgggccag                                30

SEQ ID NO: 404          moltype = AA  length = 70
FEATURE                 Location/Qualifiers
REGION                  1..70
                        note = FpL_C3KX 7d_E52Y
source                  1..70
                        mol_type = protein
                        organism = synthetic construct
SEQUENCE: 404
ETPGESAEEV TIRVNLIFAD GRIQTAEFIG TFEEATAEAY AYANLLARDY GYFTADLEDG  60
GYTINIRFAG                                                      70

SEQ ID NO: 405          moltype = DNA  length = 30
FEATURE                 Location/Qualifiers
misc_feature            1..30
                        note = FpL_C3KX 7d_Y53S forward primer
source                  1..30
                        mol_type = other DNA
                        organism = synthetic construct
SEQUENCE: 405
tatggtgact ctacggcgga cctggaagat                                30

SEQ ID NO: 406          moltype = DNA  length = 30
FEATURE                 Location/Qualifiers
misc_feature            1..30
                        note = FpL_C3KX 7d_Y53S reverse primer
source                  1..30
                        mol_type = other DNA
                        organism = synthetic construct
SEQUENCE: 406
gtccgccgta gagtcaccat aatcacgggc                                30

SEQ ID NO: 407          moltype = AA  length = 70
FEATURE                 Location/Qualifiers
REGION                  1..70
                        note = FpL_C3KX 7d_Y53S
source                  1..70
                        mol_type = protein
                        organism = synthetic construct
SEQUENCE: 407
ETPGESAEEV TIRVNLIFAD GRIQTAEFIG TFEEATAEAY AYANLLARDY GDSTADLEDG  60
GYTINIRFAG                                                      70

SEQ ID NO: 408          moltype = AA  length = 70
FEATURE                 Location/Qualifiers
REGION                  1..70
                        note = FpL_C3KX 9a
source                  1..70
                        mol_type = protein
                        organism = synthetic construct
SEQUENCE: 408
ETPGESAEEV TIRVNLIFAD GRRQTAEFIG TFEEATAEAY AYARLLARDY GEFTADLEDG  60
GYTINIRFVG                                                      70

SEQ ID NO: 409          moltype = AA  length = 70
FEATURE                 Location/Qualifiers
REGION                  1..70
                        note = FpL_C3KX 9b
source                  1..70
                        mol_type = protein
                        organism = synthetic construct
SEQUENCE: 409
ETPGESAEEV TIRVNLIFAD GRRQTAEFIG TFEEATAEAY AYAHLLARDY GEFTADLEDG  60
GYTINIRFVG                                                      70

SEQ ID NO: 410          moltype = AA  length = 70
FEATURE                 Location/Qualifiers
REGION                  1..70
                        note = FpL_C3KX 9c
source                  1..70
                        mol_type = protein
                        organism = synthetic construct
SEQUENCE: 410
ETPGESAEEV TIRVNLIFAD GRRQTAEFIG TFEEATAEAY AYANLLARDY GEFTADLEDG  60
```

```
GYTLNIRFVG                                                         70

SEQ ID NO: 411         moltype = AA  length = 70
FEATURE                Location/Qualifiers
REGION                 1..70
                       note = FpL_C3KX 9d
source                 1..70
                       mol_type = protein
                       organism = synthetic construct
SEQUENCE: 411
ETPGESAEEV TIRVNLIFAD GRIQTAEFIG TFEEATAEAY AYARLLARDY GEFTADLEDG  60
GYTLNIRFVG                                                         70

SEQ ID NO: 412         moltype = AA  length = 70
FEATURE                Location/Qualifiers
REGION                 1..70
                       note = FpL_C3KX 9e
source                 1..70
                       mol_type = protein
                       organism = synthetic construct
SEQUENCE: 412
ETPGESAEEV TIRVNLIFAD GRIQTAEFIG TFEEATAEAY AYAHLLARDY GEFTADLEDG  60
GYTLNIRFVG                                                         70

SEQ ID NO: 413         moltype = AA  length = 70
FEATURE                Location/Qualifiers
REGION                 1..70
                       note = FpL_C3KX 10a
source                 1..70
                       mol_type = protein
                       organism = synthetic construct
SEQUENCE: 413
ETPGESAEEV TIRVNLIFAD GRRQTAEFIG TFEEATAEAY AYARLLAHDY GEFTADLEDG  60
GYTLNIRFVG                                                         70

SEQ ID NO: 414         moltype = AA  length = 70
FEATURE                Location/Qualifiers
REGION                 1..70
                       note = FpL_C3KX 10b
source                 1..70
                       mol_type = protein
                       organism = synthetic construct
SEQUENCE: 414
ETPGESAEEV TIRVNLIFAD GRRQTAEFIG TFEEATAEAY AYAHLLAHDY GEFTADLEDG  60
GYTLNIRFVG                                                         70

SEQ ID NO: 415         moltype = DNA  length = 210
FEATURE                Location/Qualifiers
misc_feature           1..210
                       note = FpL_C3KX 9a_DNA
source                 1..210
                       mol_type = other DNA
                       organism = synthetic construct
SEQUENCE: 415
gaaacaccgg gagagagcgc cgaagaggtg accattcgtg taaatttgat tttcgccgac  60
ggtcgccgcc agacggctga gttcattggt accttcgagg aagcgacggc agaggcttat  120
gcgtacgcgc gtttactggc ccgcgattac ggtgagttta cagcagatct ggaggatggc  180
ggctacacca tcaacattcg ctttgtgggt                                   210

SEQ ID NO: 416         moltype = DNA  length = 210
FEATURE                Location/Qualifiers
misc_feature           1..210
                       note = FpL_C3KX 9b_DNA
source                 1..210
                       mol_type = other DNA
                       organism = synthetic construct
SEQUENCE: 416
gaaacaccgg gagagagcgc cgaagaggtg accattcgtg taaatttgat tttcgccgac  60
ggtcgccgcc agacggctga gttcattggt accttcgagg aagcgacggc agaggcttat  120
gcgtacgcgc atttactggc ccgcgattac ggtgagttta cagcagatct ggaggatggc  180
ggctacacca tcaacattcg ctttgtgggt                                   210

SEQ ID NO: 417         moltype = DNA  length = 210
FEATURE                Location/Qualifiers
misc_feature           1..210
                       note = FpL_C3KX 9c_DNA
source                 1..210
                       mol_type = other DNA
                       organism = synthetic construct
```

```
SEQUENCE: 417
gaaacaccgg gagagagcgc cgaagaggtg accattcgtg taaatttgat tttcgccgac  60
ggtcgccgcc agacggctga gttcattggt accttcgagg aagcgacggc agaggcttat  120
gcgtacgcga acttactggc ccgcgattac ggtgagttta cagcagatct ggaggatggc  180
ggctacacct taaacattcg ctttgtgggt                                  210

SEQ ID NO: 418         moltype = DNA  length = 210
FEATURE                Location/Qualifiers
misc_feature           1..210
                       note = FpL_C3KX 9d_DNA
source                 1..210
                       mol_type = other DNA
                       organism = synthetic construct
SEQUENCE: 418
gaaacaccgg gagagagcgc cgaagaggtg accattcgtg taaatttgat tttcgccgac  60
ggtcgcattc agacggctga gttcattggt accttcgagg aagcgacggc agaggcttat  120
gcgtacgcgc gcttactggc ccgcgattac ggtgagttta cagcagatct ggaggatggc  180
ggctacacct taaacattcg ctttgtgggt                                  210

SEQ ID NO: 419         moltype = DNA  length = 210
FEATURE                Location/Qualifiers
misc_feature           1..210
                       note = FpL_C3KX 9e_DNA
source                 1..210
                       mol_type = other DNA
                       organism = synthetic construct
SEQUENCE: 419
gaaacaccgg gagagagcgc cgaagaggtg accattcgtg taaatttgat tttcgccgac  60
ggtcgcattc agacggctga gttcattggt accttcgagg aagcgacggc agaggcttat  120
gcgtacgcgc atttactggc ccgcgattac ggtgagttta cagcagatct ggaggatggc  180
ggctacacct taaacattcg ctttgtgggt                                  210

SEQ ID NO: 420         moltype = DNA  length = 210
FEATURE                Location/Qualifiers
misc_feature           1..210
                       note = FpL_C3KX 10a_DNA
source                 1..210
                       mol_type = other DNA
                       organism = synthetic construct
SEQUENCE: 420
gaaacaccgg gagagagcgc cgaagaggtg accattcgtg taaatttgat tttcgccgac  60
ggtcgccgcc agacggctga gttcattggt accttcgagg aagcgacggc agaggcttat  120
gcgtacgcgc gcttactggc ccatgattac ggtgagttta cagcagatct ggaggatggc  180
ggctacacct taaacattcg ctttgtgggt                                  210

SEQ ID NO: 421         moltype = DNA  length = 210
FEATURE                Location/Qualifiers
misc_feature           1..210
                       note = FpL_C3KX 10b_DNA
source                 1..210
                       mol_type = other DNA
                       organism = synthetic construct
SEQUENCE: 421
gaaacaccgg gagagagcgc cgaagaggtg accattcgtg taaatttgat tttcgccgac  60
ggtcgccgcc agacggctga gttcattggt accttcgagg aagcgacggc agaggcttat  120
gcgtacgcgc atttactggc ccatgattac ggtgagttta cagcagatct ggaggatggc  180
ggctacacct taaacattcg ctttgtgggt                                  210

SEQ ID NO: 422         moltype = DNA  length = 30
FEATURE                Location/Qualifiers
misc_feature           1..30
                       note = N15X forward primer 1
misc_difference        10
                       note = a, c, g, or t
source                 1..30
                       mol_type = other DNA
                       organism = synthetic construct
SEQUENCE: 422
attcgtgtgn dtttaatctt cgctgatggt                                  30

SEQ ID NO: 423         moltype = DNA  length = 30
FEATURE                Location/Qualifiers
misc_feature           1..30
                       note = N15X forward primer 2
source                 1..30
                       mol_type = other DNA
                       organism = synthetic construct
SEQUENCE: 423
attcgtgtgv hgttaatctt cgctgatggt                                  30
```

```
SEQ ID NO: 424          moltype = DNA  length = 30
FEATURE                 Location/Qualifiers
misc_feature            1..30
                        note = N15X forward primer 3
source                  1..30
                        mol_type = other DNA
                        organism = synthetic construct
SEQUENCE: 424
attcgtgtgt ggttaatctt cgctgatggt                                   30

SEQ ID NO: 425          moltype = DNA  length = 30
FEATURE                 Location/Qualifiers
misc_feature            1..30
                        note = N15X reverse primer 1
misc_difference         12
                        note = a, c, g, or t
source                  1..30
                        mol_type = other DNA
                        organism = synthetic construct
SEQUENCE: 425
cacacgaata hncacacgaa tggtgacctc                                   30

SEQ ID NO: 426          moltype = DNA  length = 30
FEATURE                 Location/Qualifiers
misc_feature            1..30
                        note = N15X reverse primer 2
source                  1..30
                        mol_type = other DNA
                        organism = synthetic construct
SEQUENCE: 426
cacacgaatc dbcacacgaa tggtgacctc                                   30

SEQ ID NO: 427          moltype = DNA  length = 30
FEATURE                 Location/Qualifiers
misc_feature            1..30
                        note = N15X reverse primer 3
source                  1..30
                        mol_type = other DNA
                        organism = synthetic construct
SEQUENCE: 427
cacacgaatc cacacacgaa tggtgacctc                                   30

SEQ ID NO: 428          moltype = DNA  length = 30
FEATURE                 Location/Qualifiers
misc_feature            1..30
                        note = E34X forward primer 1
misc_difference         10
                        note = a, c, g, or t
source                  1..30
                        mol_type = other DNA
                        organism = synthetic construct
SEQUENCE: 428
acgtttgaan dtgcaaccgc cgaagcgtac                                   30

SEQ ID NO: 429          moltype = DNA  length = 30
FEATURE                 Location/Qualifiers
misc_feature            1..30
                        note = E34X forward primer 2
source                  1..30
                        mol_type = other DNA
                        organism = synthetic construct
SEQUENCE: 429
acgtttgaav hggcaaccgc cgaagcgtac                                   30

SEQ ID NO: 430          moltype = DNA  length = 30
FEATURE                 Location/Qualifiers
misc_feature            1..30
                        note = E34X forward primer 3
source                  1..30
                        mol_type = other DNA
                        organism = synthetic construct
SEQUENCE: 430
acgtttgaat gggcaaccgc cgaagcgtac                                   30

SEQ ID NO: 431          moltype = DNA  length = 30
FEATURE                 Location/Qualifiers
misc_feature            1..30
                        note = E34X reverse primer 1
```

```
misc_difference        12
                       note = a, c, g, or t
source                 1..30
                       mol_type = other DNA
                       organism = synthetic construct
SEQUENCE: 431
ttcaaacgta hnttcaaacg tcccaatgaa                                   30

SEQ ID NO: 432         moltype = DNA  length = 30
FEATURE                Location/Qualifiers
misc_feature           1..30
                       note = E34X reverse primer 2
source                 1..30
                       mol_type = other DNA
                       organism = synthetic construct
SEQUENCE: 432
ttcaaacgtc dbttcaaacg tcccaatgaa                                   30

SEQ ID NO: 433         moltype = DNA  length = 30
FEATURE                Location/Qualifiers
misc_feature           1..30
                       note = E34X reverse primer 3
source                 1..30
                       mol_type = other DNA
                       organism = synthetic construct
SEQUENCE: 433
ttcaaacgtc cattcaaacg tcccaatgaa                                   30

SEQ ID NO: 434         moltype = AA  length = 70
FEATURE                Location/Qualifiers
REGION                 1..70
                       note = FpL_C3KX 7e_N15V
source                 1..70
                       mol_type = protein
                       organism = synthetic construct
SEQUENCE: 434
ETPGESAEEV TIRVVLIFAD GRIQTAEFIG TFEEATAEAY AYANLLARDY GEFTADLEDG  60
GYTINIRFVG                                                         70

SEQ ID NO: 435         moltype = AA  length = 70
FEATURE                Location/Qualifiers
REGION                 1..70
                       note = FpL_C3KX 7e_E34D
source                 1..70
                       mol_type = protein
                       organism = synthetic construct
SEQUENCE: 435
ETPGESAEEV TIRVNLIFAD GRIQTAEFIG TFEDATAEAY AYANLLARDY GEFTADLEDG  60
GYTINIRFVG                                                         70

SEQ ID NO: 436         moltype = AA  length = 70
FEATURE                Location/Qualifiers
REGION                 1..70
                       note = FpL_C3KX 7e_E34F
source                 1..70
                       mol_type = protein
                       organism = synthetic construct
SEQUENCE: 436
ETPGESAEEV TIRVNLIFAD GRIQTAEFIG TFEFATAEAY AYANLLARDY GEFTADLEDG  60
GYTINIRFVG                                                         70

SEQ ID NO: 437         moltype = AA  length = 70
FEATURE                Location/Qualifiers
REGION                 1..70
                       note = FpL_C3KX 7e_E34L
source                 1..70
                       mol_type = protein
                       organism = synthetic construct
SEQUENCE: 437
ETPGESAEEV TIRVNLIFAD GRIQTAEFIG TFELATAEAY AYANLLARDY GEFTADLEDG  60
GYTINIRFVG                                                         70

SEQ ID NO: 438         moltype = AA  length = 70
FEATURE                Location/Qualifiers
REGION                 1..70
                       note = FpL_C3KX 7e_E34V
source                 1..70
                       mol_type = protein
                       organism = synthetic construct
```

-continued

```
SEQUENCE: 438
ETPGESAEEV TIRVNLIFAD GRIQTAEFIG TFEVATAEAY AYANLLARDY GEFTADLEDG  60
GYTINIRFVG                                                          70
```